US009233153B2

(12) United States Patent
Gall et al.

(10) Patent No.: US 9,233,153 B2
(45) Date of Patent: Jan. 12, 2016

(54) AFFENADENOVIRUS (GORILLA) OR ADENOVIRAL VECTORS AND METHODS OF USE

(71) Applicant: GenVec, Inc., Gaithersburg, MD (US)

(72) Inventors: Jason G. D. Gall, Germantown, MD (US); Duncan McVey, Derwood, MD (US); Douglas E. Brough, Gaithersburg, MD (US)

(73) Assignee: GenVec, Inc., Gaithersburg, MD (US)

( * ) Notice: Subject to any disclaimer, the term of this patent is extended or adjusted under 35 U.S.C. 154(b) by 0 days.

(21) Appl. No.: 14/349,421

(22) PCT Filed: Oct. 5, 2012

(86) PCT No.: PCT/US2012/058956
§ 371 (c)(1),
(2) Date: Apr. 3, 2014

(87) PCT Pub. No.: WO2013/052799
PCT Pub. Date: Apr. 11, 2013

(65) Prior Publication Data
US 2014/0248307 A1    Sep. 4, 2014

Related U.S. Application Data

(60) Provisional application No. 61/543,638, filed on Oct. 5, 2011.

(51) Int. Cl.
*C07K 14/005* (2006.01)
*C12N 15/86* (2006.01)
*A61K 39/155* (2006.01)

(52) U.S. Cl.
CPC ............. *A61K 39/155* (2013.01); *C07K 14/005* (2013.01); *C12N 15/86* (2013.01); *C12N 2710/10322* (2013.01); *C12N 2710/10333* (2013.01); *C12N 2710/10343* (2013.01)

(58) Field of Classification Search
CPC ................. C07K 14/005; C12N 15/86; C12N 2710/10322; C12N 2710/10333; C12N 2710/10343; C12N 7/00
See application file for complete search history.

(56) References Cited

U.S. PATENT DOCUMENTS

| 5,837,511 | A | 11/1998 | Falck-Pedersen et al. |
| 5,851,806 | A | 12/1998 | Kovesdi et al. |
| 5,994,106 | A | 11/1999 | Kovesdi et al. |
| 5,994,128 | A | 11/1999 | Fallaux et al. |
| 5,998,205 | A | 12/1999 | Hallenbeck et al. |
| 6,033,908 | A | 3/2000 | Bout et al. |
| 6,127,175 | A | 10/2000 | Vigne et al. |
| 6,225,289 | B1 | 5/2001 | Kovesdi et al. |
| 6,482,616 | B1 | 11/2002 | Kovesdi et al. |
| 6,514,943 | B2 | 2/2003 | Kovesdi et al. |
| 6,677,156 | B2 | 1/2004 | Brough et al. |
| 6,682,929 | B2 | 1/2004 | Brough et al. |
| 7,195,896 | B2 | 3/2007 | Kovesdi et al. |
| 2008/0233650 | A1 | 9/2008 | Gall et al. |
| 2014/0248308 | A1* | 9/2014 | McVey et al. ............... 424/199.1 |
| 2014/0271711 | A1* | 9/2014 | Brough et al. ............. 424/211.1 |
| 2014/0314717 | A1* | 10/2014 | Brough et al. ............... 424/93.2 |

FOREIGN PATENT DOCUMENTS

| WO | WO 94/28152 A1 | 12/1994 |
| WO | WO 95/02697 A2 | 1/1995 |
| WO | WO 95/16772 A1 | 6/1995 |
| WO | WO 95/34671 A1 | 12/1995 |
| WO | WO 96/22378 A1 | 7/1996 |
| WO | WO 97/00326 A1 | 1/1997 |
| WO | WO 97/12986 A2 | 4/1997 |
| WO | WO 97/21826 A2 | 6/1997 |
| WO | WO 00/00628 A1 | 1/2000 |
| WO | WO 00/34444 A2 | 6/2000 |
| WO | WO 03/020879 A2 | 3/2003 |
| WO | WO 03/022311 A1 | 3/2003 |
| WO | WO 2010/051367 A1 | 5/2010 |
| WO | WO 2010051367 A1 * | 5/2010 |
| WO | WO 2011/057248 A2 | 5/2011 |

OTHER PUBLICATIONS

Roy S, Calcedo R, Vandenberghe LH, Kryazhimskiy S, Yuan X, Grant R, Keough M, Somanathan S, Wang L, Sandhu A, Wang Q, Medina-Jaszek A, Plotkin JB, Wilson JM. Simian adenovirus 43, complete genome. GenBank: FJ025900. Dep. Jul. 9, 2009.*
McVey D, et. al. Gorilla beringei beringei adenovirus 7 isolate GC44 DNA polymerase gene, complete cds. GenBank: KC702816. Dep. Sep. 17, 2013.*
McVey D, et. al. Gorilla beringei beringei adenovirus 7 isolate GC44 hexon gene, complete cds. GenBank: KC702813.1. Dep. Sep. 17, 2013.*
Roy S, Calcedo R, Vandenberghe LH, Kryazhimskiy S, Yuan X, Grant R, Keough M, Somanathan S, Wang L, Sandhu A, Wang Q, Medina-Jaszek A, Plotkin JB, Wilson JM. Simian adenovirus 45, complete genome. GenBank: FJ025901. Dep. Jul. 9, 2009.*
Kohlmann R, Schwannecke S, Tippler B, Ternette N, Temchura VV, Tenbusch M, Uberla K, Grunwald T. Protective efficacy and immunogenicity of an adenoviral vector vaccine encoding the codon-optimized F protein of respiratory syncytial virus. J Virol. Dec. 2009;83(23):12601-10. Epub Sep. 23, 2009.*
Roy S, Vandenberghe LH, Kryazhimskiy S, Grant R, Calcedo R, Yuan X, Keough M, Sandhu A, Wang Q, Medina-Jaszek CA, Plotkin JB, Wilson JM. Isolation and characterization of adenoviruses persistently shed from the gastrointestinal tract of non-human primates. PLoS Pathog. Jul. 2009;5(7):e1000503. Epub Jul. 3, 2009.*

(Continued)

*Primary Examiner* — Benjamin P Blumel
*Assistant Examiner* — Rachel Gill
(74) *Attorney, Agent, or Firm* — Leydig, Voit & Mayer, Ltd.

(57) ABSTRACT

The invention provides an adenovirus or adenoviral vector characterized by comprising one or more particular nucleic acid sequences or one or more particular amino acid sequences, or portions thereof, pertaining to, for example, an adenoviral pIX protein, DNA polymerase protein, penton protein, hexon protein, and/or fiber protein.

115 Claims, No Drawings

(56) References Cited

OTHER PUBLICATIONS

Altschul et al., "Basic Local Alignment Search Tool," *J. Molecular Biol.*, 215(3): 403-410 (1990).
Altschul et al., "Gapped BLAST and PSI-BLAST: a new generation of protein database search programs," *Nucleic Acids Res.*, 25(17): 3389-3402 (1997).
Bai et al., "Mutations that alter an Arg-Gly-Asp (RGD) sequence in the adenovirus type 2 penton base protein abolish its cell-rounding activity and delay virus reproduction in flat cells," *J. Virol.*, 67(9): 5198-5205 (1993).
Biegert et al., "Sequence context-specific profiles for homology searching," *Proc. Natl. Acad. Sci. USA*, 106(10): 3770-3775 (2009).
Boulanger et al., "Characterization of adenovirus protein IX," *J. Gen. Virol.*, 44(3): 783-800 (1979).
Brough et al., "Activation of transgene expression by early region 4 is responsible for a high level of persistent transgene expression from adenovirus vectors in vivo," *J. Virol.*, 71(12): 9206-9213 (1997).
Cartier et al., "Hematopoietic stem cell gene therapy with a lentiviral vector in X-linked adrenoleukodystrophy," *Science*, 326(5954): 818-823 (2009).
Cavazzana-Calvo et al., "Gene therapy of human severe combined immunodeficiency (SCID)-X1 disease," *Science*, 288(5466): 669-672 (2000).
Chen et al., "Persistence in muscle of an adenoviral vector that lacks all viral genes," *Proc. Natl. Acad. Sci. USA*, 94(5): 1645-1650 (1997).
Chroboczek et al., "The sequence of the genome of adenovirus type 5 and its comparison with the genome of adenovirus type 2," *Virology*, 186(1): 280-285 (1992).
Crawford-Miksza et al., "Analysis of 15 adenovirus hexon proteins reveals the location and structure of seven hypervariable regions containing serotype-specific residues," *J. Virol.*, 70(3): 1836-1844 (1996).
Curiel et al., "High-efficiency gene transfer mediated by adenovirus coupled to DNA-polylysine complexes," *Hum. Gene Ther.*, 3(2): 147-154 (1992).
Devaux et al., "Structure of adenovirus fibre. I. Analysis of crystals of fibre from adenovirus serotypes 2 and 5 by electron microscopy and X-ray crystallography," *J. Molec. Biol.*, 215(4): 567-588 (1990).
Dey et al., "Molecular epidemiology of adenovirus infection among infants and children with acute gastroenteritis in Dhaka City, Bangladesh," *Infect. Genet. Evol.*, 9(4) 518-522 (2009).
Field et al., "Properties of the adenovirus DNA polymerase," *J. Biol. Chem.*, 259(15): 9487-9495 (1984).
Gall et al., "Construction and characterization of hexon-chimeric adenoviruses: specification of adenovirus serotype," *J. Virol.*, 72(12): 10260-10264 (1998).
Genbank Accession No. ABU95388.1, "hexon, partial [Human adenovirus 9]," (Jun. 2009).
Genbank Accession No. EDA88859.1, "hypothetical protein GOS_1918841, partial [marine metagenome]," (Apr. 2007).
Genbank Accession No. FJ025900.1, "Simian adenovirus 43, complete genome," (Mar. 2012).
Genbank Accession No. FJ025901.1, "Simian adenovirus 45, complete genome," (Mar. 2012).
Genbank Accession No. JN163990.1, "Gorilla gorilla beringei adenovirus 6 hexon gene, partial cds," (Dec. 2011).
Ghosh-Choudhury et al., "Protein IX, a minor component of the human adenovirus capsid, is essential for the packaging of full length genomes," *EMBO J.*, 6(6): 1733-1739 (1987).
Ginsberg et al., "A proposed terminology for the adenovirus antigens and virion morphological subunits," *Virology*, 28(4): 782-783 (1966).
Goins et al., "Herpes simplex virus vector-mediated gene delivery for the treatment of lower urinary tract pain," *Gene Ther.*, 16(4): 558-569 (2009).
Graham et al., "Characteristics of a human cell line transformed by DNA from human adenovirus type 5," *J. Gen. Virol.*, 36(1): 59-72 (1977).
Green et al., "Evidence for a repeating cross-beta sheet structure in the adenovirus fibre," *EMBO J.*, 2(8): 1357-1365 (1983).
Hacein-Bey-Abina et al., "A serious adverse event after successful gene therapy for X-linked severe combined immunodeficiency," *N. Engl. J. Med.*, 348(3): 255-256 (2003).
Henry et al., "Characterization of the knob domain of the adenovirus type 5 fiber protein expressed in *Escherichia coli*," *J. Virol.*, 68(8): 5239-5246 (1994).
Horvath et al., "Nonpermissivity of human peripheral blood lymphocytes to adenovirus type 2 infection," *J. Virology*, 62(1): 341-345 (1988).
Jornvall et al., "The adenovirus hexon protein. The primary structure of the polypeptide and its correlation with the hexon gene," *J. Biol. Chem.*, 256(12): 6181-6186 (1981).
Kannan et al., "Structural and functional diversity of the microbial kinome," *PLoS Biol.*, 5(3) E17 (2007).
Kay et al., "Viral vectors for gene therapy: the art of turning infectious agents into vehicles of therapeutics," *Nature Medicine*, 7(1): 33-40 (2001).
Kochanek et al., "High-capacity adenoviral vectors for gene transfer and somatic gene therapy," *Hum. Gene Ther.*, 10(15): 2451-2459 (1999).
Lasaro et al., "New insights on adenovirus as vaccine vectors," *Molecular Therapy*, 17(8): 1333-1339 (2009).
Lutz et al., "The product of the adenovirus intermediate gene IX is a transcriptional activator," *J. Virol.*, 71(7): 5102-5109 (1997).
Mayrhofer et al., "Nonreplicating vaccinia virus vectors expressing the H5 influenza virus hemagglutinin produced in modified Vero cells induce robust protection," *J. Virol.*, 83(10): 5192-5203 (2009).
Mease et al., "Safety, tolerability, and clinical outcomes after intraarticular injection of a recombinant adeno-associated vector containing a tumor necrosis factor antagonist gene: results of a phase 1/2 Study," *Journal of Rheumatology*, 37(4): 692-703 (2010).
Morsy et al., An adenoviral vector deleted for all viral coding sequences results in enhanced safety and extended expression of a leptin transgene, *Proc. Natl. Acad. Sci. USA*, 95: 7866-7871 (1998).
NCBI reference sequence AP_000218, "E3 12.5K [Human adenovirus 5]," (Dec. 2008).
NCBI reference sequence AP_000224.1, "*Homo sapiens* genomic DNA, chromosome 21q21.2, LL56-APP region, clone:B2017A3, complete sequence," (Nov. 1991).
Neumann et al., "Determination of the nucleotide sequence for the penton-base gene of human adenovirus type 5," *Gene*, 69(1) 153-157 (1988).
Novelli et al., "Deletion analysis of functional domains in baculovirus-expressed adenovirus type 2 fiber," *Virology*, 185(1): 365-376 (1991).
Roberts et al., "Three-dimensional structure of the adenovirus major coat protein hexon," *Science*, 232(4754): 1148-1151 (1986).
Roy et al., "Isolation and Characterization of Adenoviruses Persistently Shed from the Gastrointestinal Tract of Non-Human Primates," *PLOS Pathogens*, 5(7): E1000503, 1-9, (2009).
Rusch et al., "The Sorcerer II Global Ocean Sampling expedition: northwest Atlantic through eastern tropical Pacific," *PLoS Biol.*, 5(3) E77 (2007).
Rux et al., "Structural and phylogenetic analysis of adenovirus hexons by use of high-resolution x-ray crystallographic, molecular modeling, and sequence-based methods," *J. Virol.*, 77(17): 9553-9566 (2003).
Signas et al., Adenovirus 3 Fiber Polypeptide Gene: Implications for the Structure of the Fiber Protein, *J. Virol.*, 53(2): 672-678 (1985).
Silver et al., "Interaction of human adenovirus serotype 2 with human lymphoid cells," *Virology*, 165(2): 377-387 (1988).
Soding, "Protein homology detection by HMM-HMM comparison," *Bioinformatics*, 21(7): 951-960 (2005).
Stewart et al., "Image reconstruction reveals the complex molecular organization of adenovirus," *Cell*, 67(1): 145-154 (1991).
Stewart et al., "Difference imaging of adenovirus: bridging the resolution gap between X-ray crystallography and electron microscopy," *EMBO J.*, 12(7): 2589-99 (1993).

(56) References Cited

OTHER PUBLICATIONS

Thomas et al., "Progress and problems with the use of viral vectors for gene therapy," *Nature Review Genetics*, 4(5): 346-358 (2003).
Van Oostrum et al, "Molecular composition of the adenovirus type 2 virion," *J. Virol.*, 56(2): 439-448 (1985).
Wevers et al., "A novel adenovirus of Western lowland gorillas (Gorilla gorilla gorilla)," *J. Virology*, 7(1): 1-8 (2010).
Wevers et al., "Novel Adenoviruses in Wild Primates: a High Level of Genetic Diversity and Evidence of Zoonotic Transmissions," *J. Virology*, 85(20): 10774-10784, (2011).
Yeh et al., "Human adenovirus type 41 contains two fibers," *Virus Res.*, 33(2): 179-198 (1991).
Yooseph et al., "The Sorcerer II Global Ocean Sampling expedition: expanding the universe of protein families," *PLoS Biol.*, 5(3) E16, (2007).

* cited by examiner

SEQUENCE LISTING

```
<160> NUMBER OF SEQ ID NOS: 25

<210> SEQ ID NO 1
<211> LENGTH: 30
<212> TYPE: DNA
<213> ORGANISM: Gorilla beringei beringei

<400> SEQUENCE: 1
agctctttgg tggcgagcgg cgcggcctct                                      30

<210> SEQ ID NO 2
<211> LENGTH: 439
<212> TYPE: DNA
<213> ORGANISM: Gorilla beringei beringei

<400> SEQUENCE: 2
aacatcaata cctcaaagtc atggtcaggg acactttcgc cctcacccac acctccctcc      60
gcaaggcggc gcaggcctac gcgctgcccg tggagaaggg ctgttgcccc taccaggccg     120
tcaaccagtt ctacatgcta ggctcttacc gttcggacac ggacgggttt cccctccaag     180
agtactggaa agaccgcgaa gagttcgtcc tcaaccgcga gctgtggaaa aagaaggggg     240
aggataagta tgacatcatc cgcgagaccc tcgactactg cgcgctcgac gtccaggtca     300
ccgccgagct ggtgcacaag ctgcgcgagt cctacgcctc cttcgtcagg gactcggtgg     360
gcttgcaaga agcaagcttc aacgtcttcc agcggcccac catctcctcc aactcccatg     420
ccatcttcag gcagatcgc                                                  439
```

```
<210> SEQ ID NO 3
<211> LENGTH: 34
<212> TYPE: DNA
<213> ORGANISM: Gorilla beringei beringei

<400> SEQUENCE: 3
actgaggctg cggctaaggc tgaggtcgaa gcca                          34

<210> SEQ ID NO 4
<211> LENGTH: 45
<212> TYPE: DNA
<213> ORGANISM: Gorilla beringei beringei

<400> SEQUENCE: 4
ataggtgtgg atgccacaca ggcgggagat aaccctatat atgct             45

<210> SEQ ID NO 5
<211> LENGTH: 30
<212> TYPE: DNA
<213> ORGANISM: Gorilla beringei beringei

<400> SEQUENCE: 5
gtagcaggcc ccctagctgt ggccaatggc                              30

<210> SEQ ID NO 6
<211> LENGTH: 399
<212> TYPE: DNA
<213> ORGANISM: Gorilla beringei beringei

<400> SEQUENCE: 6
atgagcgaca ccggcaacag ctttgatgga agcatcttta gccccatatct gacagtgcgc    60 atgcctcact gggctggagt gcgtcagaat gtgatgggtt ccaacgtgga tggacgcccc   120
gttctgcctt caaattcgtc tacaatggcc tacgcgaccg tgggaggaac tccgctggac   180
gccgcgacct ccgccgccgc ctccgccgcc gccgcgaccg cgcgcagcat ggctacggac   240
ctttacagct ctttggtggc gagcggcgcg gcctctcgcg cgtctgctcg ggatgagaaa   300
ctgaccgctc tgctgcttaa actggaagac ttgacccggg agctgggtca actgacccag   360
caggtctcca gcttgcgtga gagcagcctt gcctccccc                         399

<210> SEQ ID NO 7
<211> LENGTH: 3168
<212> TYPE: DNA
<213> ORGANISM: Gorilla beringei beringei

<400> SEQUENCE: 7
atggacagct ccaatgtgcg cgatgtcgtc atcaaactcc gcccgccgag cgccgagatc    60
tggacctgcg gctctcgcgg cgtggtggtc tgctccacca tcgccctcca ggagacagat   120
gctggcggcc agacaaccaa agtagaagac caccagccac acgggacccc aggcggggga   180
cttagattcc cgctgcgctt cctcgtcaga ggtcgccagg ttcacctcgt gcaagatata   240
caacccgtgc agcgctgcca gtactgcggt cgcttttaca aaagccagca cgagtgctcg   300
gcccgcagac gggacttcta ctttcaccac atcaacagcc aatcctccaa ctggtggcgg   360
gagatccagt tcttcccgat cggctctcat cctcgcacgg agcgcctctt tgtcacctac   420
gatgtagaga cctacacttg gatgggagcc tttggcaagc agctcgtgcc cttcatgctg   480
gtcatgaaac tgggggggcga cgaggctctg tcgccgccg cgcgcgacct cgcccgagag   540
ctcagatggg accctgggga gaagacccc ctcaccttct actgcatcac ccccgaaaag   600
```

```
atggccgtgg ggcgacagtt cagaaccttc cgcgaccgcc tgcagaccct catggcccgc    660
gacctctggc gatccttcct ggcggccaac cctcacttgc aagactgggc cctggaggag    720
cacggcctgg aatcgcccga ggagctcacc tacgaggaac tcaaaaagct ccctccatc     780 aagggccagc cccgcttttt ggagctctac atcgtgggcc acaacataaa cggctttgac    840
gagatcgtcc tggccgccca ggtcatcaac aaccgctcct cggtcccagg gccctttcgc    900
atcaccagaa acttcatgcc tcgagcgggg aagatcctct tcaatgacct caccttctcc    960
ctgcccaacc cgcgctccaa aaagcgcacg actacaccc tgtgggaaca gggcggctgc    1020
gatgacacag acttcaaaca tcaataccte aaagtcatgg tcaggacac tttcgccctc    1080 acccacacct ccctccgcaa ggcggcgcag gcctacgcgc tgcccgtgga agggctgt     1140 tgccctacc aggccgtcaa ccagttctac atgctaggct cttaccgttc ggacacggac    1200
gggtttcccc tccaagagta ctggaaagac cgcgaagagt tcgtcctcaa ccgcgagctg    1260
tggaaaaaga agggggagga taagtatgac atcatccgcg agaccctcga ctactgcgcg    1320
ctcgacgtcc aggtcaccgc cgagctggtg cacaagctgc gcgagtccta cgcctccttc    1380
gtcagggact cggtgggctt gcaagaagca agcttcaacg tcttccagcg gccaccatc    1440 tcctccaact cccatgccat cttcaggcag atcgccttcc gcgccgagcg ccccagcgc    1500 accaacctcg ggcccaacat gctggccccc tcccacgagc tctatgacta cgtgcgcgcc    1560
agcatccgcg gggggcgctg ctaccccacc tacctcggca tcctcaggga acccctgtac    1620
gtgtatgaca tctgcggcat gtacgcctcc gcgctcaccc acccatgcc ctggggcccg    1680 cccctcaacc cctacgagcg cgcgctcgcc gcccgcgaat ggcagcgggc tctggacatg    1740
caagcttgca agatcgacta ctttgacccg cgcttgctcc ccggggtctt caccatcgac    1800
gcggaccccc caaacgagga ccagctggac cccctacccc ccttctgctc gcgcaagggc    1860
ggccgcctct gctggaccaa cgagcgcctg cgcggcgagg tcgccaccag cgtcgacatg    1920
gtcaccctgc acaaccgagg ctggagggtg cgcctaatcc cagacgagcg caccaccgtc    1980
ttccccgagt ggaagtgcgt ggcccgcgag tacgtgcaac tcaacatcgc ggccaaggag    2040
cgagccgacc gcgacaaaaa ccagaccctg cgctccatcg ccaagctgct ctccaacgcc    2100
ctctacgggt cgttcgccac caagcttgac aacaaaaaaa tagtgttttc tgaccagatg    2160
gacccaggta ccctcaaagg tatcacctcc ggacaggtga acatcaaatc ctcctcattt    2220
ttagaaactg acaacctgag cgctgaggtc atgcccgcct tcgagaggga atacttaccc    2280
cagcagctgg ccctcgcaga cagcgatgcg aagagagtg aagatgaaag gcgcgccacc    2340 ccctttttata ccccccgtc gggaaccccc ggtcacgtgt cctacaccta aagccaatc    2400 actttttctgg acgcggagga gggggacatg tgcctgcaca ccctggagaa ggtgacccg    2460 ctagtggaca acgaccgcta cccctcccac gtggcctcct tcgtcctggc ctggacgcgg    2520
gccttcgtct cagagtggtc agagtttctc tacgaggagg acagaggcac tccgctggaa    2580
gacaggcccc tgaagtcggt ctacggggac acggacagcc tcttcgtcac cgagaaggga    2640
caccgcctca tggagagccg aggtaagaaa cgcatcaaaa agcatggggg caacctggtt    2700
tttgaccctg accgcccgga gctcacttgg ctggtggaat cgagacggt ctgcgcttcc    2760 tgcggcgcgg acgcctactc cccagagtcc gtgtttctcg ctcccaagct ctacgccctg    2820
aagagcctgc agtgccctc gtgcggcgcc acctccaagg gaaagctccg cgccaagggg    2880
cacgccgcgg agggtctcga ctacgagacc atggtcaaat gctacctggc cgacgcgcag    2940
ggcgaagagc ggcagcgatt cagcaccagc agaaccagcc tcaagcgcac cctggccagc    3000
```

```
gcccaacccg agcgcaccc cttcaccgtg acccagacca ccctgacgag gaccctgcgc   3060
ccatggaagg acatgactct ggccccgctg gacgcccatc ggctggtgcc ctacagcgaa   3120
agccgcccca acccgcgaaa cgaggagatc tgctggatcg agatgccg                3168
```

<210> SEQ ID NO 8
<211> LENGTH: 1974
<212> TYPE: DNA
<213> ORGANISM: Gorilla beringei beringei

<400> SEQUENCE: 8

```
atgcggcgcg cggcgatgtt cgaggagggg cctccccccct cttacgagag cgcgatgggg     60
atttctcctg cggcgcccct gcagcctccc tacgtgcctc ctcggtacct gcaacctaca    120 gggggagaa atagcatctg ttactctgag ctgcagcccc tgtacgatac caccagactg     180
tacctggtgg acaacaagtc cgcggacgtg gcctccctga actaccagaa cgaccacagc    240
gattttttga ccacggtgat ccaaaacaac gacttcaccc caaccgaggc cagcaccccag   300 accataaaacc tggataacag gtcgaactgg ggcggcgacc tgaagaccat cttgcacacc    360
aacatgccca cgtgaacga gttcatgttc accaactctt ttaaggcgcg ggtgatggtg     420
gcgcgcgagc agggggaggc gaagtacgag tgggtggact tcacgctgcc cgagggcaac    480
tactcagaga ccatgactct cgacctgatg aacaatgcga tcgtggaaca ctatctgaaa    540
gtgggcaggc agaacggggt gaaggaaagc gatatcgggg tcaagtttga caccagaaac    600
ttccgtctgg gctgggaccc cgtgaccggg ctggtcatgc cggggtcta caccaacgag     660 gccttttcatc ccgacatagt gcttctgccc ggctgtgggg tggacttcac ccagagccgg    720
ctgagcaacc tgctgggcat tcgcaagcgg cagcctttcc aggagggttt caagatcacc    780
tatgaggatc tgaaggggg caacattccc gcgctccttg atctggacgc ctacgaggag    840 agcttgaaaac ccgaggagag cgctggcgac agcggcgaga gtggcgagga gcaagccggc    900
ggcggtggcg gcgcgtcggt agaaaacgaa agtacgcccg cagtggcggc ggacgctgcg    960
gaggtcgagc cggaggccat gcagcaggac gcagaggagg cgcacagga gggcgcgcag    1020 aaggacatga cgatgggga gatcagggga gacacattcg ccacccgggg cgaagaaaaa   1080
gaggcagagg cggcggcggc ggcgacggcg gaggccgaaa ccgaggttga ggcagaggca    1140
gagcccgaga ccgaagttat ggaagacatg aatgatggag aacgtagggg cgacacgttc    1200
gccacccggg gcgaagagaa ggcggcggag gcagaagccg cggctgagga ggcggctgcg    1260
gctgcggcca agactgaggc tgcggctaag gctgaggtcg aagccaatgt tgcggttgag    1320
gctcaggctg aggaggaggc ggcggctgaa gcagttaagg aaaaggccca ggcagagcag    1380
gaagagaaaa aacctgtcat tcaacctcta aagaagatca gcaaaaagcg cagttacaac    1440
gtcatcgagg gcagcacctt tacccagtac cgcagctggt acctggcgta caactacggc    1500
gacccggtca gggggtgcg ctcgtggacc ctgctctgca cgccgacgt cacctgcggc     1560 tccgagcaga tgtactggtc gctgccgaac atgatgcaag accggtgac cttccgctcc    1620 acgcggcagg ttagcaactt cccggtggtg ggcgccgaac tgctgcccgt gcactccaag    1680 agttttttaca cgagcaggc cgtctactcc cagctgatcc gccaggccac ctctctgacc    1740
cacgtgttca atcgctttcc cgagaaccag attttggcgc gccccgccggc ccccaccatc    1800 accaccgtga gtgaaaacgt tcctgccctc acagatcacg ggacgctacc gctgcgcaac    1860
agcatctcag gagtccagcg agtgaccatt actgacgcca gacgccggac ctgcccctac    1920
```

```
gtttacaagg ccttgggcat agtctcgccg cgcgtcctct ccagtcgcac tttt        1974
```

<210> SEQ ID NO 9
<211> LENGTH: 2877
<212> TYPE: DNA
<213> ORGANISM: Gorilla beringei beringei

<400> SEQUENCE: 9

```
atggcgaccc catcgatgat gcctcagtgg tcgtacatgc acatctcggg ccaggacgct      60
tcggagtacc tgagccccgg gctggtgcag ttcgcccgcg ccacagacac ctacttcaac     120
atgagtaaca agttcaggaa ccccactgtg gcgcccaccc acgatgtgac cacggaccgg     180
tcgcagcgcc tgacgctgcg gttcatcccc gtggatcggg aggacaccgc ctactcttac     240
aaggcgcggt tcacgctggc cgtgggcgac aaccgcgtgc tggacatggc ctccacttac     300
tttgacatca gggggtgct ggacaggggc cccaccttca gccctactc gggtactgcc     360
tacaactccc tggcccccaa gggcgctccc aattcttgcg agtgggaaca agatgaacca     420
gctcaggcag caatagctga agatgaagaa gaacttgaag aagaacaagc tcaggacgaa     480
caggcgccca ctaagaaaac ccatgtatac gcccaggcac ctctttctgg tgaaaaaatt     540
actaaggatg gtttgcaaat aggtgtggat gccacacagg cgggagataa ccctatatat     600
gctgataaaa cattccaacc cgaacctcag ataggtgagt ctcagtggaa cgaggctgat     660
gccacagtag caggaggcag agtcttaaaa aagaccaccc ctatgagacc ttgctatgga     720
tcctatgcca aacctactaa tgccaatggc ggtcaaggga tcatggtggc caatgatcag     780
ggagcgcttg aatctaaagt tgagatgcaa tttttctcca ccacaacgtc tcttaatgta     840
agggaaggtg aaaacaatct tcagccaaaa gtagtgctat acagcgaaga tgttaacttg     900
gaatccctg acactcattt gtcttacaaa cctaaaaagg atgacaccaa ctctaaaatc     960
atgttgggtc agcaagccat gcccaacaga cccaacctca ttgcttttag ggacaacttt    1020
attggactta tgtactacaa cagcacaggc aacatgggag tgctggcagg acaggcctcc    1080
cagctaaacg ctgtggtaga cttgcaagac agaaacacag agctgtcata ccaactgatg    1140
cttgattcca ttggagacag atcaagatac ttttccatgt ggaaccaggc agtggacagc    1200
tatgacccag atgtcagaat cattgaaaac catggggttg aagatgagct gcccaactat    1260
tgcttccc tggcggtat tggaattaca gacacatacc agtgcataaa accaaccgca    1320
gctgctaata acactacatg gtctaaggat gaagaattta gtgatcgcaa tgaaataggg    1380
gtgggaaaca acttcgccat ggagatcaac atccaggcca acctctggag gaacttcctc    1440
tatgcgaacg tggggctcta cctgccagac aagctcaagt acaaccccac caacgtggac    1500
atctctgaca ccccaacacc tatgactac atgaacaagc gtgtggtggc tcccggcctg    1560
gtggactgct ttgtcaatgt gggagccagg tggtccctgg actacatgga caacgtcaac    1620
cccttcaacc accaccgcaa tgcgggtctg cgctaccgct ccatgatcct gggcaacggg    1680
cgctacgtgc ccttccacat tcaggtgccc agaagttcct ttgccatcaa gaacctcctc    1740
ctcctgccgg gctcctacac ttacgagtgg aacttcagga aggatgtcaa catggtcctg    1800
cagagctctc tgggcaatga ccttaggtgt gacggggcca gcatcaagtt tgacagcgtc    1860
accctctatg ctaccttctt ccccatggct cacaacaccg cctccacgct cgaggccatg    1920
ctgaggaacg acaccaacga ccagtccttc aatgactacc tctctgggca acatgctc    1980
tacccccatcc ccgccaaggc caccaacgtg cccatctcca ttccctctcg caactgggcc    2040
gccttcagag gctgggcctt tacccgcctt aagaccaagg aaacccctc cctgggctcg    2100
```

```
ggttttgacc cctactttgt ctactcggga tccatcccct acctggatgg caccttctac    2160
ctcaaccaca cttttaagaa gatatccatc atgtatgact cctccgtcag ctggccgggc    2220
aatgaccgcc tgctcacccc caatgagttc gaggtcaagc gcgccgtgga cggcgagggc    2280
tacaacgtgg cccagtgcaa catgaccaag gactggttcc tggtgcagat gctggccaac    2340
tacaacatag gctaccaggg cttctacatc ccagagagct acaaggacag gatgtactcc    2400
ttcttcagaa atttccaacc catgagcagg caggtggtgg acgagaccaa atacaaggac    2460
tatcaggcca ttggcatcac tcaccagcac aacaactcgg gattcgtggg ctacctggct    2520
cccaccatgc gcgaggggca ggcctacccc gccaacttcc cctacccgtt gataggcaaa    2580
accgcggtcg acagcgtcac ccagaaaaag ttcctctgcg accgcaccct ctggcgcatc    2640
cccttctcta gcaacttcat gtccatgggt gcgctcacgg acctgggcca gaacctgctc    2700
tatgccaact ccgcccatgc gctggacatg acttttgagg tggaccccat ggacgagccc    2760
acccttctct atattgtgtt tgaagtgttc gacgtggtca gagtgcacca gccgcaccgc    2820
ggtgtcatcg agaccgtgta cctgcgcacg cccttctcgg ccggcaacgc caccacc      2877

<210> SEQ ID NO 10
<211> LENGTH: 1749
<212> TYPE: DNA
<213> ORGANISM: Gorilla beringei beringei

<400> SEQUENCE: 10
atgaaacgcg cgagatcgtc tgacgagacc ttcaacccecg tgtaccccta cgataccgag      60
atcgctccga cttctgtccc tttccttacc cctcccttgt gtcatccgc aggaatgcaa     120 gaaaatccag ctggggtgct gtccctgcac ttgtcagagc cccttaccac ccacaatggg    180
gccctgactc taaaaatggg gggcggcctg accctggaca aggaagggaa tctcacttcc    240
caaaacatca ccagtgtcga tccccctctc aaaaaagca agaacaacat cagccttcag    300
accgccgcac ccctcgccgt cagctccggg gccctaacac ttttgccac tccccccta    360 gcggtcagtg gtgacaacct tactgtgcag tctcaggccc ctctcacttt ggaagactca    420
aaactaactc tggccaccaa aggaccccta actgtgtccg aaggcaaaact tgtcctagaa    480 acagaggctc ccctgcatgc aagtgacagc agcagcctgg gcttagcgt tacggcccca    540 cttagcatta caatgacag cctaggacta gatctgcagg cacccattgt ctctcaaaat    600
ggaaaactgg ctctaaatgt agcaggcccc ctagctgtgg ccaatggcat taatgctttg    660
acagtaggca caggcaaagg tattggtcta aatgaaacca gcactcactt gcaagcaaag    720
ttggtcgccc ccctaggctt tgataccaat ggcaacatta agctaagcgt gcaggaggc    780 atgagactaa ataatgacac acttatacta gatgtaaact acccatttga agctcaaggc    840
caactaagtc taagagtggg ccagggtccg ctgtatgtag attctagcag ccataacctg    900
accattagat gccttagagg attatacata acatcgtcta ataaccaaac cggtctagag    960
gccaacataa aactaacaaa aggccttgtc tatgatggaa atgccatagc agtcaatgtt   1020
ggtcaaggat gcaatacag cactactgcc acatcggaag gtgtgtatcc tatacagtct   1080
aagataggtt tgggaatgga atatgatacc aacggagcca tgatgacaaa actaggctct   1140
ggactaagct ttgacaattc aggagccatt gtagtgggaa acaaaaatga tgacaggctt   1200
actctgtgga ctacaccaga cccatctcct aactgtagaa tttattctga aaagatact   1260 aaactaacct tggtgctgac taagtgtggc agccaaatcc taggcacagt atctgccctt   1320
```

-continued

```
gctgtcagag gcagccttgc gcccatcact aatgcatcca gcatagtcca atatttcta    1380 agatttgatg aaaatggact attgatgagc aactcatcgc tagacggtga ttactggaat    1440
tacagaaatg gggactccac taatagcaca ccatatacaa atgcagtagg ctttatgcct    1500
aatctagcag cctatcctaa aggtcaggct acagctgcaa aaagcagtat tgtaagccag    1560
gtatacatgg atggtgacac tactaaacct ataacactaa aaataaactt caatggcatt    1620
gatgaaacaa cagaaaatac ccctgttagt aaatattcca tgacattctc atggagctgg    1680
cccaccgcaa gctacatagg ccacactttt gcaacaaact cttttacttt ctcctacatc    1740
gcccaagaa                                                            1749
```

<210> SEQ ID NO 11
<211> LENGTH: 10
<212> TYPE: PRT
<213> ORGANISM: Gorilla beringei beringei

<400> SEQUENCE: 11

Ser Ser Leu Val Ala Ser Gly Ala Ala Ser
1               5                   10

<210> SEQ ID NO 12
<211> LENGTH: 147
<212> TYPE: PRT
<213> ORGANISM: Gorilla beringei beringei

<400> SEQUENCE: 12

Lys His Gln Tyr Leu Lys Val Met Val Arg Asp Thr Phe Ala Leu Thr
1               5                   10                  15

His Thr Ser Leu Arg Lys Ala Ala Gln Ala Tyr Ala Leu Pro Val Glu
            20                  25                  30

Lys Gly Cys Cys Pro Tyr Gln Ala Val Asn Gln Phe Tyr Met Leu Gly
        35                  40                  45

Ser Tyr Arg Ser Asp Thr Asp Gly Phe Pro Leu Gln Glu Tyr Trp Lys
    50                  55                  60

Asp Arg Glu Glu Phe Val Leu Asn Arg Glu Leu Trp Lys Lys Lys Gly
65                  70                  75                  80

Glu Asp Lys Tyr Asp Ile Ile Arg Glu Thr Leu Asp Tyr Cys Ala Leu
                85                  90                  95

Asp Val Gln Val Thr Ala Glu Leu Val His Lys Leu Arg Glu Ser Tyr
            100                 105                 110

Ala Ser Phe Val Arg Asp Ser Val Gly Leu Gln Glu Ala Ser Phe Asn
        115                 120                 125

Val Phe Gln Arg Pro Thr Ile Ser Ser Asn Ser His Ala Ile Phe Arg
    130                 135                 140

Gln Ile Ala
145

<210> SEQ ID NO 13
<211> LENGTH: 15
<212> TYPE: PRT
<213> ORGANISM: Gorilla beringei beringei

<400> SEQUENCE: 13

Lys Thr Glu Ala Ala Ala Lys Ala Glu Val Glu Ala Asn Val Ala
1               5                   10                  15

<210> SEQ ID NO 14
<211> LENGTH: 15

-continued

```
<212> TYPE: PRT
<213> ORGANISM: Gorilla beringei beringei

<400> SEQUENCE: 14

Ile Gly Val Asp Ala Thr Gln Ala Gly Asp Asn Pro Ile Tyr Ala
1               5                   10                  15

<210> SEQ ID NO 15
<211> LENGTH: 15
<212> TYPE: PRT
<213> ORGANISM: Gorilla beringei beringei

<400> SEQUENCE: 15

Leu Asn Val Ala Gly Pro Leu Ala Val Ala Asn Gly Ile Asn Ala
1               5                   10                  15

<210> SEQ ID NO 16
<211> LENGTH: 133
<212> TYPE: PRT
<213> ORGANISM: Gorilla beringei beringei

<400> SEQUENCE: 16

Met Ser Asp Thr Gly Asn Ser Phe Asp Gly Ser Ile Phe Ser Pro Tyr
1               5                   10                  15

Leu Thr Val Arg Met Pro His Trp Ala Gly Val Arg Gln Asn Val Met
                20                  25                  30

Gly Ser Asn Val Asp Gly Arg Pro Val Leu Pro Ser Asn Ser Ser Thr
            35                  40                  45

Met Ala Tyr Ala Thr Val Gly Gly Thr Pro Leu Asp Ala Ala Thr Ser
    50                  55                  60

Ala Ala Ala Ser Ala Ala Ala Thr Ala Arg Ser Met Ala Thr Asp
65                  70                  75                  80

Leu Tyr Ser Ser Leu Val Ala Ser Gly Ala Ala Ser Arg Ala Ser Ala
                85                  90                  95

Arg Asp Glu Lys Leu Thr Ala Leu Leu Leu Lys Leu Glu Asp Leu Thr
            100                 105                 110

Arg Glu Leu Gly Gln Leu Thr Gln Gln Val Ser Ser Leu Arg Glu Ser
        115                 120                 125

Ser Leu Ala Ser Pro
    130

<210> SEQ ID NO 17
<211> LENGTH: 1056
<212> TYPE: PRT
<213> ORGANISM: Gorilla beringei beringei

<400> SEQUENCE: 17

Met Asp Ser Ser Asn Val Arg Asp Val Val Ile Lys Leu Arg Pro Pro
1               5                   10                  15

Ser Ala Glu Ile Trp Thr Cys Gly Ser Arg Gly Val Val Cys Ser
                20                  25                  30

Thr Ile Ala Leu Gln Glu Thr Asp Ala Gly Gly Gln Thr Thr Lys Val
            35                  40                  45

Glu Asp His Gln Pro His Gly Thr Pro Gly Gly Leu Arg Phe Pro
    50                  55                  60

Leu Arg Phe Leu Val Arg Gly Arg Gln Val His Leu Val Gln Asp Ile
65                  70                  75                  80

Gln Pro Val Gln Arg Cys Gln Tyr Cys Gly Arg Phe Tyr Lys Ser Gln
                85                  90                  95
```

His Glu Cys Ser Ala Arg Arg Asp Phe Tyr Phe His His Ile Asn
            100                 105                 110

Ser Gln Ser Ser Asn Trp Trp Arg Glu Ile Gln Phe Phe Pro Ile Gly
            115                 120                 125

Ser His Pro Arg Thr Glu Arg Leu Phe Val Thr Tyr Asp Val Glu Thr
            130                 135                 140

Tyr Thr Trp Met Gly Ala Phe Gly Lys Gln Leu Val Pro Phe Met Leu
145                 150                 155                 160

Val Met Lys Leu Gly Gly Asp Glu Ala Leu Val Ala Ala Ala Arg Asp
                165                 170                 175

Leu Ala Arg Glu Leu Arg Trp Asp Pro Trp Glu Lys Asp Pro Leu Thr
            180                 185                 190

Phe Tyr Cys Ile Thr Pro Glu Lys Met Ala Val Gly Arg Gln Phe Arg
            195                 200                 205

Thr Phe Arg Asp Arg Leu Gln Thr Leu Met Ala Arg Asp Leu Trp Arg
            210                 215                 220

Ser Phe Leu Ala Ala Asn Pro His Leu Gln Asp Trp Ala Leu Glu Glu
225                 230                 235                 240

His Gly Leu Glu Ser Pro Glu Glu Leu Thr Tyr Glu Glu Leu Lys Lys
                245                 250                 255

Leu Pro Ser Ile Lys Gly Gln Pro Arg Phe Leu Glu Leu Tyr Ile Val
            260                 265                 270

Gly His Asn Ile Asn Gly Phe Asp Glu Ile Val Leu Ala Ala Gln Val
            275                 280                 285

Ile Asn Asn Arg Ser Ser Val Pro Gly Pro Phe Arg Ile Thr Arg Asn
            290                 295                 300

Phe Met Pro Arg Ala Gly Lys Ile Leu Phe Asn Asp Leu Thr Phe Ser
305                 310                 315                 320

Leu Pro Asn Pro Arg Ser Lys Lys Arg Thr Asp Tyr Thr Leu Trp Glu
                325                 330                 335

Gln Gly Gly Cys Asp Asp Thr Asp Phe Lys His Gln Tyr Leu Lys Val
            340                 345                 350

Met Val Arg Asp Thr Phe Ala Leu Thr His Thr Ser Leu Arg Lys Ala
            355                 360                 365

Ala Gln Ala Tyr Ala Leu Pro Val Glu Lys Gly Cys Cys Pro Tyr Gln
            370                 375                 380

Ala Val Asn Gln Phe Tyr Met Leu Gly Ser Tyr Arg Ser Asp Thr Asp
385                 390                 395                 400

Gly Phe Pro Leu Gln Glu Tyr Trp Lys Asp Arg Glu Glu Phe Val Leu
                405                 410                 415

Asn Arg Glu Leu Trp Lys Lys Lys Gly Glu Asp Lys Tyr Asp Ile Ile
            420                 425                 430

Arg Glu Thr Leu Asp Tyr Cys Ala Leu Asp Val Gln Val Thr Ala Glu
            435                 440                 445

Leu Val His Lys Leu Arg Glu Ser Tyr Ala Ser Phe Val Arg Asp Ser
            450                 455                 460

Val Gly Leu Gln Glu Ala Ser Phe Asn Val Phe Gln Arg Pro Thr Ile
465                 470                 475                 480

Ser Ser Asn Ser His Ala Ile Phe Arg Gln Ile Ala Phe Arg Ala Glu
                485                 490                 495

Arg Pro Gln Arg Thr Asn Leu Gly Pro Asn Met Leu Ala Pro Ser His
            500                 505                 510

```
Glu Leu Tyr Asp Tyr Val Arg Ala Ser Ile Arg Gly Arg Cys Tyr
        515                 520                 525

Pro Thr Tyr Leu Gly Ile Leu Arg Glu Pro Leu Tyr Val Tyr Asp Ile
            530                 535                 540

Cys Gly Met Tyr Ala Ser Ala Leu Thr His Pro Met Pro Trp Gly Pro
545                 550                 555                 560

Pro Leu Asn Pro Tyr Glu Arg Ala Leu Ala Ala Arg Glu Trp Gln Arg
                565                 570                 575

Ala Leu Asp Met Gln Ala Cys Lys Ile Asp Tyr Phe Asp Pro Arg Leu
            580                 585                 590

Leu Pro Gly Val Phe Thr Ile Asp Ala Asp Pro Pro Asn Glu Asp Gln
        595                 600                 605

Leu Asp Pro Leu Pro Pro Phe Cys Ser Arg Lys Gly Gly Arg Leu Cys
    610                 615                 620

Trp Thr Asn Glu Arg Leu Arg Gly Glu Val Ala Thr Ser Val Asp Met
625                 630                 635                 640

Val Thr Leu His Asn Arg Gly Trp Arg Val Arg Leu Ile Pro Asp Glu
                645                 650                 655

Arg Thr Thr Val Phe Pro Glu Trp Lys Cys Val Ala Arg Glu Tyr Val
            660                 665                 670

Gln Leu Asn Ile Ala Ala Lys Glu Arg Ala Asp Arg Asp Lys Asn Gln
        675                 680                 685

Thr Leu Arg Ser Ile Ala Lys Leu Leu Ser Asn Ala Leu Tyr Gly Ser
    690                 695                 700

Phe Ala Thr Lys Leu Asp Asn Lys Lys Ile Val Phe Ser Asp Gln Met
705                 710                 715                 720

Asp Pro Gly Thr Leu Lys Gly Ile Thr Ser Gly Gln Val Asn Ile Lys
                725                 730                 735

Ser Ser Ser Phe Leu Glu Thr Asp Asn Leu Ser Ala Glu Val Met Pro
            740                 745                 750

Ala Phe Glu Arg Glu Tyr Leu Pro Gln Gln Leu Ala Leu Ala Asp Ser
        755                 760                 765

Asp Ala Glu Glu Ser Glu Asp Glu Arg Ala Pro Thr Pro Phe Tyr Thr
    770                 775                 780

Pro Pro Ser Gly Thr Pro Gly His Val Ser Tyr Thr Tyr Lys Pro Ile
785                 790                 795                 800

Thr Phe Leu Asp Ala Glu Glu Gly Asp Met Cys Leu His Thr Leu Glu
                805                 810                 815

Lys Val Asp Pro Leu Val Asp Asn Asp Arg Tyr Pro Ser His Val Ala
            820                 825                 830

Ser Phe Val Leu Ala Trp Thr Arg Ala Phe Val Ser Glu Trp Ser Glu
        835                 840                 845

Phe Leu Tyr Glu Glu Asp Arg Gly Thr Pro Leu Glu Asp Arg Pro Leu
    850                 855                 860

Lys Ser Val Tyr Gly Asp Thr Asp Ser Leu Phe Val Thr Glu Lys Gly
865                 870                 875                 880

His Arg Leu Met Glu Ser Arg Gly Lys Lys Arg Ile Lys Lys His Gly
                885                 890                 895

Gly Asn Leu Val Phe Asp Pro Asp Arg Pro Glu Leu Thr Trp Leu Val
            900                 905                 910

Glu Cys Glu Thr Val Cys Ala Ser Cys Gly Ala Asp Ala Tyr Ser Pro
        915                 920                 925

Glu Ser Val Phe Leu Ala Pro Lys Leu Tyr Ala Leu Lys Ser Leu Gln
```

```
                930                 935                 940
Cys Pro Ser Cys Gly Ala Thr Ser Lys Gly Lys Leu Arg Ala Lys Gly
945                 950                 955                 960

His Ala Ala Glu Gly Leu Asp Tyr Glu Thr Met Val Lys Cys Tyr Leu
                965                 970                 975

Ala Asp Ala Gln Gly Glu Arg Gln Arg Phe Ser Thr Ser Arg Thr
                980                 985                 990

Ser Leu Lys Arg Thr Leu Ala Ser Ala Gln Pro Gly Ala His Pro Phe
                995                1000                1005

Thr Val Thr Gln Thr Thr Leu Thr Arg Thr Leu Arg Pro Trp Lys
    1010                1015                1020

Asp Met Thr Leu Ala Pro Leu Asp Ala His Arg Leu Val Pro Tyr
    1025                1030                1035

Ser Glu Ser Arg Pro Asn Pro Arg Asn Glu Glu Ile Cys Trp Ile
    1040                1045                1050

Glu Met Pro
    1055

<210> SEQ ID NO 18
<211> LENGTH: 658
<212> TYPE: PRT
<213> ORGANISM: Gorilla beringei beringei

<400> SEQUENCE: 18

Met Arg Arg Ala Ala Met Phe Glu Glu Gly Pro Pro Ser Tyr Glu
1               5                   10                  15

Ser Ala Met Gly Ile Ser Pro Ala Ala Pro Leu Gln Pro Pro Tyr Val
                20                  25                  30

Pro Pro Arg Tyr Leu Gln Pro Thr Gly Gly Arg Asn Ser Ile Cys Tyr
                35                  40                  45

Ser Glu Leu Gln Pro Leu Tyr Asp Thr Thr Arg Leu Tyr Leu Val Asp
50                  55                  60

Asn Lys Ser Ala Asp Val Ala Ser Leu Asn Tyr Gln Asn Asp His Ser
65                  70                  75                  80

Asp Phe Leu Thr Thr Val Ile Gln Asn Asn Asp Phe Pro Thr Glu
                85                  90                  95

Ala Ser Thr Gln Thr Ile Asn Leu Asp Asn Arg Ser Asn Trp Gly Gly
                100                 105                 110

Asp Leu Lys Thr Ile Leu His Thr Asn Met Pro Asn Val Asn Glu Phe
                115                 120                 125

Met Phe Thr Asn Ser Phe Lys Ala Arg Val Met Val Ala Arg Glu Gln
130                 135                 140

Gly Glu Ala Lys Tyr Glu Trp Val Asp Phe Thr Leu Pro Glu Gly Asn
145                 150                 155                 160

Tyr Ser Glu Thr Met Thr Leu Asp Leu Met Asn Asn Ala Ile Val Glu
                165                 170                 175

His Tyr Leu Lys Val Gly Arg Gln Asn Gly Val Lys Glu Ser Asp Ile
                180                 185                 190

Gly Val Lys Phe Asp Thr Arg Asn Phe Arg Leu Gly Trp Asp Pro Val
                195                 200                 205

Thr Gly Leu Val Met Pro Gly Val Tyr Thr Asn Glu Ala Phe His Pro
                210                 215                 220

Asp Ile Val Leu Leu Pro Gly Cys Gly Val Asp Phe Thr Gln Ser Arg
225                 230                 235                 240
```

```
Leu Ser Asn Leu Leu Gly Ile Arg Lys Arg Gln Pro Phe Gln Glu Gly
                245                 250                 255

Phe Lys Ile Thr Tyr Glu Asp Leu Lys Gly Gly Asn Ile Pro Ala Leu
            260                 265                 270

Leu Asp Leu Asp Ala Tyr Glu Glu Ser Leu Lys Pro Glu Glu Ser Ala
        275                 280                 285

Gly Asp Ser Gly Glu Ser Gly Glu Glu Gln Ala Gly Gly Gly Gly Gly
    290                 295                 300

Ala Ser Val Glu Asn Glu Ser Thr Pro Ala Val Ala Ala Asp Ala Ala
305                 310                 315                 320

Glu Val Glu Pro Glu Ala Met Gln Gln Asp Ala Glu Glu Gly Ala Gln
                325                 330                 335

Glu Gly Ala Gln Lys Asp Met Asn Asp Gly Glu Ile Arg Gly Asp Thr
            340                 345                 350

Phe Ala Thr Arg Gly Glu Glu Lys Glu Ala Glu Ala Ala Ala Ala Ala
        355                 360                 365

Thr Ala Glu Ala Glu Thr Glu Val Glu Ala Glu Ala Glu Pro Glu Thr
    370                 375                 380

Glu Val Met Glu Asp Met Asn Asp Gly Glu Arg Arg Gly Asp Thr Phe
385                 390                 395                 400

Ala Thr Arg Gly Glu Glu Lys Ala Ala Glu Ala Glu Ala Ala Ala Glu
                405                 410                 415

Glu Ala Ala Ala Ala Ala Lys Thr Glu Ala Ala Ala Lys Ala Glu
            420                 425                 430

Val Glu Ala Asn Val Ala Val Glu Ala Gln Ala Glu Glu Glu Ala Ala
        435                 440                 445

Ala Glu Ala Val Lys Glu Lys Ala Gln Ala Glu Gln Glu Glu Lys Lys
    450                 455                 460

Pro Val Ile Gln Pro Leu Lys Glu Asp Ser Lys Lys Arg Ser Tyr Asn
465                 470                 475                 480

Val Ile Glu Gly Ser Thr Phe Thr Gln Tyr Arg Ser Trp Tyr Leu Ala
                485                 490                 495

Tyr Asn Tyr Gly Asp Pro Val Lys Gly Val Arg Ser Trp Thr Leu Leu
            500                 505                 510

Cys Thr Pro Asp Val Thr Cys Gly Ser Glu Gln Met Tyr Trp Ser Leu
        515                 520                 525

Pro Asn Met Met Gln Asp Pro Val Thr Phe Arg Ser Thr Arg Gln Val
    530                 535                 540

Ser Asn Phe Pro Val Val Gly Ala Glu Leu Leu Pro Val His Ser Lys
545                 550                 555                 560

Ser Phe Tyr Asn Glu Gln Ala Val Tyr Ser Gln Leu Ile Arg Gln Ala
                565                 570                 575

Thr Ser Leu Thr His Val Phe Asn Arg Phe Pro Glu Asn Gln Ile Leu
            580                 585                 590

Ala Arg Pro Pro Ala Pro Thr Ile Thr Val Ser Glu Asn Val Pro
        595                 600                 605

Ala Leu Thr Asp His Gly Thr Leu Pro Leu Arg Asn Ser Ile Ser Gly
    610                 615                 620

Val Gln Arg Val Thr Ile Thr Asp Ala Arg Arg Thr Cys Pro Tyr
625                 630                 635                 640

Val Tyr Lys Ala Leu Gly Ile Val Ser Pro Arg Val Leu Ser Ser Arg
                645                 650                 655

Thr Phe
```

<210> SEQ ID NO 19
<211> LENGTH: 959
<212> TYPE: PRT
<213> ORGANISM: Gorilla beringei beringei

<400> SEQUENCE: 19

```
Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Asp Thr Tyr Phe Asn Met Ser Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ser Leu Ala Pro Lys Gly
        115                 120                 125

Ala Pro Asn Ser Cys Glu Trp Glu Gln Asp Glu Pro Ala Gln Ala Ala
    130                 135                 140

Ile Ala Glu Asp Glu Glu Leu Glu Glu Gln Ala Gln Asp Glu
145                 150                 155                 160

Gln Ala Pro Thr Lys Lys Thr His Val Tyr Ala Gln Ala Pro Leu Ser
                165                 170                 175

Gly Glu Lys Ile Thr Lys Asp Gly Leu Gln Ile Gly Val Asp Ala Thr
            180                 185                 190

Gln Ala Gly Asp Asn Pro Ile Tyr Ala Asp Lys Thr Phe Gln Pro Glu
        195                 200                 205

Pro Gln Ile Gly Glu Ser Gln Trp Asn Glu Ala Asp Ala Thr Val Ala
    210                 215                 220

Gly Gly Arg Val Leu Lys Lys Thr Thr Pro Met Arg Pro Cys Tyr Gly
225                 230                 235                 240

Ser Tyr Ala Lys Pro Thr Asn Ala Asn Gly Gln Gly Ile Met Val
                245                 250                 255

Ala Asn Asp Gln Gly Ala Leu Glu Ser Lys Val Glu Met Gln Phe Phe
            260                 265                 270

Ser Thr Thr Thr Ser Leu Asn Val Arg Glu Gly Glu Asn Asn Leu Gln
        275                 280                 285

Pro Lys Val Val Leu Tyr Ser Glu Asp Val Asn Leu Glu Ser Pro Asp
    290                 295                 300

Thr His Leu Ser Tyr Lys Pro Lys Lys Asp Thr Asn Ser Lys Ile
305                 310                 315                 320

Met Leu Gly Gln Gln Ala Met Pro Asn Arg Pro Asn Leu Ile Ala Phe
                325                 330                 335

Arg Asp Asn Phe Ile Gly Leu Met Tyr Tyr Asn Ser Thr Gly Asn Met
            340                 345                 350

Gly Val Leu Ala Gly Gln Ala Ser Gln Leu Asn Ala Val Val Asp Leu
        355                 360                 365

Gln Asp Arg Asn Thr Glu Leu Ser Tyr Gln Leu Met Leu Asp Ser Ile
```

```
                370                 375                 380
Gly Asp Arg Ser Arg Tyr Phe Ser Met Trp Asn Gln Ala Val Asp Ser
385                 390                 395                 400

Tyr Asp Pro Asp Val Arg Ile Ile Glu Asn His Gly Val Glu Asp Glu
                405                 410                 415

Leu Pro Asn Tyr Cys Phe Pro Leu Gly Ile Gly Ile Thr Asp Thr
                420                 425                 430

Tyr Gln Cys Ile Lys Pro Thr Ala Ala Ala Asn Asn Thr Thr Trp Ser
                435                 440                 445

Lys Asp Glu Glu Phe Ser Asp Arg Asn Glu Ile Gly Val Gly Asn Asn
450                 455                 460

Phe Ala Met Glu Ile Asn Ile Gln Ala Asn Leu Trp Arg Asn Phe Leu
465                 470                 475                 480

Tyr Ala Asn Val Gly Leu Tyr Leu Pro Asp Lys Leu Lys Tyr Asn Pro
                485                 490                 495

Thr Asn Val Asp Ile Ser Asp Asn Pro Asn Thr Tyr Asp Tyr Met Asn
                500                 505                 510

Lys Arg Val Val Ala Pro Gly Leu Val Asp Cys Phe Val Asn Val Gly
                515                 520                 525

Ala Arg Trp Ser Leu Asp Tyr Met Asp Asn Val Asn Pro Phe Asn His
                530                 535                 540

His Arg Asn Ala Gly Leu Arg Tyr Arg Ser Met Ile Leu Gly Asn Gly
545                 550                 555                 560

Arg Tyr Val Pro Phe His Ile Gln Val Pro Gln Lys Phe Phe Ala Ile
                565                 570                 575

Lys Asn Leu Leu Leu Leu Pro Gly Ser Tyr Thr Tyr Glu Trp Asn Phe
                580                 585                 590

Arg Lys Asp Val Asn Met Val Leu Gln Ser Ser Leu Gly Asn Asp Leu
                595                 600                 605

Arg Val Asp Gly Ala Ser Ile Lys Phe Asp Ser Val Thr Leu Tyr Ala
                610                 615                 620

Thr Phe Phe Pro Met Ala His Asn Thr Ala Ser Thr Leu Glu Ala Met
625                 630                 635                 640

Leu Arg Asn Asp Thr Asn Asp Gln Ser Phe Asn Asp Tyr Leu Ser Gly
                645                 650                 655

Ala Asn Met Leu Tyr Pro Ile Pro Ala Lys Ala Thr Asn Val Pro Ile
                660                 665                 670

Ser Ile Pro Ser Arg Asn Trp Ala Ala Phe Arg Gly Trp Ala Phe Thr
                675                 680                 685

Arg Leu Lys Thr Lys Glu Thr Pro Ser Leu Gly Ser Gly Phe Asp Pro
690                 695                 700

Tyr Phe Val Tyr Ser Gly Ser Ile Pro Tyr Leu Asp Gly Thr Phe Tyr
705                 710                 715                 720

Leu Asn His Thr Phe Lys Lys Ile Ser Ile Met Tyr Asp Ser Ser Val
                725                 730                 735

Ser Trp Pro Gly Asn Asp Arg Leu Leu Thr Pro Asn Glu Phe Glu Val
                740                 745                 750

Lys Arg Ala Val Asp Gly Glu Gly Tyr Asn Val Ala Gln Cys Asn Met
                755                 760                 765

Thr Lys Asp Trp Phe Leu Val Gln Met Leu Ala Asn Tyr Asn Ile Gly
                770                 775                 780

Tyr Gln Gly Phe Tyr Ile Pro Glu Ser Tyr Lys Asp Arg Met Tyr Ser
785                 790                 795                 800
```

```
Phe Phe Arg Asn Phe Gln Pro Met Ser Arg Gln Val Asp Glu Thr
                805                 810                 815

Lys Tyr Lys Asp Tyr Gln Ala Ile Gly Ile Thr His Gln His Asn Asn
            820                 825                 830

Ser Gly Phe Val Gly Tyr Leu Ala Pro Thr Met Arg Glu Gly Gln Ala
            835                 840                 845

Tyr Pro Ala Asn Phe Pro Tyr Pro Leu Ile Gly Lys Thr Ala Val Asp
        850                 855                 860

Ser Val Thr Gln Lys Lys Phe Leu Cys Asp Arg Thr Leu Trp Arg Ile
865                 870                 875                 880

Pro Phe Ser Ser Asn Phe Met Ser Met Gly Ala Leu Thr Asp Leu Gly
                885                 890                 895

Gln Asn Leu Leu Tyr Ala Asn Ser Ala His Ala Leu Asp Met Thr Phe
            900                 905                 910

Glu Val Asp Pro Met Asp Glu Pro Thr Leu Leu Tyr Ile Val Phe Glu
        915                 920                 925

Val Phe Asp Val Val Arg Val His Gln Pro His Arg Gly Val Ile Glu
    930                 935                 940

Thr Val Tyr Leu Arg Thr Pro Phe Ser Ala Gly Asn Ala Thr Thr
945                 950                 955

<210> SEQ ID NO 20
<211> LENGTH: 583
<212> TYPE: PRT
<213> ORGANISM: Gorilla beringei beringei

<400> SEQUENCE: 20

Met Lys Arg Ala Arg Ser Ser Asp Glu Thr Phe Asn Pro Val Tyr Pro
1               5                   10                  15

Tyr Asp Thr Glu Ile Ala Pro Thr Ser Val Pro Phe Leu Thr Pro Pro
            20                  25                  30

Phe Val Ser Ser Ala Gly Met Gln Glu Asn Pro Ala Gly Val Leu Ser
        35                  40                  45

Leu His Leu Ser Glu Pro Leu Thr Thr His Asn Gly Ala Leu Thr Leu
    50                  55                  60

Lys Met Gly Gly Gly Leu Thr Leu Asp Lys Glu Gly Asn Leu Thr Ser
65                  70                  75                  80

Gln Asn Ile Thr Ser Val Asp Pro Pro Leu Lys Ser Lys Asn Asn
                85                  90                  95

Ile Ser Leu Gln Thr Ala Ala Pro Leu Ala Val Ser Ser Gly Ala Leu
            100                 105                 110

Thr Leu Phe Ala Thr Pro Pro Leu Ala Val Ser Gly Asp Asn Leu Thr
        115                 120                 125

Val Gln Ser Gln Ala Pro Leu Thr Leu Glu Asp Ser Lys Leu Thr Leu
    130                 135                 140

Ala Thr Lys Gly Pro Leu Thr Val Ser Glu Gly Lys Leu Val Leu Glu
145                 150                 155                 160

Thr Glu Ala Pro Leu His Ala Ser Asp Ser Ser Ser Leu Gly Leu Ser
                165                 170                 175

Val Thr Ala Pro Leu Ser Ile Asn Asn Asp Ser Leu Gly Leu Asp Leu
            180                 185                 190

Gln Ala Pro Ile Val Ser Gln Asn Gly Lys Leu Ala Leu Asn Val Ala
        195                 200                 205

Gly Pro Leu Ala Val Ala Asn Gly Ile Asn Ala Leu Thr Val Gly Thr
```

```
              210                 215                 220
Gly Lys Gly Ile Gly Leu Asn Glu Thr Ser His Leu Gln Ala Lys
225                 230                 235                 240

Leu Val Ala Pro Leu Gly Phe Asp Thr Asn Gly Asn Ile Lys Leu Ser
                245                 250                 255

Val Ala Gly Gly Met Arg Leu Asn Asn Asp Thr Leu Ile Leu Asp Val
                260                 265                 270

Asn Tyr Pro Phe Glu Ala Gln Gly Gln Leu Ser Leu Arg Val Gly Gln
            275                 280                 285

Gly Pro Leu Tyr Val Asp Ser Ser His Asn Leu Thr Ile Arg Cys
        290                 295                 300

Leu Arg Gly Leu Tyr Ile Thr Ser Ser Asn Asn Gln Thr Gly Leu Glu
305                 310                 315                 320

Ala Asn Ile Lys Leu Thr Lys Gly Leu Val Tyr Asp Gly Asn Ala Ile
                325                 330                 335

Ala Val Asn Val Gly Gln Gly Leu Gln Tyr Ser Thr Thr Ala Thr Ser
                340                 345                 350

Glu Gly Val Tyr Pro Ile Gln Ser Lys Ile Gly Leu Gly Met Glu Tyr
            355                 360                 365

Asp Thr Asn Gly Ala Met Met Thr Lys Leu Gly Ser Gly Leu Ser Phe
        370                 375                 380

Asp Asn Ser Gly Ala Ile Val Val Gly Asn Lys Asn Asp Asp Arg Leu
385                 390                 395                 400

Thr Leu Trp Thr Thr Pro Asp Pro Ser Pro Asn Cys Arg Ile Tyr Ser
                405                 410                 415

Glu Lys Asp Thr Lys Leu Thr Leu Val Leu Thr Lys Cys Gly Ser Gln
                420                 425                 430

Ile Leu Gly Thr Val Ser Ala Leu Ala Val Arg Gly Ser Leu Ala Pro
            435                 440                 445

Ile Thr Asn Ala Ser Ser Ile Val Gln Ile Phe Leu Arg Phe Asp Glu
        450                 455                 460

Asn Gly Leu Leu Met Ser Asn Ser Ser Leu Asp Gly Asp Tyr Trp Asn
465                 470                 475                 480

Tyr Arg Asn Gly Asp Ser Thr Asn Ser Thr Pro Tyr Thr Asn Ala Val
                485                 490                 495

Gly Phe Met Pro Asn Leu Ala Ala Tyr Pro Lys Gly Gln Ala Thr Ala
                500                 505                 510

Ala Lys Ser Ser Ile Val Ser Gln Val Tyr Met Asp Gly Asp Thr Thr
            515                 520                 525

Lys Pro Ile Thr Leu Lys Ile Asn Phe Asn Gly Ile Asp Glu Thr Thr
        530                 535                 540

Glu Asn Thr Pro Val Ser Lys Tyr Ser Met Thr Phe Ser Trp Ser Trp
545                 550                 555                 560

Pro Thr Ala Ser Tyr Ile Gly His Thr Phe Ala Thr Asn Ser Phe Thr
                565                 570                 575

Phe Ser Tyr Ile Ala Gln Glu
            580

<210> SEQ ID NO 21
<211> LENGTH: 37229
<212> TYPE: DNA
<213> ORGANISM: Gorilla beringei beringei

<400> SEQUENCE: 21
```

```
catcatcaat aatatacctt attttggatt gtggccaata tgataatgag gtgggcgggg      60
agaggcgggg cgggtgacgt aggacgcgcg agtagggttg ggaggtgtgg cggaagtgtg     120
gcatttgcaa gtgggaggag ctcacatgca agcttccgtc gcggaaaatg tgacgttttt     180
gatgagcgcc gcctacctcc ggaagtgcca attttcgcgc gcttttcacc ggatatcgta     240
gtaattttgg gcgggaccat gtaagatttg gccattttcg cgcgaaaagt gaaacgggga     300
agtgaaaact gaataatagg gcgttagtca tagcgcgtaa tatttaccga gggccgaggg     360
actttgaccg attacgtgga ggactcgccc aggtgttttt tacgtgaatt ccgcgttcc      420 gggtcaaagt ctccgttttt attgtcaccg tcatttgacg cggagggtat ttaaacccgc     480
tgcgctcctc aagaggccac tcttgagtgc cagcgagaag agttttctcc tctgctccgc     540
ttcggtgatc gaaaaatgag acacatagcc tgcactccgg gtcttttgtc cggtcgggcg     600
gcggccgagc ttttggacgc tttgatcaat gatgtcctaa gcgatgattt tccgtctact     660
acccacttta gcccacctac tcttcacgaa ctgtacgatc tggatgtact ggtggatgtg     720
aacgatccca acgaggaggc ggtttctgcg tttttttccg agtctgcgct gttggccgct     780
caggagggat ttgacctaca cactccgccg cctattttag agtctccgct gccggagccc     840
agtggtatac cttatatgcc tgaactgctt cccgaagtgg tagacctgac ctgccacgag     900
cctggctttc cgcccagcga cgatgagggt gagccttttg ttttagactt tgctgagata     960
cctgggcacg gttgcaggtc ttgtgcatat catcagaggg ttaccggaga ccccgaggtt    1020
aagtgttcgc tgtgctatat gaggatgacc tcttccttta tctacagtaa gttttttgtct    1080 aggtgggctt tgggtaggt gggttttgtg tcagaacagg tgtaaacgtt gcttgtgttt    1140
tttgtacctg taggtccggt gtccgagcca gacccggagc ccgaccgcga tcccgagccg    1200
gatcccgagc ctcctcgcag gacaaggaaa ctaccttcca ttctgtgcaa gtctcagaca    1260
cctgtaagga ccagcgaggc agacagcacc gactctggca cttctacctc tcccctgaa    1320 attcacccag tggttcctct gggtatacat aaacctgttg ctgttaaagt ttgcgggcga    1380
cgccctgcag tacagtgcat tgaggacttg cttcacgatc ccgaggaacc tttggacttg    1440
agccttaaac gccctaggca ataaacccca cctaagtaat aaaccccacc taagtaataa    1500
accctgccgc ccttggttat tgagatgacg cccaatgttt gcttttgaat gacttcatgt    1560
gtgtaataaa agtgagtgtg atcataggtc tcttgtttgt ctgggcgggg cttaagggta    1620
tataagtctc ttgggctaa acttggttac acttgacccc aatggaggcg tggggtgct    1680 tggaggagtt tgcggacgtg cgccgtttgc tggacgagag ctctagcaat acctatacta    1740
tttggaggta tctgtggggc tctactcagg ccaagttggt ttccagaatt aagcaggatt    1800
acaagtgcga ttttgaagag cttttttagtt cctgcggtga gcttttgcaa tccttgaatc    1860
tgggccatca ggctattttc caggaaaagg ttctctcgac tttggatttt tccactcccg    1920
ggcgcaccgc cgcttgtgtg gcttttgtgt cttttgtgca agataaatgg agcgaggaga    1980
cccacctgag tcacggctac gtactggatt tcatggcgat ggctctttgg agggctcaca    2040
acaaatggaa gattcagaag gaactgtacg gttccgccct acgtcgtcca cttctgtcgc    2100
gacaggggct gaggtttccc gaccatcggc agcatcagaa tctggaagac gagtcggagg    2160
agcgagcgga ggagaagatc agcttgagag ccggcctgga ccctcctcag gaggaatgaa    2220
tctcccgcag gtggttgacc tgtttccaga actgagacgg gtcctgacta tcagggagga    2280
tggtcagttt gtgaagaagt ttaagaggga tcggggtgag ggagatgatg aggcggctag    2340
caatttagct tttagtctga tgactcgcca ccgaccggaa tgtattacct atcagcagat    2400
```

```
taaggagagt tgtgccaacg agctggatct tttgggtcag aagtatagca tagaacagct    2460
taccacttac tggcttcagc ctggggatga ttgggaagag gcgatcaggg tgtatgcaaa    2520
ggtggccctg cggcccgatt gcaagtataa gattactaag ttggttaata ttagaaactg    2580
ctgctatatt tctgggaacg gggccgaagt ggagatagat actcaggaca gggtggcttt    2640
taggtgttgc atgataaaca tgtggcccgg gatactgggg atggatgggg tggtattcat    2700
gaatgtgagg tttacgggcc ccaactttaa tggcacggtg ttcatgggca acaccaactt    2760
gctcctgcat ggtgcgagtt tctatgggtt taataacacc tgtatagagg cctggaccga    2820
tgtaaaggtt cgaggttgtt ccttttatag ctgttggaag gcggtggtgt gtcgccctaa    2880
aagcaggggt tctgtgaaaa aatgcttgtt tgaaggtgc accttaggca tcctctctga     2940
gggcaactcc agggtgcgcc ataatgtggc ttcgaactgc ggttgcttca tgcaagtgaa    3000
gggggtgagc gttatcaagc ataactcggt gtgtggaaac tgcgaggatc gcgcctccca    3060
gatgctgacc tgctttgatg gcaactgtca cctgttgaag accattcata taagcagcca    3120
ccccagaaag gcctggcccg tgtttgagca taacatcttg acccgctgct ccttgcatct    3180
gggggtcagg aggggtatgt tcctgcctta ccagtgtaac tttagccaca ctaaaatcct    3240
gctggaaccc gagtgcatga ccaaggtcag cctgaatggt gtgtttgatg tgactctgaa    3300
aatctgaaag gtgctgaggt atgatgagac caggaccagg tgccgaccct gcgagtgcgg    3360
cggcaagcac atgagaaatc agcctgtgat gttggatgtg accgaggagc ttaggcctga    3420
ccatctggtg ctggcctgca ccagggccga gtttgggtct agcgatgagg ataccgattg    3480
aggtgggtaa ggtgggcgtg gctagaaggg tggggcgtgt ataaattggg ggtctaaggg    3540
tctctctgtt ttgtcttgca acagccgccg ccatgagcga caccggcaac agctttgatg    3600
gaagcatctt tagcccctat ctgacagtgc gcatgcctca ctgggctgga gtgcgtcaga    3660
atgtgatggg ttccaacgtg gatggacgcc ccgttctgcc ttcaaattcg tctacaatgg    3720
cctacgcgac cgtgggagga actccgctgg acgccgcgac ctccgccgcc gcctccgccg    3780
ccgccgcgac cgcgcgcagc atggctacgg acctttacag ctctttggtg gcgagcggcg    3840
cggcctctcg cgcgtctgct cgggatgaga aactgaccgc tctgctgctt aaactggaag    3900
acttgacccg ggagctgggt caactgaccc agcaggtctc cagcttgcgt gagagcagcc    3960
ttgcctcccc ctaatggccc ataatataaa taaaagccag tctgtttgga ttaagcaagt    4020
gtatgttctt tatttaactc tccgcgcgcg gtaagcccgg gaccagcggt ctcggtcgtt    4080
tagggtgcgt tggattcttt ccaacacgtg gtacaggtgg ctctggatgt ttagatacat    4140
gggcatgagt ccatccctgg ggtggaggta gcaccactgc agagcttcgt gctcgggggt    4200
ggtgttgtat atgatccagt cgtagcagga gcgctgggcg tggtgctgaa aaatgtcctt    4260
aagcaagagg cttatagcta gggggaggcc cttggtgtaa gtgtttacaa atctgctcag    4320
ttgggagggg tgcatccggg gggatataat gtgcatcttg gactggattt ttaggttggc    4380
tatgttccca cccagatccc ttctgggatt catgttgtgc aggaccacca gcacggtata    4440
tccagtgcac ttgggaaatt tatcgtggag cttagacggg aatgcatgga agaacttgga    4500
gacgcccttg tggcctccca gattttccat acattcgtcc atgatgatgg caatgggccc    4560
gtgggaagct gcctgagcaa aaatgtttct gggatcgctc acatcgtagt tatgttccag    4620
ggtgaggtca tcataggaca tctttacgaa tcggggcgg agggtcccgg actgggggat    4680
gatggtaccc tcgggccccg gggcgtagtt cccctcacag atctgcatct cccaggcttt    4740
```

```
catttcagag ggagggatca tatccacctg cggagcgatg aaaaacacag tttctggcgc    4800 agggagatt aactgggatg agagcaggtt tctgagcagc tgtgactttc cacagccggt     4860
gggcccatat atcacgccta tcaccggctg cagctggtag ttaagagagc tgcagctgcc    4920
gtcctcccgg agcagggggg ccacctcgtt cagcatatcc ctgacgtgga tgttctccct    4980
gaccaattcc gccagaaggc gctcgccgcc cagcgaaagc agctcttgca aggaagcaaa    5040 attttcagc ggttttaggc cgtcggccgt gggcatgttt ttcagcgtct gggtcagcag     5100
ttccagcctg tcccacagct cggtgatgtg ctctacggca tctcgatcca gcagatctcc    5160
tcgtttcgcg ggttggggcg cttttcgctg tagggcacca gccgatgggc gtccagcggg    5220
gccagagtca tgtccttcca tgggcgcagg gtcctcgtca gggtggtctg ggtcacggtg    5280
aaggggtgcg ctccgggttg ggcgctggcc agggtgcgct tgaggctggt tctgctggtg    5340
ctgaatcgct gccgctcttc gccctgcgcg tcggccaggt agcatttgac catggtctcg    5400
tagtcgagac cctcggcggc gtgccccttg gcgcggagct tcccttgga ggtggcgccg     5460 cacgaggggc actgcaggct cttcagggcg tagagcttgg gagcgagaaa cacggactct    5520
ggggagtagg cgtccgcgcc gcaggaagcg cagaccgtct cgcattccac cagccaagtg    5580
agctccgggc ggtcagggtc aaaaaccagg ttgcccccat gcttttgat gcgtttctta     5640 cctcggctct ccatgaggcg tgtcccttc tcggtgacga agaggctgtc cgtgtccccg      5700
tagaccgact tcagggcct gtcttccagc ggagtgcctc tgtcctcctc gtagagaaac      5760
tctgaccact ctgagacgaa ggcccgcgtc caggccagga cgaaggaggc cacgtgggag    5820
gggtagcggt cgttgtccac tagcgggtcc accttctcca gggtgtgcag gcacatgtcc    5880
ccctcctccg cgtccagaaa agtgattggc ttgtaggtgt aggacacgtg accgggggtt    5940
cccgacgggg gggtataaaa gggggtgggc gcccttcat cttcactctc ttccgcatcg     6000
ctgtctgcga gggccagctg ctggggtaag tattccctct cgaaggcggg catgacctca    6060
gcgctcaggt tgtcagtttc taaaaatgag gaggatttga tgttcacctg tccgaggtg     6120 ataccttga gggtacctgg gtccatctgg tcagaaaaca ctatttttt gttgtcaagc       6180 ttggtggcga acgacccgta gagggcgttg gagagcagct tggcgatgga gcgcagggtc    6240 tggttttgt cgcggtcggc tcgctccttg gccgcgatgt tgagttgcac gtactcgcgg     6300
gccacgcact tccactcggg gaagacggtg gtgcgctcgt ctgggattag gcgcaccctc    6360
cagcctcggt tgtgcagggt gaccatgtcg acgctggtgg cgacctcgcc gcgcaggcgc    6420
tcgttggtcc agcagaggcg gccgcccttg gcgagcaga aggggggtag ggggtccagc     6480
tggtcctcgt ttgggggtc cgcgtcgatg gtgaagaccc cggggagcaa gcgcgggtca    6540
aagtagtcga tcttgcaagc ttgcatgtcc agagcccgct gccattcgcg ggcggcgagc    6600
gcgcgctcgt aggggttgag gggcgggccc cagggcatgg ggtgggtgag cgcggaggcg    6660
tacatgccgc agatgtcata cacgtacagg ggttccctga ggatgccgag gtaggtgggg    6720
tagcagcgcc ccccgcggat gctggcgcgc acgtagtcat agagctcgtg ggaggggcc     6780 agcatgttgg gcccgaggtt ggtgcgctgg gggcgctcgg cgcggaaggc gatctgcctg    6840
aagatggcat gggagttgga ggagatggtg ggccgctgga gacgttgaa gcttgcttct     6900 tgcaagccca ccgagtccct gacgaaggag gcgtaggact cgcgcagctt gtgcaccagc    6960
tcggcggtga cctggacgtc gagcgcgcag tagtcgaggg tctcgcggat gatgtcatac    7020
ttatcctccc ccttcttttt ccacagctcg cggttgagga cgaactcttc gcggtctttc    7080
cagtactctt ggaggggaaa cccgtccgtg tccgaacggt aagagcctag catgtagaac    7140
```

```
tggttgacgg cctggtaggg gcaacagccc ttctccacgg gcagcgcgta ggcctgcgcc   7200
gccttgcgga gggaggtgtg ggtgagggcg aaagtgtccc tgaccatgac tttgaggtat   7260
tgatgtttga agtctgtgtc atcgcagccg ccctgttccc acagggtgta gtccgtgcgc   7320
tttttggagc gcgggttggg cagggagaag gtgaggtcat tgaagaggat cttccccgct   7380
cgaggcatga agtttctggt gatgcgaaag ggccctggga ccgaggagcg gttgttgatg   7440
acctgggcgc ccaggacgat ctcgtcaaag ccgtttatgt tgtggcccac gatgtagagc   7500
tccaaaaagc ggggctggcc cttgatggag gggagctttt tgagttcctc gtaggtgagc   7560
tcctcgggcg attccaggcc gtgctcctcc agggcccagt cttgcaagtg agggttggcc   7620
gccaggaagg atcgccagag gtcgcgggcc atgagggtct gcaggcggtc gcggaaggtt   7680
ctgaactgtc gccccacggc catcttttcg ggggtgatgc agtagaaggt gaggggggtct   7740 ttctcccagg ggtcccatct gagctctcgg gcgaggtcgc gcgcggcggc gaccagagcc   7800
tcgtcgcccc ccagtttcat gaccagcatg aagggcacga gctgcttgcc aaaggctccc   7860
atccaagtgt aggtctctac atcgtaggtg acaaagaggc gctccgtgcg aggatgagag   7920
ccgatcggga agaactggat ctcccgccac cagttggagg attggctgtt gatgtggtga   7980
aagtagaagt cccgtctgcg ggccgagcac tcgtgctggc ttttgtaaaa gcgaccgcag   8040
tactggcagc gctgcacggg ttgtatatct tgcacgaggt gaacctggcg acctctgacg   8100
aggaagcgca gcgggaatct aagtcccccg cctggggtcc cgtgtggctg gtggtcttct   8160
actttggttg tctggccgcc agcatctgtc tcctggaggg cgatggtgga gcagaccacc   8220
acgccgcgag agccgcaggt ccagatctcg gcgctcggcg ggcggagttt gatgacgaca   8280
tcgcgcacat tggagctgtc catggtctcc agctcccgcg gcggcaggtc agctgggagt   8340
tcctggaggt tcacctcgca gagacgggtc aaggcgcggg cagtgttgag atggtatctg   8400
atttcaaggg gcgtgttggc ggcggagtcg atggcttgca ggaggccgca gccccggggg   8460
gccacgatgg ttccccgcgg ggcgcgaggg gaggcggaag ctgggggtgt gttcagaagc   8520
ggtgacgcgg gcgggccccc ggaggtaggg gggggttccgg ccccacaggc atgggcggca   8580
ggggcacgtc ttcgccgcgc gcgggcaggg gctggtgctg gctccgaaga gcgcttgcgt   8640
gcgcgacgac gcgacggttg gtgtcctgta tctgacgcct ctgagtgaag accacgggtc   8700
ccgtgacctt gaacctgaaa gagagttcga cagaatcaat ctcggcatcg ttgacagcgg   8760
cctggcgcag gatctcctgc acgtcgcccg agttgtcctg gtaggcgatc tctgccatga   8820
actgctcgat ctcttcttcc tggagatctc ctcgtccggc gcgctccacg gtggccgcca   8880
ggtcgttgga gatgcgaccc atgagctgtg agaaggcgtt gagcccgccc tcgttccaga   8940
cccggctgta gaccacgccc ccctcggcgt cgcgagcgcg catgaccacc tgggccaggt   9000
tgagctccac gtgtcgcgtg aagacggcgt agttgcgcag gcgctggaaa aggtagttca   9060
gggtggtggc ggtgtgctcg gcgacgaaga agtacatgac ccagcgccgc aacgtggatt   9120
cattgatgtc ccccaaggcc tccaggcgct ccatggcctc gtagaagtcc acggcgaagt   9180
tgaaaaactg ggagttgcga gcggacacgg tcaactcctc ctccagaaga cggatgagct   9240
cggcgacagt gttgcgcacc tcgcgctcga aggccacggg gggcgcttct tcctcttcca   9300
cctcttcttc catgatcgct tcttcttctt cctcagccgg gacgggaggg ggcggcggcg   9360 gcggggggagg ggcgcggcgg cggcggcggc gcacgggag gcggtcgatg aagcgctcga   9420
tcatctcccc ccgcatgcgg cgcatggtct cggtgacggc gcggccgttc tcccgggggc   9480
```

```
gcagctcgaa gacgccgcct ctcatctcgc cgcggggcga gcggccgtga ggtagcgaga    9540
cggcgctgac tatgcatctt aacaattgct gtgtaggtac accgccgagg gacctgattg    9600
agtccagatc caccggatcc gaaaaccttt ggaggaaagc gtctatccag tcgcagtcgc    9660
aaggtaggct gagcaccgtg gcgggcgggg gcgggtctgg agagttcctg gcggagatgc    9720
tgctgatgat gtaattaaag taggcggtct tgagaaggcg gatggtggac aggagcacca    9780
tgtctttggg tccggcctgt tggatgcgga ggcggtcggc catgccccag gcctcgttct    9840
gacaccggcg caggtctttg tagtagtctt gcatgagtct ttccaccggc acctcttctc    9900
cttcctcttc tccatctcgc cggtggtttc tcgcgccgcc catgcgcgtg accccaaagc    9960
ccctgagcgg ctgcagcagg gccaggtcgg cgaccacgcg ctcggccaag atggcctgct   10020
gcacctgagt gagggtcctc tcgaagtcat ccatgtccac gaagcggtgg taggcgcccg   10080
tgttgatggt gtaggtgcag ttggccatga cggaccagtt gacggtctgg tgtcccggct   10140
gcgagagctc cgtgtaccgc aggcgcgaga aggcgcggga atcgaacacg tagtcgttgc   10200
aagtccgcac cagatactgg tagccccacca ggaagtgcgg cggaggttgg cgatagaggg   10260
gccagcgctg ggtggcgggg gcgccgggcg ccaggtcttc cagcatgagg cggtggtatc   10320
cgtagatgta cctggacatc caggtgatgc cggcggcggt ggtggtggcg cgcgcgtagt   10380
cgcggacccg gttccagatg tttcgcaggg gcgagaagtg ttccatggtc ggcacgctct   10440
ggccggtgag gcgcgcgcag tcgttgacgc tctatacaca cacaaaaacg aaagcgttta   10500
cagggctttc gttctgtagc ctggaggaaa gtaaatgggt tgggttgcgg tgtgccccgg   10560
ttcgagacca agctgagctc ggccggctga agccgcagct aacgtggtat tggcagtccc   10620
gtctcgaccc aggccctgta tcctccagga tacggtcgag agccctttg ctttcttggc   10680
caagcgcccg tggcgcgatc tgggatagat ggtcgcgatg agaggacaaa agcggctcgc   10740
ttccgtagtc tggagaaaca atcgccaggg ttgcgttgcg gcgtaccccg gttcgagccc   10800
ctatggcggc ttgaatcggc cggaaccgcg gctaacgagg gccgtggcag ccccgtcctc   10860
aggaccccgc cagccgactt ctccagttac gggagcgagc cccttttgtt ttttatttt   10920
tagatgcatc ccgtgctgcg gcagatgcgc ccctcgcccc ggcccgatca gcagcagcaa   10980
cagcaggcat gcagaccccc ctctcccctt tccgccccgg tcaccacggc cgcggcggcc   11040
gtgtcgggcg cggggggcgc gctggagtca gatgagccac cgcggcggcg acctaggcag   11100
tatctggact tggaagaggg cgagggactg gcgcggctgg gggcgaactc tccagagcgc   11160
cacccgcggg tgcagttgaa aagggacgcg cgcgaggcgt acctgccgcg gcagaacctg   11220
tttcgcgacc gcggggggcga ggagcccgag gagatgcgag actgcaggtt ccaagcgggg   11280
cgcgagctgc ggcgcgggct ggacagacag cgcctgctgc gcgaggagga ctttgagccc   11340
gacacgcaga cgggcatcag ccccgcgcgc gcgcacgtag ccgcggccga cctggtgacc   11400
gcctacgagc agacggtaaa ccaggagcgc aacttccaaa agagcttcaa caaccacgtg   11460
cgcacgctgg tggcgcgcga ggaggtgacc ctgggtctca tgcatctgtg ggacctggtg   11520
gaggcgatcg tgcagaaccc cagcagcaag cccctgaccg cgcagctgtt cctggtggtg   11580
cagcacagca gggacaacga ggccttcagg gaggcgctgc tgaacatcac cgagccgag   11640
gggcgctggc tcctggacct gataaacatc ctgcagagca tagtggtgca ggagcgcagc   11700
ctgagcctgg ccgagaaggt ggcggccatc aactactcta tgctgagcct gggcaagttc   11760
tacgcccgca agatctacaa gaccccctac gtgccccatg acaaggaggt gaagatagac   11820
agcttctaca tgcgcatggc gctgaaggtg ctgaccctga gcgacgacct gggagtgtac   11880
```

```
cgcaacgagc gcatccacaa ggccgtgagc gccagccggc ggcgcgagct gagcgaccgc   11940
gagctgatgc acagtctgca gcgcgcgctg accggcgcgg gcgagggcga cagggaggtc   12000
gagtcctact tcgacatggg ggccgacctg cactggcagc cgagccgccg cgccctggag   12060
gcggcggggg cgtacggcgg cccctggcg gccgatgacc aggaagagga ggactatgag   12120
ctagaggagg gcgagtacct ggaggactga cctggctggt ggtgttttgg tatagatgca   12180
agatccgaac gtggcggacc cggcggtccg ggcggcgctg caaagccagc cgtccggcat   12240
taactcctct gacgactggg ccgcggccat gggtcgcatc atggccctga ccgcgcgcaa   12300
ccccgaggct ttcaggcagc agcctcaggc caaccggctg gcggccatct tggaagcggt   12360
agtgcccgcg cgctccaacc ccacccacga aaggtgctg gccatagtca acgcgctggc   12420
ggagagcagg gccatccgcg cggacgaggc cggactggtg tacgatgcgc tgctgcagcg   12480
ggtggcgcgg tacaacagcg gcaacgtgca gaccaacctg gaccgcctgg tgacggacgt   12540
gcgcgaggcc gtggcgcagc gcgagcgctt gcatcaggac ggtaacctgg gctcgctggt   12600
ggcgctaaac gccttcctca gcacccagcc ggccaacgta ccgcggggc aggaggacta   12660 caccaacttt ttgagcgcgc tgcggctgat ggtgaccgag gtccctcaga gcgaggtgta   12720
ccagtcgggg cccgactact tcttccagac cagcagacag ggcttgcaaa ccgtgaacct   12780
gagccaggct ttcaagaacc tgcggggggct gtgggggagtg aaggcgccca ccggcgaccg   12840
ggctacggtg tccagcctgc taacccccaa ctcgcgcctg ctgctgctgc tgatcgcgcc   12900
cttcacggac agcgggagcg tctcgcggga gacctatctg ggccacctgc tgacgctgta   12960
ccgcgaggcc atcgggcagg cgcaggtgga cgagcacacc ttccaagaga tcaccagcgt   13020
gagccacgcg ctggggcagg aggacacggg cagcctgcag gcgaccctga actacctgct   13080
gaccaacagg cggcagaaga ttcccacgct gcacagcctg acccaggagg aggagcgcat   13140
cttgcgctac gtgcagcaga gcgtgagcct gaacctgatg cgcgacgcg tgacgcccag   13200 cgtggcgctg gacatgaccg cgcgcaacat ggaaccgggc atgtacgcct cccaccggcc   13260
gtttatcaac cgcctgatgg actacttgca tcgggcggcg gccgtgaacc ccgagtactt   13320
cactaatgcc attctgaatc cccactggat gccccctccg ggtttctaca acggggactt   13380
tgaggtgccc gaggtcaacg acgggttcct ctgggatgac atggatgaca gtgtgttctc   13440
acccaacccg ctgcgcgccg cgtctctgcg attgaaggag ggctctgaca gggaaggacc   13500
gaggagtctg gcctcctccc tggctctggg agcggtgggc gccacgggcg cggcggcgcg   13560
gggcagtagc cccttcccca gcctggcaga ctctctgaac agcgggcggg tgagcaggcc   13620
ccgcttgcta ggcgaggagg agtatctgaa caactccctg ctgcagcccg cgagggacaa   13680
gaacgctcag cggcagcagt ttcccaacaa tgggatagag agcctggtgg acaagatgtc   13740
cagatggaag acgtatgcgc aggagtacaa ggagtgggag gaccgccagc gcggggccctt   13800 gccgccccct aggcagcgct ggcagcggcg cgcgtccaac cgccgctgga ggcagggggc   13860
cgaggacgat gatgactctg cagatgacag cagcgtgttg gacctgggcg ggagcgggaa   13920 cccctttcg cacctgcgcc cacgcctggg caagatgttt taaagaaaaa aaaaaataaa   13980
actcaccaag gccatggcga cgagcgttgg ttttttgttc ccttccttag tatgcggcgc   14040
gcggcgatgt tcgaggaggg gcctcccccc tcttacgaga gcgcgatggg gatttctcct   14100
gcggcgcccc tgcagcctcc ctacgtgcct cctcggtacc tgcaacctac agggggagaga   14160 aatagcatct gttactctga gctgcagccc ctgtacgata ccaccagact gtacctggtg   14220
```

```
gacaacaagt ccgcggacgt ggcctccctg aactaccaga acgaccacag cgatttttg    14280
accacggtga tccaaaacaa cgacttcacc ccaaccgagg ccagcaccca gaccataaac   14340
ctggataaca ggtcgaactg gggcggcgac ctgaagacca tcttgcacac caacatgccc   14400
aacgtgaacg agttcatgtt caccaactct tttaaggcgc gggtgatggt ggcgcgcgag   14460
caggggagg cgaagtacga gtgggtggac ttcacgctgc ccgagggcaa ctactcagag    14520
accatgactc tcgacctgat gaacaatgcg atcgtggaac actatctgaa agtgggcagg   14580
cagaacgggg tgaaggaaag cgatatcggg gtcaagtttg acaccagaaa cttccgtctg   14640
ggctgggacc ccgtgaccgg gctggtcatg ccggggtct acaccaacga ggcctttcat    14700
cccgacatag tgcttctgcc cggctgtggg gtggacttca cccagagccg gctgagcaac   14760
ctgctgggca ttcgcaagcg gcagccttc caggagggtt tcaagatcac ctatgaggat    14820
ctgaaggggg gcaacattcc cgcgctcctt gatctggacg cctacgagga gagcttgaaa   14880
cccgaggaga gcgctggcga cagcggcgag agtggcgagg agcaagccgg cggcggtggc   14940
ggcgcgtcgg tagaaaacga aagtacgccc gcagtggcgg cggacgctgc ggaggtcgag   15000
ccggaggcca tgcagcagga cgcagaggag ggcgcacagg agggcgcgca aaggacatg    15060
aacgatgggg agatcagggg agacacattc gccacccggg gcgaagaaaa agaggcagag   15120
gcggcggcgg cggcgacggc ggaggccgaa accgaggttg aggcagaggc agagcccgag   15180
accgaagtta tggaagacat gaatgatgga gaacgtaggg gcgacacgtt cgccacccgg   15240
ggcgaagaga aggcggcgga ggcagaagcc gcggctgagg aggcggctgc ggctgcggcc   15300
aagactgagg ctgcggctaa ggctgaggtc gaagccaatg ttgcggttga ggctcaggct   15360
gaggaggagg cggcggctga agcagttaag gaaaaggccc aggcagagca ggaagagaaa   15420
aaacctgtca ttcaacctct aaaagaagat agcaaaaagc gcagttacaa cgtcatcgag   15480
ggcagcacct ttacccagta ccgcagctgg tacctggcgt acaactacgg cgacccggtc   15540
aagggggtgc gctcgtggac cctgctctgc acgccgacg tcacctgcgg ctccgagcag    15600
atgtactggt cgctgccgaa catgatgcaa gacccggtga ccttccgctc cacgcggcag   15660
gttagcaact tcccggtggt gggcgccgaa ctgctgcccg tgcactccaa gagttttac     15720
aacgagcagg ccgtctactc ccagctgatc cgccaggcca cctctctgac ccacgtgttc   15780
aatcgctttc ccgagaacca gattttggcg cgcccgccgg cccccaccat caccaccgtg   15840
agtgaaaacg ttcctgccct cacagatcac gggacgctac cgctgcgcaa cagcatctca   15900
ggagtccagc gagtgaccat tactgacgcc agacgccgga cctgccccta cgtttacaag   15960
gccttgggca tagtctcgcc gcgcgtcctc tccagtcgca ctttttaaaa cacatctacc   16020
cacacgttcc aaaatcatgt ccgtactcat ctcacccagc aacaacaccg gctgggggct    16080
gcgcgcgccc agcaagatgt ttggagggc gaggaagcgc tccgaccagc accctgtgcg     16140
cgtgcgcggc cactaccgcg cgccctgggg agcgcacaag gcgggcgca cagggcgcac     16200
cactgtggac gacgtcattg actccgtagt ggagcaagcg cgccactaca cacccggcgc   16260
gccgaccgcc ccgccgtgt ccaccgtgga ccaggcgatc gaaagcgtgg tacagggcgc     16320
gcggcactat gccaacctta aaagtcgccc ccgccgcgtg gcccgccgcc atcgccgag    16380
accccgggcc accgccgccg cgcgccttac taaggctctg ctcaggcgcg ccaggcgaac   16440
tggccaccgg gccgccatga gggccgcacg gcgggctgcc gctgccgcaa gcgtcgtggc   16500
cccgcgggca cgaaggcgcg cggccgctgc cgccgccgcc gccatttcca gcttggcctc   16560
gacgcggcgc ggtaacatat actgggtgcg cgactcggta accggcacgc gggtacccgt   16620
```

```
gcgctttcgc cccccgcgga attagcacaa gacaacatac acactgagtc tcctgctgtt   16680
gtgtatccca gcggcgaccg tcagcagcgg cgacatgtcc aagcgcaaaa ttaaagaaga   16740
gatgctccag gtcatcgcgc cggagatcta tgggcccccg aagaaggagg aggatgatta   16800
caagccccgc aagctaaagc gggtcaaaaa gaaaaagaaa gatgatgatg acgaggcggt   16860
ggagtttgtc cgccgcatgg cacccaggcg ccccgtgcag tggaagggcc ggcgcgtgca   16920
gcgcgttttg cgcccccggca ccgcggtggt cttcacgccc ggcgagcgct ccacgcgcac   16980
tttcaagcgg gtgtacgatg aggtgtacgg cgacgaggac ctgttggagc aggccaacca   17040
gcgctttggg gagtttgcat atgggaaacg ccccgcgag agtctaaaag aggacctgct   17100
ggcgctaccg ctggacgagg gcaatcccac cccgagtctg aagccggtaa ccctgcaaca   17160
ggtgctgcct ttgagcgcgc ccagcgagca taagcgaggg ttgaagcgcg aaggcgggga   17220
cctggcgccc accgtgcagt tgatggtgcc caagcggcag aagctggagg acgtgctgga   17280
gaaaatgaaa gtagagcccg ggatccagcc cgagatcaag gtccgcccca tcaagcaggt   17340
ggcgcccggc gtgggagtcc agaccgtgga cgttaggatt cccacggagg agatggaaac   17400
ccaaaccgcc actccctctt cggcggccag cgccaccacc ggcaccgctt cggtagaggt   17460
gcagacggac ccctggctac ccgccaccgc tgttgccgcc gccgcccccc gttcgcgcgg   17520
gcgcaagaga aattatccag cggccagcgc gctcatgccc cagtacgcac tgcatccatc   17580
catcgtgccc accccggct accgcgggta ctcgtaccgc ccgcgcagat cagccggcac   17640
tcgcggccgc cgccgccgtg cgaccacaac cagccgccgc cgtcgccgcc gccgccagcc   17700
agtgctgacc cccgtgtctg taaggaaggt ggctcgctcg gggagcacgc tggtggtgcc   17760
cagagcgcgc taccaccca gcatcgttta agccggtct ctgtatggtt cttgcagata   17820
tggccctcac ttgtcgcctc cgcttcccgg tgccgggata ccgaggaaga actcaccgcc   17880
gcagaggcat ggcgggcagc ggtctccgcg gcggccgtcg ccatcgccgg cgcgcaaaaa   17940
gcaggcgcat gcgcggcggt gtgctgcctc tgctaatccc gctaatcgcc gcggcgatcg   18000
gtgccgtacc cgggatcgcc tccgtggccc tgcaggcgtc ccagaaacgt tgactcttgc   18060
aaccttgcaa gcttgcattt tttggaggaa aaataaaaaa aagtctagac tctcacgctc   18120
gcttggtcct gtgactattt tgtagaaaaa aagatggaag acatcaactt gcgtcgctg    18180 gccccgcgtc acgctcgcg cccgttcatg ggagactgga cagatatcgg caccagcaat   18240
atgagcggtg gcgccttcag ctggggcagt ctgtggagcg gccttaaaaa ttttggttcc   18300
accattaaga actatggcaa caaagcgtgg aacagcagca cggccagat gctgagagac   18360 aagttgaaag agcagaactt ccaggagaag gtggcgcagg gcctggcctc tggcatcagc   18420
ggggtggtgg acatagctaa ccaggccgtg cagaaaaaga taaacagtca tctgaccccc   18480
cgtcctcagg tggaggaaat gcctccagcg atggagacgg tgtctcccga gggcaaaggc   18540
gaaaagcgcc gcggcccga cagagaagag accctggtgt cacacaccga ggagccgccc   18600
tcttacgagg aggcagtcaa ggccggcctg cccaccactc gcccatagc ccccatggcc   18660 accggtgtgg tgggccacag gcaacacact cccgcaacac tagatctgcc cccgccgtcc   18720
gagccgccgc gccagccaaa ggcggcgacg gtgcccgctc cctccacttc cgccgccaac   18780
agagtgcccc tgcgccgcgc gcgagcggc ccccgggcct cgcgagttag cggcaactgg   18840
cagagcacac tgaacagcat cgtgggcctg ggagtgagga gtgtgaagcg ccgccgttgc   18900
tactgaatga gcaagctagc taacgtgttg tatgtgtgta tgcgtcctat gtcgccgcca   18960
```

```
gaggagctgt tgagccgccg gcgccgtctg cactccagcg aatttcaaga tggcgacccc   19020
atcgatgatg cctcagtggt cgtacatgca catctcgggc caggacgctt cggagtacct   19080
gagccccggg ctggtgcagt tcgcccgcgc cacagacacc tacttcaaca tgagtaacaa   19140
gttcaggaac cccactgtgg cgcccaccca cgatgtgacc acggaccggt cgcagcgcct   19200
gacgctgcgg ttcatccccg tggatcggga ggacaccgcc tactcttaca aggcgcggtt   19260
cacgctggcc gtgggcgaca accgcgtgct ggacatggcc tccacttact ttgacatcag   19320
gggggtgctg gacaggggcc ccaccttcaa gccctactcg ggtactgcct acaactccct   19380
ggcccccaag ggcgctccca attcttgcga gtgggaacaa gatgaaccag ctcaggcagc   19440
aatagctgaa gatgaagaag aacttgaaga agaacaagct caggacgaac aggcgcccac   19500
taagaaaacc catgtatacg cccaggcacc tctttctggt gaaaaaatta ctaaggatgg   19560
tttgcaaata ggtgtggatg ccacacaggc gggagataac cctatatatg ctgataaaac   19620
attccaaccc gaacctcaga taggtgagtc tcagtggaac gaggctgatg ccacagtagc   19680
aggaggcaga gtcttaaaaa agaccacccc tatgagacct tgctatggat cctatgccaa   19740
acctactaat gccaatggcg gtcaagggat catggtggcc aatgatcagg agcgcttga   19800
atctaaagtt gagatgcaat ttttctccac cacaacgtct cttaatgtaa gggaaggtga   19860
aaacaatctt cagccaaaag tagtgctata cagcgaagat gttaacttgg aatcccctga   19920
cactcatttg tcttacaaac ctaaaaagga tgacaccaac tctaaaatca tgttgggtca   19980
gcaagccatg cccaacagac ccaacctcat tgcttttagg gacaacttta ttggacttat   20040
gtactacaac agcacaggca acatgggagt gctggcagga caggcctccc agctaaacgc   20100
tgtggtagac ttgcaagaca gaaacacaga gctgtcatac caactgatgc ttgattccat   20160
tggagacaga tcaagatact tttccatgtg gaaccaggca gtggacagct atgacccaga   20220
tgtcagaatc attgaaaacc atggggttga agatgagctg cccaactatt gctttcccct   20280
gggcggtatt ggaattacag acacatacca gtgcataaaa ccaaccgcag ctgctaataa   20340
cactacatgg tctaaggatg aagaatttag tgatcgcaat gaaataggg tgggaaacaa   20400
cttcgccatg gagatcaaca tccaggccaa cctctggagg aacttcctct atgcgaacgt   20460
ggggctctac ctgccagaca agctcaagta caaccccacc aacgtggaca tctctgacaa   20520
ccccaacacc tatgactaca tgaacaagcg tgtggtggct cccggcctgg tggactgctt   20580
tgtcaatgtg ggagccaggt ggtccctgga ctacatggac aacgtcaacc ccttcaacca   20640
ccaccgcaat gcgggtctgc gctaccgctc catgatcctg ggcaacgggc gctacgtgcc   20700
cttccacatt caggtgcccc agaagttctt tgccatcaag aacctcctcc tcctgccggg   20760
ctcctacact tacgagtgga cttcaggaa ggatgtcaac atggtcctgc agagctctct   20820
gggcaatgac cttagggtgg acggggccag catcaagttt gacagcgtca ccctctatgc   20880
taccttcttc cccatggctc acaacaccgc ctccacgctc gaggccatgc tgaggaacga   20940
caccaacgac cagtccttca tgactacctc tctggggcc aacatgctct accccatccc   21000
cgccaaggcc accaacgtgc ccatctccat tccctctcgc aactgggccg ccttcagagg   21060
ctgggccttt acccgcctta agaccaagga accccctcc ctgggctcgg ttttgacccc   21120
ctactttgtc tactcgggat ccatccccta cctggatggc accttctacc tcaaccacac   21180
ttttaagaag atatccatca tgtatgactc ctccgtcagc tggccgggca atgaccgcct   21240
gctcaccccc aatgagttcg aggtcaagcg cgccgtggac ggcgagggct acaacgtggc   21300
ccagtgcaac atgaccaagg actggttcct ggtgcagatg ctggccaact acaacatagg   21360
```

```
ctaccagggc ttctacatcc cagagagcta caaggacagg atgtactcct tcttcagaaa    21420
tttccaaccc atgagcaggc aggtggtgga cgagaccaaa tacaaggact atcaggccat    21480
tggcatcact caccagcaca acaactcggg attcgtgggc tacctggctc ccaccatgcg    21540
cgaggggcag gcctaccccg ccaacttccc ctacccgttg ataggcaaaa ccgcggtcga    21600
cagcgtcacc cagaaaaagt tcctctgcga ccgcaccctc tggcgcatcc ccttctctag    21660
caacttcatg tccatgggtg cgctcacgga cctgggccag aacctgctct atgccaactc    21720
cgcccatgcg ctggacatga cttttgaggt ggaccccatg gacgagccca cccttctcta    21780
tattgtgttt gaagtgttcg acgtggtcag agtgcaccag ccgcaccgcg gtgtcatcga    21840
gaccgtgtac ctgcgcacgc ccttctcggc cggcaacgcc accacctaag agacagcgc    21900 cgccgcctgc atgacgggtt ccaccgagca agagctcagg gccatcgcca gagacctggg    21960
atgcggaccc tattttttgg gcacctatga caaacgcttc ccgggcttca tctcccgaga    22020
caagctcgcc tgcgccatcg tcaacacggc cgcgcgcgag accgggggcg tgcactggct    22080
ggcctttggc tgggacccgc gctccaaaac ctgctacctc ttcgaccect ttggcttctc    22140 cgatcagcgc ctcagacaga tctatgagtt tgagtacgag gggctgctgc ccgcagcgc    22200 gcttgcctcc tcgcccgacc gctgcatcac ccttgagaag tccaccgaga ccgtgcaggg    22260
gccccactcg gccgcctgcg gtctcttctg ctgcatgttt ttgcacgcct tgtgcgctg    22320 gccccagagt cccatggatc gcaaccccac catgaacttg ctcaagggag tgcccaacgc    22380
catgctccag agcccccagg tccagcccac cctgcgccac aaccaggaac agctctaccg    22440
cttcctggag cgccactccc cctacttccg cagtcacagc gcgcacatcc gggggccac    22500 ctctttctgc cacttgcaag aaaacatgca agacggaaaa tgatgtacag ctcgcttttt    22560
aataaatgta aagactgtgc actttattta tacacgggct cttttctggtt atttattcaa    22620 caccgccgtc gccatctaga aatcgaaagg gttctgccgc gcgtcgccgt gcgccacggg    22680
cagagacacg ttgcgatact ggaagcggct cgcccactta aactcgggca ccaccatgcg    22740
gggcagtggt tcctcgggga agttctcgcc ccacagggtg cgggtcagct gcagcgcgct    22800
caggaggtcg ggagccgaga tcttgaagtc gcagttgggg ccggaaccct gcgcgcgcga    22860
gttgcggtac acggggttgc agcactggaa caccagcagg gccggattat gcacgctggc    22920
cagcaggctc tcgtcgctga tcatgtcgct gtccagatcc tccgcgttgc tcagggcgaa    22980
cggggtcatc ttgcagacct gcctgcccag gaaaggcggc agcccgggct gccgttgca    23040 gtcgcagcgc aggggcatca gcaggtgccc gcggcccgac tgcgcctgcg ggtacagcgc    23100
gcgcatgaag gcttcgatct gcctgaaagc cacctgcgtc ttggctccct ccgaaaagaa    23160
catcccacag gacttgctgg agaactggtt cgcgggacag ctggcatcgt gcaggcagca    23220
gcgcgcgtcg gtgttggcga tctgcaccac gttgcgaccc caccggttct tcactatctt    23280
ggccttggaa gcctgctcct tcagcgcgcg ctggccgttc tcgctggtca catccatctc    23340
tatcacctgc tccttgttga tcatgtttgt accgtgcaga cacttcaggt cgccctccgt    23400
ctgggtgcag cggtgctccc acagcgcgca accggtgggc tcccaatttt tgtgggtcac    23460
ccccgcgtag gcctgcaggt aggcctgcaa gaagcgcccc atcatggcca caaaggtctt    23520
ctggctcgta aaggtcagct gcaggccgcg atgctcttcg ttcagccagg tcttgcagat    23580
ggcggccagc gcctcggtct gctcgggcag catcctaaaa tttgtcttca ggtcgttatc    23640
cacgtggtac ttgtccatca tggcgcgcgc cgcctccatg cccttctccc aggcggacac    23700
```

-continued

```
catgggcagg cttagggggt ttatcacttc caccggcgag acaccgtac tttcgatttc    23760
ttcttcctcc ccctcttccc ggcgcgcgcc cacgctgctg cgcgctctca ccgcctgcac    23820
caagggtcg tcttcaggca agcgccgcac cgagcgcttg ccgcccttga cctgcttaat    23880
cagcaccggc gggttgctga agcccaccat ggtcagcgcc gcctgctctt cttcgtcttc    23940
gctgtctacc actatctctg gggaagggct tctccgctct gcggcggcgc gcttcttttt    24000
tttcttggga gcggccgtga tggagtccgc cacggcgacg gaggtcgagg gcgtggggct    24060
gggggtgcgc ggtaccaggg cctcgtcgcc ctcggactct tcctctgact ccaggcggcg    24120
gcggagtcgc ttctttgggg gcgcgcgcgt cagcggcggc ggagacgggg acggggacgg    24180
ggacgggacg ccctccacag ggggtggtct tcgcgcagac ccgcggccgc gctcggggt     24240
cttctcgagc tggtcttggt cccgactggc cattgtatcc tcctcctcct aggcagagag    24300
acataaggag tctatcatgc aagtcgagaa ggaggagagc ttaaccaccc cctctgagac    24360
cgccgatgcg cccgccgtcg ccgtcgcccc cgctgccgcc gacgcgcccg ccacaccgag    24420
cgacaccccc gcggaccccc ccgccgacgc acccctgttc gaggaagcgg ccgtggagca    24480
ggacccgggc tttgtctcgg cagaggagga tttgcgagag gaggaggata aggagaagaa    24540
gccctcagtg ccaaaagatg ataaagagca agacgagcac gacgcagatg cacaccaggg    24600
tgaagtcggg cgggggggacg gagggcatga cggcgccgac tacctagacg aagggaacga    24660
cgtgctcttg aagcacctgc atcgtcagtg cgccattgtt tgcgacgctc tgcaggagcg    24720
cagcgaagtg cccctcagcg tggcggaggt cagccacgcc tacgagctca gcctcttctc    24780
cccccgggtg ccccccgcc gccgcgaaaa cggcacatgc gagcccaacc cgcgcctcaa    24840
cttctacccc gcctttgtgg tacccgaggt cctggccacc tatcacatct tctttcaaaa    24900
ttgcaagatc cccctctcgt gccgcgccaa ccgtagccgc gccgataaga tgctggccct    24960
gcgccagggc gaccacatac ctgatatcgc cgctttggaa gatgtaccaa agatcttcga    25020
gggtctgggt cgcaacgaga agcgggcagc aaactctctg caacaggaaa acagcgaaaa    25080
tgagagtcac accggggtac tggtggagct cgagggcgac aacgcccgcc tggcggtggt    25140
caagcgcagc atcgaggtca cccactttgc ctaccccgcg ctaaacctgc cccccaaagt    25200
catgaacgcg gccatggacg ggctgatcat gcgccgcggc cggcccctcg ctccagatgc    25260
aaacttgcat gaggagaccg aggacggcca gcccgtggtc agcgacgagc agctggcgcg    25320
ctggctggag accgcggacc ccgccgaact ggaggagcgg cgcaagatga tgatggccgt    25380
ggtgctggtc accgtagagc tggagtgtct gcagcgcttc ttcggcgacc ccagagatgca    25440
gagaaaggtc gaggagaccc tgcactacac cttccgccag ggctacgtgc gccaggcttg    25500
caagatctcc aacgtggagc tcagcaacct ggtgtcctac ctgggcatct tgcatgagaa    25560
ccgcctcggg cagagcgtgc tgcactccac cctgcgcggg gaggcgcgcc gcgactacgt    25620
gcgcgactgc gtttacctct tcctctgcta cacctggcag acggccatgg gggtctggca    25680
gcagtgcctg gaggagcgca acctcaagga gctgagaaag ctcctgcagc gcgcgctcaa    25740
agatctctgg acgggctaca acgagcgctc ggtggccgcc gcgctggccg acctcatctt    25800
ccccgagcgc ctgctcaaaa ccctccagca ggggctgccc gacttcacca gccaaagcat    25860
gttgcaaaac ttcaggaact ttatcctgga gcgttctggc atcctacccg ccacctgctg    25920
cgccctgccc agcgactttg tccccctcgt gtaccgcgag tgcccccgc cgctgtgggg    25980
tcactgctac ctgttccaac tggccaacta ccctgtcctac cacgcggacc tcatggagga    26040
ctccagcggc gaggggctca tggagtgcca ctgccgctgc aacctctgca cgccccaccg    26100
```

```
ctccctggtc tgcaacaccc aactgctcag cgagagtcag attatcggta ccttcgagct    26160
acagggtccg tcctcctcag acgagaagtc cgcggctccg gggctaaaac tcactccggg    26220
gctgtggact tccgcctacc tgcgcaaatt tgtacctgaa gactaccacg cccacgagat    26280
caggttttac gaagaccaat cccgcccgcc caaggcggga ctgaccgcct gcgtcatcac    26340
ccagggcgag atcctaggcc aattgcaagc catccaaaaa gcccgccaag acttttgct     26400 gaagaagggt cggggggtgt atctggaccc ccagtcgggt gaggagctca acccggttcc    26460
cccgctgccg ccgccgcggg accttgcttc ccaggataag catcgccatg gctcccagaa    26520
agaagcagca gcgccgcca  ctgccgccac cccacatgct ggaggaagag gaggaatact    26580
gggacagtca ggcagaggag gtttcggacg aggaggagcc ggagacggag atggaagagt    26640
gggaggagga cagcttagac gaggaggctt ccgaagccga agaggcagac gcaacaccgt    26700
caccctcggc cgcagccccc tcgcaggcgc ccccgaagtc cgctcccagc atcagcagca    26760
acagcagcgc tataacctcc gctcctccac cgccgcgacc cacggccgac cgcagaccca    26820
accgtagatg ggacaccacc ggaaccgggg ccggtaagtc ctccgggaga ggcaagcaag    26880 cgcagccgcca aggctaccgc tcgtggcgcg ctcacaagaa cgccatagtc gcttgcttgc    26940
aagactgcgg ggggaacatc tccttcgccc gccgcttcct gctcttccac cacggtgtgg    27000 ccttccccccg taacgtcctg cattactacc gtcatctcta cagcccctac tgcggcggca    27060
gtgagccaga cacggtcggc ggcggcggcg gcgcccgttt cggcgcctag aagacccag    27120 ggcaagactt cagccaagaa actcgcggcg gccgcggcga acgcggtcgc gggggccctg    27180
cgcctgacgg tgaacgaacc cctgtcgacc cgcgaactga ggaaccgaat cttccccact    27240
ctctatgcca tcttccagca gagcagaggg caggatcagg aactgaaagt aaaaaacagg    27300
tctctgcgct ccctcacccg cagctgtctg tatcacaaga gcgaagacca gcttcggcgc    27360
acgctggagg acgctgaggc actcttcagc aaatactgcg cgctcactct taaggactag    27420
ctccgcgccc ttctcgaatt taggcgggaa cgcctacgtc atcgcagcgc cgccgtcatg    27480
agcaaggaca ttcccacgcc atacatgtgg agctatcagc cgcagatggg actcgcggcg    27540
ggcgcctccc aagactactc caccccgcatg aactggctca gtgccggccc acacatgatc    27600
tcacaggtta atgatatccg cacccatcga aaccaaatat tggtggagca ggcggcaatt    27660
accaccacgc cccgcaataa tcccaacccc agggagtggc ccgcgtccct ggtgtatcag    27720
gaaattcccg gccccaccac cgtactactt ccgcgtgatt cccaggccga agtccaaatg    27780
actaactcag gggcacagct cgcgggcggc tgtcgtcaca gggtgcggcc tcctcgccag    27840
ggtataactc acctggagat ccgaggcaga ggtattcagc tcaacgacga gtcggtgagc    27900
tcctcgctcg gtctcagacc tgacgggacc ttccagatag ccggagccgg ccgatcttcc    27960
ttcacgcccc gccaggcgta cctgactctg caaagctcgt cctcggcgcc gcgctcgggc    28020
ggcatcggga ctctccagtt cgtgcaggag tttgtgccct cggtctactt caacccctc    28080 tcgggctctc ccggtcgcta cccggaccag ttcatctcga actttgacgc cgcgagggac    28140
tcggtggacg gctacgactg aatgtcgggt ggacccggtg cagagcaact tcgcctgaag    28200
cacctcgacc actgccgccg ccctcagtgc tttgcccgct gtcagaccgg tgagttccag    28260
tacttttccc tgcccgactc gcacccggac ggcccggcgc acggggtgcg cttttttcatc    28320 ccgagtcagg tgcgctctac cctaatcagg gagtttaccg cccgtcccct actgcggag    28380 ttggaaaagg ggccttctat cctaaccatt gcctgcatct gctctaaccc tggattgcac    28440
```

```
caagatctttt gctgtcattt gtgtgctgag tataataaag gctgagatca gaatctactc   28500
gggctcctgt cgccatcctg tcaacgccac cgtccaagcc cggcccgatc agcccgaggt   28560
gaacctcacc tgcggtctgc accggcgcct gaggaaatac ctagcttggt actacaacag   28620
cactcccttt gtggtttaca acagctttga ccaggacggg gtctcactga gggataacct   28680
ctcgaacctg agctactcca tcaggaagaa cagcaccctc gagctacttc ctccttacct   28740
gcccgggact taccagtgtg tcaccggtcc ctgcacccac acccacctgt tgatcgtaaa   28800
cgactctctt ccgagaacag acctcaataa ctcctcttcg cagttcccca aacaggagg    28860 tgagctcagg aaaccccggg taaagaaggg tggacgagag ttaacacttg tggggtttct   28920
ggtgtatgtg acgctggtgg tggctctttt gattaaggct tttccttcca tgtctgaact   28980
ctccctcttc ttttatgaac aactcgacta gtgctaacgg gacccctaccc aacgaatcgg  29040 gattgaatat cggtaaccag gttgcagttt cacttttgat taccttcata gtcctcttcc   29100
tgctagtgct gtcgcttctg tgcctgcgga tcggggctg ctgcatccac gtttatatct    29160
ggtgctggct gtttagaagg ttcggagacc atcgcaggta gaataaacat gctgctgctt   29220
accctctttg tcctggcgct ggccgccagc tgccaagcct tttccgaggc tgactttata   29280
gagccccagt gtaatgtgac ttttaaagcc catgcacagc gttgtcatac tataatcaaa   29340
tgtgccaccg aacacgatga ataccttatc cagtataaag ataaatcaca caaagtggca   29400
cttgttgaca tctggaaacc cgaagaccct ttgaataca atgtgaccgt tttccagggt    29460
gacctcttca aaatttacaa ttacactttc ccatttgacc agatgtgtga ctttgtcatg   29520
tacatggaaa agcagcacaa gctgtggcct ccgactcccc agggctgtgt ggaaaatcca   29580
ggctctttct gcatgatctc tctctgtgta actgtgctgg cactaatact cacgcttttg   29640
tatatcagat ttaaatcaag gcaaagcttc attgatgaaa agaaaatgcc ttaatcgctt   29700
tcacgcttga ttgctaacac cgggttttta tccgcagaat gattggaatc accctactaa   29760
tcacctccct ccttgcgatt gcccatgggt tggaacgaat cgaagtccct gtgggggcca   29820
atgttaccct ggtgggggcct gtcggcaatg ctacattaat gtgggaaaaa tatactaaaa  29880
atcaatgggt ctcttactgc actaacaaaa atagccacaa gcccagagcc atctgcgatg   29940
ggcaaaatct aaccttgatt gatgttcaat tgctggatgc gggctactat tatgggcagc   30000
tgggtacaat gattaattac tggagacccc acagagatta catgctccac gtagtaaagg   30060
gtccccttag cagcccaccc actaccacct ctactacccc cactaccacc actactccca   30120
ccaccagcac tgccgcccag cctcctcata gcagaacaac cacttttatc aattccaagt   30180
cccactcccc ccacattgcc ggcgggccct ccgcctcaga ctccgaaacc accgagatct   30240
gcttctgcaa atgctctgac gccattgccc aggatttgga agatcacgag gaagatgagc   30300
atgacttcgc agatgcatgc caggcatcag agccagaagc gctgccggtg ccctcaaac    30360 agtatgcaga ccccacacc accccgacc ttcctccacc ttcccagaag ccaagtttcc      30420
tgggggaaaa tgaaactctg cctctctcca tactcgctct gacatctgtt gctatgttga   30480
ccgctctgct ggtgcttcta tgctctatat gctacctgat ctgctgcaga aagaaaaaat   30540
ctcacggcca tgctcaccag cccctcatgc acttcccttg ccctccagag ctgggcgacc   30600
acaaacttta agtctgcagt aactatctgc ccatcccttg tcagtcgaca gcgatgagcc   30660
ccactaatct aacggcctct ggacttacaa catcgtctct taatgagacc accgctcctc   30720
aagacctgta cgatggtgtc tccgcgctgg ttaaccagtg ggatcacctg gcatatggt    30780 ggctcctcat aggagcagtg accctgtgcc taatcctggt ctggatcatc tgctgcatca   30840
```

```
aaagcagaag acccaggcgg cggcccatct acaggccctt tgtcatcaca cctgaagatg    30900
atgatgacac cacttccagg ctgcagaggc taaagcagct actcttctct tttacagcat    30960
ggtaaattga atcatgcctc gcattttcat ctacttgtct ctccttccac tttttctggg    31020
ctcttctaca ttggccgctg tgtcccacat cgaggtagac tgcctcacgc ccttcacagt    31080
ctacctgctt ttcggctttg tcatctgcac ctttgtctgc agcgttatca ctgtagtgat    31140
ctgcttcata cagtgcatcg actacgtctg cgtgcgggtg gcttacttta gacaccaccc    31200
ccagtatcgc aacagggaca tagcggctct cctaagactt gtttaaaatc atggccaaat    31260
taactgtgat tggtcttctg atcatctgct gcgtcctagc cgcgattggg actcaagctc    31320
ctaccaccac cagcgctccc agaaagagac atgtatcctg cagcttcaag cgtccctgga    31380
atataccccca atgctttact gatgaacctg aaatctcttt ggcttggtac ttcagcgtca    31440
ccgcccttct tatcttctgc agtacggtta ttgcccttgc catctaccct tcccttgacc    31500
tgggctggaa tgctgtcaac tctatggaat atcccacctt cccagaacca gacctgccag    31560
acctggttgt tctaaacgcg tttcctcctc ctgctcccgt tcaaaatcag tttcgccctc    31620
cgtcccccac gcccactgag gtcagctact ttaatctaac aggcggagat gactgaaaac    31680
ctagacctag aaatggacgg tctctgcagc gagcaacgca cactagagag gcgccggcaa    31740
aaagagctcg agcgtcttaa acaagagctc caagacgcgg tggccataca ccagtgcaaa    31800
aaggtgtctc tctgtctggt aaaacaggcc acgctcacct atgaaaaaac aggtgacacc    31860
caccgcctag gatacaagct gcccacacag cgccaaaagt tcgccctcat gataggcgaa    31920
caacccatca ccgtgaccca gcactccgtg gagacagaag gctgcataca tgctccctgt    31980
aggggcgctg actgcctcta caccttgatc aaaaccctct gcggtctcag agaccttatc    32040
cctttcaatt aatcataact gtaatcaata aaaaatcact tacttgaaat ctgatagcaa    32100
gcctctgtcc aatttttttca gcaacacttc cttccccctcc tcccaactct ggtactctag    32160
gcgcctccta gctgcaaact tcctccacag tctgaaggga atgtcagatt cctcctcctg    32220
tccctccgca cccacgatct tcatgttgtt gcagatgaaa cgcgcgagat cgtctgacga    32280
gaccttcaac cccgtgtacc cctacgatac cgagatcgct ccgacttctg tccctttcct    32340
tacccctccc tttgtgtcat ccgcaggaat gcaagaaaat ccagctgggg tgctgtccct    32400
gcacttgtca gagcccctta ccacccacaa tggggccctg actctaaaaa tggggggcgg    32460
cctgaccctg gacaaggaag ggaatctcac ttcccaaaac atcaccagtg tcgatccccc    32520
tctcaaaaaa agcaagaaca acatcagcct tcagaccgcc gcaccccctcg ccgtcagctc    32580
cggggcccta acacttttttg ccactccccc cctagcggtc agtggtgaca accttactgt    32640
gcagtctcag gcccctctca ctttggaaga ctcaaaacta actctggcca ccaaaggacc    32700
cctaactgtg tccgaaggca aacttgtcct agaaacagag gctcccctgc atgcaagtga    32760
cagcagcagc ctgggcctta cgttacggc cccacttagc attaacaatg acagcctagg    32820
actagatctg caggcaccca ttgtctctca aaatggaaaa ctggctctaa atgtagcagg    32880
cccccctagct gtggccaatg gcattaatgc tttgacagta ggcacaggca aaggtattgg    32940
tctaaatgaa accagcactc acttgcaagc aaagttggtc gccccctag ctttgatac    33000
caatggcaac attaagctaa gcgttgcagg aggcatgaga ctaaataatg acacacttat    33060
actagatgta aactacccat ttgaagctca aggccaacta agtctaagag tgggccaggg    33120
tccgctgtat gtagattcta gcagccataa cctgaccatt agatgcctta gaggattata    33180
```

```
cataacatcg tctaataacc aaaccggtct agaggccaac ataaaactaa caaaaggcct    33240
tgtctatgat ggaaatgcca tagcagtcaa tgttggtcaa ggattgcaat acagcactac    33300
tgccacatcg gaaggtgtgt atcctataca gtctaagata ggtttgggaa tggaatatga    33360
taccaacgga gccatgatga caaaactagg ctctggacta agctttgaca attcaggagc    33420
cattgtagtg ggaaacaaaa atgatgacag gcttactctg tggactacac cagacccatc    33480
tcctaactgt agaatttatt ctgaaaaaga tactaaacta accttggtgc tgactaagtg    33540
tggcagccaa atcctaggca cagtatctgc ccttgctgtc agaggcagcc ttgcgcccat    33600
cactaatgca tccagcatag tccaaatatt tctaagattt gatgaaaatg gactattgat    33660
gagcaactca tcgctagacg gtgattactg gaattacaga aatggggact ccactaatag    33720
cacaccatat acaaatgcag taggctttat gcctaatcta gcagcctatc ctaaaggtca    33780
ggctacagct gcaaaaagca gtattgtaag ccaggtatac atggatggtg acactactaa    33840
acctataaca ctaaaaataa acttcaatgg cattgatgaa acaacagaaa atacccctgt    33900
tagtaaatat tccatgacat tctcatggag ctggccacc gcaagctaca taggccacac    33960
ttttgcaaca aactctttta ctttctccta catcgcccaa gaataaagaa agcacagaga    34020
tgcttgtttt gatttcaaaa ttgtgtgctt ttatttattt tcagcttaca gtatttccag    34080
tagtcattcg aataaagctt aatcaaactg catgagaacc cttccacata gcttaaatta    34140
gcaccagtgc aaatggagaa aattcaacat acctttttta tccagatatc agagaactct    34200
agtggtcagt tttcccccac cctcccagct cacagaatac acagtccttt cccccggct    34260 ggctttaaac aacactatct cattggtaac agacatattc ttaggtgtaa taatccacac    34320
ggtctcttgg cgggccaagc gctggtcggt gatgttaata aactccccag gcagctcttt    34380
caagttcacg tcgctgtcca actgctgaag cgctcgcggc tccgactgcg cctctagcgg    34440
aggcaacggc aacacccgat ccttgatcta taaggagta gagtcataat cccccataag    34500 aatagggcg tgatgcagca acaaggcgcg cagcaactcc tgccgccgcc tctccgtacg    34560
acaggaatgc aacggcgtgg tggtctcctc cgcgataatc cgcaccgctc gcagcatcag    34620
catcctcgtc ctccgggcac agcagcgcat cctgatctca ctgagatcgg cgcagtaagt    34680
gcagcacaaa accaagatgt tatttaagat cccacagtgc aaagcactgt acccaaagct    34740 catgcggga aggacagccc ccacgtgacc atcataccag atccttaggt aaatcaaatg    34800
acgacctctc ataaacacgc tggacatgta catccacctcc ttgggcatgc gctgattcac    34860
cacctctcga taccaaagc atcgctgatt aattaaagac ccctcaagca ccatcctgaa    34920
ccaggaagcc agcacctgac cccccgccag gcactgcagg gaccccggtg aattgcagtg    34980
gcagtgaaga ctccagcgct cgtagccgtg aaccatagag ccggtcatta tatccacatt    35040
ggcacaacac aaacacactt tcatacactt tttcatgatt agcagctcct ctctagtcag    35100
gaccatatcc caaggaatca cccactcttg aatcaaggta atcccacac agcagggcag    35160 gcctctcaca taactcacgt tatgcatagt gagcgtgtcg caatctggaa ataccggatg    35220
atcttccatc accgaagctc gcgtctccgt ctcaaggga ggtaaacggt ccctcgtgta    35280
gggacagtgg cgggataatc gagatcgtgt tgaacgtaga gtcatgccaa agggaacagc    35340
ggacgtactc atatttcctc cagcagaacc aagtgcgcgc gtggcagcta tccctgcgtc    35400
ttctgtctcg ccgcctgccc cgctcggtgt agtagttgta atacagccac tccctcagac    35460
cgtcaaggcg ctccctggcg tccggatcta taacaacacc gtcctgcagc gccgcctga    35520 tgacatccac caccgtagag tatgccaagc ccagccagga aatgcattca ctttgacagc    35580
```

```
gagagatagg aggagcggga agagatggaa gaaccatgat agtaaaagac ttttattcca    35640
atcgatcctc tacaatgtca aagtgtagat ctataagatg acactggtct cctccgctga    35700
gtcgatcaaa ataacagct aaaccacaaa caacacgatt ggtcaaatgc tccacaaggg     35760
cttgcagcat aaaatcgcct cgaaagtcca ccgcaagcat aacatcaaag ccaccgcccc    35820
tatcatgatc tataataaaa accccacagc tatccaccag acccataaag ttttcatctc    35880
tccatcgtga aaaatatttt acaagctcct cctttaaatc acctccaacc aattgaaaaa    35940
gttgagccaa accgccctcc accttcattt tcagcaagcg catcatgatt gcaaaaattc    36000
aggctcctga gacacctgta taagattgag aagcggaacg ttaacgtcaa tgtttcgctc    36060
gcgaagatcg cgcctcagtg caagcatgat ataatcccac aggtcggagc ggatcagcga    36120
ggacatctcc ccgccaggaa ccaactcaac ggagcctatg ctgattataa tacgcatatt    36180
cggggctatg ctgaccagca cggcccccaa ataggcgtac tgcataggcg gcgacaaaaa    36240
gtgaacagtt tgggttaaaa aatcaggcaa acagtcgcgc aaaaaagcaa gaacatcata    36300
accatgctca tgcaaataga tgcaagtaag ctcaggaacg accacagaaa aatgcacaat    36360
ttttctctca aacatgactg cgagccctgc aaaaaataaa aaagaaacat tacacaagag    36420
tagcctgtct tacgatggga tagactactc taaccaacat aagacgggcc acaacatcgc    36480
ccgcgtggcc ataaaaaaaa ttgtccgtgt gattaaaaag aagcacagat agctggccag    36540
tcatatccgg agtcatcacg tgtgaacccg tgtagacccc cgggttggac acatcggcca    36600
aacaaagaaa gcggccaatg tacccaggag gaatcataac actaagacga agatacaaca    36660
gaataacccc atgaggggga ataacaaagt tagtaggtga ataaaaacga taaacacccg    36720
aaactccctc ctgcgtaggc aaaatagcac cctcccttc caaaacaaca tatagcgctt     36780
ccacagcagc catgacaaaa gactcaaaac actcaaaaga ctcagtctta ccaggaaaat    36840
aaaagcactc tcacagcacc agcactaatc agagtgtgaa gagggccaag tgccgaacga    36900
gtatatatag gaataaaaaa tgacgtaaat gtgtaaaggt cagaaacgc ccagaaaaat     36960 acacagacca acgcccgaaa cgaaaacccg cgaaaaaata cccagaactt cctcaacaac    37020
cgccacttcc ggtttctcac ggtacgtcac ttccgcaaga aaagcaaaac tacatttccc    37080
acatgtgtaa aaacgaaacc ccgcccctgg taactgccca caacttacat catcaaaaca    37140
taaactccta cgtcacccgc cccgcctctc ccgcccacc tcattatcat attggccaca     37200
atccaaaata aggtatatta ttgatgatg                                      37229

<210> SEQ ID NO 22
<211> LENGTH: 37232
<212> TYPE: DNA
<213> ORGANISM: Gorilla beringei beringei

<400> SEQUENCE: 22
catcatcaat aatatacctt attttggatt gtggccaata tgataatgag gtgggcgggg      60
agaggcgggg cgggtgacgt aggacgcgcg agtagggttg ggaggtgtgg cggaagtgtg     120
gcatttgcaa gtgggaggag ctcacatgca agcttccgtc gcggaaaatg tgacgttttt     180
gatgagcgcc gcctacctcc ggaagtgcca attttcgcgc gcttttcacc ggatatcgta     240
gtaattttgg gcgggaccat gtaagatttg gccatttcg cgcgaaaagt gaaacgggga      300
agtgaaaact gaataatagg gcgttagtca tagcgcgtaa tatttaccga gggccgaggg     360
actttgaccg attacgtgga ggactcgccc aggtgttttt tacgtgaatt tccgcgttcc     420
```

```
gggtcaaagt ctccgttttt attgtcaccg tcatttgacg cggagggtat ttaaacccgc    480
tgcgctcctc aagaggccac tcttgagtgc cagcgagaag agttttctcc tctgctccgc    540
ttcggtgatc gaaaaatgag acacatagcc tgcactccgg gtcttttgtc cggtcgggcg    600
gcggccgagc ttttggacgc tttgatcaat gatgtcctaa gcatgatttt tccgtctact    660
acccacttta gcccacctac tcttcacgaa ctgtacgatc tggatgtact ggtggatgtg    720
aacgatccca acgaggaggc ggtttctgcg tttttccccg agtctgcgct gttgccgct    780 caggagggat ttgacctaca cactccgccg cctattttag agtctccgct gccggagccc    840
agtggtatac cttatatgcc tgaactgctt cccgaagtgg tagacctgac ctgccacgag    900
cctggctttc cgcccagcga cgatgagggt gagccttttg ttttagactt tgctgagata    960
cctgggcacg gttgcaggtc ttgtgcatat catcagaggg ttaccggaga ccccgaggtt   1020
aagtgttcgc tgtgctatat gaggatgacc tcttccttta tctacagtaa gtttttgtct   1080
aggtgggctt tgggtaggt gggttttgtg tcagaacagg tgtaaacgtt gcttgtgttt   1140
tttgtacctg taggtccggt gtccgagcca gacccgagc ccgaccgcga tcccgagccg   1200
gatcccgagc ctcctcgcag gacaaggaaa ctaccttcca ttctgtgcaa gtctcagaca   1260
cctgtaagga ccagcgaggc agacagcacc gactctggca cttctacctc tccccctgaa   1320
attcacccag tggttcctct gggtatacat aaacctgttg ctgttaaagt ttgcgggcga   1380
cgccctgcag tacagtgcat tgaggacttg cttcacgatc ccgaggaacc tttggacttg   1440
agccttaaac gccctaggca ataaacccca cctaagtaat aaaccсссacc taagtaataa   1500 accctgccgc ccttggttat tgagatgacg cccaatgttt gcttttgaat gacttcatgt   1560
gtgtaataaa agtgagtgtg atcataggtc tcttgtttgt ctgggcgggg cttaagggta   1620

tataagtctc ttggggctaa acttggttac acttgacccc aatggaggcg tgggggtgct   1680
tggaggagtt tgcggacgtg cgccgtttgc tggacgagag ctctagcaat acttatacta   1740

tttgggagta tctgtggggc tctactcagg ccaagttggt ttccagaatt aagcaggatt   1800 acaagtgcga тттттgaagag ctttttagtt cctgcggtga gcttttgcaa tccttgaatc   1860

tgggccatca ggctattttc caggaaaagg ttctctcgac tttggatttt tccactcccg   1920
ggcgcaccgc cgcttgtgtg gcтттттgтgт cтттттgтgca agataaatgg agcgaggaga   1980
cccacctgag tcacggctac gtactggatt tcatggcgat ggctctttgg aggggctcaca   2040 acaaatggaa gattcagaag gaactgtacg gttccgccct acgtcgtcca cttctgtcgc   2100 gacagggct gaggtttccc gaccatcggc agcatcagaa tctggaagac gagtcggagg   2160
agcgagcgga ggagaagatc agcttgagag ccggcctgga ccctcctcag gaggaatgaa   2220

tctcccgcag gtggttgacc tgtttccaga actgagacgg gtcctgacta tcagggagga   2280
tggtcagttt gtgaagaagt ttaagaggga tcggggtgag ggagatgatg aggcggctag   2340
caattaggct tttagtctga tgactcgcca ccgaccggaa tgtattacct atcagcagat   2400

taaggagagt tgtgccaacg agctggatct tttgggtcag aagtatagca tagaacagct   2460

taccacttac tggcttcagc ctggggatga ttgggaagag gcgatcaggg tgtatgcaaa   2520
ggtggccctg cggcccgatt gcaagtataa gattactaag ttggttaata тттagaaacтg   2580 ctgctatatt tctgggaacg gggccgaagt ggagatagat actcaggaca gggtggcttt   2640

taggtgttgc atgataaaca тgтggccccgg gatactgggg atggatgggg tggtattcat   2700
gaatgtgagg tttacgggcc ccaactttaa tggcacggtg ttcatgggca acaccaactt   2760
gctcctgcat ggtgcgagtt tctatgggtt taataacacc tgtatagagg cctggaccga   2820
```

```
tgtaaaggtt cgaggttgtt cctttatag ctgttggaag gcggtggtgt gtcgccctaa   2880 aagcagggt tctgtgaaaa aatgcttgtt tgaaaggtgc accttaggca tcctctctga   2940
gggcaactcc agggtgcgcc ataatgtggc ttcgaactgc ggttgcttca tgcaagtgaa   3000
gggggtgagc gttatcaagc ataactcggt gtgtggaaac tgcgaggatc gcgcctccca   3060
gatgctgacc tgctttgatg gcaactgtca cctgttgaag accattcata taagcagcca   3120
ccccagaaag gcctggcccg tgtttgagca taacatcttg acccgctgct ccttgcatct   3180
gggggtcagg aggggtatgt tcctgcctta ccagtgtaac tttagccaca ctaaaatcct   3240 gctgaaccc gagtgcatga ccaaggtcag cctgaatggt gtgtttgatg tgactctgaa   3300
aatctggaag gtgctgaggt atgatgagac caggaccagg tgccgaccct gcgagtgcgg   3360
cggcaagcac atgagaaatc agcctgtgat gttggatgtg accgaggagc ttaggcctga   3420
ccatctggtg ctggcctgca ccagggccga gtttgggtct agcgatgagg ataccgattg   3480
aggtgggtaa ggtgggcgtg gctagaaggg tggggcgtgt ataaattggg ggtctaaggg   3540
tctctctgtt ttgtcttgca acagccgccg ccatgagcga caccggcaac agctttgatg   3600
gaagcatctt tagcccctat ctgacagtgc gcatgcctca ctgggctgga gtgcgtcaga   3660
atgtgatggg ttccaacgtg gatggacgcc ccgttctgcc ttcaaattcg tctacaatgg   3720
cctacgcgac cgtgggagga actccgctgg acgccgcgac ctccgccgcc gcctccgccg   3780
ccgccgcgac cgcgcgcagc atggctacgg acctttacag ctctttggtg gcgagcggcg   3840
cggcctctcg cgcgtctgct cgggatgaga aactgaccgc tctgctgctt aaactggaag   3900
acttgacccg ggagctgggt caactgaccc agcaggtctc cagcttgcgt gagagcagcc   3960
ttgcctcccc ctaatggccc ataatataaa taaaagccag tctgtttgga ttaagcaagt   4020
gtatgttctt tatttaactc tccgcgcgcg gtaagcccgg gaccagcggt ctcggtcgtt   4080
tagggtgcgg tggattcttt ccaacacgtg gtacaggtgg ctctggatgt ttagatacat   4140
gggcatgagt ccatccctgg ggtggaggta gcaccactgc agagcttcgt gctcgggggt   4200
ggtgttgtat atgatccagt cgtagcagga gcgctgggcg tggtgctgaa aaatgtcctt   4260
aagcaagagg cttatagcta gggggaggcc cttggtgtaa gtgtttacaa atctgctcag   4320 ttggagggg tgcatccggg gggatataat gtgcatcttg gactggattt ttaggttggc   4380
tatgttccca cccagatccc ttctgggatt catgttgtgc aggaccacca gcacggtata   4440
tccagtgcac ttgggaaatt tatcgtggag cttagacggg aatgcatgga agaacttgga   4500
gacgcccttg tggcctccca gattttccat acattcgtcc atgatgatgg caatgggccc   4560
gtgggaagct gcctgagcaa aaatgtttct gggatcgctc acatcgtagt tatgttccag   4620
ggtgaggtca tcataggaca tctttacgaa tcggggcgg agggtcccgg actggggat   4680 gatggtaccc tcgggccccg gggcgtagtt cccctcacag atctgcatct cccaggcttt   4740
catttcagag ggagggatca tatccacctg cggagcgatg aaaaacacag tttctggcgc   4800 agggagatt aactgggatg agagcaggtt tctgagcagc tgtgactttc cacagccggt   4860
gggcccatat atcacgccta tcaccggctg cagctggtag ttaagagagc tgcagctgcc   4920
gtcctcccgg agcaggggg ccacctcgtt cagcatatcc ctgacgtgga tgttctccct   4980
gaccaattcc gccagaaggc gctcgccgcc cagcgaaagc agctcttgca aggaagcaaa   5040 attttcagc ggtttaggc cgtcggccgt gggcatgttt ttcagcgtct gggtcagcag   5100
ttccagcctg tcccacagct cggtgatgtg ctctacggca tctcgatcca gcagatctcc   5160
```

```
tcgtttcgcg ggttggggcg gctttcgctg tagggcacca gccgatgggc gtccagcggg   5220
gccagagtca tgtccttcca tgggcgcagg gtcctcgtca gggtggtctg ggtcacggtg   5280
aaggggtgcg ctccggggttg ggcgctggcc agggtgcgct tgaggctggt tctgctggtg   5340
ctgaatcgct gccgctcttc gccctgcgcg tcggccaggt agcatttgac catggtctcg   5400
tagtcgagac cctcggcggc gtgccccttg gcgcggagct ttcccttgga ggtggcgccg   5460
cacgaggggc actgcaggct cttcaggcg tagagcttgg gagcgagaaa cacggactct   5520
ggggagtagg cgtccgcgcc gcaggaagcg cagaccgtct cgcattccac cagccaagtg   5580
agctccgggc ggtcagggtc aaaaaccagg ttgcccccat gcttttgat gcgtttctta   5640 cctcggctct ccatgaggcg gtgtcccttc tcggtgacga agaggctgtc cgtgtccccg   5700
tagaccgact tcaggggcct gtcttccagc ggagtgcctc tgtcctcctc gtagagaaac   5760
tctgaccact ctgagacgaa ggcccgcgtc caggccagga cgaaggaggc cacgtgggag   5820
gggtagcggt cgttgtccac tagcgggtcc accttctcca gggtgtgcag gcacatgtcc   5880
ccctcctccg cgtccagaaa agtgattggc ttgtaggtgt aggacacgtg accgggggtt   5940
cccgacgggg gggtataaaa ggggtgggc gccctttcat cttcactctc ttccgcatcg   6000
ctgtctgcga gggccagctg ctgggtaag tattccctct cgaaggcggg catgacctca   6060
gcgctcaggt tgtcagtttc taaaaatgag gaggatttga tgttcacctg tccggaggtg   6120 ataccttttga gggtacctgg gtccatctgg tcagaaaaca ctattttttt gttgtcaagc   6180
ttggtggcga acgacccgta gagggcgttg gagagcagct ggcgatgga gcgcagggtc   6240 tggttttttgt cgcggtcggc tcgctccttg gccgcgatgt tgagttgcac gtactcgcgg   6300
gccacgcact tccactcggg gaagacggtg gtgcgctcgt ctgggattag gcgcaccctc   6360
cagcctcggt tgtgcagggt gaccatgtcg acgctggtgg cgacctcgcc gcgcaggcgc   6420
tcgttggtcc agcagaggcg gccgcccttg cgcgagcaga aggggggtag ggggtccagc   6480
tggtcctcgt ttgggggtc cgcgtcgatg gtgaagaccc cggggagcaa gcgcgggtca   6540
aagtagtcga tcttgcaagc ttgcatgtcc agagcccgct gccattcgcg ggcggcgagc   6600
gcgcgctcgt aggggttgag gggcgggccc cagggcatgg ggtgggtgag cgcggaggcg   6660
tacatgccgc agatgtcata cacgtacagg ggttccctga ggatgccgag gtaggtgggg   6720
tagcagcgcc ccccgcggat gctggcgcgc acgtagtcat agagctcgtg ggagggggcc   6780
agcatgttgg gcccgaggtt ggtgcgctgg gggcgctcgg cgcggaaggc gatctgcctg   6840
aagatggcat gggagttgga ggagatggtg ggccgctgga agacgttgaa gcttgcttct   6900
tgcaagccca ccgagtccct gacgaaggag gcgtaggact cgcgcagctt gtgcaccagc   6960
tcggcggtga cctggacgtc gagcgcgcag tagtcgaggg tctcgcggat gatgtcatac   7020
ttatcctccc ccttcttttt ccacagctcg cggttgagga cgaactcttc gcggtctttc   7080
cagtactctt ggaggggaaa cccgtccgtg tccgaacggt aagagcctag catgtagaac   7140
tggttgacgg cctggtaggg gcaacagccc ttctccacgg gcagcgcgta ggcctgcgcc   7200
gccttgcgga gggaggtgtg ggtgagggcg aaagtgtccc tgaccatgac tttgaggtat   7260
tgatgtttga agtctgtgtc atcgcagccg ccctgttccc acagggtgta gtccgtgcgc   7320
tttttggagc gcgggttggg cagggagaag gtgaggtcat tgaagaggat cttccccgct   7380
cgaggcatga agtttctggt gatgcgaaag ggcctgggga ccgaggagcg gttgttgatg   7440
acctgggcgg ccaggacgat ctcgtcaaag ccgtttatgt tgtggcccac gatgtagagc   7500
tccaaaaagc ggggctggcc cttgatggag gggagctttt tgagttcctc gtaggtgagc   7560
```

```
tcctcgggcg attccaggcc gtgctcctcc agggcccagt cttgcaagtg agggttggcc    7620
gccaggaagg atcgccagag gtcgcgggcc atgagggtct gcaggcggtc gcggaaggtt    7680
ctgaactgtc gccccacggc catcttttcg ggggtgatgc agtagaaggt gagggggtct    7740
ttctcccagg ggtcccatct gagctctcgg gcgaggtcgc gcgcggcggc gaccagagcc    7800
tcgtcgcccc ccagtttcat gaccagcatg aagggcacga gctgcttgcc aaaggctccc    7860
atccaagtgt aggtctctac atcgtaggtg acaaagaggc gctccgtgcg aggatgagag    7920
ccgatcggga agaactggat ctcccgccac cagttggagg attggctgtt gatgtggtga    7980
aagtagaagt cccgtctgcg ggccgagcac tcgtgctggc ttttgtaaaa gcgaccgcag    8040
tactggcagc gctgcacggg ttgtatatct tgcacgaggt gaacctggcg acctctgacg    8100
aggaagcgca gcgggaatct aagtcccccg cctggggtcc cgtgtggctg gtggtcttct    8160
actttggttg tctggccgcc agcatctgtc tcctggaggg cgatggtgga gcagaccacc    8220
acgccgcgag agccgcaggt ccagatctcg gcgctcggcg ggcggagttt gatgacgaca    8280
tcgcgcacat tggagctgtc catggtctcc agctcccgcg gcggcaggtc agctgggagt    8340
tcctggaggt tcacctcgca gagacgggtc aaggcgcggg cagtgttgag atggtatctg    8400
atttcaaggg gcgtgttggc ggcggagtcg atggcttgca ggaggccgca gccccggggg    8460
gccacgatgt tccccgcgg ggcgcgaggg gaggcggaag ctgggggtgt gttcagaagc    8520
ggtgacgcgg gcgggccccc ggaggtaggg ggggttccgg ccccacaggc atgggcggca    8580 gggcacgtc ttcgccgcgc gcgggcaggg gctggtgctg gctccgaaga gcgcttgcgt    8640
gcgcgacgac gcgacggttg gtgtcctgta tctgacgcct ctgagtgaag accacgggtc    8700
ccgtgacctt gaacctgaaa gagagttcga cagaatcaat ctcggcatcg ttgacagcgg    8760
cctggcgcag gatctcctgc acgtcgcccg agttgtcctg gtaggcgatc tctgccatga    8820
actgctcgat ctcttcttcc tggagatctc ctcgtccggc gcgctccacg gtggccgcca    8880
ggtcgttgga gatgcgaccc atgagctgtg agaaggcgtt gagcccgccc tcgttccaga    8940
cccggctgta gaccacgccc ccctcggcgt cgcgagcgcg catgaccacc tgggccaggt    9000
tgagctccac gtgtcgcgtg aagacggcgt agttgcgcag gcgctggaaa aggtagttca    9060
gggtggtggc ggtgtgctcg gcgacgaaga agtacatgac ccagcgccgc aacgtggatt    9120
cattgatgtc ccccaaggcc tccaggcgct ccatggcctc gtagaagtcc acggcgaagt    9180
tgaaaaactg ggagttgcga gcggacacgg tcaactcctc ctccagaaga cggatgagct    9240
cggcgacagt gttgcgcacc tcgcgctcga aggccacggg gggcgcttct tcctcttcca    9300
cctcttcttc catgatcgct tcttcttctt cctcagccgg gacgggaggg ggcggcggcg    9360 gcggggagg ggcgcggcgg cggcggcggc gcacgggag gcggtcgatg aagcgctcga    9420
tcatctcccc ccgcatgcgg cgcatggtct cggtgacggc gcggccgttc tcccgggggc    9480
gcagctcgaa gacgccgcct ctcatctcgc cgcggggcga gcggccgtga ggtagcgaga    9540
cggcgctgac tatgcatctt aacaattgct gtgtaggtac accgccgagg gacctgattg    9600
agtccagatc caccggatcc gaaaaccttt ggaggaaagc gtctatccag tcgcagtcgc    9660
aaggtaggct gagcaccgtg gcgggcgggg gcggtctgg agagttcctg gcggagatgc    9720
tgctgatgat gtaattaaag taggcggtct tgagaaggcg gatggtggac aggagcacca    9780
tgtctttggg tccggcctgt tggatgcgga ggcggtcggc catgcccag gcctcgttct    9840 gacaccggcg caggtctttg tagtagtctt gcatgagtct ttccaccggc acctcttctc    9900
```

```
cttcctcttc tccatctcgc cggtggtttc tcgcgccgcc catgcgcgtg accccaaagc    9960
ccctgagcgg ctgcagcagg gccaggtcgg cgaccacgcg ctcggccaag atggcctgct   10020
gcacctgagt gagggtcctc tcgaagtcat ccatgtccac gaagcggtgg taggcgcccg   10080
tgttgatggt gtaggtgcag ttggccatga cggaccagtt gacggtctgg tgtcccggct   10140
gcgagagctc cgtgtaccgc aggcgcgaga aggcgcggga atcgaacacg tagtcgttgc   10200
aagtccgcac cagatactgg tagcccacca ggaagtgcgg cggaggttgg cgatagaggg   10260
gccagcgctg ggtggcgggg gcgccgggcg ccaggtcttc cagcatgagg cggtggtatc   10320
cgtagatgta cctggacatc caggtgatgc cggcggcggt ggtggtggcg cgcgcgtagt   10380
cgcggacccg gttccagatg tttcgcaggg gcgagaagtg ttccatggtc ggcacgctct   10440
ggccggtgag gcgcgcgcag tcgttgacgc tctatacaca cacaaaaacg aaagcgttta   10500
cagggctttc gttctgtagc ctggaggaaa gtaaatgggt tgggttgcgg tgtgccccgg   10560
ttcgagacca agctgagctc ggccggctga agccgcagct aacgtggtat tggcagtccc   10620
gtctcgaccc aggccctgta tcctccagga tacggtcgag agccttttg ctttcttggc   10680
caagcgcccg tggcgcgatc tgggatagat ggtcgcgatg agaggacaaa agcggctcgc   10740
ttccgtagtc tggagaaaca atcgccaggg ttgcgttgcg gcgtacccg gttcgagccc   10800
ctatggcggc ttgaatcggc cggaaccgcg gctaacgagg gccgtggcag ccccgtcctc   10860
aggacccgc cagccgactt ctccagttac gggagcgagc cccttttgtt ttttattttt   10920
tagatgcatc ccgtgctgcg gcagatgcgc ccctcgcccc ggcccgatca gcagcagcaa   10980
cagcaggcat gcagaccccc ctctccccctt tccgccccgg tcaccacggc cgcggcggcc   11040
gtgtcgggcg cggggggcgc gctggagtca gatgagccac cgcggcggcg acctaggcag   11100
tatctggact tggaagaggg cgagggactg gcgcggctgg gggcgaactc tccagagcgc   11160
cacccgcggg tgcagttgaa aagggacgcg cgcgaggcgt acctgccgcg gcagaacctg   11220
tttcgcgacc gcggggggcga ggagcccgag gagatgcgag actgcaggtt ccaagcgggg   11280
cgcgagctgc ggcgcgggct ggacagacag cgcctgctgc gcgaggagga ctttgagccc   11340
gacacgcaga cgggcatcag ccccgcgcgc gcgcacgtag ccgcggccga cctggtgacc   11400
gcctacgagc agacggtaaa ccaggagcgc aacttccaaa agagcttcaa caaccacgtg   11460
cgcacgctgg tggcgcgcga ggaggtgacc ctgggtctca tgcatctgtg ggacctggtg   11520
gaggcgatcg tgcagaaccc cagcagcaag ccctgaccg cgcagctgtt cctggtggtg   11580
cagcacagca gggacaacga ggccttcagg gaggcgctgc tgaacatcac cgagccggag   11640
gggcgctggc tcctggacct gataaacatc ctgcagagca tagtggtgca ggagcgcagc   11700
ctgagcctgg ccgagaaggt ggcggccatc aactactcta tgctgagcct gggcaagttc   11760
tacgcccgca agatctacaa gacccccctac gtgcccatag acaaggaggt gaagatagac   11820
agcttctaca tgcgcatggc gctgaaggtg ctgaccctga cgacgacct gggagtgtac   11880
cgcaacgagc gcatccacaa ggccgtgagc gccagccggc ggcgcgagct gagcgaccgc   11940
gagctgatgc acagtctgca gcgcgcgctg accggcgcgg gcgagggcga cagggaggtc   12000
gagtcctact tcgacatggg ggccgacctg cactggcagc cgagccgccg cgccctggag   12060
gcggcggggg cgtacggcgg cccctggcg gccgatgacc aggaagagga ggactatgag   12120
ctagaggagg cgagtacct ggaggactga cctggctggt ggtgttttgg tatagatgca   12180
agatccgaac gtggcggacc cggcggtccg ggcggcgctg caaagccagc cgtccggcat   12240
taactcctct gacgactggg ccgcggccat gggtcgcatc atggccctga ccgcgcgcaa   12300
```

```
ccccgaggct tcaggcagc agcctcaggc caaccggctg gcggccatct tggaagcggt    12360
agtgcccgcg cgctccaacc ccacccacga gaaggtgctg gccatagtca acgcgctggc    12420
ggagagcagg gccatccgcg cggacgaggc cggactggtg tacgatgcgc tgctgcagcg    12480
ggtggcgcgg tacaacagcg gcaacgtgca gaccaacctg gaccgcctgg tgacggacgt    12540
gcgcgaggcc gtggcgcagc gcgagcgctt gcatcaggac ggtaacctgg gctcgctggt    12600
ggcgctaaac gccttcctca gcacccagcc ggccaacgta ccgcggggc aggaggacta    12660 caccaacttt ttgagcgcgc tgcggctgat ggtgaccgag gtccctcaga gcgaggtgta    12720
ccagtcgggg cccgactact tcttccagac cagcagacag ggcttgcaaa ccgtgaacct    12780
gagccaggct ttcaagaacc tgcggggct gtggggagtg aaggcgccca ccggcgaccg    12840
ggctacggtg tccagcctgc taaccccca ctcgcgcctg ctgctgctgc tgatcgcgcc    12900
cttcacggac agcgggagcg tctcgcggga gacctatctg gccacctgc tgacgctgta    12960 ccgcgaggcc atcgggcagg cgcaggtgga cgagcacacc ttccaagaga tcaccagcgt    13020
gagccacgcg ctggggcagg aggacacggg cagcctgcag gcgaccctga actacctgct    13080
gaccaacagg cggcagaaga ttcccacgct gcacagcctg acccaggagg aggagcgcat    13140
cttgcgctac gtgcagcaga gcgtgagcct gaacctgatg cgcgacggcg tgacgcccag    13200
cgtggcgctg gacatgaccg cgcgcaacat ggaaccgggc atgtacgcct cccaccggcc    13260
gtttatcaac cgcctgatgg actacttgca tcgggcggcg gccgtgaacc ccgagtactt    13320
cactaatgcc attctgaatc cccactggat gccccctccg ggtttctaca acggggactt    13380
tgaggtgccc gaggtcaacg acgggttcct ctgggatgac atggatgaca gtgtgttctc    13440
acccaacccg ctgcgcgccg cgtctctgcg attgaaggag ggctctgaca gggaaggacc    13500
gaggagtctg gcctcctccc tggctctggg agcggtgggc gccacgggcg cggcggcgcg    13560
gggcagtagc cccttcccca gcctggcaga ctctctgaac agcgggcggg tgagcaggcc    13620
ccgcttgcta ggcgaggagg agtatctgaa caactccctg ctgcagcccg cgagggacaa    13680
gaacgctcag cggcagcagt tcccaacaa tgggatagag agcctggtgg acaagatgtc    13740
cagatggaag acgtatgcgc aggagtacaa ggagtgggag gaccgccagc gcggccctt    13800 gccgccccct aggcagcgct ggcagcggcg cgcgtccaac cgccgctgga ggcaggggcc    13860
cgaggacgat gatgactctg cagatgacag cagcgtgttg gacctgggcg ggagcgggaa    13920 cccctttcg cacctgcgcc cacgcctggg caagatgttt taaaagaaaa aaaaaataa    13980 aactcaccaa ggccatggcg acgagcgttg gttttttgtt cccttcctta gtatgcggcg    14040
cgcggcgatg ttcgaggagg ggcctccccc ctcttacgag agcgcgatgg ggatttctcc    14100
tgcggcgccc ctgcagcctc cctacgtgcc tcctcggtac ctgcaaccta cagggggag    14160 aaatagcatc tgttactctg agctgcagcc cctgtacgat accaccagac tgtacctggt    14220
ggacaacaag tccgcggacg tggcctccct gaactaccag aacgaccaca gcgattttt    14280 gaccacggtg atccaaaaca acgacttcac cccaaccgag gccagcaccc agaccataaa    14340
cctggataac aggtcgaact ggggcggcga cctgaagacc atcttgcaca ccaacatgcc    14400
caacgtgaac gagttcatgt tcaccaactc ttttaaggcg cgggtgatgg tggcgcgcga    14460
gcagggggag gcgaagtacg agtgggtgga cttcacgctg cccgagggca actactcaga    14520
gaccatgact ctcgacctga tgaacaatgc gatcgtggaa cactatctga aagtgggcag    14580
gcagaacggg gtgaaggaaa gcgatatcgg ggtcaagttt gacaccagaa acttccgtct    14640
```

```
gggctgggac cccgtgaccg ggctggtcat gccgggggtc tacaccaacg aggcctttca    14700
tcccgacata gtgcttctgc ccggctgtgg ggtggacttc acccagagcc ggctgagcaa    14760
cctgctgggc attcgcaagc ggcagccttt ccaggagggt ttcaagatca cctatgagga    14820
tctgaagggg ggcaacattc ccgcgctcct tgatctggac gcctacgagg agagcttgaa    14880
acccgaggag agcgctggcg acagcggcga gagtggcgag gagcaagccg gcggcggtgg    14940
cggcgcgtcg gtagaaaacg aaagtacgcc cgcagtggcg gcggacgctg cggaggtcga    15000
gccggaggcc atgcagcagg acgcagagga gggcgcacag gagggcgcgc agaaggacat    15060
gaacgatggg gagatcaggg gagacacatt cgccacccgg ggcgaagaaa aagaggcaga    15120
ggcggcggcg gcggcgacgg cggaggccga aaccgaggtt gaggcagagg cagagcccga    15180
gaccgaagtt atggaagaca tgaatgatgg agaacgtagg ggcgacacgt tcgccacccg    15240
gggcgaagag aaggcggcgg aggcagaagc cgcggctgag gaggcggctg cggctgcggc    15300
caagactgag gctgcggcta aggctgaggt cgaagccaat gttgcggttg aggctcaggc    15360
tgaggaggag gcggcggctg aagcagttaa ggaaaaggcc caggcagagc aggaagagaa    15420
aaaacctgtc attcaacctc taaaagaaga tagcaaaaag cgcagttaca acgtcatcga    15480
gggcagcacc tttacccagt accgcagctg gtacctggcg tacaactacg gcgacccggt    15540 caaggggtg cgctcgtgga ccctgctctg cacgccggac gtcacctgcg gctccgagca    15600
gatgtactgg tcgctgccga acatgatgca agacccggtg accttccgct ccacgcggca    15660
ggttagcaac ttcccggtgg tgggcgccga actgctgccc gtgcactcca agagttttta    15720
caacgagcag gccgtctact cccagctgat ccgccaggcc acctctctga cccacgtgtt    15780
caatcgcttt cccgagaacc agattttggc gcgcccgccg gccccacca tcaccaccgt    15840 gagtgaaaac gttcctgccc tcacagatca cgggacgcta ccgctgcgca acagcatctc    15900
aggagtccag cgagtgacca ttactgacgc cagacgccgg acctgcccct acgtttacaa    15960
ggccttgggc atagtctcgc cgcgcgtcct ctccagtcgc actttttaaa acacatctac    16020
ccacacgttc caaaatcatg tccgtactca tctcacccag caacaacacc ggctggggc    16080 tgcgcgcgcc cagcaagatg tttgaggggg cgaggaagcg ctccgaccag cacctgtgc    16140 gcgtgcgcgg ccactaccgc gcgccctggg gagcgcacaa gcgcgggcgc acagggcgca    16200
ccactgtgga cgacgtcatt gactccgtag tggagcaagc gcgccactac acacccggcg    16260
cgccgaccgc ccccgccgtg tccaccgtgg accaggcgat cgaaagcgtg gtacagggcg    16320
cgcggcacta tgccaacctt aaaagtcgcc gccgccgcgt ggcccgccgc catcgccgga    16380
gaccccgggc caccgccgcc gcgcgccctta ctaaggctct gctcaggcgc gccaggcgaa    16440
ctggccaccg ggccgccatg agggccgcac ggcgggctgc cgctgccgca agcgtcgtgg    16500
ccccgcgggc acgaaggcgc gcggccgctg ccgccgccgc cgccatttcc agcttggcct    16560
cgacgcggcc cggtaacata tactgggtgc gcgactcggt aaccggcacg cgggtacccg    16620
tgcgctttcg ccccccgcgg aattagcaca agacaacata cacactgagt ctcctgctgt    16680
tgtgtatccc agcggcgacc gtcagcagcg gcgacatgtc caagcgcaaa attaaagaag    16740
agatgctcca ggtcatcgcg ccggagatct atgggccccc gaagaaggag gaggatgatt    16800 acaagcccg caagctaaag cgggtcaaaa agaaaaagaa agatgatgat gacgaggcgg    16860
tggagtttgt ccgccgcatg gcacccaggc gcccgtgca gtggaagggc cggcgcgtgc    16920
agcgcgtttt gcgccccggc accgcggtgg tcttcacgcc cggcgagcgc tccacgcgca    16980 cttttcaagcg ggtgtacgat gaggtgtacg gcgacgagga cctgttggag caggccaacc    17040
```

```
agcgctttgg ggagtttgca tatgggaaac ggccccgcga gagtctaaaa gaggacctgc   17100
tggcgctacc gctggacgag ggcaatccca ccccgagtct gaagccggta accctgcaac   17160
aggtgctgcc tttgagcgcg cccagcgagc ataagcgagg gttgaagcgc gaaggcgggg   17220
acctggcgcc caccgtgcag ttgatggtgc ccaagcggca gaagctggag gacgtgctgg   17280
agaaaatgaa agtagagccc gggatccagc ccgagatcaa ggtccgcccc atcaagcagg   17340
tggcgcccgg cgtgggagtc cagaccgtgg acgttaggat tcccacggag gagatggaaa   17400
cccaaaccgc cactccctct tcggcggcca gcgccaccac cggcaccgct tcggtagagg   17460
tgcagacgga cccctggcta cccgccaccg ctgttgccgc cgccgccccc cgttcgcgcg   17520
ggcgcaagag aaattatcca gcggccagcg cgctcatgcc ccagtacgca ctgcatccat   17580
ccatcgtgcc cacccccggc taccgcgggt actcgtaccg cccgcgcaga tcagccggca   17640
ctcgcggccg ccgccgccgt gcgaccacaa ccagccgccg ccgtcgccgc cgccgccagc   17700
cagtgctgac ccccgtgtct gtaaggaagg tggctcgctc ggggagcacg ctggtggtgc   17760
ccagagcgcg ctaccacccc agcatcgttt aaagccggtc tctgtatggt tcttgcagat   17820
atggccctca cttgtcgcct ccgcttcccg gtgccgggat accgaggaag aactcaccgc   17880
cgcagaggca tggcgggcag cggtctccgc ggcggccgtc gccatcgccg gcgcgcaaaa   17940
agcaggcgca tgcgcggcgg tgtgctgcct ctgctaatcc cgctaatcgc cgcggcgatc   18000
ggtgccgtac ccgggatcgc ctccgtggcc ctgcaggcgt cccagaaacg ttgactcttg   18060
caaccttgca agcttgcatt ttttggagga aaaataaaa aaaagtcta gactctcacg   18120
ctcgcttggt cctgtgacta ttttgtagaa aaaagatgg aagacatcaa ctttgcgtcg   18180
ctggccccgc gtcacggctc gcgcccgttc atgggagact ggacagatat cggcaccagc   18240
aatatgagcg gtggcgcctt cagctggggc agtctgtgga gcggccttaa aaattttggt   18300
tccaccatta agaactatgg caacaaagcg tggaacagca gcacgggcca gatgctgaga   18360
gacaagttga aagagcagaa cttccaggag aaggtggcgc agggcctggc ctctggcatc   18420
agcggggtgg tggacatagc taaccaggcc gtgcagaaaa agataaacag tcatctggac   18480
ccccgtcctc aggtggagga aatgcctcca gcgatggaga cggtgtctcc cgagggcaaa   18540
ggcgaaaagc gcccgcggcc cgacagagaa gagaccctgg tgtcacacac cgaggagccg   18600
ccctcttacg aggaggcagt caaggccggc ctgcccacca ctcgccccat agcccccatg   18660
gccaccggtg tggtgggcca caggcaacac actcccgcaa cactagatct gccccgccg   18720
tccgagccgc cgcgccagcc aaaggcggcg acggtgcccg ctccctccac ttccgccgcc   18780
aacagagtgc ccctgcgccg cgccgcgagc ggccccggg cctcgcgagt tagcggcaac   18840
tggcagagca cactgaacag catcgtgggc ctggagtga ggagtgtgaa gcgccgccgt   18900
tgctactgaa tgagcaagct agctaacgtg ttgtatgtgt gtatgcgtcc tatgtcgccg   18960
ccagaggagc tgttgagccg ccggcgccgt ctgcactcca gcgaatttca agatggcgac   19020
cccatcgatg atgcctcagt ggtcgtacat gcacatctcg ggccaggacg cttcggagta   19080
cctgagcccc gggctggtgc agttcgcccg cgccacagac acctacttca acatgagtaa   19140
caagttcagg aaccccactg tggcgcccac ccacgatgtg accacggacc ggtcgcagcg   19200
cctgacgctg cggttcatcc ccgtggatcg ggaggacacc gcctactctt acaaggcgcg   19260
gttcacgctg gccgtgggcg acaaccgcgt gctggacatg gcctccactt actttgacat   19320
caggggggtg ctggacaggg gccccacctt caagccctac tcgggtactg cctacaactc   19380
```

```
cctggccccc aagggcgctc ccaattcttg cgagtgggaa caagatgaac cagctcaggc    19440
agcaatagct gaagatgaag aagaacttga agaagaacaa gctcaggacg aacaggcgcc    19500
cactaagaaa acccatgtat acgcccaggc acctctttct ggtgaaaaaa ttactaagga    19560
tggtttgcaa ataggtgtgg atgccacaca ggcgggagag aaccctatat atgctgataa    19620
aacattccaa cccgaacctc agataggtga gtctcagtgg aacgaggctg atgccacagt    19680
agcaggaggc agagtcttaa aaaagaccac ccctatgaga ccttgctatg gatcctatgc    19740
caaacctact aatgccaatg gcggtcaagg gatcatggtg gccaatgatc agggagcgct    19800
tgaatctaaa gttgagatgc aattttttctc caccacaacg tctcttaatg taagggaagg    19860
tgaaaacaat cttcagccaa aagtagtgct atacagcgaa gatgttaact tggaatcccc    19920
tgacactcat ttgtcttaca aacctaaaaa ggatgacacc aactctaaaa tcatgttggg    19980
tcagcaagcc atgcccaaca gacccaacct cattgctttt agggacaact ttattggact    20040
tatgtactac aacagcacag gcaacatggg agtgctggca ggacaggcct cccagctaaa    20100
cgctgtggta gacttgcaag acagaaacac agagctgtca taccaactga tgcttgattc    20160
cattggagac agatcaagat acttttccat gtggaaccag gcagtggaca gctatgaccc    20220
agatgtcaga atcattgaaa accatggggt tgaagatgag ctgcccaact attgctttcc    20280
cctgggcggt attggaatta cagacacata ccagtgcata aaaccaaccg cagctgctaa    20340
taacactaca tggtctaagg atgaagaatt tagtgatcgc aatgaaatag gggtgggaaa    20400
caacttcgcc atggagatca acatccaggc caacctctgg aggaacttcc tctatgcgaa    20460 cgtgggctc tacctgccag acaagctcaa gtacaacccc accaacgtgg acatctctga    20520
caaccccaac acctatgact acatgaacaa gcgtgtggtg gctcccggcc tggtggactg    20580
ctttgtcaat gtgggagcca ggtggtccct ggactacatg gacaacgtca cccccttcaa    20640
ccaccaccgc aatgcgggtc tgcgctaccg ctccatgatc ctgggcaacg ggcgctacgt    20700
gcccttccac attcaggtgc cccagaagtt cttttgccatc aagaacctcc tcctcctgcc    20760
gggctcctac acttacgagt ggaacttcag gaaggatgtc aacatggtcc tgcagagctc    20820
tctgggcaat gacctagggg tggacggggc cagcatcaag tttgacagcg tcaccctcta    20880
tgctaccttc ttccccatgg ctcacaacac cgcctccacg ctcgaggcca tgctgaggaa    20940
cgacaccaac gaccagtcct tcaatgacta cctctctggg gccaacatgc tctacccat    21000 ccccgccaag gccaccaacg tgcccatctc cattccctct cgcaactggg ccgccttcag    21060 aggctgggc tttacccgcc ttaagaccaa ggaaaccccc tccctgggct cgggttttga    21120 ccccctacttt gtctactcgg gatccatccc ctacctggat ggcaccttct acctcaacca    21180
cacttttaag aagatatcca tcatgtatga ctcctccgtc agctggccgg gcaatgaccg    21240
cctgctcacc cccaatgagt tcgaggtcaa gcgcgccgtg gacggcgagg gctacaacgt    21300
ggcccagtgc aacatgacca aggactggtt cctggtgcag atgctggcca actacaacat    21360
aggctaccag ggcttctaca tcccagagag ctacaaggac aggatgtact ccttcttcag    21420
aaatttccaa cccatgagca ggcaggtggt ggacgagacc aaatacaagg actatcaggc    21480
cattggcatc actcaccagc acaacaactc gggattcgtg ggctacctgg ctcccaccat    21540
gcgcgagggg caggcctacc ccgccaactt cccctacccg ttgataggca aaaccgcggt    21600
cgacagcgtc acccagaaaa agttcctctg cgaccgcacc ctctggcgca tcccttctc    21660 tagcaacttc atgtccatgg gtgcgctcac ggacctgggc cagaacctgc tctatgccaa    21720
ctccgcccat gcgctggaca tgactttttga ggtggacccc atggacgagc ccaccctcct    21780
```

```
ctatattgtg tttgaagtgt tcgacgtggt cagagtgcac cagccgcacc gcggtgtcat   21840
cgagaccgtg tacctgcgca cgcccttctc ggccggcaac gccaccacct aaggagacag   21900
cgccgccgcc tgcatgacgg gttccaccga gcaagagctc agggccatcg ccagagacct   21960
gggatgcgga ccctattttt tgggcaccta tgacaaacgc ttcccgggct tcatctcccg   22020
agacaagctc gcctgcgcca tcgtcaacac ggccgcgcgc gagaccgggg gcgtgcactg   22080
gctggccttt ggctgggacc cgcgctccaa aacctgctac ctcttcgacc cctttggctt   22140
ctccgatcag cgcctcagac agatctatga gtttgagtac gaggggctgc tgcgccgcag   22200
cgcgcttgcc tcctcgcccg accgctgcat caccccttgag aagtccaccg agaccgtgca   22260 ggggcccac tcggccgcct gcggtctctt ctgctgcatg ttttttgcacg cctttgtgcg   22320 ctggcccag agtcccatgg atcgcaaccc caccatgaac ttgctcaagg gagtgcccaa   22380
cgccatgctc cagagccccc aggtccagcc caccctgcgc cacaaccagg aacagctcta   22440
ccgcttcctg gagcgccact cccctactt ccgcagtcac agcgcgcaca tccgggggc    22500 cacctctttc tgccacttgc aagaaaacat gcaagacgga aaatgatgta cagctcgctt   22560
tttaataaat gtaaagactg tgcactttat ttatacacgg gctctttctg gttatttatt   22620
caacaccgcc gtcgccatct agaaatcgaa agggttctgc cgcgcgtcgc cgtgcgccac   22680
gggcagagac acgttgcgat actggaagcg gctcgcccac ttaaactcgg gcaccaccat   22740
gcggggcagt ggttcctcgg ggaagttctc gccccacagg gtgcgggtca gctgcagcgc   22800
gctcaggagg tcgggagccg agatcttgaa gtcgcagttg gggccggaac cctgcgcgcg   22860
cgagttgcgg tacacggggt tgcagcactg gaacaccagc agggccggat tatgcacgct   22920
ggccagcagg ctctcgtcgc tgatcatgtc gctgtccaga tcctccgcgt tgctcagggc   22980
gaacggggtc atcttgcaga cctgcctgcc caggaaaggc ggcagccgg gcttgccgtt    23040 gcagtcgcag cgcaggggca tcagcaggtc cccgcggccc gactgcgcct gcgggtacag   23100
cgcgcgcatg aaggcttcga tctgcctgaa agccacctgc gtcttggctc cctccgaaaa   23160
gaacatccca caggacttgc tggagaactg gttcgcggga cagctggcat cgtgcaggca   23220
gcagcgcgcg tcggtgttgg cgatctgcac cacgttgcga ccccaccggt tcttcactat   23280
cttggccttg gaagcctgct ccttcagcgc gcgctggccg ttctcgctgg tcacatccat   23340
ctctatcacc tgctccttgt tgatcatgtt tgtaccgtgc agacacttca ggtcgccctc   23400
cgtctgggtg cagcggtgct cccacagcgc gcaaccggtg ggctcccaat ttttgtgggt   23460
cacccccgcg taggcctgca ggtaggcctg caagaagcgc cccatcatgg ccacaaaggt   23520
cttctggctc gtaaaggtca gctgcaggcc gcgatgctct tcgttcagcc aggtcttgca   23580 gatgcggcc agcgcctcgg tctgctcggg cagcatccta aaatttgtct tcaggtcgtt   23640
atccacgtgg tacttgtcca tcatggcgcg cgccgcctcc atgcccttct cccaggcgga   23700
caccatgggc aggcttaggg ggtttatcac ttccaccggc gaggacaccg tactttcgat   23760
ttcttcttcc tcccctctt cccggcgcgc gcccacgctg ctgcgcgctc tcaccgcctg   23820
caccaagggg tcgtcttcag gcaagcgccg caccgagcgc ttgccgccct tgacctgctt   23880
aatcagcacc ggcgggttgc tgaagcccac catggtcagc gccgcctgct cttcttcgtc   23940
ttcgctgtct accactatct ctggggaagg gcttctccgc tctgcggcgg cgcgcttctt   24000
ttttttcttg ggagcggccg tgatggagtc cgccacggcg acggaggtcg agggcgtggg   24060
gctgggggtg cgcggtacca gggcctcgtc gccctcggac tcttcctctg actccaggcg   24120
```

```
gcggcggagt cgcttctttg ggggcgcgcg cgtcagcggc ggcggagacg gggacgggga    24180
cggggacggg acgccctcca caggggtgg tcttcgcgca gacccgcggc cgcgctcggg     24240
ggtcttctcg agctggtctt ggtcccgact ggccattgta tcctcctcct cctaggcaga    24300
gagacataag gagtctatca tgcaagtcga aaggaggag agcttaacca ccccctctga     24360
gaccgccgat gcgcccgccg tcgccgtcgc ccccgctgcc gccgacgcgc cgccacacc     24420
gagcgacacc cccgcggacc cccccgccga cgcaccsctg ttcgaggaag cggcegtgga    24480
gcaggacccg ggctttgtct cggcagagga ggatttgcga gaggaggagg ataaggagaa    24540
gaagccctca gtgccaaaag atgataaaga gcaagacgag cacgacgcag atgcacacca    24600
gggtgaagtc gggcggggg acggagggca tgacggcgcc gactacctag acgaagggaa     24660
cgacgtgctc ttgaagcacc tgcatcgtca gtgcgccatt gtttgcgacg ctctgcagga    24720
gcgcagcgaa gtgcccctca gcgtggcgga ggtcagccac gcctacgagc tcagcctctt    24780
ctccccccgg gtgccccccc gccgccgcga aaacggcaca tgcgagccca acccgcgcct    24840
caacttctac cccgcctttg tggtacccga ggtcctggcc acctatcaca tcttctttca    24900
aaattgcaag atcccsctct cgtgccgcgc caaccgtagc cgccgcgata agatgctggc    24960
cctgcgccag ggcgaccaca tacctgatat cgccgctttg gaagatgtac caaagatctt    25020
cgagggtctg ggtcgcaacg agaagcgggc agcaaactct ctgcaacagg aaaacagcga    25080
aaatgagagt cacaccgggg tactggtgga gctcgagggc gacaacgccc gcctggcggt    25140
ggtcaagcgc agcatcgagg tcacccactt tgcctacccc gcgctaaacc tgccccccaa    25200
agtcatgaac gcgccatgg acgggctgat catgcgccgc ggccggcccc tcgctccaga     25260
tgcaaacttg catgaggaga ccgaggacgg ccagcccgtg gtcagcgacg agcagctggc    25320
gcgctggctg gagaccgcgg accccgccga actggaggag cggcgcaaga tgatgatggc    25380
cgtggtgctg gtcaccgtag agctggagtg tctgcagcgc ttcttcggcg accccgagat    25440
gcagagaaag gtcgaggaga ccctgcacta caccttccgc cagggctacg tgcgccaggc    25500
ttgcaagatc tccaacgtgg agctcagcaa cctggtgtcc tacctgggca tcttgcatga    25560
gaaccgcctc gggcagagcg tgctgcactc caccctgcgc ggggaggcgc gccgcgacta    25620
cgtgcgcgac tgcgtttacc tcttcctctg ctacacctgg cagacggcca tgggggtctg    25680
gcagcagtgc ctggaggagc gcaacctcaa ggagctggag aagctcctgc agcgcgcgct    25740
caaagatctc tggacgggct acaacgagcg ctcggtggcc gccgcgctgg ccgacctcat    25800
cttccccgag cgcctgctca aaaccctcca gcaggggctg cccgacttca ccagccaaag    25860
catgttgcaa aacttcagga actttatcct ggagcgttct ggcatcctac ccgccacctg    25920
ctgcgccctg cccagcgact ttgtcccct cgtgtaccgc gagtgccccc cgccgctgtg    25980
gggtcactgc tacctgttcc aactggccaa ctacctgtcc taccacgcgg acctcatgga    26040
ggactccagc ggcgagggc tcatggagtg ccactgccgc tgcaacctct gcacgccca     26100
ccgctccctg gtctgcaaca cccaactgct cagcgagagt cagattatcg gtaccttcga    26160
gctacagggt ccgtcctcct cagacgagaa gtccgcggct ccggggctaa aactcactcc    26220
ggggctgtgg acttccgcct acctgcgcaa atttgtacct gaagactacc acgcccacga    26280
gatcaggttt tacgaagacc aatcccgccc gcccaaggcg gagctgaccg cctgcgtcat    26340
cacccagggc gagatcctag gccaattgca agccatccaa aaagcccgcc aagactttt     26400
gctgaagaag gtcggggg tgtatctgga ccccagtcg ggtgaggagc tcaacccggt       26460
tcccccgctg ccgccgccgc gggaccttgc ttcccaggat aagcatcgcc atggctccca    26520
```

-continued

```
gaaagaagca gcagcggccg ccactgccgc caccccacat gctggaggaa gaggaggaat    26580
actgggacag tcaggcagag gaggtttcgg acgaggagga gccggagacg gagatggaag    26640
agtgggagga ggacagctta gacgaggagg cttccgaagc cgaagaggca gacgcaacac    26700
cgtcaccctc ggccgcagcc ccctcgcagg cgccccgaa gtccgctccc agcatcagca    26760
gcaacagcag cgctataacc tccgctcctc caccgccgcg acccacggcc gaccgcagac    26820
ccaaccgtag atgggacacc accggaaccg gggccggtaa gtcctccggg agaggcaagc    26880
aagcgcagcg ccaaggctac cgctcgtggc gcgctcacaa gaacgccata gtcgcttgct    26940
tgcaagactg cgggggaac atctccttcg cccgccgctt cctgctcttc caccacggtg    27000
tggccttccc ccgtaacgtc ctgcattact accgtcatct ctacagcccc tactgcggcg    27060
gcagtgagcc agagacggtc ggcggcggcg gggcgcccg tttcggcgcc taggaagacc    27120
cagggcaaga cttcagccaa gaaactcgcg gcggccgcgg cgaacgcggt cgcggggcc    27180
ctgcgcctga cggtgaacga acccctgtcg acccgcgaac tgaggaaccg aatcttcccc    27240
actctctatg ccatcttcca gcagagcaga gggcaggatc aggaactgaa agtaaaaaac    27300
aggtctctgc gctccctcac ccgcagctgt ctgtatcaca agagcgaaga ccagcttcgg    27360
cgcacgctgg aggacgctga ggcactcttc agcaaatact gcgcgctcac tcttaaggac    27420
tagctccgcg cccttctcga atttaggcgg gaacgcctac gtcatcgcag cgccgccgtc    27480
atgagcaagg acattcccac gccatacatg tggagctatc agccgcagat gggactcgcg    27540
gcgggcgcct cccaagacta ctccaccgcc atgaactggc tcagtgccgg cccacacatg    27600
atctcacagg ttaatgatat ccgcacccat cgaaaccaaa tattggtgga gcaggcggca    27660
attaccacca cgccccgcaa taatcccaac cccagggagt ggcccgcgtc cctggtgtat    27720
caggaaattc ccggccccac caccgtacta cttccgcgtg attcccaggc cgaagtccaa    27780
atgactaact caggggcaca gctcgcgggc ggctgtcgtc acagggtgcg gcctcctcgc    27840
cagggtataa ctcacctgga gatccgaggc agaggtattc agctcaacga cgagtcggtg    27900
agctcctcgc tcggtctcag acctgacggg accttccaga tagccggagc cggccgatct    27960
tccttcacgc cccgccaggc gtacctgact ctgcaaagct cgtcctcggc gccgcgctcg    28020
ggcggcatcg ggactctcca gttcgtgcag gagtttgtgc cctcggtcta cttcaacccc    28080
ttctcgggct ctcccggtcg ctacccggac cagttcatct cgaactttga cgccgcgagg    28140
gactcggtgg acggctacga ctgaatgtcg ggtggacccg gtgcagagca acttcgcctg    28200
aagcacctcg accactgccg ccgccctcag tgctttgccc gctgtcagac cggtgagttc    28260
cagtactttt ccctgcccga ctcgcacccg gacggcccgg cgcacggggt gcgcttttc    28320
atcccgagtc aggtgcgctc taccctaatc agggagttta ccgcccgtcc cctactggcg    28380
gagttggaaa aggggccttc tatcctaacc attgcctgca tctgctctaa ccctggattg    28440
caccaagatc tttgctgtca tttgtgtgct gagtataata aaggctgaga tcagaatcta    28500
ctcgggctcc tgtcgccatc ctgtcaacgc caccgtccaa gcccggcccg atcagcccga    28560
ggtgaacctc acctgcggtc tgcaccggcc cctgaggaaa tacctagctt ggtactacaa    28620
cagcactccc tttgtggttt acaacagctt tgaccaggac ggggtctcac tgagggataa    28680
cctctcgaac ctgagctact ccatcaggaa gaacagcacc ctcgagctac ttcctcctta    28740
cctgcccggg acttaccagt gtgtcaccgg tccctgcacc cacacccacc tgttgatcgt    28800
aaacgactct cttccgagaa cagacctcaa taactcctct tcgcagttcc ccagaacagg    28860
```

```
aggtgagctc aggaaacccc gggtaaagaa gggtggacga gagttaacac ttgtggggtt    28920
tctggtgtat gtgacgctgg tggtggctct tttgattaag gcttttcctt ccatgtctga    28980
actctccctc ttcttttatg aacaactcga ctagtgctaa cgggacccta cccaacgaat    29040
cgggattgaa tatcggtaac caggttgcag tttcactttt gattaccttc atagtcctct    29100
tcctgctagt gctgtcgctt ctgtgcctgc ggatcggggg ctgctgcatc cacgtttata    29160
tctggtgctg gctgtttaga aggttcggag accatcgcag gtagaataaa catgctgctg    29220
cttaccctct ttgtcctggc gctggccgcc agctgccaag ccttttccga ggctgacttt    29280
atagagcccc agtgtaatgt gacttttaaa gcccatgcac agcgttgtca tactataatc    29340
aaatgtgcca ccgaacacga tgaataccct atccagtata agataaaatc acacaaagtg    29400
gcacttgttg acatctggaa acccgaagac cctttggaat acaatgtgac cgttttccag    29460
ggtgacctct tcaaaattta caattacact ttcccatttg accagatgtg tgactttgtc    29520
atgtacatgg aaaagcagca caagctgtgg cctccgactc cccagggctg tgtggaaaat    29580
ccaggctctt tctgcatgat ctctctctgt gtaactgtgc tggcactaat actcacgctt    29640
ttgtatatca gatttaaatc aaggcaaagc ttcattgatg aaaagaaaat gccttaatcg    29700 cttttcacgct tgattgctaa caccgggttt ttatccgcag aatgattgga atcaccctac    29760
taatcacctc cctccttgcg attgcccatg ggttggaacg aatcgaagtc cctgtggggg    29820
ccaatgttac cctggtgggg cctgtcggca atgctacatt aatgtgggaa aaatatacta    29880
aaaatcaatg ggtctcttac tgcactaaca aaaatagcca caagcccaga gccatctgcg    29940
atgggcaaaa tctaaccttg attgatgttc aattgctgga tgcgggctac tattatgggc    30000
agctgggtac aatgattaat tactggagac cccacagaga ttacatgctc cacgtagtaa    30060
agggtcccct tagcagccca cccactacca cctctactac ccccactacc accactactc    30120
ccaccaccag cactgccgcc cagcctcctc atagcagaac aaccacttttt atcaattcca    30180 agtcccactc cccccacatt gccggcgggc cctccgcctc agactccgaa accaccgaga    30240
tctgcttctg caaatgctct gacgccattg cccaggattt ggaagatcac gaggaagatg    30300
agcatgactt cgcagatgca tgccaggcat cagagccaga agcgctgccg gtggccctca    30360
aacagtatgc agaccccacac accaccccccg accttcctcc accttcccag aagccaagtt    30420
tcctggggga aaatgaaact ctgcctctct ccatactcgc tctgcatctt gttgctatgt    30480
tgaccgctct gctggtgctt ctatgctcta tatgctacct gatctgctgc agaaagaaaa    30540
aatctcacgg ccatgctcac cagccctca tgcacttccc ttaccctcca gagctgggcg    30600
accacaaact ttaagtctgc agtaactatc tgcccatccc ttgtcagtcg acagcgatga    30660
gccccactaa tctaacggcc tctggactta caacatcgtc tcttaatgag accaccgctc    30720
ctcaagacct gtacgatggt gtctccgcgc tggttaacca gtgggatcac ctgggcatat    30780
ggtggctcct cataggagca gtgacccgt gcctaatcct ggtctggatc atctgctgca    30840
tcaaaagcag aagacccagg cggcggccca tctacaggcc ctttgtcatc acacctgaag    30900
atgatgatga caccacttcc aggctgcaga ggctaaagca gctactcttc tcttttacag    30960
catggtaaat tgaatcatgc ctcgcatttt catctacttg tctctccttc cactttttct    31020
gggctcttct acattggccg ctgtgtccca catcgaggta gactgcctca cgcccttcac    31080
agtctacctg cttttcggct ttgtcatctg cacctttgtc tgcagcgtta tcactgtagt    31140
gatctgcttc atacagtgca tcgactacgt ctgcgtgcgg gtggcttact ttagacacca    31200
cccccagtat cgcaacaggg acatagcggc tctcctaaga cttgtttaaa atcatggcca    31260
```

```
aattaactgt gattggtctt ctgatcatct gctgcgtcct agccgcgatt gggactcaag   31320
ctcctaccac caccagcgct cccagaaaga gacatgtatc ctgcagcttc aagcgtccct   31380
ggaatatacc ccaatgcttt actgatgaac ctgaaatctc tttggcttgg tacttcagcg   31440
tcaccgccct tcttatcttc tgcagtacgg ttattgccct tgccatctac ccttcccttg   31500
acctgggctg gaatgctgtc aactctatgg aatatcccac cttcccagaa ccagacctgc   31560
cagacctggt tgttctaaac gcgtttcctc tcctgctcc cgttcaaaat cagtttcgcc    31620
ctccgtcccc cacgcccact gaggtcagct actttaatct aacaggcgga gatgactgaa   31680
aacctagacc tagaaatgga cggtctctgc agcgagcaac gcacactaga gaggcgccgg   31740
caaaaagagc tcgagcgtct taaacaagag ctccaagacg cggtggccat acaccagtgc   31800
aaaaaaggtg tcttctgtct ggtaaaacag gccacgctca cctatgaaaa aacaggtgac   31860
acccaccgcc taggatacaa gctgcccaca cagcgccaaa agttcgccct catgataggc   31920
gaacaaccca tcaccgtgac ccagcactcc gtggagacag aaggctgcat acatgctccc   31980
tgtaggggcg ctgactgcct ctacaccttg atcaaaaccc tctgcggtct cagagacctt   32040 atcccttttca attaatcata actgtaatca ataaaaaatc acttacttga aatctgatag   32100
caagcctctg tccaattttt tcagcaacac ttccttcccc tcctcccaac tctggtactc   32160
taggcgcctc ctagctgcaa acttcctcca cagtctgaag ggaatgtcag attcctcctc   32220
ctgtccctcc gcacccacga tcttcatgtt gttgcagatg aaacgcgcga gatcgtctga   32280
cgagaccttc aaccccgtgt acccctacga taccgagatc gctccgactt ctgtcccttt   32340
ccttacccct cccttttgtgt catccgcagg aatgcaagaa aatccagctg gggtgctgtc   32400
cctgcacttg tcagagcccc ttaccaccca caatgggggcc ctgactctaa aaatgggggg   32460
cggcctgacc ctggacaagg aagggaatct cacttcccaa acatcacca gtgtcgatcc    32520 ccctctcaaa aaaagcaaga acaacatcag ccttcagacc gccgcacccc tcgccgtcag   32580
ctccggggcc ctaacacttt ttgccactcc ccccctagcg gtcagtggtg acaaccttac   32640
tgtgcagtct caggcccctc tcactttgga agactcaaaa ctaactctgg ccaccaaagg   32700
acccctaact gtgtccgaag gcaaacttgt cctagaaaca gaggctcccc tgcatgcaag   32760
tgacagcagc agcctgggcc ttagcgttac ggccccactt agcattaaca atgacagcct   32820
aggactagat ctgcaggcac ccattgtctc tcaaaatgga aaactggctc taaatgtagc   32880
aggcccccta gctgtggcca atggcattaa tgctttgaca gtaggcacag gcaaaggtat   32940
tggtctaaat gaaaccagca ctcacttgca agcaaagttg gtcgccccc taggctttga    33000 taccaatggc aacattaagc taagcgttgc aggaggcatg agactaaata atgacacact   33060
tatactagat gtaaactacc catttgaagc tcaaggccaa ctaagtctaa gagtgggcca   33120
gggtccgctg tatgtagatt ctagcagcca taacctgacc attagatgcc ttagaggatt   33180
atacataaca tcgtctaata accaaaccgg tctagaggcc aacataaaac taacaaaagg   33240
ccttgtctat gatggaaatg ccatagcagt caatgttggt caaggattgc aatacagcac   33300
tactgccaca tcggaaggtg tgtatcctat acagtctaag ataggttttgg gaatggaata   33360 tgataccaac ggagccatga tgacaaaact aggctctgga ctaagctttg acaattcagg   33420
agccattgta gtgggaaaca aaaatgatga caggcttact ctgtggacta caccagaccc   33480
atctcctaac tgtagaattt attctgaaaa agatactaaa ctaaccttgg tgctgactaa   33540
gtgtggcagc caaatcctag gcacagtatc tgcccttgct gtcagaggca gccttgcgcc   33600
```

```
catcactaat gcatccagca tagtccaaat atttctaaga tttgatgaaa atggactatt    33660
gatgagcaac tcatcgctag acggtgatta ctggaattac agaaatgggg actccactaa    33720
tagcacacca tatacaaatg cagtaggctt tatgcctaat ctagcagcct atcctaaagg    33780
tcaggctaca gctgcaaaaa gcagtattgt aagccaggta tacatggatg gtgacactac    33840
taaacctata acactaaaaa taaacttcaa tggcattgat gaaacaacag aaaataccc    33900 tgttagtaaa tattccatga cattctcatg gagctggccc accgcaagct acataggcca    33960 cactttgca acaaactctt ttactttctc ctacatcgcc caagaataaa gaaagcacag    34020
agatgcttgt tttgatttca aaattgtgtg cttttattta ttttcagctt acagtatttc    34080
cagtagtcat tcgaataaag cttaatcaaa ctgcatgaga acccttccac atagcttaaa    34140
ttagcaccag tgcaaatgga gaaaattcaa cataccttt ttatccagat atcagagaac    34200
tctagtggtc agttttcccc caccctccca gctcacagaa tacacagtcc tttccccccg    34260
gctggcttta acaacacta tctcattggt aacagacata tcttaggtg taataatcca    34320 cacggtctct tggcgggcca agcgctggtc ggtgatgtta ataaactccc caggcagctc    34380
tttcaagttc acgtcgctgt ccaactgctg aagcgctcgc ggctccgact gcgcctctag    34440
cggaggcaac ggcaacaccc gatccttgat ctataaagga gtagagtcat aatcccccat    34500
aagaataggg cggtgatgca gcaacaaggc gcgcagcaac tcctgccgcc gcctctccgt    34560
acgacaggaa tgcaacggcg tggtggtctc ctccgcgata tccgcaccg ctcgcagcat    34620 cagcatcctc gtcctccggg cacagcagcg catcctgatc tcactgagat cggcgcagta    34680
agtgcagcac aaaaccaaga tgttatttaa gatcccacag tgcaaagcac tgtacccaaa    34740
gctcatggcg ggaaggacag ccccacgtg accatcatac cagatcctta ggtaaatcaa    34800
atgacgacct ctcataaaca cgctggacat gtacatcacc tccttgggca tgcgctgatt    34860
caccacctct cgataccaca agcatcgctg attaattaaa gacccctcaa gcaccatcct    34920
gaaccaggaa gccagcacct gaccccccgc caggcactgc agggaccccg gtgaattgca    34980
gtggcagtga agactccagc gctcgtagcc gtgaaccata gagccggtca ttatatccac    35040
attggcacaa cacaaacaca ctttcataca cttttcatg attagcagct cctctctagt    35100
caggaccata tcccaaggaa tcacccactc ttgaatcaag gtaaatccca cacagcaggg    35160
caggcctctc acataactca cgttatgcat agtgagcgtg tcgcaatctg gaaataccgg    35220
atgatcttcc atcaccgaag ctcgcgtctc cgtctcaaag ggaggtaaac ggtccctcgt    35280
gtagggacag tggcgggata atcgagatcg tgttgaacgt agagtcatgc caaagggaac    35340
agcggacgta ctcatatttc ctccagcaga accaagtgcg cgcgtggcag ctatccctgc    35400
gtcttctgtc tcgccgcctg ccccgctcgg tgtagtagtt gtaatacagc cactccctca    35460
gaccgtcaag gcgctccctg gcgtccggat ctataacaac accgtcctgc agcgccgccc    35520
tgatgacatc caccaccgta gagtatgcca agcccagcca ggaaatgcat tcactttgac    35580
agcgagagat aggaggagcg ggaagagatg gaagaaccat gatagtaaaa gactttatt    35640 ccaatcgatc ctctacaatg tcaaagtgta gatctataag atgacactgg tctcctccgc    35700
tgagtcgatc aaaaataaca gctaaaccac aaacaacacg attggtcaaa tgctccacaa    35760
gggcttgcag cataaaatcg cctcgaaagt ccaccgcaag cataacatca aagccaccgc    35820
ccctatcatg atctataata aaaacccac agctatccac cagacccata agttttcat    35880 ctctccatcg tgaaaaaata tttacaagct cctcctttaa atcacctcca accaattgaa    35940
aaagttgagc caaaccgccc tccaccttca tttttcagcaa gcgcatcatg attgcaaaaa    36000
```

```
ttcaggctcc tgagacacct gtataagatt gagaagcgga acgttaacgt caatgtttcg    36060
ctcgcgaaga tcgcgcctca gtgcaagcat gatataatcc cacaggtcgg agcggatcag    36120
cgaggacatc tccccgccag gaaccaactc aacggagcct atgctgatta taatacgcat    36180
attcggggct atgctgacca gcacggcccc caaataggcg tactgcatag gcggcgacaa    36240
aaagtgaaca gtttgggtta aaaaatcagg caaacagtcg cgcaaaaaag caagaacatc    36300
ataaccatgc tcatgcaaat agatgcaagt aagctcagga acgaccacag aaaaatgcac    36360 aattttctc tcaaacatga ctgcgagccc tgcaaaaaat aaaaagaaa cattacacaa     36420 gagtagcctg tcttacgatg ggatagacta ctctaaccaa cataagacgg ccacaacat    36480 cgcccgcgtg gccataaaaa aaattgtccg tgtgattaaa aagaagcaca gatagctggc    36540
cagtcatatc cggagtcatc acgtgtgaac ccgtgtagac ccccgggttg gacacatcgg   36600
ccaaacaaag aaagcggcca atgtacccag gaggaatcat aacactaaga cgaagataca    36660
acagaataac cccatgaggg ggaataacaa agttagtagg tgaataaaaa cgataaacac    36720
ccgaaactcc ctcctgcgta ggcaaaatag cacctcccc ttccaaaaca acatatagcg    36780
cttccacagc agccatgaca aaagactcaa aacactcaaa agactcagtc ttaccaggaa    36840
aataaaagca ctctcacagc accagcacta atcagagtgt gaagagggcc aagtgccgaa    36900
cgagtatata taggaataaa aaatgacgta aatgtgtaaa ggtcagaaaa cgcccagaaa    36960
aatacacaga ccaacgcccg aaacgaaaac ccgcgaaaaa atacccagaa cttcctcaac    37020
aaccgccact tccggtttct cacggtacgt cacttccgca agaaaagcaa aactacattt    37080
cccacatgtg taaaaacgaa accccgcccc ttgtaactgc ccacaactta catcatcaaa    37140
acataaactc ctacgtcacc cgccccgcct ctccccgccc acctcattat catattggcc    37200
acaatccaaa ataaggtata ttattgatga tg                                 37232

<210> SEQ ID NO 23
<211> LENGTH: 37213
<212> TYPE: DNA
<213> ORGANISM: Gorilla beringei beringei

<400> SEQUENCE: 23
ataatatacc ttattttgga ttgtggccaa tatgataatg aggtgggcgg ggagaggcgg       60
ggcgggtgac gtaggacgcg cgagtagggt tgggaggtgt ggcggaagtg tggcatttgc      120
aagtgggagg agctcacatg caagcttccg tcgcggaaaa tgtgacgttt ttgatgagcg      180
ccgcctacct ccggaagtgc caattttcgc gcgcttttca ccggatatcg tagtaatttt      240
gggcgggacc atgtaagatt tggccatttt cgcgcgaaaa gtgaaacggg gaagtgaaaa      300
ctgaataata gggcgttagt catagcgcgt aatatttacc gagggccgag ggactttgac      360
cgattacgtg gaggactcgc ccaggtgttt tttacgtgaa tttccgcgtt ccgggtcaaa      420
gtctccgttt ttattgtcac cgtcatttga cgcggagggt atttaaaccc gctgcgctcc      480
tcaagaggcc actcttgagt gccagcgaga agagttttct cctctgctcc gcttcggtga      540
tcgaaaaatg agacacatag cctgcactcc gggtcttttg tccggtcggg cggcggccga      600
gcttttggac gctttgatca atgatgtcct aagcgatgat tttccgtcta ctacccactt      660
tagcccacct actcttcacg aactgtacga tctggatgta ctggtggatg tgaacgatcc      720
caacgaggag gcggtttctg cgttttttcc cgagtctgcg ctgttggccg ctcaggaggg      780
atttgaccta cacactccgc cgcctatttt agagtctccg ctgccggagc ccagtggtat      840
```

```
accttatatg cctgaactgc ttcccgaagt ggtagacctg acctgccacg agcctggctt    900
tccgcccagc gacgatgagg gtgagccttt tgttttagac tttgctgaga tacctgggca    960
cggttgcagg tcttgtgcat atcatcagag ggttaccgga gaccccgagg ttaagtgttc   1020
gctgtgctat atgaggatga cctcttcctt tatctacagt aagttttgt ctaggtgggc    1080 ttttgggtag gtgggttttg tgtcagaaca ggtgtaaacg ttgcttgtgt tttttgtacc   1140
tgtaggtccg gtgtccgagc cagacccgga gcccgaccgc gatcccgagc cggatcccga   1200
gcctcctcgc aggacaagga aactaccttc cattctgtgc aagtctcaga cacctgtaag   1260
gaccagcgag gcagacagca ccgactctgg cacttctacc tctccccctg aaattcaccc   1320
agtggttcct ctgggtatac ataaacctgt tgctgttaaa gtttgcgggc gacgccctgc   1380
agtacagtgc attgaggact tgcttcacga tcccgaggaa cctttggact tgagccttaa   1440
acgccctagg caataaaccc cacctaagta ataaacccca cctaagtaat aaaccctgcc   1500
gcccttggtt attgagatga cgcccaatgt ttgcttttga atgacttcat gtgtgtaata   1560
aaagtgagtg tgatcatagg tctcttgttt gtctgggcgg ggcttaaggg tatataagtc   1620
tcttggggct aaacttggtt acacttgacc ccaatggagg cgtggggtg cttggaggag   1680 tttgcggacg tgcgccgttt gctggacgag agctctagca atacctatac tatttggagg   1740
tatctgtggg gctctactca ggccaagttg gtttccagaa ttaagcagga ttacaagtgc   1800
gattttgaag agctttttag ttcctgcggt gagcttttgc aatccttgaa tctgggccat   1860
caggctattt tccaggaaaa ggttctctcg actttggatt tttccactcc cgggcgcacc   1920
gccgcttgtg tggcttttgt gtcttttgtg caagataaat ggagcgagga gacccacctg   1980
agtcacggct acgtactgga tttcatggcg atggctcttt ggagggctca caacaaatgg   2040
aagattcaga aggaactgta cggttccgcc ctacgtcgtc cacttctgtc gcgacagggg   2100
ctgaggtttc ccgaccatcg gcagcatcag aatctggaag acgagtcgga ggagcgagcg   2160
gaggagaaga tcagcttgag agccggcctg gaccctcctc aggaggaatg aatctcccgc   2220
aggtggttga cctgtttcca gaactgagac gggtcctgac tatcagggag gatggtcagt   2280
ttgtgaagaa gtttaagagg gatcggggtg agggagatga tgaggcggct agcaatttag   2340
cttttagtct gatgactcgc caccgaccgg aatgtattac ctatcagcag attaaggaga   2400
gttgtgccaa cgagctggat cttttgggtc agaagtatag catagaacag cttaccactt   2460
actggcttca gcctggggat gattgggaag aggcgatcag ggtgtatgca aaggtggccc   2520
tgcggcccga ttgcaagtat aagattacta agttggttaa tattagaaac tgctgctata   2580
tttctgggaa cggggccgaa gtggagatag atactcagga cagggtggct tttaggtgtt   2640
gcatgataaa catgtggccc gggatactgg ggatggatgg ggtggtattc atgaatgtga   2700
ggtttacggg ccccaacttt aatggcacgg tgttcatggg caacaccaac ttgctcctgc   2760
atggtgcgag tttctatggg tttaataaca cctgtataga ggcctggacc gatgtaaagg   2820
ttcgaggttg ttccttttat agctgttgga aggcggtggt gtgtcgccct aaaagcaggg   2880
gttctgtgaa aaaatgcttg tttgaaaggt gcaccttagg catcctctct gagggcaact   2940
ccagggtgcg ccataatgtg gcttcgaact gcggttgctt catgcaagtg aaggggtgaa   3000
gcgttatcaa gcataactcg gtgtgtggaa actgcgagga tcgcgcctcc cagatgctga   3060
cctgctttga tggcaactgt cacctgttga agaccattca tataagcagc caccccagaa   3120
aggcctggcc cgtgtttgag cataacatct tgacccgctg ctccttgcat ctgggggtca   3180 ggagggggtat gttcctgcct taccagtgta actttagcca cactaaaatc ctgctggaac   3240
```

```
ccgagtgcat gaccaaggtc agcctgaatg gtgtgtttga tgtgactctg aaaatctgga    3300
aggtgctgag gtatgatgag accaggacca ggtgccgacc ctgcgagtgc ggcggcaagc    3360
acatgagaaa tcagcctgtg atgttggatg tgaccgagga gcttaggcct gaccatctgg    3420
tgctggcctg caccagggcc gagtttgggt ctagcgatga ggataccgat tgaggtgggt    3480
aaggtgggcg tggctagaag ggtggggcgt gtataaattg ggggtctaag ggtctctctg    3540
ttttgtcttg caacagccgc cgccatgagc gacaccggca acagctttga tggaagcatc    3600
tttagcccct atctgacagt gcgcatgcct cactgggctg gagtgcgtca gaatgtgatg    3660
ggttccaacg tggatggacg ccccgttctg ccttcaaatt cgtctacaat ggcctacgcg    3720
accgtgggag gaactccgct ggacgccgcg acctccgccg ccgcctccgc cgccgccgcg    3780
accgcgcgca gcatggctac ggacctttac agctctttgg tggcgagcgg cgcggcctct    3840
cgcgcgtctg ctcgggatga gaaactgacc gctctgctgc ttaaactgga agacttgacc    3900
cgggagctgg gtcaactgac ccagcaggtc tccagcttgc gtgagagcag ccttgcctcc    3960
ccctaatggc ccataatata aataaaagcc agtctgtttg gattaagcaa gtgtatgttc    4020
tttatttaac tctccgcgcg cggtaagccc gggaccagcg gtctcggtcg tttagggtgc    4080
ggtggattct ttccaacacg tggtacaggt ggctctggat gtttagatac atgggcatga    4140
gtccatccct ggggtggagg tagcaccact gcagagcttc gtgctcgggg gtggtgttgt    4200
atatgatcca gtcgtagcag gagcgctggg cgtggtgctg aaaaatgtcc ttaagcaaga    4260
ggcttatagc tagggggagg cccttggtgt aagtgtttac aaatctgctc agttgggagg    4320
ggtgcatccg gggggatata atgtgcatct tggactggat ttttaggttg gctatgttcc    4380
cacccagatc ccttctggga ttcatgttgt gcaggaccac cagcacggta tatccagtgc    4440
acttgggaaa tttatcgtgg agcttagacg ggaatgcatg gaagaacttg gagacgccct    4500
tgtggcctcc cagattttcc atacattcgt ccatgatgat ggcaatgggc ccgtgggaag    4560
ctgcctgagc aaaaatgttt ctgggatcgc tcacatcgta gttatgttcc agggtgaggt    4620
catcatagga catctttacg aatcggggc ggagggtccc ggactggggg atgatggtac    4680
cctcgggccc cggggcgtag ttcccctcac agatctgcat ctcccaggct ttcatttcag    4740
agggagggat catatccacc tgcggagcga tgaaaaacac agtttctggc gcaggggaga    4800
ttaactggga tgagagcagg tttctgagca gctgtgactt tccacagccg gtgggcccat    4860
atatcacgcc tatcaccggc tgcagctggt agttaagaga gctgcagctg ccgtcctccc    4920
ggagcagggg ggccacctcg ttcagcatat ccctgacgtg gatgttctcc ctgaccaatt    4980
ccgccagaag gcgctcgccg cccagcgaaa gcagctcttg caaggaagca aaattttca    5040
gcggttttag gccgtcggcc gtgggcatgt ttttcagcgt ctgggtcagc agttccagcc    5100
tgtcccacag ctcggtgatg tgctctacgg catctcgatc cagcagatct cctcgtttcg    5160
cgggttgggg cggcttttcgc tgtagggcac cagccgatgg cgtccagcg gggccagagt    5220
catgtccttc catgggcgca gggtcctcgt cagggtggtc tgggtcacgg tgaagggtg    5280
cgctccgggt tgggcgctgg ccagggtgcg cttgaggctg gttctgctgg tgctgaatcg    5340
ctgccgctct tcgccctgcg cgtcggccag gtagcatttg accatggtct cgtagtcgag    5400
accctcggcg gcgtgcccct tggcgcggag cttcccttg gaggtggcgc gcacgaggg    5460
gcactgcagg ctcttcaggg cgtagagctt gggagcgaga aacacggact ctggggagta    5520
ggcgtccgcg ccgcaggaag cgcagaccgt ctcgcattcc accagccaag tgagctccgg    5580
```

-continued

```
gcggtcaggg tcaaaaacca ggttgccccc atgcttttg atgcgtttct tacctcggct      5640
ctccatgagg cggtgtccct tctcggtgac gaagaggctg tccgtgtccc cgtagaccga      5700
cttcaggggc ctgtcttcca gcggagtgcc tctgtcctcc tcgtagagaa actctgacca     5760
ctctgagacg aaggcccgcg tccaggccag gacgaaggag gccacgtggg aggggtagcg     5820
gtcgttgtcc actagcgggt ccaccttctc cagggtgtgc aggcacatgt cccctcctc     5880 cgcgtccaga aaagtgattg gcttgtaggt gtaggacacg tgaccggggg ttcccgacgg      5940
gggggtataa aaggggtggg gcgcccttc atcttcactc tcttccgcat cgctgtctgc      6000
gagggccagc tgctggggta agtattccct ctcgaaggcg ggcatgacct cagcgctcag     6060
gttgtcagtt tctaaaaatg aggaggattt gatgttcacc tgtccggagg tgataccttt     6120
gagggtacct gggtccatct ggtcagaaaa cactattttt ttgttgtcaa gcttggtggc      6180
gaacgacccg tagagggcgt tggagagcag cttggcgatg gagcgcaggg tctggttttt      6240
gtcgcggtcg gctcgctcct tggccgcgat gttgagttgc acgtactcgc gggccacgca     6300
cttccactcg gggaagacgg tggtgcgctc gtctgggatt aggcgcaccc tccagcctcg     6360
gttgtgcagg gtgaccatgt cgacgctggt ggcgacctcg ccgcgcaggc gctcgttggt      6420
ccagcagagg cggccgccct tgcgcgagca aagggggggt aggggtcca gctggtcctc     6480 gtttggggggg tccgcgtcga tggtgaagac cccggggagc aagcgcgggt caaagtagtc     6540
gatcttgcaa gcttgcatgt ccagagcccg ctgccattcg cgggcggcga gcgcgcgctc     6600
gtaggggttg aggggcgggc cccagggcat ggggtgggtg agcgcggagg cgtacatgcc     6660
gcagatgtca tacacgtaca gggggttccct gaggatgccg aggtaggtgg ggtagcagcg     6720
ccccccgcgg atgctggcgc gcacgtagtc atagagctcg tgggaggggg ccagcatgtt     6780
gggcccgagg ttggtgcgct gggggcgctc ggcgcggaag gcgatctgcc tgaagatggc     6840
atgggagttg gaggagatgg tgggccgctg gaagacgttg aagcttgctt cttgcaagcc     6900
caccgagtcc ctgacgaagg aggcgtagga ctcgcgcagc ttgtgcacca gctcggcggt     6960
gacctggacg tcgagcgcgc agtagtcgag ggtctcgcgg atgatgtcat acttatcctc     7020
ccccttcttt ttccacagct cgcggttgag gacgaactct tcgcggtctt tccagtactc     7080
ttggagggga aacccgtccg tgtccgaacg gtaagagcct agcatgtaga actggttgac      7140
ggcctggtag gggcaacagc ccttctccac gggcagcgcg taggcctgcg ccgccttgcg     7200
gagggaggtg tgggtgaggg cgaaagtgtc cctgaccatg actttgaggt attgatgttt      7260
gaagtctgtg tcatcgcagc cgccctgttc ccacagggtg tagtccgtgc gcttttttgga     7320 gcgcggggttg ggcagggaga aggtgaggtc attgaagagg atcttccccg ctcgaggcat     7380
gaagtttctg gtgatgcgaa agggccctgg gaccgaggag cggttgttga tgacctgggc     7440
ggccaggacg atctcgtcaa agccgtttat gttgtggccc acgatgtaga gctccaaaaa     7500
gcggggctgg cccttgatgg aggggagctt tttgagttcc tcgtaggtga gctcctcggg     7560
cgattccagg ccgtgctcct ccagggccca gtcttgcaag tgagggttgg ccgccaggaa     7620
ggatcgccag aggtcgcggg ccatgagggt ctgcaggcgg tcgcggaagg ttctgaactg     7680
tcgccccacg gccatctttt cggggtgat gcagtagaag gtgagggggt ctttctccca      7740
ggggtcccat ctgagctctc gggcgaggtc gcgcgcggcg gcgaccagag cctcgtcgcc      7800
ccccagtttc atgaccagca tgaagggcac gagctgcttg ccaaaggctc ccatccaagt    7860
gtaggtctct acatcgtagg tgacaaagag gcgctccgtg cgaggatgag agccgatcgg     7920
gaagaactgg atctcccgcc accagttgga ggattggctg ttgatgtggt gaaagtagaa     7980
```

```
gtcccgtctg cgggccgagc actcgtgctg gcttttgtaa aagcgaccgc agtactggca    8040
gcgctgcacg ggttgtatat cttgcacgag gtgaacctgg cgacctctga cgaggaagcg    8100
cagcgggaat ctaagtcccc cgcctggggt cccgtgtggc tggtggtctt ctactttggt    8160
tgtctggccg ccagcatctg tctcctggag ggcgatggtg gagcagacca ccacgccgcg    8220
agagccgcag gtccagatct cggcgctcgg cgggcggagt ttgatgacga catcgcgcac    8280
attggagctg tccatggtct ccagctcccg cggcggcagg tcagctggga gttcctggag    8340
gttcacctcg cagagacggg tcaaggcgcg ggcagtgttg agatggtatc tgatttcaag    8400
gggcgtgttg gcgcggagt cgatggcttg caggaggccg cagccccggg gggccacgat     8460
ggttccccgc ggggcgcgag gggaggcgga agctgggggt gtgttcagaa gcggtgacgc    8520
gggcgggccc ccggaggtag ggggggttcc ggccccacag gcatgggcgg caggggcacg    8580
tcttcgccgc gcgcgggcag gggctggtgc tggctccgaa gagcgcttgc gtgcgcgacg    8640
acgcgacggt tggtgtcctg tatctgacgc ctctgagtga agaccacggg tcccgtgacc    8700
ttgaacctga aagagagttc gacagaatca atctcggcat cgttgacagc ggcctggcgc    8760
aggatctcct gcacgtcgcc cgagttgtcc tggtaggcga tctctgccat gaactgctcg    8820
atctcttctt cctggagatc tcctcgtccg gcgcgctcca cggtggccgc caggtcgttg    8880
gagatgcgac ccatgagctg tgagaaggcg ttgagcccgc cctcgttcca gacccggctg    8940
tagaccacgc ccccctcggc gtcgcgagcg cgcatgacca cctgggccag gttgagctcc    9000
acgtgtcgcg tgaagacggc gtagttcgcg aggcgctgga aaaggtagtt cagggtggtg    9060
gcggtgtgct cggcgacgaa gaagtacatg acccagcgcc gcaacgtgga ttcattgatg    9120
tcccccaagg cctccaggcg ctccatggcc tcgtagaagt ccacggcgaa gttgaaaaac    9180
tgggagttgc gagcggacac ggtcaactcc tcctccagaa gacggatgag ctcggcgaca    9240
gtgttgcgca cctcgcgctc gaaggccacg ggggcgcttc cttcctcttc cacctcttct    9300
tccatgatcg cttcttcttc ttcctcagcc gggacggag gggcggcgg cggcggggga    9360 ggggcgcggc ggcggcggcg gcgcaccggg aggcggtcga tgaagcgctc gatcatctcc    9420
ccccgcatgc ggcgcatggt ctcggtgacg gcgcggccgt tctcccgggg gcgcagctcg    9480
aagacgccgc ctctcatctc gccgcggggc gagcggccgt gaggtagcga gacggcgctg    9540
actatgcatc ttaacaattg ctgtgtaggt acaccgccga gggacctgat tgagtccaga    9600
tccaccggat ccgaaaacct ttggaggaaa gcgtctatcc agtcgcagtc gcaaggtagg    9660
ctgagcaccg tggcgggcgg gggcgggtct ggagagttcc tggcggagat gctgctgatg    9720
atgtaattaa agtaggcggt cttgagaagg cggatggtgg acaggagcac catgtctttg    9780
ggtccggcct gttggatgcg gaggcggtcg gccatgcccc aggcctcgtt ctgacaccgg    9840
cgcaggtctt tgtagtagtc ttgcatgagt cttttccaccg gcacctcttc tccttcctct    9900
tctccatctc gccggtggtt tctcgcgccg cccatgcgcg tgaccccaaa gcccctgagc    9960
ggctgcagca gggccaggtc ggcgaccacg cgctcggcca agatggcctg ctgcacctga   10020
gtgagggtcc tctcgaagtc atccatgtcc acgaagcggt ggtaggcgcc cgtgttgatg   10080
gtgtaggtgc agttggccat gacgaccag ttgacggtct ggtgtcccgg ctgcgagagc    10140
tccgtgtacc gcaggcgcga gaaggcgcgg gaatcgaaca cgtagtcgtt gcaagtccgc   10200
accagatact ggtagcccac caggaagtgc ggcggaggtt ggcgatagag gggccagcgc   10260
tgggtggcgg gggcgccggg cgccaggtct tccagcatga ggcggtggta tccgtagatg   10320
```

```
tacctggaca tccaggtgat gccggcggcg gtggtggtgg cgcgcgcgta gtcgcggacc    10380
cggttccaga tgtttcgcag gggcgagaag tgttccatgg tcggcacgct ctggccggtg    10440
aggcgcgcgc agtcgttgac gctctataca cacacaaaaa cgaaagcgtt tacagggctt    10500
tcgttctgta gcctggagga aagtaaatgg gttgggttgc ggtgtgcccc ggttcgagac    10560
caagctgagc tcggccggct gaagccgcag ctaacgtggt attggcagtc ccgtctcgac    10620
ccaggccctg tatcctccag gatacggtcg agagcccttt tgctttcttg gccaagcgcc    10680
cgtggcgcga tctgggatag atggtcgcga tgagaggaca aaagcggctc gcttccgtag    10740
tctggagaaa caatcgccag ggttgcgttg cggcgtaccc cggttcgagc ccctatggcg    10800
gcttgaatcg gccggaaccg cggctaacga gggccgtggc agccccgtcc tcaggacccc    10860
gccagccgac ttctccagtt acgggagcga gcccctttg ttttttattt tttagatgca     10920
tcccgtgctg cggcagatgc gccccctcgcc ccggcccgat cagcagcagc aacagcaggc    10980
atgcagaccc cctctccccc tttccgcccc ggtcaccacg gccgcggcgg ccgtgtcggg    11040
cgcgggggc gcgctggagt cagatgagcc accgcggcgg cgacctaggc agtatctgga     11100
cttggaagag ggcgagggac tggcgcggct gggggcgaac tctccagagc gccacccgcg    11160
ggtgcagttg aaaagggacg cgcgcgaggc gtacctgccg cggcagaacc tgtttcgcga    11220
ccgcgggggc gaggagcccg aggagatgcg agactgcagg ttccaagcgg ggcgcgagct    11280
gcggcgcggg ctggacagac agcgcctgct gcgcgaggag gactttgagc ccgacacgca    11340
gacgggcatc agccccgcgc gcgcgcacgt agccgcggcc gacctggtga ccgcctacga    11400
gcagacggta aaccaggagc gcaacttcca aaagagcttc aacaaccacg tgcgcacgct    11460
ggtggcgcgc gaggaggtga ccctgggtct catgcatctg tgggacctgg tggaggcgat    11520
cgtgcagaac cccagcagca agccctgac cgcgcagctg ttcctggtgg tgcagcacag     11580
cagggacaac gaggccttca gggaggcgct gctgaacatc accgagccgg aggggcgctg    11640
gctcctggac ctgataaaca tcctgcagag catagtggtg caggagcgca gcctgagcct    11700
ggccgagaag gtggcggcca tcaactactc tatgctgagc ctgggcaagt tctacgcccg    11760
caagatctac aagaccccct acgtgcccat agacaaggag gtgaagatag acagcttcta    11820
catgcgcatg gcgctgaagg tgctgaccct gagcgacgac ctgggagtgt accgcaacga    11880
gcgcatccac aaggccgtga gcgccagccg cggcgcgag ctgagcgacc gcagctgat      11940
gcacagtctg cagcgcgcgc tgaccggcgc gggcgagggc gacagggagg tcgagtccta    12000
cttcgacatg ggggccgacc tgcactggca gccgagccgc cgcgccctgg aggcggcggg    12060
ggcgtacggc ggcccctgg cggccgatga ccaggaagag gaggactatg agctagagga     12120
gggcgagtac ctggaggact gacctggctg gtggtgtttt ggtatagatg caagatccga    12180
acgtggcgga cccggcggtc cgggcggcgc tgcaaagcca gccgtccggc attaactcct    12240
ctgacgactg ggccgcggcc atgggtcgca tcatggccct gaccgcgcgc aaccccgagg    12300
ctttcaggca gcagcctcag gccaaccggc tggcggccat cttggaagcg gtagtgcccg    12360
cgcgctccaa ccccacccac gagaaggtgc tggccatagt caacgcgctg gcggagagca    12420
gggccatccg cgcggacgag gccggactgg tgtacgatgc gctgctgcag cgggtggcgc    12480
ggtacaacag cggcaacgtg cagaccaacc tggaccgcct ggtgacggac gtgcgcgagg    12540
ccgtggcgca gcgcgagcgc ttgcatcagg acggtaacct gggctcgctg gtggcgctaa    12600
acgccttcct cagcacccag ccggccaacg taccgcgggg gcaggaggac tacaccaact    12660
ttttgagcgc gctgcggctg atggtgaccg aggtccctca gagcgaggtg taccagtcgg    12720
```

```
ggcccgacta cttcttccag accagcagac agggcttgca aaccgtgaac ctgagccagg   12780
ctttcaagaa cctgcggggg ctgtggggag tgaaggcgcc caccggcgac cgggctacgg   12840
tgtccagcct gctaaccccc aactcgcgcc tgctgctgct gctgatcgcg cccttcacgg   12900
acagcgggag cgtctcgcgg gagacctatc tgggccacct gctgacgctg taccgcgagg   12960
ccatcgggca ggcgcaggtg gacgagcaca ccttccaaga gatcaccagc gtgagccacg   13020
cgctggggca ggaggacacg ggcagcctgc aggcgaccct gaactacctg ctgaccaaca   13080
ggcggcagaa gattcccacg ctgcacagcc tgacccagga ggaggagcgc atcttgcgct   13140
acgtgcagca gagcgtgagc ctgaacctga tgcgcgacgg cgtgacgccc agcgtggcgc   13200
tggacatgac cgcgcgcaac atggaaccgg gcatgtacgc ctcccaccgg ccgtttatca   13260
accgcctgat ggactacttg catcgggcgg cggccgtgaa ccccgagtac ttcactaatg   13320
ccattctgaa tccccactgg atgccccctc cgggtttcta caacggggac tttgaggtgc   13380
ccgaggtcaa cgacgggttc ctctgggatg acatggatga cagtgtgttc tcacccaacc   13440
cgctgcgcgc cgcgtctctg cgattgaagg agggctctga cagggaagga ccgaggagtc   13500
tggcctcctc cctggctctg ggagcggtgg gcgccacggg cgcggcggcg cggggcagta   13560 gcccttccc cagcctggca gactctctga acagcgggcg ggtgagcagg ccccgcttgc   13620
taggcgagga ggagtatctg aacaactccc tgctgcagcc cgcgagggac aagaacgctc   13680
agcggcagca gtttcccaac aatgggatag agagcctggt ggacaagatg tccagatgga   13740
agacgtatgc gcaggagtac aaggagtggg aggaccgcca gccgcggccc ttgccgcccc   13800
ctaggcagcg ctggcagcgg cgcgcgtcca accgccgctg gaggcagggg cccgaggacg   13860
atgatgactc tgcagatgac agcagcgtgt tggacctggg cgggagcggg aaccccttt   13920 cgcacctgcg cccacgcctg ggcaagatgt tttaaaagaa aaaaaaaata aaactcacca   13980
aggccatggc gacgagcgtt ggttttttgt tcccttcctt agtatgcggc gcgcggcgat   14040
gttcgaggag gggcctcccc cctcttacga gagcgcgatg gggatttctc ctgcggcgcc   14100
cctgcagcct ccctacgtgc ctcctcggta cctgcaacct acaggggga gaaatagcat   14160 ctgttactct gagctgcagc ccctgtacga taccaccaga ctgtacctgg tggacaacaa   14220
gtccgcggac gtggcctccc tgaactacca gaacgaccac agcgatttt tgaccacggt   14280 gatccaaaac aacgacttca ccccaaccga ggccagcacc cagaccataa acctggataa   14340
caggtcgaac tggggcggcg acctgaagac catcttgcac accaacatgc caacgtgaa   14400 cgagttcatg ttcaccaact cttttaaggc gcggtgatg gtggcgcgcg agcagggga   14460 ggcgaagtac gagtgggtgg acttcacgct gcccgagggc aactactcag agaccatgac   14520
tctcgacctg atgaacaatg cgatcgtgga acactatctg aaagtgggca ggcagaacgg   14580
ggtgaaggaa agcgatatcg gggtcaagtt tgacaccaga aacttccgtc tgggctggga   14640
ccccgtgacc gggctggtca tgccgggggt ctacaccaac gaggcctttc atcccgacat   14700
agtgcttctg cccggctgtg gggtggactt cacccagagc cggctgagca acctgctggg   14760
cattcgcaag cggcagcctt tccaggaggg tttcaagatc acctatgagg atctgaaggg   14820
gggcaacatt cccgcgctcc ttgatctgga cgcctacgag gagagcttga aacccgagga   14880
gagcgctggc gacagcggcg agagtggcga ggagcaagcc ggcggcggtg gcggcgcgtc   14940
ggtagaaaac gaaagtacgc ccgcagtggc ggcggacgct gcggaggtcg agccggaggc   15000
catgcagcag gacgcagagg agggcgcaca ggagggcgcg cagaaggaca tgaacgatgg   15060
```

```
ggagatcagg ggagacacat tcgccacccg gggcgaagaa aaagaggcag aggcggcggc  15120
ggcggcgacg gcggaggccg aaaccgaggt tgaggcagag gcagagcccg agaccgaagt  15180
tatggaagac atgaatgatg gagaacgtag gggcgacacg ttcgccaccc ggggcgaaga  15240
gaaggcggcg gaggcagaag ccgcggctga ggaggcggct gcggctgcgg ccaagactga  15300
ggctgcggct aaggctgagg tcgaagccaa tgttgcggtt gaggctcagg ctgaggagga  15360
ggcggcggct gaagcagtta aggaaaaggc ccaggcagag caggaagaga aaaaacctgt  15420
cattcaacct ctaaaagaag atagcaaaaa gcgcagttac aacgtcatcg agggcagcac  15480
ctttacccag taccgcagct ggtacctggc gtacaactac ggcgaccggg tcaagggggt  15540
gcgctcgtgg accctgctct gcacgccgga cgtcacctgc ggctccgagc agatgtactg  15600
gtcgctgccg aacatgatgc aagacccggt gaccttccgc tccacgcggc aggttagcaa  15660
cttcccggtg gtgggcgccg aactgctgcc cgtgcactcc aagagttttt acaacgagca  15720
ggccgtctac tcccagctga tccgccaggc cacctctctg acccacgtgt tcaatcgctt  15780
tcccgagaac cagattttgg cgcgcccgcc ggcccccacc atcaccaccg tgagtgaaaa  15840
cgttcctgcc ctcacagatc acgggacgct accgctgcgc aacagcatct caggagtcca  15900
gcgagtgacc attactgacg ccagacgccg gacctgcccc tacgtttaca aggccttggg  15960
catagtctcg ccgcgcgtcc tctccagtcg cacttttttaa aacacatcta cccacacgtt  16020
ccaaaatcat gtccgtactc atctcaccca gcaacaacac cggctggggg ctgcgcgcgc  16080
ccagcaagat gtttggaggg gcgaggaagc gctccgacca gcaccctgtg cgcgtgcgcg  16140
gccactaccg cgcgccctgg ggagcgcaca agcgcgggcg cacagggcgc accactgtgg  16200
acgacgtcat tgactccgta gtggagcaag cgccgccacta cacacccggc gcgccgaccg  16260
cccccgccgt gtccaccgtg gaccaggcga tcgaaagcgt ggtacagggc gcgcggcact  16320
atgccaacct taaaagtcgc cgccgccgcg tggcccgccg ccatcgccgg agaccccggg  16380
ccaccgccgc cgcgcgcctt actaaggctc tgctcaggcg cgccaggcga actgccaccc  16440
gggccgccat gagggccgca cggcgggctg ccgctgccgc aagcgtcgtg gccccgcggg  16500
cacgaaggcg cgcggccgct gccgccgccg ccgccatttc cagcttggcc tcgacgcggc  16560
gcggtaacat atactgggtg cgcgactcgg taaccggcac gcgggtaccc gtgcgctttc  16620
gccccccgcg gaattagcac aagacaacat acacactgag tctcctgctg ttgtgtatcc  16680
cagcggcgac cgtcagcagc ggcgacatgt ccaagcgcaa aattaaagaa gagatgctcc  16740
aggtcatcgc gccggagatc tatgggcccc gaagaaggga ggaggatgat tacaagcccc  16800
gcaagctaaa gcgggtcaaa agaaaaaga aagatgatga tgacgaggcg gtggagtttg  16860
tccgccgcat ggcacccagg cgccccgtgc agtggaaggg ccggcgcgtg cagcgcgttt  16920
tgcgccccgg caccgcggtg gtcttcacgc ccggcgagcg ctccacgcgc actttcaagc  16980
gggtgtacga tgaggtgtac ggcgacgagg acctgttgga gcaggccaac cagcgctttg  17040
gggagtttgc atatgggaaa cggccccgcg agagtctaaa agaggacctg ctggcgctac  17100
cgctggacga gggcaatccc accccgagtc tgaagccggt aaccctgcaa caggtgctgc  17160
ctttgagcgc gcccagcgag cataagcgag ggttgaagcg cgaaggcggg gacctggcgc  17220
ccaccgtgca gttgatggtg cccaagcggc agaagctgga ggacgtgctg gagaaaatga  17280
aagtagagcc cgggatccag cccgagatca aggtccgccc catcaagcag gtggcgcccg  17340
gcgtgggagt ccagaccgtg gacgttagga ttcccacgga ggagatggaa acccaaaccg  17400
ccactcccct ttcggcggcc agcgccacca ccggcaccgc ttcggtagag gtgcagacgg  17460
```

```
accccctggct acccgccacc gctgttgccg ccgccgcccc ccgttcgcgc gggcgcaaga  17520
gaaattatcc agcggccagc gcgctcatgc cccagtacgc actgcatcca tccatcgtgc  17580
ccaccccgg ctaccgcggg tactcgtacc gcccgcgcag atcagccggc actcgcggcc   17640
gccgccgccg tgcgaccaca accagccgcc gccgtcgccg ccgccgccag ccagtgctga  17700
cccccgtgtc tgtaaggaag gtggctcgct cggggagcac gctggtggtg cccagagcgc  17760
gctaccaccc cagcatcgtt taaagccggt ctctgtatgg ttcttgcaga tatgcccctc  17820
acttgtcgcc tccgcttccc ggtgccggga taccgaggaa gaactcaccg ccgcagaggc  17880
atggcgggca gcggtctccg cggcggccgt cgccatcgcc ggcgcgcaaa aagcaggcgc  17940
atgcgcggcg gtgtgctgcc tctgctaatc ccgctaatcg ccgcggcgat cggtgccgta  18000
cccgggatcg cctccgtggc cctgcaggcg tcccagaaac gttgactctt gcaaccttgc  18060
aagcttgcat ttttggagg aaaaataaaa aaaagtctag actctcacgc tcgcttggtc   18120
ctgtgactat tttgtagaaa aaagatgga agacatcaac tttgcgtcgc tggccccgcg   18180
tcacggctcg cgcccgttca tgggagactg gacagatatc ggcaccagca atatgagcgg  18240
tggcgccttc agctggggca gtctgtggag cggccttaaa aatttttggtt ccaccattaa  18300
gaactatggc aacaaagcgt ggaacagcag cacgggccag atgctgagag acaagttgaa  18360
agagcagaac ttccaggaga aggtggcgca gggcctggcc tctggcatca gcggggtggt  18420
ggacatagct aaccaggccg tgcagaaaaa gataaacagt catctggacc cccgtcctca  18480
ggtggaggaa atgcctccag cgatggagac ggtgtctccc gagggcaaag gcgaaaagcg  18540
cccgcggccc gacagagaag agaccctggt gtcacacacc gaggagccgc cctcttacga  18600
ggaggcagtc aaggcggcc tgcccaccac tcgccccata gccccatgg ccaccggtgt    18660
ggtgggccac aggcaacaca ctcccgcaac actagatctg ccccgccgt ccgagccgcc   18720
gcgccagcca aaggcggcga cggtgcccgc tccctccact tccgccgcca acagagtgcc  18780
cctgcgccgc gccgcgagcg gcccccgggc ctcgcgagtt agcggcaact ggcagagcac  18840
actgaacagc atcgtgggcc tgggagtgag gagtgtgaag cgccgccgtt gctactgaat  18900
gagcaagcta gctaacgtgt tgtatgtgtg tatgcgtcct atgtcgccgc cagaggagct  18960
gttgagccgc cggcgccgtc tgcactccag cgaatttcaa gatggcgacc ccatcgatga  19020
tgcctcagtg gtcgtacatg cacatctcgg gccaggacgc ttcggagtac ctgagccccg  19080
ggctggtgca gttcgcccgc gccacagaca cctacttcaa catgagtaac aagttcagga  19140
accccactgt ggcgcccacc cacgatgtga ccacggaccg gtcgcagcgc ctgacgctgc  19200
ggttcatccc cgtggatcgg gaggacaccg cctactctta caaggcgcgg ttcacgctgg  19260
ccgtgggcga caaccgcgtg ctggacatgg cctccactta cttgacatc aggggggtgc   19320
tggacagggg ccccaccttc aagccctact cgggtactgc ctacaactcc ctggccccca  19380
agggcgctcc caattcttgc gagtgggaac aagatgaacc agctcaggca gcaatagctg  19440
aagatgaaga agaacttgaa gaagaacaag ctcaggacga acaggcgccc actaagaaaa  19500
cccatgtata cgcccaggca cctctttctg gtgaaaaaat tactaaggat ggtttgcaaa  19560
taggtgtgga tgccacacag gcgggagata accctatata tgctgataaa acattccaac  19620
ccgaacctca gataggtgag tctcagtgga acgaggctga tgccacagta gcaggaggca  19680
gagtcttaaa aaagaccacc cctatgagac cttgctatgg atcctatgcc aaacctacta  19740
atgccaatgg cggtcaaggg atcatggtgg ccaatgatca gggagcgctt gaatctaaag  19800
```

```
ttgagatgca attttctcc accacaacgt ctcttaatgt aagggaaggt gaaaacaatc   19860
ttcagccaaa agtagtgcta tacagcgaag atgttaactt ggaatcccct gacactcatt   19920
tgtcttacaa acctaaaaag gatgacacca actctaaaat catgttgggt cagcaagcca   19980
tgcccaacag acccaacctc attgctttta gggacaactt tattggactt atgtactaca   20040
acagcacagg caacatggga gtgctggcag acaggcctc ccagctaaac gctgtggtag   20100
acttgcaaga cagaaacaca gagctgtcat accaactgat gcttgattcc attggagaca   20160
gatcaagata cttttccatg tggaaccagg cagtggacag ctatgaccca gatgtcagaa   20220
tcattgaaaa ccatggggtt gaagatgagc tgcccaacta ttgctttccc ctgggcggta   20280
ttggaattac agacacatac cagtgcataa accaaccgc agctgctaat aacactacat   20340
ggtctaagga tgaagaattt agtgatcgca atgaaatagg ggtgggaaac aacttcgcca   20400
tggagatcaa catccaggcc aacctctgga ggaacttcct ctatgcgaac gtggggctct   20460
acctgccaga caagctcaag tacaacccca ccaacgtgga catctctgac aaccccaaca   20520
cctatgacta catgaacaag cgtgtggtgg ctcccggcct ggtggactgc tttgtcaatg   20580
tgggagccag gtggtccctg gactacatgg acaacgtcaa ccccttcaac caccaccgca   20640
atgcgggtct gcgctaccgc tccatgatcc tgggcaacgg gcgctacgtg cccttccaca   20700
ttcaggtgcc ccagaagttc tttgccatca gaacctcct cctcctgccg ggctcctaca   20760
cttacgagtg gaacttcagg aaggatgtca acatggtcct gcagagctct ctgggcaatg   20820
accttagggt ggacggggcc agcatcaagt ttgacagcgt caccctctat gctaccttct   20880
tccccatggc tcacaacacc gcctccacgc tcgaggccat gctgaggaac gacaccaacg   20940
accagtcctt caatgactac ctctctgggg ccaacatgct ctaccccatc cccgccaagg   21000
ccaccaacgt gccatctcc attccctctc gcaactgggc cgccttcaga ggctgggcct   21060
ttacccgcct taagaccaag gaaacccct cctgggctc gggttttgac ccctactttg   21120
tctactcggg atccatcccc tacctggatg gcaccttcta cctcaaccac acttttaaga   21180
agatatccat catgtatgac tcctccgtca gctggccggg caatgaccgc ctgctcaccc   21240
ccaatgagtt cgaggtcaag cgcgccgtgg acggcgaggg ctacaacgtg cccagtgca   21300 acatgaccaa ggactggttc ctggtgcaga tgctggccaa ctacaacata ggctaccagg   21360
gcttctacat cccagagagc tacaaggaca ggatgtactc cttcttcaga aatttccaac   21420
ccatgagcag gcaggtggtg gacgagacca aatacaagga ctatcaggcc attggcatca   21480
ctcaccagca caacaactcg ggattcgtgg gctacctggc tcccaccatg cgcgagggc   21540 aggcctaccc cgccaacttc ccctacccgt tgataggcaa aaccgcggtc gacagcgtca   21600
cccagaaaaa gttcctctgc gaccgcaccc tctggcgcat cccttctct agcaacttca   21660 tgtccatggg tgcgctcacg gacctgggcc agaacctgct ctatgccaac tccgcccatg   21720
cgctggacat gacttttgag gtggaccccca tggacgagcc cacccttctc tatattgtgt   21780
ttgaagtgtt cgacgtggtc agagtgcacc agccgcaccg cggtgtcatc gagaccgtgt   21840
acctgcgcac gccttctcg gccggcaacg ccaccaccta aggagacagc gccgccgcct   21900
gcatgacggg ttccaccgag caagagctca gggccatcgc cagagacctg ggatgcggac   21960 cctattttt gggcacctat gacaaacgct tcccgggctt catctcccga acaagctcg   22020 cctgcgccat cgtcaacacg gccgcgcgcg agaccggggg cgtgcactgg ctggcctttg   22080
gctgggaccc gcgctccaaa acctgctacc tcttcgaccc ctttggcttc tccgatcagc   22140
gcctcagaca gatctatgag tttgagtacg aggggctgct gcgccgcagc gcgcttgcct   22200
```

```
cctcgcccga ccgctgcatc acccttgaga agtccaccga gaccgtgcag gggcccact   22260
cggccgcctg cggtctcttc tgctgcatgt ttttgcacgc ctttgtgcgc tggcccaga   22320
gtcccatgga tcgcaacccc accatgaact tgctcaaggg agtgcccaac gccatgctcc   22380
agagccccca ggtccagccc accctgcgcc acaaccagga acagctctac cgcttcctgg   22440
agcgccactc cccctacttc cgcagtcaca gcgcgcacat ccgggggggcc acctcttcct   22500
gccacttgca agaaaacatg caagacggaa aatgatgtac agctcgcttt ttaataaatg   22560
taaagactgt gcactttatt tatacacggg ctctttctgg ttatttattc aacaccgccg   22620
tcgccatcta gaaatcgaaa gggttctgcc gcgcgtcgcc gtgcgccacg ggcagagaca   22680
cgttgcgata ctggaagcgg ctcgcccact taaactcggg caccaccatg cggggcagtg   22740
gttcctcggg gaagttctcg ccccacaggg tgcgggtcag ctgcagcgcg ctcaggaggt   22800
cgggagccga gatcttgaag tcgcagttgg ggccggaacc ctgcgcgcgc gagttgcggt   22860
acacggggtt gcagcactgg aacaccagca gggccggatt atgcacgctg ccagcaggc   22920
tctcgtcgct gatcatgtcg ctgtccagat cctccgcgtt gctcagggcg aacggggtca   22980
tcttgcagac ctgcctgccc aggaaaggcg gcagcccggg cttgccgttg cagtcgcagc   23040
gcaggggcat cagcaggtgc ccgcggcccg actgcgcctg cgggtacagc gcgcgcatga   23100
aggcttcgat ctgcctgaaa gccacctgcg tcttggctcc ctccgaaaag aacatcccac   23160
aggacttgct ggagaactgg ttcgcgggac agctggcatc gtgcaggcag cagcgcgcgt   23220
cggtgttggc gatctgcacc acgttgcgac cccaccggtt cttcactatc ttggccttgg   23280
aagcctgctc cttcagcgcg cgctggccgt tctcgctggt cacatccatc tctatcacct   23340
gctccttgtt gatcatgttt gtaccgtgca gacacttcag gtcgccctcc gtctgggtgc   23400
agcggtgctc ccacagcgcg caaccggtgg gctcccaatt tttgtgggtc accccgcgt   23460
aggcctgcag gtaggcctgc aagaagcgcc ccatcatggc cacaaaggtc ttctggctcg   23520
taaaggtcag ctgcaggccg cgatgctctt cgttcagcca ggtcttgcag atggcggcca   23580
gcgcctcggt ctgctcgggc agcatcctaa aatttgtctt caggtcgtta tccacgtggt   23640
acttgtccat catggcgcgc gccgcctcca tgcccttctc ccaggcggac accatgggca   23700
ggcttagggg gtttatcact tccaccggcg aggacaccgt actttcgatt tcttcttcct   23760
ccccctcttc ccggcgcgcg cccacgctgc tgcgcgctct caccgcctgc accaagggt   23820
cgtcttcagg caagcgccgc accgagcgct tgccgccctt gacctgctta atcagcaccg   23880
gcgggttgct gaagcccacc atggtcagcg ccgcctgctc ttcttcgtct tcgctgtcta   23940
ccactatctc tggggaaggg cttctccgct ctgcggcggc gcgcttcttt ttttcttgg   24000
gagcggccgt gatggagtcc gccacggcga cggaggtcga gggcgtgggg ctggggtgc   24060
gcggtaccag ggcctcgtcg ccctcggact cttcctctga ctccaggcgg cggcggagtc   24120
gcttctttgg gggcgcgcgc gtcagcggcg cggagacgg ggacggggac ggggacggga   24180
cgccctccac aggggtggt cttcgcgcag acccgcggcc gcgctcgggg gtcttctcga   24240
gctggtcttg gtcccgactg gccattgtat cctcctcctc ctaggcagag agacataagg   24300
agtctatcat gcaagtcgag aaggaggaga gcttaaccac cccctctgag accgccgatg   24360
cgcccgccgt cgccgtcgcc cccgctgccg ccgacgcgcc cgccacaccg agcgacaccc   24420
ccgcggaccc ccccgccgac gcaccccgt tcgaggaagc ggccgtggag caggaccccgg   24480
gctttgtctc ggcagaggag gatttgcgag aggaggagga taaggagaag aagccctcag   24540
```

```
tgccaaaaga tgataaagag caagacgagc acgacgcaga tgcacaccag ggtgaagtcg   24600
ggcgggggga cggagggcat gacggcgccg actacctaga cgaagggaac gacgtgctct   24660
tgaagcacct gcatcgtcag tgcgccattg tttgcgacgc tctgcaggag cgcagcgaag   24720
tgcccctcag cgtggcggag gtcagccacg cctacgagct cagcctcttc tcccccgggg   24780
tgcccccccg ccgccgcgaa aacggcacat gcgagcccaa cccgcgcctc aacttctacc   24840
ccgcctttgt ggtacccgag gtcctggcca cctatcacat cttctttcaa aattgcaaga   24900 tcccctctc gtgccgcgcc aaccgtagcc gcgccgataa gatgctggcc ctgcgccagg   24960
gcgaccacat acctgatatc gccgctttgg aagatgtacc aaagatcttc gagggtctgg   25020
gtcgcaacga gaagcgggca gcaaactctc tgcaacagga aaacagcgaa aatgagagtc   25080 acaccgggt actggtggag ctcgagggcg acaacgcccg cctggcggtg gtcaagcgca   25140
gcatcgaggt cacccacttt gcctaccccg cgctaaacct gccccccaaa gtcatgaacg   25200
cggccatgga cgggctgatc atgcgccgcg gccggcccct cgctccagat gcaaacttgc   25260
atgaggagac cgaggacggc cagcccgtgg tcagcgacga gcagctggcg cgctggctgg   25320
agaccgcgga ccccgccgaa ctggaggagc ggcgcaagat gatgatggcc gtggtgctgg   25380
tcaccgtaga gctggagtgt ctgcagcgct tcttcggcga cccgagatg cagagaaagg   25440 tcgaggagac cctgcactac accttccgcc agggctacgt gcgccaggct tgcaagatct   25500
ccaacgtgga gctcagcaac ctggtgtcct acctgggcat cttgcatgag aaccgcctcg   25560
ggcagagcgt gctgcactcc accctgcgcg gggaggcgcg ccgcgactac gtgcgcgact   25620
gcgtttacct cttcctctgc tacacctggc agacggccat gggggtctgg cagcagtgcc   25680
tggaggagcg caacctcaag gagctggaga agctcctgca gcgcgcgctc aaagatctct   25740
ggacgggcta caacgagcgc tcggtggccg ccgcgctggc cgacctcatc ttccccgagc   25800
gcctgctcaa aaccctccag caggggctgc ccgacttcac cagccaaagc atgttgcaaa   25860
acttcaggaa ctttatcctg gagcgttctg gcatcctacc cgccacctgc tgcgccctgc   25920
ccagcgactt tgtcccccctc gtgtaccgcg agtgccccc gccgctgtgg ggtcactgct   25980
acctgttcca actggccaac tacctgtcct accacgcgga cctcatggag gactccagcg   26040
gcgaggggct catggagtgc cactgccgct gcaacctctg cacgccccac cgctccctgg   26100
tctgcaacac ccaactgctc agcgagagtc agattatcgg taccttcgag ctacagggtc   26160
cgtcctcctc agacgagaag tccgcggctc cggggctaaa actcactccg gggctgtgga   26220
cttccgccta cctgcgcaaa tttgtacctg aagactacca cgcccacgag atcaggtttt   26280
acgaagacca atcccgcccg cccaaggcgg agctgaccgc ctgcgtcatc acccagggcg   26340
agatcctagg ccaattgcaa gccatccaaa aagcccgcca agactttttg ctgaagaagg   26400
gtcggggggt gtatctggac cccagtcgg gtgaggagct caacccggtt cccccgctgc   26460
cgccgccgcg ggaccttgct tcccaggata gcatcgcca tggctcccag aaagaagcag   26520
cagcggccgc cactgccgcc accccacatg ctggaggaag aggaggaata ctgggacagt   26580
caggcagagg aggtttcgga cgaggaggag ccggagacgg agatggaaga gtgggaggag   26640
gacagcttag acgaggaggc ttccgaagcc gaagaggcag acgcaacacc gtcaccctcg   26700
gccgcagccc cctcgcaggc gcccccgaag tccgctccca gcatcagcag caacagcagc   26760
gctataacct ccgctcctcc accgccgcga cccacggccg accgcagacc caaccgtaga   26820
tgggacacca ccggaaccgg ggccggtaag tcctccggga gaggcaagca agcgcagcgc   26880
caaggctacc gctcgtggcg cgctcacaag aacgccatag tcgcttgctt gcaagactgc   26940
```

```
gggggaaca tctccttcgc ccgccgcttc ctgctcttcc accacggtgt ggccttcccc   27000
cgtaacgtcc tgcattacta ccgtcatctc tacagcccct actgcggcgg cagtgagcca   27060
gagacggtcg gcggcggcgg cggcgcccgt ttcggcgcct aggaagaccc agggcaagac   27120
ttcagccaag aaactcgcgg cggccgcggc gaacgcggtc gcggggggcc tgcgcctgac   27180
ggtgaacgaa cccctgtcga cccgcgaact gaggaaccga atcttcccca ctctctatgc   27240
catcttccag cagagcagag ggcaggatca ggaactgaaa gtaaaaaaca ggtctctgcg   27300
ctccctcacc cgcagctgtc tgtatcacaa gagcgaagac cagcttcggc gcacgctgga   27360
ggacgctgag gcactcttca gcaaatactg cgcgctcact cttaaggact agctccgcgc   27420
ccttctcgaa tttaggcggg aacgcctacg tcatcgcagc gccgccgtca tgagcaagga   27480
cattcccacg ccatacatgt ggagctatca gccgcagatg ggactcgcgg cgggcgcctc   27540
ccaagactac tccacccgca tgaactggct cagtgccggc ccacacatga tctcacaggt   27600
taatgatatc cgcacccatc gaaaccaaat attggtggag caggcggcaa ttaccaccac   27660
gccccgcaat aatcccaacc ccagggagtg gcccgcgtcc ctggtgtatc aggaaattcc   27720 cggcccacc accgtactac ttccgcgtga ttcccaggcc gaagtccaaa tgactaactc   27780
aggggcacag ctcgcgggcg gctgtcgtca cagggtgcgg cctcctcgcc agggtataac   27840
tcacctggag atccgaggca gaggtattca gctcaacgac gagtcggtga gctcctcgct   27900
cggtctcaga cctgacggga ccttccagat agccggagcc ggccgatctt ccttcacgcc   27960
ccgccaggcg tacctgactc tgcaaagctc gtcctcggcg ccgcgctcgg gcggcatcgg   28020
gactctccag ttcgtgcagg agtttgtgcc ctcggtctac ttcaaccccct tctcgggctc   28080 tcccggtcgc tacccggacc agttcatctc gaactttgac gccgcgaggg actcggtgga   28140
cggctacgac tgaatgtcgg gtggacccgg tgcagagcaa cttcgcctga agcacctcga   28200
ccactgccgc cgccctcagt gctttgcccg ctgtcagacc ggtgagttcc agtacttttc   28260
cctgcccgac tcgcacccgg acggcccggc gcacggggtg cgcttttttca tcccgagtca   28320 ggtgcgctct accctaatca gggagtttac cgcccgtccc ctactggcgg agttggaaaa   28380
ggggccttct atcctaacca ttgcctgcat ctgctctaac cctggattgc accaagatct   28440
ttgctgtcat ttgtgtgctg agtataataa aggctgagat cagaatctac tcgggctcct   28500
gtcgccatcc tgtcaacgcc accgtccaag cccggcccga tcagcccgag gtgaacctca   28560
cctgcggtct gcaccggcgc ctgaggaaat acctagcttg gtactacaac agcactccct   28620
ttgtggttta caacagcttt gaccaggacg gggtctcact gagggataac ctctcgaacc   28680
tgagctactc catcaggaag aacagcaccc tcgagctact tcctccttac ctgcccggga   28740
cttaccagtg tgtcaccggt ccctgcaccc acacccacct gttgatcgta aacgactctc   28800
ttccgagaac agacctcaat aactcctctt cgcagttccc cagaacagga ggtgagctca   28860 ggaaacccccg ggtaaagaag ggtggacgag agttaacact tgtgggggttt ctggtgtatg   28920 tgacgctggt ggtggctctt ttgattaagg ccttttccttc catgtctgaa ctctccctct   28980
tcttttatga acaactcgac tagtgctaac gggaccctac ccaacgaatc gggattgaat   29040
atcggtaacc aggttgcagt ttcacttttg attaccttca tagtcctctt cctgctagtg   29100
ctgtcgcttc tgtgcctgcg gatcgggggc tgctgcatcc acgtttatat ctggtgctgg   29160
ctgtttagaa ggttccggaga ccatcgcagg tagaataaac atgctgctgc ttaccctctt   29220
tgtcctggcg ctggccgcca gctgccaagc cttttccgag gctgacttta tagagcccca   29280
```

```
gtgtaatgtg acttttaaag cccatgcaca gcgttgtcat actataatca aatgtgccac    29340
cgaacacgat gaataccttta tccagtataa agataaatca cacaaagtgg cacttgttga   29400
catctggaaa cccgaagacc ctttggaata caatgtgacc gttttccagg gtgacctctt    29460
caaaatttac aattcacttt tcccatttga ccagatgtgt gactttgtca tgtacatgga    29520
aaagcagcac aagctgtggc ctccgactcc ccagggctgt gtggaaaatc caggctcttt    29580
ctgcatgatc tctctctgtg taactgtgct ggcactaata ctcacgcttt tgtatatcag    29640
atttaaatca aggcaaagct tcattgatga aaagaaaatg ccttaatcgc tttcacgctt    29700
gattgctaac accgggtttt tatccgcaga atgattggaa tcaccctact aatcacctcc    29760
ctccttgcga ttgcccatgg gttggaacga atcgaagtcc ctgtgggggc caatgttacc    29820
ctggtggggc ctgtcggcaa tgctacatta atgtgggaaa aatatactaa aaatcaatgg    29880
gtctcttact gcactaacaa aaatagccac aagcccagag ccatctgcga tgggcaaaat    29940
ctaaccttga ttgatgttca attgctggat gcgggctact attatgggca gctgggtaca    30000
atgattaatt actggagacc ccacagagat tacatgctcc acgtagtaaa gggtcccctt    30060
agcagcccac ccactaccac ctctactacc cccactacca ccactactcc caccaccagc    30120
actgccgccc agcctcctca tagcagaaca accactttta tcaattccaa gtcccactcc    30180
ccccacattg ccggcgggcc ctccgcctca gactccgaaa ccaccgagat ctgcttctgc    30240
aaatgctctg acgccattgc ccaggatttg gaagatcacg aggaagatga gcatgacttc    30300
gcagatgcat gccaggcatc agagccagaa gcgctgccgg tggccctcaa acagtatgca    30360
gacccccaca ccaccccccga ccttcctcca ccttcccaga agccaagttt cctgggggaa    30420
aatgaaactc tgcctctctc catactcgct ctgacatctg ttgctatgtt gaccgctctg    30480
ctggtgcttc tatgctctat atgctacctg atctgctgca gaaagaaaaa atctcacggc    30540
catgctcacc agcccctcat gcacttccct taccctccag agctgggcga ccacaaactt    30600
taagtctgca gtaactatct gcccatccct tgtcagtcga cagcgatgag ccccactaat    30660
ctaacggcct ctggacttac aacatcgtct cttaatgaga ccaccgctcc tcaagacctg    30720
tacgatggtg tctccgcgct ggttaaccag tgggatcacc tgggcatatg gtggctcctc    30780
ataggagcag tgaccctgtg cctaatcctg gtctggatca tctgctgcat caaaagcaga    30840
agacccaggc ggcggcccat ctacaggccc tttgtcatca cacctgaaga tgatgatgac    30900
accacttcca ggctgcagag gctaaagcag ctactcttct cttttacagc atggtaaatt    30960
gaatcatgcc tcgcattttc atctacttgt ctctccttcc acttttttctg ggctcttcta    31020
cattggccgc tgtgtcccac atcgaggtag actgcctcac gcccttcaca gtctacctgc    31080
ttttcggctt tgtcatctgc acctttgtct gcagcgttat cactgtagtg atctgcttca    31140
tacagtgcat cgactacgtc tgcgtgcggg tggcttactt tagacaccac ccccagtatc    31200
gcaacaggga catagcggct ctcctaagac ttgtttaaaa tcatggccaa attaactgtg    31260
attggtcttc tgatcatctg ctgcgtccta gccgcgattg ggactcaagc tcctaccacc    31320
accagcgctc ccagaaagag acatgtatcc tgcagcttca agcgtccctg gaatataccc    31380
caatgcttta ctgatgaacc tgaaatctct ttggcttggt acttcagcgt caccgccctt    31440
cttatcttct gcagtacggt tattgccctt gccatctacc cttcccttga cctgggctgg    31500
aatgctgtca actctatgga atatcccacc ttcccagaac cagacctgcc agacctggtt    31560
gttctaaacg cgtttcctcc tcctgctccc gttcaaaatc agtttcgccc tccgtccccc    31620
acgcccactg aggtcagcta cttttaatcta acaggcggag atgactgaaa acctagacct    31680
```

```
agaaatggac ggtctctgca gcgagcaacg cacactagag aggcgccggc aaaaagagct    31740
cgagcgtctt aaacaagagc tccaagacgc ggtggccata caccagtgca aaaaaggtgt    31800
cttctgtctg gtaaaacagg ccacgctcac ctatgaaaaa acaggtgaca cccaccgcct    31860
aggatacaag ctgcccacac agcgccaaaa gttcgccctc atgataggcg aacaacccat    31920
caccgtgacc cagcactccg tggagacaga aggctgcata catgctccct gtagggcgc    31980 tgactgcctc tacaccttga tcaaaaccct ctgcggtctc agagacctta tccctttcaa    32040
ttaatcataa ctgtaatcaa taaaaaatca cttacttgaa atctgatagc aagcctctgt    32100
ccaatttttt cagcaacact tccttcccct cctcccaact ctggtactct aggcgcctcc    32160
tagctgcaaa cttcctccac agtctgaagg gaatgtcaga ttcctcctcc tgtccctccg    32220
cacccacgat cttcatgttg ttgcagatga acgcgcgag atcgtctgac gagaccttca    32280
accccgtgta ccctacgat accgagatcg ctccgacttc tgtcccttc cttacccctc    32340 cctttgtgtc atccgcagga atgcaagaaa atccagctgg ggtgctgtcc ctgcacttgt    32400
cagagcccct taccacccac aatggggccc tgactctaaa aatgggggc ggcctgaccc    32460 tggacaagga agggaatctc acttcccaaa acatcaccag tgtcgatccc cctctcaaaa    32520
aaagcaagaa caacatcagc cttcagaccg ccgcacccct cgccgtcagc tccggggccc    32580
taacactttt tgccactccc cccctagcgg tcagtggtga caaccttact gtgcagtctc    32640
aggcccctct cactttggaa gactcaaaac taactctggc caccaaagga ccctaactg    32700 tgtccgaagg caaacttgtc ctagaaacag aggctcccct gcatgcaagt gacagcagca    32760
gcctgggcct tagcgttacg gccccactta gcattaacaa tgacagccta ggactagatc    32820
tgcaggcacc cattgtctct caaaatggaa aactggctct aaatgtagca ggccccctag    32880
ctgtggccaa tggcattaat gctttgacag taggcacagg caaaggtatt ggtctaaatg    32940
aaaccagcac tcacttgcaa gcaaagttgg tcgcccccct aggctttgat accaatggca    33000
acattaagct aagcgttgca ggaggcatga gactaaataa tgcacacttt atactagatg    33060
taaactaccc atttgaagct caaggccaac taagtctaag agtgggccag ggtccgctgt    33120
atgtagattc tagcagccat aacctgacca ttagatgcct tagaggatta tacataacat    33180
cgtctaataa ccaaaccggt ctagaggcca acataaaact aacaaaaggc cttgtctatg    33240
atggaaatgc catagcagtc aatgttggtc aaggattgca atacagcact actgccacat    33300
cggaaggtgt gtatcctata cagtctaaga taggtttggg aatggaatat gataccaacg    33360
gagccatgat gacaaaacta ggctctggac taagctttga caattcagga gccattgtag    33420
tgggaaacaa aaatgatgac aggcttactc tgtggactac accagaccca tctcctaact    33480
gtagaattta ttctgaaaaa gatactaaac taaccttggt gctgactaag tgtggcagcc    33540
aaatcctagg cacagtatct gcccttgctg tcagaggcag ccttgcgccc atcactaatg    33600
catccagcat agtccaaata tttctaagat ttgatgaaaa tggactattg atgagcaact    33660
catcgctaga cggtgattac tggaattaca gaaatgggga ctccactaat agcacaccat    33720
atacaaatgc agtaggcttt atgcctaatc tagcagccta tcctaaaggt caggctacag    33780
ctgcaaaaag cagtattgta agccaggtat acatggatgg tgcacactact aaacctataa    33840 cactaaaaat aaacttcaat ggcattgatg aaacaacaga aaatacccct gttagtaaat    33900
attccatgac attctcatgg agctggccca ccgcaagcta cataggccac acttttgcaa    33960
caaactcttt tactttctcc tacatcgccc aagaataaag aaagcacaga gatgcttgtt    34020
```

```
ttgatttcaa aattgtgtgc ttttatttat tttcagctta cagtatttcc agtagtcatt    34080
cgaataaagc ttaatcaaac tgcatgagaa cccttccaca tagcttaaat tagcaccagt    34140
gcaaatggag aaaattcaac ataccttttt tatccagata tcagagaact ctagtggtca    34200
gttttccccc accctcccag ctcacagaat acacagtcct ttcccccccgg ctggctttaa    34260
acaacactat ctcattggta acagacatat tcttaggtgt aataatccac acggtctctt    34320
ggcgggccaa gcgctggtcg gtgatgttaa taaactcccc aggcagctct ttcaagttca    34380
cgtcgctgtc caactgctga agcgctcgcg gctccgactg cgcctctagc ggaggcaacg    34440
gcaacacccg atccttgatc tataaaggag tagagtcata atcccccata gaatagggc    34500
ggtgatgcag caacaaggcg cgcagcaact cctgccgccg cctctccgta cgacaggaat    34560
gcaacgcgt ggtggtctcc tccgcgataa tccgcaccgc tcgcagcatc agcatcctcg    34620
tcctccgggc acagcagcgc atcctgatct cactgagatc ggcgcagtaa gtgcagcaca    34680
aaaccaagat gttatttaag atcccacagt gcaaagcact gtacccaaag ctcatggcgg    34740
gaaggacagc ccccacgtga ccatcatacc agatccttag gtaaatcaaa tgacgacctc    34800
tcataaacac gctggacatg tacatcacct ccttgggcat gcgctgattc accacctctc    34860
gataccacaa gcatcgctga ttaattaaag accccctcaag caccatcctg aaccaggaag    34920
ccagcacctg accccccgcc aggcactgca gggaccccgg tgaattgcag tggcagtgaa    34980
gactccagcg ctcgtagccg tgaaccatag agccggtcat tatatccaca ttggcacaac    35040
acaaacacac tttcatacac ttttttcatga ttagcagctc ctctctagtc aggaccatat    35100
cccaaggaat cacccactct tgaatcaagg taaatcccac acagcagggc aggcctctca    35160
cataactcac gttatgcata gtgagcgtgt cgcaatctgg aaataccgga tgatcttcca    35220
tcaccgaagc tcgcgtctcc gtctcaaagg gaggtaaacg gtccctcgtg tagggacagt    35280
ggcgggataa tcgagatcgt gttgaacgta gagtcatgcc aaagggaaca gcggacgtac    35340
tcatatttcc tccagcagaa ccaagtgcgc gcgtggcagc tatccctgcg tcttctgtct    35400
cgccgcctgc cccgctcggt gtagtagttg taatacagcc actccctcag accgtcaagg    35460
cgctccctgg cgtccggatc tataacaaca ccgtcctgca gcgccgccct gatgacatcc    35520
accaccgtag agtatgccaa gcccagccag gaaatgcatt cactttgaca gcgagagata    35580
ggaggagcgg gaagagatgg aagaaccatg atagtaaaag acttttattc caatcgatcc    35640
tctacaatgt caaagtgtag atctataaga tgacactggt ctcctccgct gagtcgatca    35700
aaaataacag ctaaaccaca aacaacacga ttggtcaaat gctccacaag ggcttgcagc    35760
ataaaatcgc ctcgaaagtc caccgcaagc ataacatcaa agccaccgcc cctatcatga    35820
tctataataa aaaccccaca gctatccacc agacccataa agttttcatc tctccatcgt    35880
gaaaaaatat ttacaagctc ctcctttaaa tcacctccaa ccaattgaaa aagttgagcc    35940
aaaccgccct ccaccttcat tttcagcaag cgcatcatga ttgcaaaaat tcaggctcct    36000
gagacacctg tataagattg agaagcggaa cgttaacgtc aatgtttcgc tcgcgaagat    36060
cgcgcctcag tgcaagcatg atataatccc acaggtcgga gcggatcagc gaggacatct    36120
ccccgccagaa accaactca acggagccta tgctgattat aatacgcata ttcggggcta    36180
tgctgaccag cacggcccc aaataggcgt actgcatagg cggcgacaaa aagtgaacag    36240
tttgggttaa aaaatcaggc aaacagtcgc gcaaaaaagc aagaacatca taaccatgct    36300
catgcaaata gatgcaagta agctcaggaa cgaccacaga aaaatgcaca attttttctct    36360
caaacatgac tgcgagccct gcaaaaaata aaaaagaaac attacacaag agtagcctgt    36420
```

```
cttacgatgg gatagactac tctaaccaac ataagacggg ccacaacatc gcccgcgtgg   36480
ccataaaaaa aattgtccgt gtgattaaaa agaagcacag atagctggcc agtcatatcc   36540
ggagtcatca cgtgtgaacc cgtgtagacc cccgggttgg acacatcggc caaacaaaga   36600
aagcggccaa tgtacccagg aggaatcata acactaagac gaagatacaa cagaataacc   36660
ccatgagggg gaataacaaa gttagtaggt gaataaaaac gataaacacc cgaaactccc   36720
tcctgcgtag gcaaaatagc accctcccct tccaaaacaa catatagcgc ttccacagca   36780
gccatgacaa aagactcaaa acactcaaaa gactcagtct taccaggaaa ataaaagcac   36840
tctcacagca ccagcactaa tcagagtgtg aagagggcca agtgccgaac gagtatatat   36900
aggaataaaa aatgacgtaa atgtgtaaag gtcagaaaac gcccagaaaa atacacagac   36960
caacgcccga aacgaaaacc cgcgaaaaaa tacccgaaac ttcctcaaca accgccactt   37020
ccggtttctc acgtacgtc acttccgcaa gaaaagcaaa actacatttc ccacatgtgt   37080
aaaaacgaaa ccccgcccct tgtaactgcc cacaacttac atcatcaaaa cataaactcc   37140
tacgtcaccc gccccgcctc tccccgccca cctcattatc atattggcca caatccaaaa   37200
taaggtatat tat                                                     37213

<210> SEQ ID NO 24
<211> LENGTH: 37216
<212> TYPE: DNA
<213> ORGANISM: Gorilla beringei beringei

<400> SEQUENCE: 24
ataatatacc ttattttgga ttgtggccaa tatgataatg aggtgggcgg ggagaggcgg     60
ggcgggtgac gtaggacgcg cgagtagggt tgggaggtgt ggcggaagtg tggcatttgc    120
aagtgggagg agctcacatg caagcttccg tcgcggaaaa tgtgacgttt ttgatgagcg    180
ccgcctacct ccggaagtgc caattttcgc gcgcttttca ccggatatcg tagtaatttt    240
gggcgggacc atgtaagatt tggccatttt cgcgcgaaaa gtgaaacggg gaagtgaaaa    300
ctgaataata gggcgttagt catagcgcgt aatatttacc gagggccgag ggactttgac    360
cgattacgtg gaggactcgc ccaggtgttt tttacgtgaa tttccgcgtt ccgggtcaaa    420
gtctccgttt ttattgtcac cgtcatttga cgcggagggt atttaaaccc gctgcgctcc    480
tcaagaggcc actcttgagt gccagcgaga agagttttct cctctgctcc gcttcggtga    540
tcgaaaaatg agacacatag cctgcactcc gggtcttttg tccggtcggg cggcggccga    600
gcttttggac gctttgatca atgatgtcct aagcgatgat tttccgtcta ctacccactt    660
tagcccacct actcttcacg aactgtacga tctggatgta ctggtggatg tgaacgatcc    720
caacgaggag gcggtttctg cgttttttcc cgagtctgcg ctgttggccg ctcaggaggg    780
atttgaccta cacactccgc cgcctatttt agagtctccg ctgccggagc ccagtggtat    840
accttatatg cctgaactgc ttcccgaagt ggtagacctg acctgccacg agcctggctt    900
tccgcccagc gacgatgagg gtgagccttt tgttttagac tttgctgaga tacctgggca    960
cggttgcagg tcttgtgcat atcatcagag ggttaccgga gaccccgagg ttaagtgttc   1020
gctgtgctat atgaggatga cctcttcctt tatctacagt aagttttgt ctaggtgggc   1080 ttttgggtag gtgggttttg tgtcagaaca ggtgtaaacg ttgcttgtgt tttttgtacc   1140
tgtaggtccg gtgtccgagc cagacccgga gcccgaccgc gatcccgagc cggatcccga   1200
gcctcctcgc aggacaagga aactaccttc cattctgtgc aagtctcaga cacctgtaag   1260
```

```
gaccagcgag gcagacagca ccgactctgg cacttctacc tctcccctg aaattcaccc    1320
agtggttcct ctgggtatac ataaacctgt tgctgttaaa gtttgcgggc gacgccctgc    1380
agtacagtgc attgaggact tgcttcacga tcccgaggaa cctttggact tgagccttaa    1440
acgccctagg caataaaccc cacctaagta ataaaccca cctaagtaat aaaccctgcc      1500
gcccttggtt attgagatga cgcccaatgt ttgcttttga atgacttcat gtgtgtaata    1560
aaagtgagtg tgatcatagg tctcttgttt gtctgggcgg ggcttaaggg tatataagtc    1620
tcttggggct aaacttggtt acacttgacc ccaatggagg cgtggggtg cttggaggag      1680
tttgcggacg tgcgccgttt gctggacgag agctctagca ataccatac tatttggagg      1740
tatctgtggg gctctactca ggccaagttg gtttccagaa ttaagcagga ttacaagtgc    1800
gattttgaag agcttttag ttcctgcggt gagcttttgc aatccttgaa tctgggccat      1860
caggctattt tccaggaaaa ggttctctcg actttggatt tttccactcc cgggcgcacc    1920
gccgcttgtg tggcttttgt gtcttttgtg caagataaat ggagcgagga gacccacctg    1980
agtcacggct acgtactgga tttcatggcg atggctcttt ggagggctca caacaaatgg    2040
aagattcaga aggaactgta cggttccgcc ctacgtcgtc cacttctgtc gcgacagggg    2100
ctgaggtttc ccgaccatcg gcagcatcag aatctggaag acgagtcgga ggagcagcg      2160
gaggagaaga tcagcttgag agccggcctg daccctcctc aggaggaatg aatctcccgc    2220
aggtggttga cctgtttcca gaactgagac gggtcctgac tatcagggag gatggtcagt    2280
ttgtgaagaa gtttaagagg gatcggggtg agggagatga tgaggcggct agcaatttag    2340
cttttagtct gatgactcgc caccgaccgg aatgtattac ctatcagcag attaaggaga    2400
gttgtgccaa cgagctggat cttttgggtc agaagtatag catagaacag cttaccactt    2460
actggcttca gcctggggat gattgggaag aggcgatcag ggtgtatgca aaggtggccc    2520
tgcggcccga ttgcaagtat aagattacta agttggttaa tattagaaac tgctgctata    2580
tttctgggaa cggggccgaa gtggagatag atactcagga cagggtggct tttaggtgtt    2640
gcatgataaa catgtggccc gggatactgg ggatggatgg ggtggtattc atgaatgtga    2700
ggtttacggg ccccaacttt aatggcacgg tgttcatggg caacaccaac ttgctcctgc    2760
atggtgcgag tttctatggg tttaataaca cctgtataga ggcctggacc gatgtaaagg    2820
ttcgaggttt ttccttttat agctgttgga aggcggtggt gtgtcgccct aaaagcaggg    2880
gttctgtgaa aaaatgcttg tttgaaaggt gcaccttagg catcctctct gagggcaact    2940
ccagggtgcg ccataatgtg gcttcgaact gcggttgctt catgcaagtg aagggggtga    3000
gcgttatcaa gcataactcg gtgtgtggaa actgcgagga tcgcgcctcc cagatgctga    3060
cctgctttga tggcaactgt cacctgttga agaccattca tataagcagc cacccagaa      3120
aggcctggcc cgtgtttgag cataacatct tgacccgctg ctccttgcat ctgggggtca    3180
ggaggggtat gttcctgcct taccagtgta actttagcca cactaaaatc ctgctggaac    3240
ccgagtgcat gaccaaggtc agcctgaatg gtgtgtttga tgtgactctg aaaatctgga    3300
aggtgctgag gtatgatgag accaggacca ggtgccgacc ctgcgagtgc ggcggcaagc    3360
acatgagaaa tcagcctgtg atgttggatg tgaccgagga gcttaggcct gaccatctgg    3420
tgctggcctg caccagggcc gagtttgggt ctagcgatga ggataccgat tgaggtgggt    3480
aaggtggggcg tggctagaag ggtggggcgt gtataaattg ggggtctaag ggtctctctg    3540
ttttgtcttg caacagccgc cgccatgagc gacaccggca acagcttga tggaagcatc    3600
tttagcccct atctgacagt gcgcatgcct cactgggctg gagtgcgtca gaatgtgatg    3660
```

```
ggttccaacg tggatggacg ccccgttctg ccttcaaatt cgtctacaat ggcctacgcg    3720
accgtgggag gaactccgct ggacgccgcg acctccgccg ccgcctccgc cgccgccgcg    3780
accgcgcgca gcatggctac ggacctttac agctctttgg tggcgagcgg cgcggcctct    3840
cgcgcgtctg ctcgggatga gaaactgacc gctctgctgc ttaaactgga agacttgacc    3900
cgggagctgg gtcaactgac ccagcaggtc tccagcttgc gtgagagcag ccttgcctcc    3960
ccctaatggc ccataatata aataaaagcc agtctgtttg gattaagcaa gtgtatgttc    4020
tttatttaac tctccgcgcg cggtaagccc gggaccagcg gtctcggtcg tttagggtgc    4080
ggtggattct ttccaacacg tggtacaggt ggctctggat gtttagatac atgggcatga    4140
gtccatccct ggggtggagg tagcaccact gcagagcttc gtgctcgggg tggtgttgt     4200
atatgatcca gtcgtagcag gagcgctggg cgtggtgctg aaaaatgtcc ttaagcaaga    4260
ggcttatagc taggggaggg cccttggtgt aagtgtttac aaatctgctc agttgggagg    4320
ggtgcatccg gggggatata atgtgcatct tggactggat ttttaggttg ctatgttcc     4380
cacccagatc ccttctggga ttcatgttgt gcaggaccac cagcacggta tatccagtgc    4440
acttgggaaa tttatcgtgg agcttagacg ggaatgcatg gaagaacttg agacgccct     4500
tgtggcctcc cagattttcc atacattcgt ccatgatgat ggcaatgggc ccgtgggaag    4560
ctgcctgagc aaaaatgttt ctgggatcgc tcacatcgta gttatgttcc agggtgaggt    4620
catcatagga catctttacg aatcgggggc ggagggtccc ggactggggg atgatggtac    4680
cctcgggccc cggggcgtag ttcccctcac agatctgcat ctcccaggct ttcatttcag    4740
agggagggat catatccacc tgcggagcga tgaaaaacac agtttctggc gcaggggaga    4800
ttaactggga tgagagcagg tttctgagca gctgtgactt tccacagccg gtgggcccat    4860
atatcacgcc tatcaccggc tgcagctggt agttaagaga gctgcagctg ccgtcctccc    4920
ggagcagggg ggccacctcg ttcagcatat ccctgacgtg gatgttctcc ctgaccaatt    4980
ccgccagaag gcgctcgccg cccagcgaaa gcagctcttg caaggaagca aaattttttca   5040
gcggttttag gccgtcggcc gtgggcatgt ttttcagcgt ctgggtcagc agttccagcc    5100
tgtcccacag ctcggtgatg tgctctacgg catctcgatc cagcagatct cctcgtttcg    5160
cggggttgggg cggctttcgc tgtagggcac cagccgatgg gcgtccagcg ggccagagt    5220
catgtccttc catgggcgca gggtcctcgt cagggtggtc tgggtcacgg tgaaggggtg    5280
cgctccgggt tgggcgctgg ccagggtgcg cttgaggctg gttctgctgg tgctgaatcg    5340
ctgccgctct tcgccctgcg cgtcggccag gtagcatttg accatggtct cgtagtcgag    5400
accctcggcg gcgtgcccct tggcgcggag cttttcccttg gaggtggcgc gcacgaggg    5460
gcactgcagg ctcttcaggg cgtagagctt gggagcgaga acacggact ctggggagta     5520
ggcgtccgcg ccgcaggaag cgcagaccgt ctcgcattcc accagccaag tgagctccgg    5580
gcggtcaggg tcaaaaacca ggttgccccc atgcttttg atgcgtttct tacctcggct     5640
ctccatgagg cggtgtccct tctcggtgac gaagaggctg tccgtgtccc cgtagaccga    5700
cttcaggggc ctgtcttcca gcggagtgcc tctgtcctcc tcgtagagaa actctgacca    5760
ctctgagacg aaggcccgcg tccaggccag gacgaaggag gccacgtggg aggggtagcg    5820
gtcgttgtcc actagcgggt ccaccttctc cagggtgtgc aggcacatgt cccctcctc    5880
cgcgtccaga aaagtgattg gcttgtaggt gtaggcacacg tgaccgggg ttcccgacgg    5940
ggggtataa aaggggtgg gcgcccttc atcttcactc tcttccgcat cgctgtctgc       6000
```

```
gagggccagc tgctggggta agtattccct ctcgaaggcg ggcatgacct cagcgctcag    6060
gttgtcagtt tctaaaaatg aggaggattt gatgttcacc tgtccggagg tgatacccttt   6120 gagggtacct gggtccatct ggtcagaaaa cactattttt ttgttgtcaa gcttggtggc    6180
gaacgacccg tagagggcgt tggagagcag cttggcgatg gagcgcaggg tctggttttt    6240
gtcgcggtcg gctcgctcct tggccgcgat gttgagttgc acgtactcgc gggccacgca    6300
cttccactcg gggaagacgg tggtgcgctc gtctgggatt aggcgcaccc tccagcctcg    6360
gttgtgcagg gtgaccatgt cgacgctggt ggcgacctcg ccgcgcaggc gctcgttggt    6420
ccagcagagg cggccgccct tgcgcgagca aagggggggt aggggtcca gctggtcctc     6480 gtttgggggg tccgcgtcga tggtgaagac cccggggagc aagcgcgggt caaagtagtc    6540
gatcttgcaa gcttgcatgt ccagagcccg ctgccattcg cgggcggcga gcgcgcgctc    6600
gtaggggttg aggggcgggc cccagggcat ggggtgggtg agcgcggagg cgtacatgcc    6660
gcagatgtca tacacgtaca ggggttccct gaggatgccg aggtaggtgg ggtagcagcg    6720 cccccccgcgg atgctggcgc gcacgtagtc atagagctcg tgggaggggg ccagcatgtt  6780
gggcccgagg ttggtgcgct gggggcgctc ggcgcggaag gcgatctgcc tgaagatggc   6840
atgggagttg gaggagatgg tgggccgctg gaagacgttg aagcttgctt cttgcaagcc    6900
caccgagtcc ctgacgaagg aggcgtagga ctcgcgcagc ttgtgcacca gctcggcggt    6960
gacctggacg tcgagcgcgc agtagtcgag ggtctcgcgg atgatgtcat acttatcctc    7020 cccctttcttt ttccacagct cgcggttgag gacgaactct cgcggtctt tccagtactc   7080 ttggaggga aacccgtccg tgtccgaacg gtaagagcct agcatgtaga actggttgac    7140
ggcctggtag gggcaacagc ccttctccac gggcagcgcg taggcctgcg ccgccttgcg    7200
gagggaggtg tgggtgaggg cgaaagtgtc cctgaccatg actttgaggt attgatgttt    7260
gaagtctgtg tcatcgcagc cgccctgttc ccacagggtg tagtccgtgc gcttttgga     7320 gcgcgggttg ggcagggaga aggtgaggtc attgaagagg atcttccccg ctcgaggcat    7380
gaagtttctg gtgatgcgaa agggccctgg gaccgaggag cggttgttga tgacctgggc    7440
ggccaggacg atctcgtcaa agccgtttat gttgtggccc acgatgtaga gctccaaaaa    7500
gcggggctgg cccttgatgg aggggagctt tttgagttcc tcgtaggtga gctcctcggg    7560
cgattccagg ccgtgctcct ccagggccca gtcttgcaag tgaggggttgg ccgccaggaa   7620 ggatcgccag aggtcgcggg ccatgagggt ctgcaggcgg tcgcggaagg ttctgaactg    7680
tcgccccacg gccatctttt cggggtgat gcagtagaag gtgaggggt cttttctccca   7740 ggggtcccat ctgagctctc gggcgaggtc gcgcgcggcg gcgaccagag cctcgtcgcc    7800
ccccagtttc atgaccagca tgaagggcac gagctgcttg ccaaaggctc ccatccaagt    7860
gtaggtctct acatcgtagg tgacaaagag gcgctccgtg cgaggatgag agccgatcgg    7920
gaagaactgg atctcccgcc accagttgga ggattggctg ttgatgtggt gaaagtagaa    7980
gtcccgtctg cgggccgagc actcgtgctg gcttttgtaa aagcgaccgc agtactggca    8040
gcgctgcacg ggttgtatat cttgcacgag gtgaacctgg cgacctctga cgaggaagcg    8100
cagcgggaat ctaagtcccc cgcctggggt ccgtgtggc tggtggtctt ctactttggt     8160
tgtctggccg ccagcatctg tctcctggag ggcgatggtg gagcagacca ccacgccgcg    8220
agagccgcag gtccagatct cggcgctcgg cgggcggagt ttgatgacga catcgcgcac    8280
attggagctg tccatggtct ccagctcccg cggcggcagg tcagctggga gttcctggag    8340
gttcacctcg cagagacggg tcaaggcgcg ggcagtgttg agatggtatc tgatttcaag    8400
```

```
gggcgtgttg gcggcggagt cgatggcttg caggaggccg cagccccggg gggccacgat    8460
ggttccccgc ggggcgcgag gggaggcgga agctgggggt gtgttcagaa gcggtgacgc    8520
gggcgggccc ccggaggtag gggggttcc ggccccacag gcatgggcgg caggggcacg    8580
tcttcgccgc gcgcgggcag gggctggtgc tggctccgaa gagcgcttgc gtgcgcgacg    8640
acgcgacggt tggtgtcctg tatctgacgc ctctgagtga agaccacggg tcccgtgacc    8700
ttgaacctga aagagagttc gacagaatca atctcggcat cgttgacagc ggcctggcgc    8760
aggatctcct gcacgtcgcc cgagttgtcc tggtaggcga tctctgccat gaactgctcg    8820
atctcttctt cctggagatc tcctcgtccg gcgcgctcca cggtggccgc caggtcgttg    8880
gagatgcgac ccatgagctg tgagaaggcg ttgagcccgc cctcgttcca gacccggctg    8940
tagaccacgc cccctcggc gtcgcgagcg cgcatgacca cctgggccag gttgagctcc    9000
acgtgtcgcg tgaagacggc gtagttgcgc aggcgctgga aaaggtagtt cagggtggtg    9060
gcggtgtgct cggcgacgaa gaagtacatg acccagcgcc gcaacgtgga ttcattgatg    9120
tcccccaagg cctccaggcg ctccatggcc tcgtagaagt ccacggcgaa gttgaaaaac    9180
tgggagttgc gagcggacac ggtcaactcc tcctccagaa gacggatgag ctcggcgaca    9240
gtgttgcgca cctcgcgctc gaaggccacg gggcgcgctt cttcctcttc cacctcttct    9300
tccatgatcg cttcttcttc ttcctcagcc gggacgggag ggggcggcgg cggcggggga    9360
ggggcgcggc ggcggcggcg gcgcaccggg aggcggtcga tgaagcgctc gatcatctcc    9420
ccccgcatgc ggcgcatggt ctcggtgacg gcgcggccgt tctcccgggg gcgcagctcg    9480
aagacgccgc ctctcatctc gccgcggggc gagcggccgt gaggtagcga gacggcgctg    9540
actatgcatc ttaacaattg ctgtgtaggt acaccgccga gggacctgat tgagtccaga    9600
tccaccggat ccgaaaacct ttggaggaaa gcgtctatcc agtcgcagtc gcaaggtagg    9660
ctgagcaccg tggcgggcgg gggcgggtct ggagagttcc tggcggagat gctgctgatg    9720
atgtaattaa agtaggcggt cttgagaagg cggatggtgg acaggagcac catgtctttg    9780
ggtccggcct gttggatgcg gaggcggtcg gccatgcccc aggcctcgtt ctgacaccgg    9840
cgcaggtctt tgtagtagtc ttgcatgagt cttttccaccg gcacctcttc tccttcctct    9900
tctccatctc gccggtggtt tctcgcgccg cccatgcgcg tgaccccaaa gcccctgagc    9960
ggctgcagca gggccaggtc ggcgaccacg cgctcggcca agatggcctg ctgcacctga   10020
gtgagggtcc tctcgaagtc atccatgtcc acgaagcggt ggtaggcgcc cgtgttgatg   10080
gtgtaggtgc agttggccat gacgaccag ttgacggtct ggtgtcccgg ctgcgagagc   10140
tccgtgtacc gcaggcgcga gaaggcgcgg gaatcgaaca cgtagtcgtt gcaagtccgc   10200
accagatact ggtagcccac caggaagtgc ggcggaggtt ggcgatagag gggccagcgc   10260
tgggtggcgg gggcgccggg cgccaggtct tccagcatga ggcggtggta tccgtagatg   10320
tacctggaca tccaggtgat gccggcgcg gtggtggtgg cgcgcgcgta gtcgcggacc   10380
cggttccaga tgtttcgcag gggcgagaag tgttccatgg tcggcacgct ctggccggtg   10440
aggcgcgcgc agtcgttgac gctctataca cacacaaaaa cgaaagcgtt tacagggctt   10500
tcgttctgta gcctggagga aagtaaatgg gttgggttgc ggtgtgcccc ggttcgagac   10560
caagctgagc tcggccggct gaagccgcag ctaacgtggt attggcagtc ccgtctcgac   10620
ccaggccctg tatcctccag gatacggtcg agagcccttt tgctttcttg gccaagcgcc   10680
cgtggcgcga tctgggatag atggtcgcga tgagaggaca aaagcggctc gcttccgtag   10740
```

```
tctggagaaa caatcgccag ggttgcgttg cggcgtaccc cggttcgagc ccctatggcg   10800
gcttgaatcg gccggaaccg cggctaacga gggccgtggc agcccgtcc tcaggacccc    10860
gccagccgac ttctccagtt acgggagcga gcccttttg ttttttattt tttagatgca    10920
tcccgtgctg cggcagatgc gcccctcgcc ccggccgat cagcagcagc aacagcaggc    10980
atgcagaccc ccctctcccc tttccgcccc ggtcaccacg gccgcggcgg ccgtgtcggg   11040
cgcggggggc gcgctggagt cagatgagcc accgcggcgg cgacctaggc agtatctgga   11100
cttggaagag ggcgagggac tggcgcggct gggggcgaac tctccagagc gccacccgcg   11160
ggtgcagttg aaaagggacg cgcgcgaggc gtacctgccg cggcagaacc tgtttcgcga   11220
ccgcgggggc gaggagcccg aggagatgcg agactgcagg ttccaagcgg ggcgcgagct   11280
gcggcgcggg ctggacagac agcgcctgct gcgcgaggag gactttgagc ccgacacga    11340
gacgggcatc agccccgcgc gcgcgcacgt agccgcggcc gacctggtga ccgcctacga   11400
gcagacggta aaccaggagc gcaacttcca aaagagcttc aacaaccacg tgcgcacgct   11460
ggtggcgcgc gaggaggtga ccctgggtct catgcatctg tgggacctgg tggaggcgat   11520
cgtgcagaac cccagcagca agcccctgac cgcgcagctg ttcctggtgg tgcagcacag   11580
caggacaac gaggccttca gggaggcgct gctgaacatc accgagccgg aggggcgctg    11640
gctcctggac ctgataaaca tcctgcagag catagtggtg caggagcgca gcctgagcct   11700
ggccgagaag gtggcggcca tcaactactc tatgctgagc ctgggcaagt tctacgcccg   11760
caagatctac aagaccccct acgtgccat agacaaggag gtgaagatag acagcttcta    11820
catgcgcatg gcgctgaagg tgctgaccct gagcgacgac ctgggagtgt accgcaacga   11880
gcgcatccac aaggccgtga gcgccagccg gcggcgcgag ctgagcgacc gcgagctgat   11940
gcacagtctg cagcgcgcgc tgaccggcgc gggcgaggc gacagggagg tcgagtccta    12000
cttcgacatg ggggccgacc tgcactggca gccgagccgc cgcgccctgg aggcggcggg   12060
ggcgtacggc ggccccctgg cggccgatga ccaggaagag gaggactatg agctagagga   12120
gggcgagtac ctggaggact gacctggctg gtggtgtttt ggtatagatg caagatccga   12180
acgtggcgga cccggcggtc cggcggcgc tgcaaagcca gccgtccggc attaactcct    12240
ctgacgactg ggccgcggcc atgggtcgca tcatggccct gaccgcgcgc aaccccgagg   12300
ctttcaggca gcagcctcag gccaaccggc tggcggccat cttggaagcg gtagtgcccg   12360
cgcgctccaa ccccacccac gagaaggtgc tggccatagt caacgcgctg gcggagagca   12420
gggccatccg cgcggacgag gccggactgg tgtacgatgc gctgctgcag cgggtggcgc   12480
ggtacaacag cggcaacgtg cagaccaacc tggaccgcct ggtgacggac gtgcgcgagg   12540
ccgtggcgca gcgcgagcgc ttgcatcagg acggtaacct gggctcgctg gtggcgctaa   12600
acgccttcct cagcacccag ccggccaacg taccgcgggg gcaggaggac tacaccaact   12660
ttttgagcgc gctgcggctg atggtgaccg aggtccctca gagcgaggtg taccagtcgg   12720
ggcccgacta cttcttccag accagcagac agggcttgca aaccgtgaac ctgagccagg   12780
ctttcaagaa cctgcggggg ctgtgggag tgaaggcgcc caccggcgac cgggctacgg    12840
tgtccagcct gctaaccccc aactcgcgcc tgctgctgct gctgatcgcg cccttcacgg   12900
acagcgggag cgtctcgcgg gagacctatc tgggccacct gctgacgctg taccgcgagg   12960
ccatcgggca ggcgcaggtg gacgagcaca ccttccaaga gatcaccagc gtgagccacg   13020
cgctggggca ggaggacacg ggcagcctgc aggcgaccct gaactacctg ctgaccaaca   13080
ggcggcagaa gattcccacg ctgcacagcc tgacccagga ggaggagcgc atcttgcgct   13140
```

```
acgtgcagca gagcgtgagc ctgaacctga tgcgcgacgg cgtgacgccc agccgtggcgc   13200 tggacatgac cgcgcgcaac atggaaccgg gcatgtacgc ctcccaccgg ccgtttatca   13260
accgcctgat ggactacttg catcgggcgg cggccgtgaa ccccgagtac ttcactaatg   13320
ccattctgaa tccccactgg atgccccctc cgggtttcta caacggggac tttgaggtgc   13380
ccgaggtcaa cgacgggttc ctctgggatg acatggatga cagtgtgttc tcacccaacc   13440
cgctgcgcgc cgcgtctctg cgattgaagg agggctctga cagggaagga ccgaggagtc   13500
tggcctcctc cctggctctg ggagcggtgg gcgccacggg cgcggcggcg cggggcagta   13560
gccccttccc cagcctggca gactctctga cagcgggcg ggtgagcagg ccccgcttgc   13620
taggcgagga ggagtatctg aacaactccc tgctgcagcc cgcgagggac aagaacgctc   13680
agcggcagca gtttcccaac aatgggatag agagcctggt ggacaagatg tccagatgga   13740
agacgtatgc gcaggagtac aaggagtggg aggaccgcca gccgcggccc ttgccgcccc   13800
ctaggcagcg ctggcagcgg cgcgcgtcca accgccgctg gaggcagggg cccgaggacg   13860
atgatgactc tgcagatgac agcagcgtgt tggacctggg cgggagcggg aaccccttt   13920 cgcacctgcg cccacgcctg ggcaagatgt tttaaaagaa aaaaaaaaat aaaactcacc   13980
aaggccatgg cgacgagcgt tggtttttg ttcccttcct tagtatgcgg cgcgcggcga   14040
tgttcgagga ggggcctccc ccctcttacg agagcgcgat ggggatttct cctgcgcgc   14100 ccctgcagcc tccctacgtg cctcctcggt acctgcaacc tacaggggg agaaatagca   14160 tctgttactc tgagctgcag cccctgtacg ataccaccag actgtacctg gtggacaaca   14220
agtccgcgga cgtggcctcc ctgaactacc agaacgacca cagcgatttt ttgaccacgg   14280
tgatccaaaa caacgacttc accccaaccg aggccagcac ccagaccata aacctggata   14340
acaggtcgaa ctggggcggc gacctgaaga ccatcttgca caccaacatg cccaacgtga   14400 acagttcat gttcaccaac tcttttaagg cgcgggtgat ggtggcgcgc gagcagggg   14460 aggcgaagta cgagtgggtg gacttcacgc tgcccgaggg caactactca gagaccatga   14520
ctctcgacct gatgaacaat gcgatcgtgg aacactatct gaaagtgggc aggcagaacg   14580
gggtgaagga aagcgatatc ggggtcaagt ttgacaccaa aaacttccgt ctgggctggg   14640
accccgtgac cggcgctggtc atgccggggg tctacaccaa cgaggccttt catcccgaca   14700
tagtgcttct gcccggctgt ggggtggact tcacccagag ccggctgagc aacctgctgg   14760
gcattcgcaa gcggcagcct ttccaggagg gtttcaagat cacctatgag gatctgaagg   14820
ggggcaacat tcccgcgctc cttgatctgg acgcctacga ggagagcttg aaacccgagg   14880
agagcgctgg cgacagcggc gagagtggcg aggagcaagc cggcggcggt ggcggcgcgt   14940
cggtagaaaa cgaaagtacg cccgcagtgg cggcggacgc tgcggaggtc gagccggagg   15000
ccatgcagca ggacgcagag gagggcgcac aggagggcgc gcagaaggac atgaacgatg   15060
gggagatcag gggagacaca ttcgccaccc ggggcgaaga aaagaggca gaggcggcgg   15120 cggcggcgac ggcggaggcc gaaaccgagg ttgaggcaga ggcagagccc gagaccgaag   15180
ttatggaaga catgaatgat ggagaacgta ggggcgacac gttcgccacc cggggcgaag   15240
agaaggcggc ggaggcagaa gccgcggctg aggaggcggc tgcggctgcg gccaagactg   15300
aggctgcggc taaggctgag gtcgaagcca atgttgcggt tgaggctcag gctgaggagg   15360
aggcggcggc tgaagcagtt aaggaaaagg cccaggcaga gcaggaagag aaaaaacctg   15420
tcattcaacc tctaaaagaa gatagcaaaa agcgcagtta caacgtcatc gagggcagca   15480
```

```
cctttaccca gtaccgcagc tggtacctgg cgtacaacta cggcgacccg gtcaaggggg   15540
tgcgctcgtg gaccctgctc tgcacgccgg acgtcacctg cggctccgag cagatgtact   15600
ggtcgctgcc gaacatgatg caagacccgg tgaccttccg ctccacgcgg caggttagca   15660
acttcccggt ggtgggcgcc gaactgctgc ccgtgcactc caagagtttt tacaacgagc   15720
aggccgtcta ctcccagctg atccgccagg ccacctctct gacccacgtg ttcaatcgct   15780
ttcccgagaa ccagattttg gcgcgccccg cggcccccac catcaccacc gtgagtgaaa   15840
acgttcctgc cctcacagat cacgggacgc taccgctgcg caacagcatc tcaggagtcc   15900
agcgagtgac cattactgac gccagacgcc ggacctgccc ctacgtttac aaggccttgg   15960
gcatagtctc gccgcgcgtc ctctccagtc gcactttta aaacacatct acccacacgt   16020
tccaaaatca tgtccgtact catctcaccc agcaacaaca ccggctgggg gctgcgcgcg   16080
cccagcaaga tgtttggagg ggcgaggaag cgctccgacc agcaccctgt gcgcgtgcgc   16140
ggccactacc gcgcgccctg gggagcgcac aagcgcgggc gcacagggcg caccactgtg   16200
gacgacgtca ttgactccgt agtggagcaa gcgcgccact acacacccgg cgcgccgacc   16260
gcccccgccg tgtccaccgt ggaccaggcg atcgaaagcg tggtacaggg cgcgcggcac   16320
tatgccaacc ttaaaagtcg ccgccgccgc gtggcccgcc gccatcgccg gagacccgg   16380 gccaccgccg ccgcgcgcct tactaaggct ctgctcaggc gcgccaggcg aactggccac   16440
cgggccgcca tgagggccgc acggcgggct gccgctgccg caagcgtcgt ggccccgcgg   16500
gcacgaaggc gcgcggccgc tgccgccgcc gccgccattt ccagcttggc ctcgacgcgg   16560
cgcggtaaca tatactgggt gcgcgactcg gtaaccggca cgcgggtacc cgtgcgcttt   16620
cgccccccgc ggaattagca caagacaaca tacacactga gtctcctgct gttgtgtatc   16680
ccagcggcga ccgtcagcag cggcgacatg tccaagcgca aaattaaaga agagatgctc   16740
caggtcatcg cgccggagat ctatgggccc ccgaagaagg aggaggatga ttacaagccc   16800
cgcaagctaa agcgggtcaa aaagaaaaag aaagatgatg atgacgaggc ggtggagttt   16860
gtccgccgca tggcacccag gcgccccgtg cagtggaagg gccggcgcgt gcagcgcgtt   16920
ttgcgccccg gcaccgcggt ggtcttcacg cccggcgagc gctccacgcg cacttttcaag   16980 cgggtgtacg atgaggtgta cggcgacgag gacctgttgg agcaggccaa ccagcgcttt   17040
ggggagtttg catatgggaa acggccccgc gagagtctaa aagaggacct gctggcgcta   17100
ccgctggacg agggcaatcc caccccgagt ctgaagccgg taaccctgca acaggtgctg   17160
cctttgagcg cgcccagcga gcataagcga gggttgaagc gcgaaggcgg ggacctggcg   17220
cccaccgtgc agttgatggt gcccaagcgg cagaagctgg aggacgtgct ggagaaaatg   17280
aaagtagagc ccgggatcca gcccgagatc aaggtccgcc ccatcaagca ggtggcgccc   17340
ggcgtgggag tccagaccgt ggacgttagg attcccacgg aggagatgga aacccaaacc   17400
gccactccct cttcggcggc cagcgccacc accggcaccg cttcggtaga ggtgcagacg   17460
gacccctggc tacccgccac cgctgttgcc gccgccgccc ccgttcgcg cgggcgcaag   17520 agaaattatc cagcggccag cgcgctcatg ccccagtacg cactgcatcc atccatcgtg   17580 cccaccccg gctaccgcgg gtactcgtac cgccgcgca gatcagccgg cactcgcggc   17640
cgccgccgcc gtgcgaccac aaccagccgc cgccgtcgcc gccgccgcca gccagtgctg   17700 accccgtgt ctgtaaggaa ggtggctcgc tcggggagca cgctggtggt gcccagagcg   17760
cgctaccacc ccagcatcgt ttaaagccgg tctctgtatg gttcttgcag atatggccct   17820
cacttgtcgc ctccgcttcc cggtgccggg ataccgagga agaactcacc gccgcagagg   17880
```

```
catggcgggc agcggtctcc gcggcggccg tcgccatcgc cggcgcgcaa aaagcaggcg    17940
catgcgcggc ggtgtgctgc ctctgctaat cccgctaatc gccgcggcga tcggtgccgt    18000
acccgggatc gcctccgtgg ccctgcaggc gtcccagaaa cgttgactct tgcaaccttg    18060
caagcttgca ttttttggag gaaaaaataa aaaaaagtc tagactctca cgctcgcttg    18120
gtcctgtgac tattttgtag aaaaaaagat ggaagacatc aactttgcgt cgctggcccc    18180
gcgtcacggc tcgcgcccgt tcatgggaga ctggacagat atcggcacca gcaatatgag    18240
cggtggcgcc ttcagctggg gcagtctgtg gagcggcctt aaaaattttg gttccaccat    18300
taagaactat ggcaacaaag cgtggaacag cagcacgggc cagatgctga gagacaagtt    18360
gaaagagcag aacttccagg agaaggtggc gcagggcctg gcctctggca tcagcggggt    18420
ggtggacata gctaaccagg ccgtgcagaa aaagataaac agtcatctgg accccgtcc    18480
tcaggtggag gaaatgcctc cagcgatgga gacggtgtct cccgagggca aaggcgaaaa    18540
gcgcccgcgg cccgacagag aagagaccct ggtgtcacac accgaggagc cgccctctta    18600
cgaggaggca gtcaaggccg gcctgcccac cactcgcccc atagccccca tggccaccgg    18660
tgtggtgggc cacaggcaac acactcccgc aacactagat ctgcccccgc cgtccgagcc    18720
gccgcgccag ccaaaggcgg cgacggtgcc cgctccctcc acttccgccg ccaacagagt    18780
gccctgcgc cgcgccgcga gcggccccg ggcctgcga gttagcggca actggcagag    18840
cacactgaac agcatcgtgg gcctgggagt gaggagtgtg aagcgccgcc gttgctactg    18900
aatgagcaag ctagctaacg tgttgtatgt gtgtatgcgt cctatgtcgc cgccagagga    18960
gctgttgagc cgccggcgcc gtctgcactc cagcgaattt caagatggcg accccatcga    19020
tgatgcctca gtggtcgtac atgcacatct cgggccagga cgcttcggag tacctgagcc    19080
ccgggctggt gcagttcgcc cgcgccacag acacctactt caacatgagt aacaagttca    19140
ggaaccccac tgtggcgccc acccacgatg tgaccacgga ccggtcgcag cgcctgacgc    19200
tgcggttcat ccccgtggat cgggaggaca ccgcctactc ttacaaggcg cggttcacgc    19260
tggccgtggg cgacaaccgc gtgctggaca tggcctccac ttactttgac atcagggggg    19320
tgctggacag ggcccccacc ttcaagccct actcgggtac tgcctacaac tccctggccc    19380
ccaagggcgc tcccaattct tgcgagtggg aacaagatga accagctcag gcagcaatag    19440
ctgaagatga agaagaactt gaagaagaac aagctcagga cgaacaggcg cccactaaga    19500
aaacccatgt atacgcccag gcacctcttt ctggtgaaaa aattactaag gatggtttgc    19560
aaataggtgt ggatgccaca caggcgggag ataaccctat atatgctgat aaaacattcc    19620
aacccgaacc tcagataggt gagtctcagt ggaacgaggc tgatgccaca gtagcaggag    19680
gcagagtctt aaaaaagacc accctatga gaccttgcta tggatcctat gccaaaccta    19740
ctaatgccaa tggcggtcaa gggatcatgg tggccaatga tcagggagcg cttgaatcta    19800
aagttgagat gcaatttttc tccaccacaa cgtctcttaa tgtaagggaa ggtgaaaaca    19860
atcttcagcc aaaagtagtg ctatacagcg aagatgttaa cttggaatcc cctgacactc    19920
atttgtctta caaacctaaa aaggatgaca ccaactctaa aatcatgttg ggtcagcaag    19980
ccatgcccaa cagacccaac ctcattgctt ttagggacat cttattgga cttatgtact    20040
acaacagcac aggcaacatg ggagtgctgg caggacaggc ctcccagcta aacgctgtgg    20100
tagacttgca agacagaaac acagagctgt cataccaact gatgcttgat tccattggag    20160
acagatcaag atacttttcc atgtggaacc aggcagtgga cagctatgac ccagatgtca    20220
```

```
gaatcattga aaaccatggg gttgaagatg agctgcccaa ctattgcttt ccccctgggcg   20280 gtattggaat tacagacaca taccagtgca taaaaccaac cgcagctgct aataacacta   20340
catggtctaa ggatgaagaa tttagtgatc gcaatgaaat aggggtggga aacaacttcg   20400
ccatggagat caacatccag gccaacctct ggaggaactt cctctatgcg aacgtggggc   20460
tctacctgcc agacaagctc aagtacaacc ccaccaacgt ggacatctct gacaacccca   20520
acacctatga ctacatgaac aagcgtgtgg tggctcccgg cctggtggac tgctttgtca   20580
atgtgggagc caggtggtcc ctggactaca tggacaacgt caaccccttc aaccaccacc   20640
gcaatgcggg tctgcgctac cgctccatga tcctgggcaa cgggcgctac gtgcccttcc   20700
acattcaggt gccccagaag ttctttgcca tcaagaacct cctcctcctg ccgggctcct   20760
acacttacga gtggaacttc aggaaggatg tcaacatggt cctgcagagc tctctgggca   20820
atgaccttag ggtggacggg gccagcatca agtttgacag cgtcaccctc tatgctacct   20880
tcttccccat ggctcacaac accgcctcca cgctcgaggc catgctgagg aacgacacca   20940
acgaccagtc cttcaatgac tacctctctg ggccaacat gctctacccc atccccgcca   21000
aggccaccaa cgtgcccatc tccattccct ctcgcaactg gccgccttc agaggctggg   21060 cctttacccg ccttaagacc aaggaaaccc cctccctggg ctcgggtttt gacccctact   21120
ttgtctactc gggatccatc ccctacctgg atggcacctt ctacctcaac cacacttttta   21180 agaagatatc catcatgtat gactcctccg tcagctggcc gggcaatgac cgcctgctca   21240
cccccaatga gttcgaggtc aagcgcgccg tggacggcga gggctacaac gtggcccagt   21300
gcaacatgac caaggactgg ttcctggtgc agatgctggc caactacaac ataggctacc   21360
agggcttcta catcccagag agctacaagg acaggatgta ctccttcttc agaaatttcc   21420
aacccatgag caggcaggtg gtggacgaga ccaaatacaa ggactatcag gccattggca   21480
tcactcacca gcacaacaac tcgggattcg tgggctacct ggctccacc atgcgcgagg   21540 ggcaggccta ccccgccaac ttcccctacc cgttgatagg caaaaccgcg gtcgacagcg   21600
tcacccagaa aaagttcctc tgcgaccgca ccctctggcg catccccttc tctagcaact   21660
tcatgtccat gggtgcgctc acggacctgg gccagaacct gctctatgcc aactccgccc   21720
atgcgctgga catgactttt gaggtggacc ccatggacga gcccacccttt ctctatattg   21780 tgtttgaagt gttcgacgtg gtcagagtgc accagccgca ccgcggtgtc atcgagaccg   21840
tgtacctgcg cacgcccttc tcggccggca acgccaccac ctaaggagac agcgccgccg   21900
cctgcatgac gggttccacc gagcaagagc tcagggccat cgccagagac ctgggatgcg   21960
gaccctattt tttgggcacc tatgacaaac gcttcccggg cttcatctcc cgagacaagc   22020
tcgcctgcgc catcgtcaac acggccgcgc gcgagaccgg gggcgtgcac tggctggcct   22080
ttggctggga cccgcgctcc aaaacctgct acctcttcga cccctttggc ttctccgatc   22140
agcgcctcag acagatctat gagtttgagt acgagggggct gctgcgccgc agcgcgcttg   22200
cctcctcgcc cgaccgctgc atcacccttg agaagtccac cgagaccgtg caggggcccc   22260
actcggccgc ctgcggtctc ttctgctgca tgtttttgca cgcctttgtg cgctggcccc   22320
agagtcccat ggatcgcaac cccaccatga acttgctcaa gggagtgccc aacgccatgc   22380
tccagagccc ccaggtccag cccaccctgc gccacaacca ggaacagctc taccgcttcc   22440
tggagcgcca ctcccctac ttccgcagtc acagcgcgca catccgggg gccacctctt   22500 tctgccactt gcaagaaaac atgcaagacg gaaaatgatg tacagctcgc tttttaataa   22560
atgtaaagac tgtgcacttt atttatacac gggctctttc tggttatta tcaacaccg   22620
```

```
ccgtcgccat ctagaaatcg aaagggttct gccgcgcgtc gccgtgcgcc acgggcagag   22680
acacgttgcg atactggaag cggctcgccc acttaaactc gggcaccacc atgcggggca   22740
gtggttcctc ggggaagttc tcgccccaca gggtgcgggt cagctgcagc gcgctcagga   22800
ggtcgggagc cgagatcttg aagtcgcagt tggggccgga accctgcgcg cgcgagttgc   22860
ggtacacggg gttgcagcac tggaacacca gcagggccgg attatgcacg ctggccagca   22920
ggctctcgtc gctgatcatg tcgctgtcca gatcctccgc gttgctcagg gcgaacgggg   22980
tcatcttgca gacctgcctg cccaggaaag gcggcagccc gggcttgccg ttgcagtcgc   23040
agcgcagggg catcagcagg tgcccgcggc ccgactgcgc ctgcgggtac agcgcgcgca   23100
tgaaggcttc gatctgcctg aaagccacct gcgtcttggc tccctccgaa aagaacatcc   23160
cacaggactt gctggagaac tggttcgcgg acagctggc atcgtgcagg cagcagcgcg    23220
cgtcggtgtt ggcgatctgc accacgttgc gaccccaccg gttcttcact atcttggcct   23280
tggaagcctg ctccttcagc gcgcgctggc cgttctcgct ggtcacatcc atctctatca   23340
cctgctcctt gttgatcatg tttgtaccgt gcagacactt caggtcgccc tccgtctggg   23400
tgcagcggtc ctcccacagc gcgcaaccgg tgggctccca attttgtgg gtcacccccg    23460
cgtaggcctg caggtaggcc tgcaagaagc gccccatcat ggccacaaag gtcttctggc   23520
tcgtaaaggt cagctgcagg ccgcgatgct cttcgttcag ccaggtcttg cagatggcgg   23580
ccagcgcctc ggtctgctcg ggcagcatcc taaaatttgt cttcaggtcg ttatccacgt   23640
ggtacttgtc catcatggcg cgcgccgcct ccatgcccct tctcccaggcg acaccatgg   23700
gcaggcttag ggggtttatc acttccaccg gcgaggacac cgtactttcg atttcttctt   23760
cctcccccctc ttcccggcgc gcgcccacgc tgctgcgcgc tctcaccgcc tgcaccaagg   23820
ggtcgtcttc aggcaagcgc cgcaccgagc gcttgccgcc cttgacctgc ttaatcagca   23880
ccggcgggtt gctgaagccc accatggtca gcgccgcctg ctcttcttcg tcttcgctgt   23940
ctaccactat ctctggggaa gggcttctcc gctctgcggc ggcgcgcttc ttttttttct   24000
tgggagcggc cgtgatggag tccgccacgg cgacggaggt cgaggcgtg gggctggggg    24060
tgcgcggtac cagggcctcg tcgccctcgg actcttcctc tgactccagg cggcggcgga   24120
gtcgcttctt tggggcgcg cgcgtcagcg gcggcggaga cggggacggg gacggggacg    24180
ggacgccctc cacaggggt ggtcttcgcg cagacccgcg gccgcgctcg gggtcttct     24240
cgagctggtc ttggtcccga ctggccattg tatcctcctc ctcctaggca gagagacata   24300
aggagtctat catgcaagtc gagaaggagg agagcttaac caccccctct gagaccgccg   24360
atgcgcccgc cgtcgccgtc gccccgcctg ccgccgacgc gcccgccaca ccgagcgaca   24420
ccccccgcgga ccccccgcc gacgcacccc tgttcgagga gcggccgtg gagcaggacc    24480
cgggctttgt ctcggcagag gaggatttgc gagaggagga ggataaggag aagaagccct   24540
cagtgccaaa agatgataaa gagcaagacg agcacgacgc agatgcacac cagggtgaag   24600
tcgggcgggg ggacggaggg catgacggcg ccgactacct agacgaaggg aacgacgtgc   24660
tcttgaagca cctgcatcgt cagtgcgcca ttgtttgcga cgctctgcag gagcgcagcg   24720
aagtgcccct cagcgtggcg gaggtcagcc acgcctacga gctcagcctc ttctcccccc   24780
gggtgcccc cgccgccgc gaaaacggca catgcgagcc caacccgcgc ctcaacttct     24840
accccgcctt tgtggtaccc gaggtcctgg ccacctatca catcttcttt caaaattgca   24900
agatcccct ctcgtgccgc gccaaccgta gccgcgccga taagatgctg gccctgcgcc    24960
```

```
agggcgacca catacctgat atcgccgctt ggaagatgt accaaagatc ttcgagggtc   25020
tgggtcgcaa cgagaagcgg gcagcaaact ctctgcaaca ggaaaacagc gaaaatgaga   25080
gtcacaccgg ggtactggtg gagctcgagg gcgacaacgc ccgcctggcg gtggtcaagc   25140
gcagcatcga ggtcacccac tttgcctacc ccgcgctaaa cctgccccccc aaagtcatga  25200
acgcggccat ggacgggctg atcatgcgcc gcggccggcc cctcgctcca gatgcaaact   25260
tgcatgagga gaccgaggac ggccagcccg tggtcagcga cgagcagctg gcgcgctggc   25320
tggagaccgc ggaccccgcc gaactggagg agcggcgcaa gatgatgatg gccgtggtgc   25380
tggtcaccgt agagctggag tgtctgcagc gcttcttcgg cgaccccgag atgcagagaa   25440
aggtcgagga gaccctgcac tacaccttcc gccagggcta cgtgcgccag gcttgcaaga   25500
tctccaacgt ggagctcagc aacctggtgt cctacctggg catcttgcat gagaaccgcc   25560
tcgggcagag cgtgctgcac tccaccctgc gcggggaggc gcgccgcgac tacgtgcgcg   25620
actgcgttta cctcttcctc tgctacacct ggcagacggc catgggggtc tggcagcagt   25680
gcctggagga gcgcaacctc aaggagctgg agaagctcct gcagcgcgcg ctcaaagatc   25740
tctggacggg ctacaacgag cgctcggtgg ccgccgcgct ggccgacctc atcttccccg   25800
agcgcctgct caaaaccctc cagcaggggc tgcccgactt caccagccaa agcatgttgc   25860
aaaacttcag gaactttatc ctggagcgtt ctggcatcct acccgccacc tgctgcgccc   25920
tgcccagcga ctttgtcccc ctcgtgtacc gcgagtgccc ccgccgctg tggggtcact   25980
gctacctgtt ccaactggcc aactacctgt cctaccacgc ggacctcatg gaggactcca   26040
gcggcgaggg gctcatggag tgccactgcc gctgcaacct ctgcacgccc caccgctccc   26100
tggtctgcaa cacccaactg ctcagcgaga gtcagattat cggtaccttc gagctacagg   26160
gtccgtcctc ctcagacgag aagtccgcgg ctccgggct aaaactcact ccggggctgt    26220
ggacttccgc ctacctgcgc aaatttgtac ctgaagacta ccacgcccac gagatcaggt   26280
tttacgaaga ccaatcccgc ccgcccaagg cggagctgac cgcctgcgtc atcccccagg   26340
gcgagatcct aggccaattg caagccatcc aaaaagcccg ccaagacttt tgctgaaga   26400
agggtcgggg ggtgtatctg gaccccccagt cgggtgagga gctcaacccg gttccccccgc   26460
tgccgccgcc gcgggaccttt gcttcccagg ataagcatcg ccatggctcc cagaaagaag   26520
cagcagcggc cgccactgcc gccacccccac atgctggagg aagaggagga atactgggac   26580
agtcaggcag aggaggtttc ggacgaggag gagccggaga cggagatgga agagtgggag   26640
gaggacagct tagacgagga ggcttccgaa gccgaagagg cagacgcaac accgtcaccc   26700
tcggccgcag cccccctcgca ggcgcccccg aagtccgctc ccagcatcag cagcaacagc   26760
agcgctataa cctccgctcc tccaccgccg cgacccacgg ccgaccgcag acccaaccgt   26820
agatgggaca ccaccggaac cggggccggt aagtcctccg ggagaggcaa gcaagcgcag   26880
cgccaaggct accgctcgtg gcgcgctcac aagaacgcca tagtcgcttg cttgcaagac   26940
tgcgggggga acatctcctt cgcccgccgc ttcctgctct tccaccacgg tgtggccttc   27000
ccccgtaacg tcctgcatta ctaccgtcat ctctacagcc cctactgcgg cggcagtgag   27060
ccagagacgg tcgcggcgg cggcggcgcc cgtttcggcg cctaggaaga cccagggcaa   27120
gacttcagcc aagaaactcg cggcggccgc ggcgaacgcg gtcgcgggg ccctgcgcct    27180
gacggtgaac gaaccccctgt cgaccgcgca actgaggaac cgaatcttcc ccactctcta   27240
tgccatcttc cagcagagca gagggcagga tcaggaactg aaagtaaaaa acaggtctct   27300
gcgctccctc acccgcagct gtctgtatca caagagcgaa gaccagcttc ggcgcacgct   27360
```

```
ggaggacgct gaggcactct tcagcaaata ctgcgcgctc actcttaagg actagctccg   27420
cgcccttctc gaatttaggc gggaacgcct acgtcatcgc agcgccgccg tcatgagcaa   27480
ggacattccc acgccataca tgtggagcta tcagccgcag atgggactcg cggcgggcgc   27540
ctcccaagac tactccaccc gcatgaactg gctcagtgcc ggcccacaca tgatctcaca   27600
ggttaatgat atccgcaccc atcgaaacca aatattggtg gagcaggcgg caattaccac   27660
cacgccccgc aataatccca accccaggga gtgcccgcg tccctggtgt atcaggaaat   27720
tcccggcccc accaccgtac tacttccgcg tgattcccag gccgaagtcc aaatgactaa   27780
ctcaggggca cagctcgcgg gcggctgtcg tcacagggtg cggcctcctc gccagggtat   27840
aactcacctg gagatccgag gcagaggtat tcagctcaac gacgagtcgg tgagctcctc   27900
gctcggtctc agacctgacg ggaccttcca gatagccgga gccggccgat cttccttcac   27960
gccccgccag gcgtacctga ctctgcaaag ctcgtcctcg gcgccgcgct cgggcggcat   28020
cgggactctc cagttcgtgc aggagtttgt gccctcggtc tacttcaacc ccttctcggg   28080
ctctcccggt cgctacccgg accagttcat ctcgaacttt gacgccgcga gggactcggt   28140
ggacggctac gactgaatgt cgggtggacc cggtgcagag caacttcgcc tgaagcacct   28200
cgaccactgc cgccgccctc agtgctttgc ccgctgtcag accggtgagt tccagtactt   28260
ttccctgccc gactcgcacc cggacggccc ggcgcacggg gtgcgctttt tcatcccgag   28320
tcaggtgcgc tctaccctaa tcagggagtt taccgcccgt ccctactgg cggagttgga   28380 aaaggggcct tctatcctaa ccattgcctg catctgctct aaccctggat tgcaccaaga   28440
tctttgctgt catttgtgtg ctgagtataa taaaggctga gatcagaatc tactcgggct   28500
cctgtcgcca tcctgtcaac gccaccgtcc aagcccggcc cgatcagccc gaggtgaacc   28560
tcacctgcgg tctgcaccgg cgcctgagga aatacctagc ttggtactac aacagcactc   28620
cctttgtggt ttacaacagc tttgaccagg acggggtctc actgagggat aacctctcga   28680
acctgagcta ctccatcagg aagaacagca ccctcgagct acttcctcct tacctgcccg   28740
ggacttacca gtgtgtcacc ggtccctgca cccacaccca cctgttgatc gtaaacgact   28800
ctcttccgag aacagacctc aataactcct cttcgcagtt ccccagaaca ggaggtgagc   28860
tcaggaaacc ccgggtaaag aagggtggac gagagttaac acttgtgggg tttctggtgt   28920
atgtgacgct ggtggtggct cttttgatta aggcttttcc ttccatgtct gaactctccc   28980
tcttctttta tgaacaactc gactagtgct aacgggaccc tacccaacga atcgggattg   29040
aatatcggta accaggttgc agtttcactt ttgattacct tcatagtcct cttcctgcta   29100
gtgctgtcgc ttctgtgcct gcggatcggg ggctgctgca tccacgttta tatctggtgc   29160
tggctgttta gaaggttcgg agaccatcgc aggtagaata aacatgctgc tgcttaccct   29220
ctttgtcctg gcgctggccg ccagctgcca agccttttcc gaggctgact ttatagagcc   29280
ccagtgtaat gtgactttta agcccatgc acagcgttgt catactataa tcaaatgtgc   29340
caccgaacac gatgaatacc ttatccagta taaagataaa tcacacaaag tggcacttgt   29400
tgacatctgg aaacccgaag acccttttgga atacaatgtg accgttttcc agggtgacct   29460
cttcaaaatt tacaattaca cttccccatt tgaccagatg tgtgactttg tcatgtacat   29520
ggaaaagcag cacaagctgt ggcctccgac tcccccaggc tgtgtggaaa atccaggctc   29580
tttctgcatg atctctctct gtgtaactgt gctggcacta atactcacgc ttttgtatat   29640
cagatttaaa tcaaggcaaa gcttcattga tgaaaagaaa atgccttaat cgctttcacg   29700
```

```
cttgattgct aacaccgggt ttttatccgc agaatgattg gaatcaccct actaatcacc   29760
tccctccttg cgattgccca tgggttggaa cgaatcgaag tccctgtggg ggccaatgtt   29820
accctggtgg ggcctgtcgg caatgctaca ttaatgtggg aaaaatatac taaaaatcaa   29880
tgggtctctt actgcactaa caaaaatagc cacaagccca gagccatctg cgatgggcaa   29940
aatctaacct tgattgatgt tcaattgctg gatgcgggct actattatgg gcagctgggt   30000
acaatgatta attactggag accccacaga gattacatgc tccacgtagt aaagggtccc   30060
cttagcagcc cacccactac cacctctact acccccacta ccaccactac tcccaccacc   30120
agcactgccg cccagcctcc tcatagcaga acaaccactt ttatcaattc caagtcccac   30180
tcccccaca ttgccggcgg gccctccgcc tcagactccg aaaccaccga gatctgcttc   30240
tgcaaatgct ctgacgccat tgcccaggat ttggaagatc acgaggaaga tgagcatgac   30300
ttcgcagatg catgccaggc atcagagcca gaagcgctgc cggtggccct caaacagtat   30360
gcagaccccc acaccacccc cgaccttcct ccaccttccc agaagccaag tttcctgggg   30420
gaaaatgaaa ctctgcctct ctccatactc gctctgacat ctgttgctat gttgaccgct   30480
ctgctggtgc ttctatgctc tatatgctac ctgatctgct gcagaaagaa aaaatctcac   30540
ggccatgctc accagcccct catgcacttc ccttaccctc cagagctggg cgaccacaaa   30600
ctttaagtct gcagtaacta tctgcccatc ccttgtcagt cgacagcgat gagcccact   30660
aatctaacgg cctctggact tacaacatcg tctcttaatg agaccaccgc tcctcaagac   30720
ctgtacgatg gtgtctccgc gctggttaac cagtgggatc acctgggcat atggtggctc   30780
ctcataggag cagtgaccct gtgcctaatc ctggtctgga tcatctgctg catcaaaagc   30840
agaagaccca ggcggcggcc catctacagg cccttgtca tcacacctga agatgatgat   30900
gacaccactt ccaggctgca gaggctaaag cagctactct tctcttttac agcatggtaa   30960
attgaatcat gcctcgcatt ttcatctact tgtctctcct tccactttt ctgggctctt   31020
ctacattggc cgctgtgtcc cacatcgagg tagactgcc cacgcccttc acagtctacc   31080
tgcttttcgg ctttgtcatc tgcacctttg tctgcagcgt tatcactgta gtgatctgct   31140
tcatacagtg catcgactac gtctgcgtgc gggtggctta ctttagacac cacccccagt   31200
atcgcaacag ggacatagcg gctctcctaa gacttgttta aaatcatggc caaattaact   31260
gtgattggtc ttctgatcat ctgctgcgtc ctagccgcga ttgggactca agctcctacc   31320
accaccagcg ctcccagaaa gagacatgta tcctgcagct tcaagcgtcc ctggaatata   31380
ccccaatgct ttactgatga acctgaaatc tctttggctt ggtacttcag cgtcaccgcc   31440
cttcttatct tctgcagtac ggttattgcc cttgccatct acccttccct tgacctgggc   31500
tggaatgctg tcaactctat ggaatatccc accttcccag aaccagacct gccagacctg   31560
gttgttctaa acgcgtttcc tcctcctgct cccgttcaaa atcagtttcg ccctccgtcc   31620
cccacgccca ctgaggtcag ctactttaat ctaacaggcg gagatgactg aaaacctaga   31680
cctagaaatg gacggtctct gcagcgagca acgcacacta gagaggcgcc ggcaaaaaga   31740
gctcgagcgt cttaaacaag agctccaaga cgcggtggcc atacaccagt gcaaaaaagg   31800
tgtcttctgt ctggtaaaac aggccacgct cacctatgaa aaaacaggtg acacccaccg   31860
cctaggatac aagctgccca cacagcgcca aaagttcgcc ctcatgatag gcgaacaacc   31920
catcaccgtg acccagcact ccgtggagac agaaggctgc atacatgctc cctgtagggg   31980
cgctgactgc ctctacacct tgatcaaaac cctctgcgt ctcagagacc ttatccttt   32040
caattaatca taactgtaat caataaaaaa tcacttactt gaaatctgat agcaagcctc   32100
```

```
tgtccaattt tttcagcaac acttccttcc cctcctccca actctggtac tctaggcgcc  32160
tcctagctgc aaacttcctc cacagtctga agggaatgtc agattcctcc tcctgtccct  32220
ccgcacccac gatcttcatg ttgttgcaga tgaaacgcgc gagatcgtct gacgagacct  32280
tcaaccccgt gtaccsctac gataccgaga tcgctccgac ttctgtccct ttccttaccc  32340
ctcccttcgt gtcatccgca ggaatgcaag aaaatccagc tgggtgctg tccctgcact  32400 tgtcagagcc ccttaccacc cacaatgggg ccctgactct aaaaatgggg gcggcctga  32460 ccctggacaa ggaagggaat ctcacttccc aaaacatcac cagtgtcgat ccccctctca  32520
aaaaaagcaa gaacaacatc agccttcaga ccgccgcacc cctcgccgtc agctccgggg  32580
ccctaacact ttttgccact ccccccctag cggtcagtgg tgacaacctt actgtgcagt  32640
ctcaggcccc tctcactttg gaagactcaa aactaactct ggccaccaaa ggaccctaa  32700 ctgtgtccga aggcaaactt gtcctagaaa cagaggctcc cctgcatgca agtgacagca  32760
gcagcctggg ccttagcgtt acggcccac ttagcattaa caatgacagc ctaggactag  32820
atctgcaggc acccattgtc tctcaaaatg gaaaactggc tctaaatgta gcaggccccc  32880
tagctgtggc caatggcatt aatgctttga cagtaggcac aggcaaaggt attggtctaa  32940
atgaaaccag cactcacttg caagcaaagt tggtcgcccc cctaggcttt gataccaatg  33000
gcaacattaa gctaagcgtt gcaggaggca tgagactaaa taatgacaca cttatactag  33060
atgtaaacta cccatttgaa gctcaaggcc aactaagtct aagagtgggc cagggtccgc  33120
tgtatgtaga ttctagcagc cataacctga ccattagatg ccttagagga ttatacataa  33180
catcgtctaa taaccaaacc ggtctagagg ccaacataaa actaacaaaa ggccttgtct  33240
atgatggaaa tgccatagca gtcaatgttg gtcaaggatt gcaatacagc actactgcca  33300
catcggaagg tgtgtatcct atacagtcta agataggttt gggaatggaa tatgatacca  33360
acggagccat gatgacaaaa ctaggctctg gactaagctt tgacaattca ggagccattg  33420
tagtgggaaa caaaaatgat gacaggctta ctctgtggac tacaccagac ccatctccta  33480
actgtagaat ttattctgaa aaagatacta actaaccttt ggtgctgact aagtgtggca  33540
gccaaatcct aggcacagta tctgcccttg ctgtcagagg cagccttgcg cccatcacta  33600
atgcatccag catagtccaa atatttctaa gatttgatga aaatggacta ttgatgagca  33660
actcatcgct agacggtgat tactggaatt acagaaatgg ggactccact aatagcacac  33720
catatacaaa tgcagtaggc tttatgccta atctagcagc ctatcctaaa ggtcaggcta  33780
cagctgcaaa aagcagtatt gtaagccagg tatacatgga tggtgacact actaaaccta  33840
taacactaaa aataaacttc aatggcattg atgaaacaac agaaaatacc cctgttagta  33900
aatattccat gacattctca tggagctggc ccaccgcaag ctacataggc cacacttttg  33960
caacaaactc tttttacttc tcctacatcg cccaagaata agaaagcac agagatgctt  34020 gttttgattt caaaattgtg tgcttttatt tattttcagc ttacagtatt tccagtagtc  34080
attcgaataa agcttaatca aactgcatga gaacccttcc acatagctta aattagcacc  34140
agtgcaaatg gagaaaattc aacataccct ttttatccag atatcagaga actctagtgg  34200
tcagttttcc cccaccctcc cagctcacag aatacacagt ccttcccccc cggctggctt  34260
taaacaacac tatctcattg gtaacagaca tattcttagg tgtaataatc cacacggtct  34320
cttggcgggc caagcgctgg tcggtgatgt taataaactc cccaggcagc tctttcaagt  34380
tcacgtcgct gtccaactgc tgaagcgctc gcggctccga ctgcgcctct agcggaggca  34440
```

```
acggcaacac ccgatccttg atctataaag gagtagagtc ataatccccc ataagaatag   34500
ggcggtgatg cagcaacaag gcgcgcagca actcctgccg ccgcctctcc gtacgacagg   34560
aatgcaacgg cgtggtggtc tcctccgcga taatccgcac cgctcgcagc atcagcatcc   34620
tcgtcctccg ggcacagcag cgcatcctga tctcactgag atcggcgcag taagtgcagc   34680
acaaaaccaa gatgttattt aagatcccac agtgcaaagc actgtaccca aagctcatgg   34740
cgggaaggac agcccccacg tgaccatcat accagatcct taggtaaatc aaatgacgac   34800
ctctcataaa cacgctggac atgtacatca cctccttggg catgcgctga ttcaccacct   34860
ctcgatacca caagcatcgc tgattaatta agaccccctc aagcaccatc ctgaaccagg   34920
aagccagcac ctgacccccc gccaggcact gcagggaccc cggtgaattg cagtggcagt   34980
gaagactcca gcgctcgtag ccgtgaacca tagagccggt cattatatcc acattggcac   35040
aacacaaaca cactttcata cacttttttca tgattagcag ctcctctcta gtcaggacca   35100
tatcccaagg aatcacccac tcttgaatca aggtaaatcc cacacagcag ggcaggcctc   35160
tcacataact cacgttatgc atagtgagcg tgtcgcaatc tggaaatacc ggatgatctt   35220
ccatcaccga agctcgcgtc tccgtctcaa agggaggtaa acggtccctc gtgtagggac   35280
agtggcggga taatcgagat cgtgttgaac gtagagtcat gccaaaggga acagcggacg   35340
tactcatatt tcctccagca gaaccaagtg cgcgcgtggc agctatccct gcgtcttctg   35400
tctcgccgcc tgccccgctc ggtgtagtag ttgtaataca gccactccct cagaccgtca   35460
aggcgctccc tggcgtccgg atctataaca acaccgtcct gcagcgccgc cctgatgaca   35520
tccaccaccg tagagtatgc caagcccagc caggaaatgc attcactttg acagcgagag   35580
ataggaggag cgggaagaga tggaagaacc atgatagtaa aagacttta ttccaatcga   35640 tcctctacaa tgtcaaagtg tagatctata agatgacact ggtctcctcc gctgagtcga   35700
tcaaaaataa cagctaaacc acaaacaaca cgattggtca aatgctccac aagggcttgc   35760
agcataaaat cgcctcgaaa gtccaccgca agcataacat caaagccacc gcccctatca   35820
tgatctataa taaaaacccc acagctatcc accagaccca taaagttttc atctctccat   35880
cgtgaaaaaa tatttacaag ctcctccttt aaatcacctc caaccaattg aaaaagttga   35940
gccaaaccgc cctccacctt catttttcagc aagcgcatca tgattgcaaa aattcaggct   36000
cctgagacac ctgtataaga ttgagaagcg gaacgttaac gtcaatgttt cgctcgcgaa   36060
gatcgcgcct cagtgcaagc atgatataat cccacaggtc ggagcggatc agcgaggaca   36120
tctccccgcc aggaaccaac tcaacggagc ctatgctgat tataatacgc atattcgggg   36180
ctatgctgac cagcacggcc cccaaatagg cgtactgcat aggcggcgac aaaaagtgaa   36240
cagtttgggt taaaaaatca ggcaaacagt gcgcaaaaa agcaagaaca tcataaccat   36300
gctcatgcaa atagatgcaa gtaagctcag gaacgaccac agaaaaatgc acaattttc   36360 tctcaaacat gactgcgagc cctgcaaaaa ataaaaaaga aacattacac aagagtagcc   36420
tgtcttacga tgggatagac tactctaacc aacataagac gggccacaac atcgcccgcg   36480
tggccataaa aaaaattgtc cgtgtgatta aaagaagca cagatagctg gccagtcata   36540
tccggagtca tcacgtgtga acccgtgtag accccgggt tggacacatc ggccaaacaa   36600
agaaagcggc caatgtaccc aggaggaatc ataacactaa gacgaagata caacagaata   36660
accccatgag ggggaataac aaagttagta ggtgaataaa aacgataaac acccgaaact   36720
ccctcctgcg taggcaaaat agcacccctcc ccttccaaaa caacatatag cgcttccaca   36780
gcagccatga caaaagactc aaaacactca aaagactcag tcttaccagg aaaataaaag   36840
```

| | |
|---|---:|
| cactctcaca gcaccagcac taatcagagt gtgaagaggg ccaagtgccg aacgagtata | 36900 |
| tataggaata aaaaatgacg taaatgtgta aaggtcagaa aacgcccaga aaaatacaca | 36960 |
| gaccaacgcc cgaaacgaaa acccgcgaaa aaatacccag aacttcctca acaaccgcca | 37020 |
| cttccggttt ctcacggtac gtcacttccg caagaaaagc aaaactacat ttcccacatg | 37080 |
| tgtaaaaacg aaaccccgcc ccttgtaact gcccacaact tacatcatca aaacataaac | 37140 |
| tcctacgtca cccgccccgc ctctccccgc ccacctcatt atcatattgg ccacaatcca | 37200 |
| aaataaggta tattat | 37216 |

<210> SEQ ID NO 25
<211> LENGTH: 34029
<212> TYPE: DNA
<213> ORGANISM: Gorilla beringei beringei

<400> SEQUENCE: 25

| | |
|---|---:|
| catcatcaat aatatacctt attttggatt gtggccaata tgataatgag gtgggcgggg | 60 |
| agaggcgggg cggtgacgt aggacgcgcg agtagggttg ggaggtgtgg cggaagtgtg | 120 |
| gcatttgcaa gtgggaggag ctcacatgca agcttccgtc gcggaaaatg tgacgttttt | 180 |
| gatgagcgcc gcctacctcc ggaagtgcca attttcgcgc gcttttcacc ggatatcgta | 240 |
| gtaattttgg gcgggaccat gtaagatttg gccattttcg cgcgaaaagt gaacggggga | 300 |
| agtgaaaact gaataatagg gcgttagtca tagtgcgtaa tatttaccga gggccgaggg | 360 |
| actttgaccg attacgtgga ggactcgccc aggtgttttt tacgtgaatt tccgcgttcc | 420 |
| gggtcaaagt ctccgtttta ttgtcaccgt catttgacgc ttaggcctga ccatctggtg | 480 |
| ctggcctgca ccagggccga gtttgggtct agcgatgagg ataccgattg aggtgggtaa | 540 |
| ggtgggcgtg gctagaaggg tggggcgtgt ataaattggg ggtctaaggg tctctctgtt | 600 |
| ttgtcttgca acagccgccg ccatgagcga caccggcaac agctttgatg gaagcatctt | 660 |
| tagcccctat ctgacagtgc gcatgcctca ctgggctgga gtgcgtcaga atgtgatggg | 720 |
| ttccaacgtg gatggacgcc ccgttctgcc ttcaaattcg tctacaatgg cctacgcgac | 780 |
| cgtgggagga actccgctgg acgccgcgac ctccgccgcc gcctccgccg ccgccgcgac | 840 |
| cgcgcgcagc atggctacgg acctttacag ctctttggtg gcgagcggcg cggcctctcg | 900 |
| cgcgtctgct cgggatgaga aactgaccgc tctgctgctt aaactggaag acttgacccg | 960 |
| ggagctgggt caactgaccc agcaggtctc cagcttgcgt gagagcagcc ttgcctcccc | 1020 |
| ctaatggccc ataatataaa taaaagccag tctgtttgga ttaagcaagt gtatgttctt | 1080 |
| tatttaactc tccgcgcgcg gtaagcccgg gaccagcggt ctcggtcgtt tagggtgcgg | 1140 |
| tggattcttt ccaacacgtg gtacaggtgg ctctggatgt ttagatacat gggcatgagt | 1200 |
| ccatccctgg ggtggaggta gcaccactgc agagcttcgt gctcgggggt ggtgttgtat | 1260 |
| atgatccagt cgtagcagga gcgctgggcg tggtgctgaa aaatgtcctt aagcaagagg | 1320 |
| cttatagcta gggggaggcc cttggtgtaa gtgtttacaa atctgctcag ttgggagggg | 1380 |
| tgcatccggg gggatataat gtgcatcttg gactggattt ttaggttggc tatgttccca | 1440 |
| cccagatccc ttctgggatt catgttgtgc aggaccacca gcacggtata tccagtgcac | 1500 |
| ttgggaaatt tatcgtggag cttagacggg aatgcatgga agaacttgga gacgcccttg | 1560 |
| tggcctccca gattttccat acattcgtcc atgatgatgg caatgggccc gtgggaagct | 1620 |
| gcctgagcaa aaatgtttct gggatcgctc acatcgtagt tatgttccag ggtgaggtca | 1680 |

```
tcataggaca tctttacgaa tcggggggcgg agggtcccgg actgggggat gatggtaccc   1740
tcgggccccg gggcgtagtt ccctcacag atctgcatct cccaggcttt catttcagag     1800
ggagggatca tatccacctg cggagcgatg aaaaacacag tttctggcgc aggggagatt    1860
aactgggatg agagcaggtt tctgagcagc tgtgactttc cacagccggt gggcccatat    1920
atcacgccta tcaccggctg cagctggtag ttaagagagc tgcagctgcc gtcctcccgg    1980
agcagggggg ccacctcgtt cagcatatcc ctgacgtgga tgttctccct gaccaattcc    2040
gccagaaggc gctcgccgcc cagcgaaagc agctcttgca aggaagcaaa attttcagc     2100
ggttttaggc cgtcggccgt gggcatgttt tcagcgtct gggtcagcag ttccagcctg     2160
tcccacagct cggtgatgtg ctctacggca tctcgatcca gcagatctcc tcgtttcgcg    2220
ggttggggcg gctttcgctg tagggcacca gccgatgggc gtccagcggg gccagagtca    2280
tgtccttcca tgggcgcagg gtcctcgtca gggtggtctg ggtcacggtg aagggggtgcg   2340
ctccggggttg ggcgctggcc agggtgcgct tgaggctggt tctgctggtg ctgaatcgct   2400
gccgctcttc gccctgcgcg tcggccaggt agcatttgac catggtctcg tagtcgagac    2460
cctcggcggc gtgcccttg gcgcggagct ttcccttgga ggtggcgccg cacgaggggc     2520
actgcaggct cttcagggcg tagagcttgg gagcgagaaa cacggactct ggggagtagg    2580
cgtccgcgcc gcaggaagcg cagaccgtct cgcattccac cagccaagtg agctccgggc   2640
ggtcagggtc aaaaaccagg ttgccccat gcttttttgat gcgtttctta cctcggctct   2700
ccatgaggcg gtgtcccttc tcggtgacga agaggctgtc cgtgtccccg tagaccgact   2760
tcaggggcct gtcttccagc ggagtgcctc tgtcctcctc gtagagaaac tctgaccact   2820
ctgagacgaa ggcccgcgtc caggccagga cgaaggaggc cacgtgggag gggtagcggt   2880
cgttgtccac tagcgggtcc accttctcca gggtgtgcag gcacatgtcc ccctcctccg   2940
cgtccagaaa agtgattggc ttgtaggtgt aggacacgtg accggggggtt cccgacgggg   3000
gggtataaaa gggggtgggc gccctttcat cttcactctc ttccgcatcg ctgtctgcga   3060
gggccagctg ctggggtaag tattccctct cgaaggcggg catgacctca gcgctcaggt   3120
tgtcagtttc taaaaatgag gaggatttga tgttcacctg tccggaggtg ataccctttga  3180
gggtacctgg gtccatctgg tcagaaaaca ctattttttt gttgtcaagc ttggtggcga   3240
acgacccgta gagggcgttg gagagcagct tggcgatgga gcgcagggtc tggttttttgt  3300
cgcggtcggc tcgctccttg ccgcgatgt tgagttgcac gtactcgcgg ccacgcact     3360
tccactcggg gaagacggtg gtgcgctcgt ctgggattag gcgcaccctc cagcctcggt   3420
tgtgcagggt gaccatgtcg acgctggtgg cgacctcgcc gcgcaggcgc tcgttggtcc   3480
agcagaggcg gccgcccttg cgcgagcaga agggggtag ggggtccagc tggtcctcgt    3540
ttgggggggtc cgcgtcgatg gtgaagaccc cggggagcaa gcgcgggtca aagtagtcga  3600
tcttgcaagc ttgcatgtcc agagcccgct gccattcgcg ggcggcgagc gcgcgctcgt   3660
aggggttgag gggcgggccc cagggcatgg ggtgggtgag cgcggaggcg tacatgccgc   3720
agatgtcata cacgtacagg ggttccctga ggatgccgag gtaggtgggg tagcagcgcc   3780
ccccgcggat gctggcgcgc acgtagtcat agagctcgtg ggagggggcc agcatgttgg   3840
gcccgaggtt ggtgcgctgg gggcgctcgg cgcggaaggc gatctgcctg aagatggcat   3900
gggagttgga ggagatggtg ggccgctgga agacgttgaa gcttgcttct tgcaagccca   3960
ccgagtccct gacgaaggag gcgtaggact cgcgcagctt gtgcaccagc tcggcggtga   4020
cctggacgtc gagcgcgcag tagtcgaggg tctcgcggat gatgtcatac ttatcctccc   4080
```

| | |
|---|---|
| ccttcttttt ccacagctcg cggttgagga cgaactcttc gcggtctttc cagtactctt | 4140 |
| ggagggaaa cccgtccgtg tccgaacggt aagagcctag catgtagaac tggttgacgg | 4200 |
| cctggtaggg gcaacagccc ttctccacgg gcagcgcgta ggcctgcgcc gccttgcgga | 4260 |
| gggaggtgtg ggtgagggcg aaagtgtccc tgaccatgac tttgaggtat tgatgtttga | 4320 |
| agtctgtgtc atcgcagccg ccctgttccc acagggtgta gtccgtgcgc tttttggagc | 4380 |
| gcgggttggg cagggagaag gtgaggtcat tgaagaggat cttccccgct cgaggcatga | 4440 |
| agtttctggt gatgcgaaag ggccctggga ccgaggagcg gttgttgatg acctgggcgg | 4500 |
| ccaggacgat ctcgtcaaag ccgtttatgt tgtggcccac gatgtagagc tccaaaaagc | 4560 |
| ggggctggcc cttgatggag gggagctttt tgagttcctc gtaggtgagc tcctcgggcg | 4620 |
| attccaggcc gtgctcctcc agggcccagt cttgcaagtg agggttggcc gccaggaagg | 4680 |
| atcgccagag gtcgcgggcc atgagggtct gcaggcggtc gcggaaggtt ctgaactgtc | 4740 |
| gccccacggc catcttttcg ggggtgatgc agtagaaggt gaggggtct ttctcccagg | 4800 |
| ggtcccatct gagctctcgg gcgaggtcgc gcgcggcggc gaccagagcc tcgtcgcccc | 4860 |
| ccagtttcat gaccagcatg aagggcacga gctgcttgcc aaaggctccc atccaagtgt | 4920 |
| aggtctctac atcgtaggtg acaaagaggc gctccgtgcg aggatgagag ccgatcggga | 4980 |
| agaactggat ctcccgccac cagttggagg attggctgtt gatgtggtga aagtagaagt | 5040 |
| cccgtctgcg ggccgagcac tcgtgctggc ttttgtaaaa gcgaccgcag tactggcagc | 5100 |
| gctgcacggt ttgtatatct tgcacgaggt gaacctggcg acctctgacg aggaagcgca | 5160 |
| gcgggaatct aagtcccccg cctggggtcc cgtgtggctg gtggtcttct actttggttg | 5220 |
| tctggccgcc agcatctgtc tcctggaggg cgatggtgga gcagaccacc acgccgcgag | 5280 |
| agccgcaggt ccagatctcg gcgctcggcg ggcggagttt gatgacgaca tcgcgcacat | 5340 |
| tggagctgtc catggtctcc agctcccgcg gcggcaggtc agctgggagt tcctggaggt | 5400 |
| tcacctcgca gagacgggtc aaggcgcggg cagtgttgag atggtatctg atttcaaggg | 5460 |
| gcgtgttggc ggcggagtcg atggcttgca ggaggccgca gccccggggg gccacgatgg | 5520 |
| ttccccgcgg ggcgcgaggg gaggcggaag ctggggggtgt gttcagaagc ggtgacgcgg | 5580 |
| gcgggccccc ggaggtaggg ggggttccgg ccccacaggc atgggcggca ggggcacgtc | 5640 |
| ttcgccgcgc gcgggcaggg gctggtgctg gctccgaaga gcgcttgcgt gcgcgacgac | 5700 |
| gcgacggttg gtgtcctgta tctgacgcct ctgagtgaag accacgggtc ccgtgacctt | 5760 |
| gaacctgaaa gagagttcga cagaatcaat ctcggcatcg ttgacagcgg cctggcgcag | 5820 |
| gatctcctgc acgtcgcccg agttgtcctg gtaggcgatc tctgccatga actgctcgat | 5880 |
| ctcttcttcc tggagatctc ctcgtccggc gcgctccacg gtggccgcca ggtcgttgga | 5940 |
| gatgcgaccc atgagctgtg agaaggcgtt gagcccgccc tcgttccaga cccggctgta | 6000 |
| gaccacgccc cctcggcgt cgcgagcgcg catgaccacc tgggccaggt tgagctccac | 6060 |
| gtgtcgcgtg aagacggcgt agttgcgcag gcgctggaaa aggtagttca gggtggtggc | 6120 |
| ggtgtgctcg gcgacgaaga agtacatgac ccagcgccgc aacgtggatt cattgatgtc | 6180 |
| ccccaaggcc tccaggcgct ccatggcctc gtagaagtcc acggcgaagt tgaaaaactg | 6240 |
| ggagttgcga gcggacacgg tcaactcctc ctccagaaga cggatgagct cggcgacagt | 6300 |
| gttgcgcacc tcgcgctcga aggccacggg gggcgcttct tcctcttcca cctcttcttc | 6360 |
| catgatcgct tcttcttctt cctcagccgg gacgggaggg ggcggcggcg gcggggagg | 6420 |

```
ggcgcggcgg cggcggcggc gcaccgggag gcggtcgatg aagcgctcga tcatctcccc    6480
ccgcatgcgg cgcatggtct cggtgacggc gcggccgttc tcccggggc gcagctcgaa     6540
gacgccgcct ctcatctcgc cgcggggcga gcggccgtga ggtagcgaga cggcgctgac    6600
tatgcatctt aacaattgct gtgtaggtac accgccgagg gacctgattg agtccagatc    6660
caccggatcc gaaaaccttt ggaggaaagc gtctatccag tcgcagtcgc aaggtaggct    6720
gagcaccgtg gcgggcgggg gcgggtctgg agagttcctg gcggagatgc tgctgatgat    6780
gtaattaaag taggcggtct tgagaaggcg gatggtggac aggagcacca tgtctttggg    6840
tccggcctgt tggatgcgga ggcggtcggc catgccccag gcctcgttct gacaccggcg    6900
caggtctttg tagtagtctt gcatgagtct ttccaccggc acctcttctc cttcctcttc    6960
tccatctcgc cggtggtttc tcgcgccgcc catgcgcgtg accccaaagc ccctgagcgg    7020
ctgcagcagg gccaggtcgg cgaccacgcg ctcggccaag atggcctgct gcacctgagt    7080
gagggtcctc tcgaagtcat ccatgtccac gaagcggtgg taggcgcccg tgttgatggt    7140
gtaggtgcag ttggccatga cggaccagtt gacggtctgg tgtcccggct gcgagagctc    7200
cgtgtaccgc aggcgcgaga aggcgcggga atcgaacacg tagtcgttgc aagtccgcac    7260
cagatactgg tagcccacca ggaagtgcgg cggaggttgg cgatagaggg gccagcgctg    7320
ggtggcgggg gcgccgggcg ccaggtcttc cagcatgagg cggtggtatc cgtagatgta    7380
cctggacatc caggtgatgc cggcggcggt ggtggtggcg cgcgcgtagt cgcggacccg    7440
gttccagatg tttcgcaggg gcgagaagtg ttccatggtc ggcacgctct ggccggtgag    7500
gcgcgcgcag tcgttgacgc tctatacaca cacaaaaacg aaagcgttta cagggctttc    7560
gttctgtagc ctggaggaaa gtaaatgggt tgggttgcgg tgtgccccgg ttcgagacca    7620
agctgagctc ggccggctga agccgcagct aacgtggtat tggcagtccc gtctcgaccc    7680
aggccctgta tcctccagga tacggtcgag agccctttg ctttcttggc caagcgcccg    7740
tggcgcgatc tgggatagat ggtcgcgatg agaggacaaa agcggctcgc ttccgtagtc    7800
tggagaaaca atcgccaggg ttgcgttgcg gcgtacccg gttcgagccc ctatggcggc     7860
ttgaatcggc cggaaccgcg gctaacgagg gccgtgcag ccccgtcctc aggacccgc      7920
cagccgactt ctccagttac gggagcgagc ccctttgtt ttttattttt tagatgcatc     7980
ccgtgctgcg gcagatgcgc ccctcgcccc ggcccgatca gcagcagcaa cagcaggcat    8040
gcagaccccc ctctccccett tccgcccegg tcaccacgge cgcggcggcc gtgtcgggcg   8100
cgggggggcgc gctggagtca gatgagccac cgcggcggcg acctaggcag tatctggact   8160
tggaagaggg cgagggactg gcgcggctgg gggcgaactc tccagagcgc cacccgcggg    8220
tgcagttgaa aagggacgcg cgcgaggcgt acctgccgcg gcagaacctg tttcgcgacc    8280
gcggggcga ggagcccgag gagatgcgag actgcaggtt ccaagcgggg cgcgagctgc     8340
ggcgcgggct ggacagacag cgcctgctgc gcgaggagga ctttgagccc gacacgcaga    8400
cgggcatcag ccccgcgcgc gcgcacgtag ccgcggccga cctggtgacc gcctacgagc    8460
agacggtaaa ccaggagcgc aacttccaaa agagcttcaa caaccacgtg cgcacgctgg    8520
tggcgcgcga ggaggtgacc ctgggtctca tgcatctgtg ggacctggtg gaggcgatcg    8580
tgcagaaccc cagcagcaag cccctgaccg cgcagctgtt cctggtggtg cagcacagca    8640
gggacaacga ggccttcagg gaggcgctgc tgaacatcac cgagccggag gggcgctggc    8700
tcctggacct gataaacatc ctgcagagca tagtggtgca ggagcgcagc ctgagcctgg    8760
ccgagaaggt ggcggccatc aactactcta tgctgagcct gggcaagttc tacgcccgca    8820
```

```
agatctacaa gaccccctac gtgcccatag acaaggaggt gaagatagac agcttctaca   8880
tgcgcatggc gctgaaggtg ctgaccctga gcgacgacct gggagtgtac cgcaacgagc   8940
gcatccacaa ggccgtgagc gccagccggc ggcgcgagct gagcgaccgc gagctgatgc   9000
acagtctgca gcgcgcgctg accggcgcgg gcgagggcga cagggaggtc gagtcctact   9060
tcgacatggg ggccgacctg cactggcagc cgagccgccg cgccctggag gcggcggggg   9120
cgtacggcgg ccccctggcg gccgatgacc aggaagagga ggactatgag ctagaggagg   9180
gcgagtacct ggaggactga cctggctggt ggtgttttgg tatagatgca agatccgaac   9240
gtggcggacc cggcggtccg ggcggcgctg caaagccagc cgtccggcat taactcctct   9300
gacgactggg ccgcggccat gggtcgcatc atggccctga ccgcgcgcaa ccccgaggct   9360
ttcaggcagc agcctcaggc caaccggctg gcggccatct tggaagcggt agtgcccgcg   9420
cgctccaacc ccacccacga gaaggtgctg gccatagtca acgcgctggc ggagagcagg   9480
gccatccgcg cggacgaggc cggactggtg tacgatgcgc tgctgcagcg ggtggcgcgg   9540
tacaacagcg gcaacgtgca gaccaacctg gaccgcctgg tgacggacgt gcgcgaggcc   9600
gtggcgcagc gcgagcgctt gcatcaggac ggtaacctgg gctcgctggt ggcgctaaac   9660
gccttcctca gcacccagcc ggccaacgta ccgcgggggc aggaggacta caccaacttt   9720
ttgagcgcgc tgcggctgat ggtgaccgag gtccctcaga gcgaggtgta ccagtcgggg   9780
cccgactact tcttccagac cagcagacag ggcttgcaaa ccgtgaacct gagccaggct   9840
ttcaagaacc tgcgggggct gtggggagtg aaggcgccca ccggcgaccg ggctacggtg   9900
tccagcctgc taaccccaa ctcgcgcctg ctgctgctgc tgatcgcgcc cttcacggac   9960
agcgggagcg tctcgcggga gacctatctg ggccacctgc tgacgctgta ccgcgaggcc  10020
atcgggcagg cgcaggtgga cgagcacacc ttccaagaga tcaccagcgt gagccacgcg  10080
ctggggcagg aggacacggg cagcctgcag gcgaccctga actacctgct gaccaacagg  10140
cggcagaaga ttcccacgct gcacagcctg acccaggagg aggagcgcat cttgcgctac  10200
gtgcagcaga gcgtgagcct gaacctgatg cgcgacggcg tgacgccag cgtggcgctg  10260
gacatgaccg cgcgcaacat ggaaccgggc atgtacgcct cccaccggcc gtttatcaac  10320
cgcctgatgg actacttgca tcgggcggcg gccgtgaacc ccgagtactt cactaatgcc  10380
attctgaatc cccactggat gccccctccg ggtttctaca acgggacttt gaggtgccc   10440
gaggtcaacg acgggttcct ctgggatgac atggatgaca gtgtgttctc acccaacccg  10500
ctgcgcgccc cgtctctgcg attgaaggag ggctctgaca gggaaggacc gaggagtctg  10560
gcctcctccc tggctctggg agcggtgggc gccacgggcg cggcggcgcg gggcagtagc  10620
cccttcccca gcctggcaga ctctctgaac agcgggcggg tgagcaggcc ccgcttgcta  10680
ggcgaggagg agtatctgaa caactccctg ctgcagcccg cgaggacaa gaacgctcag  10740
cggcagcagt ttcccaacaa tgggatagag agcctggtgg acaagatgtc cagatggaag  10800
acgtatgcgc aggagtacaa ggagtgggag gaccgccagc cgcggccctt gccgcccct   10860
aggcagcgct ggcagcggcg cgcgtccaac cgccgctgga ggcaggggcc cgaggacgat  10920
gatgactctg cagatgacag cagcgtgttg gacctgggcg ggagcgggaa ccccttttcg  10980
cacctgcgcc cacgcctggg caagatgttt taaaagaaaa aaaaaataaa actcaccaag  11040
gccatggcga cgagcgttgg ttttttgttc ccttccttag tatgcggcgc gcggcgatgt  11100
tcgaggaggg gcctcccccc tcttacgaga gcgcgatggg gatttctcct gcggcgcccc  11160
```

```
tgcagcctcc ctacgtgcct cctcggtacc tgcaacctac aggggggaga aatagcatct   11220
gttactctga gctgcagccc ctgtacgata ccaccagact gtacctggtg gacaacaagt   11280
ccgcggacgt ggcctccctg aactaccaga acgaccacag cgatttttg accacggtga    11340 tccaaaacaa cgacttcacc ccaaccgagg ccagcaccca gaccataaac ctggataaca   11400
ggtcgaactg gggcggcgac ctgaagacca tcttgcacac caacatgccc aacgtgaacg   11460
agttcatgtt caccaactct tttaaggcgc gggtgatggt ggcgcgcgag caggggaggg   11520
cgaagtacga gtgggtggac ttcacgctgc ccgagggcaa ctactcagag accatgactc   11580
tcgacctgat gaacaatgcg atcgtggaac actatctgaa agtgggcagg cagaacgggg   11640
tgaaggaaag cgatatcggg gtcaagtttg acaccagaaa cttccgtctg ggctgggacc   11700
ccgtgaccgg gctggtcatg ccgggggtct acaccaacga ggcctttcat cccgacatag   11760
tgcttctgcc cggctgtggg gtggacttca cccagagccg gctgagcaac ctgctgggca   11820
ttcgcaagcg gcagcctttc caggagggtt tcaagatcac ctatgaggat ctgaaggggg   11880
gcaacattcc cgcgctcctt gatctggacg cctacgagga gagcttgaaa cccgaggaga   11940
gcgctggcga cagcggcgag agtggcgagg agcaagccgg cggcggtggc ggcgcgtcgg   12000
tagaaaacga aagtacgccc gcagtggcgg cggacgctgc ggaggtcgag ccggaggcca   12060
tgcagcagga cgcagaggag ggcgcacagg agggcgcgca aaggacatg aacgatgggg    12120 agatcagggg agacacattc gccacccggg gcgaagaaaa agaggcagag gcggcggcgg   12180
cggcgacggc ggaggccgaa accgaggttg aggcagaggc agagcccgag accgaagtta   12240
tggaagacat gaatgatgga gaacgtaggg gcgacacgtt cgccacccgg ggcgaagaga   12300
aggcggcgga ggcagaagcc gcggctgagg aggcggctgc ggctgcggcc aagactgagg   12360
ctgcggctaa ggctgaggtc gaagccaatg ttgcggttga ggctcaggct gaggaggagg   12420
cggcggctga agcagttaag gaaaaggccc aggcagagca ggaagagaaa aaacctgtca   12480
ttcaacctct aaaagaagat agcaaaaagc gcagttacaa cgtcatcgag ggcagcacct   12540
ttacccagta ccgcagctgg tacctggcgt acaactacgg cgacccggtc aagggggtgc   12600
gctcgtggac cctgctctgc acgcggacg tcacctgcgg ctccgagcag atgtactggt    12660
cgctgccgaa catgatgcaa gacccggtga ccttccgctc cacgcggcag gttagcaact   12720
tcccggtggt gggcgccgaa ctgctgcccg tgcactccaa gagtttttac aacgagcagg   12780
ccgtctactc ccagctgatc cgccaggcca cctctctgac ccacgtgttc aatcgctttc   12840
ccgagaacca gattttggcg cgcccgccgg ccccaccat caccaccgtg agtgaaaacg    12900
ttcctgccct cacagatcac gggacgctac cgctgcgcaa cagcatctca ggagtccagc   12960
gagtgaccat tactgacgcc agacgccgga cctgccccta cgtttacaag gccttgggca   13020
tagtctcgcc gcgcgtcctc tccagtcgca cttttttaaaa cacatctacc cacacgttcc   13080
aaaatcatgt ccgtactcat ctcacccagc aacaacaccg gctgggggct gcgcgcgccc   13140
agcaagatgt ttggagggc gaggaagcgc tccgaccagc accctgtgcg cgtgcgcggc    13200
cactaccgcg cgccctgggg agcgcacaag cgcgggcgca cagggcgcac cactgtggac   13260
gacgtcattg actccgtagt ggagcaagcg cgccactaca caccccggcgc ccgaccgcc   13320 cccgccgtgt ccaccgtgga ccaggcgatc gaaagcgtgg tacagggcgc gcggcactat   13380
gccaacctta aaagtcgccg ccgccgcgtg gccgccgcc atcgccggag accccgggcc    13440
accgccgccg cgcgccttac taaggctctg ctcaggcgcg ccaggcgaac tggccaccgg   13500
gccgccatga gggccgcacg gcgggctgcc gctgccgcaa gcgtcgtggc cccgcgggca   13560
```

```
cgaaggcgcg cggccgctgc cgccgccgcc gccatttcca gcttggcctc gacgcggcgc    13620
ggtaacatat actgggtgcg cgactcggta accggcacgc gggtacccgt gcgctttcgc    13680
cccccgcgga attagcacaa gacaacatac acactgagtc tcctgctgtt gtgtatccca    13740
gcggcgaccg tcagcagcgg cgacatgtcc aagcgcaaaa ttaaagaaga gatgctccag    13800
gtcatcgcgc cggagatcta tgggcccccg aagaaggagg aggatgatta caagcccgc     13860 aagctaaagc gggtcaaaaa gaaaagaaa gatgatgatg acgaggcggt ggagtttgtc     13920
cgccgcatgg cacccaggcg ccccgtgcag tggaagggcc ggcgcgtgca gcgcgttttg    13980
cgccccggca ccgcggtggt cttcacgccc ggcgagcgct ccacgcgcac tttcaagcgg    14040
gtgtacgatg aggtgtacgg cgacgaggac ctgttggagc aggccaacca gcgctttggg    14100
gagtttgcat atgggaaacg gccccgcgag agtctaaaag aggacctgct ggcgctaccg    14160
ctggacgagg gcaatcccac cccgagtctg aagccggtaa ccctgcaaca ggtgctgcct    14220
ttgagcgcgc ccagcgagca taagcgaggg ttgaagcgcg aaggcgggga cctggcgccc    14280
accgtgcagt tgatggtgcc caagcggcag aagctggagg acgtgctgga gaaaatgaaa    14340
gtagagcccg ggatccagcc cgagatcaag gtccgccca tcaagcaggt ggcgcccggc     14400
gtgggagtcc agaccgtgga cgttaggatt cccacggagg agatgaaac ccaaaccgcc     14460 actccctctt cggcggccag cgccaccacc ggcaccgctt cggtagaggt gcagacggac    14520
ccctggctac ccgccaccgc tgttgccgcc gccgccccc gttcgcgcgg gcgcaagaga     14580
aattatccag cggccagcgc gctcatgccc cagtacgcac tgcatccatc catcgtgccc    14640
acccccggct accgcgggta ctcgtaccgc ccgcgcagat cagccggcac tcgcggccgc    14700
cgccgccgtg cgaccacaac cagccgccgc cgtcgccgcc gccgccagcc agtgctgacc    14760
cccgtgtctg taaggaaggt ggctcgctcg gggagcacgc tggtggtgcc cagagcgcgc    14820
taccacccca gcatcgttta aagccggtct ctgtatggtt cttgcagata tggccctcac    14880
ttgtcgcctc cgcttcccgg tgccgggata ccgaggaaga actcaccgcc gcagaggcat    14940
ggcgggcagc ggtctccgcg gcggccgtcg ccatcgccgg cgcgcaaaaa gcaggcgcat    15000
gcgcggcggt gtgctgcctc tgctaatccc gctaatcgcc gcggcgatcg gtgccgtacc    15060
cgggatcgcc tccgtggccc tgcaggcgtc ccagaaacgt tgactcttgc aaccttgcaa    15120
gcttgcattt tttggaggaa aaataaaaaa aagtctagac tctcacgctc gcttggtcct    15180
gtgactattt tgtagaaaaa aagatggaag acatcaactt gcgtcgctg ccccgcgtc     15240 acggctcgcg cccgttcatg ggagactgga cagatatcgg caccagcaat atgagcggtg    15300
gcgccttcag ctggggcagt ctgtggagcg gccttaaaaa ttttggttcc accattaaga    15360
actatggcaa caaagcgtgg aacagcagca cgggccagat gctgagagac aagttgaaag    15420
agcagaactt ccaggagaag gtggcgcagg gcctggcctc tggcatcagc ggggtggtgg    15480
acatagctaa ccaggccgtg cagaaaaaga taaacagtca tctggacccc cgtcctcagg    15540
tggaggaaat gcctccagcg atggagacgg tgtctcccga gggcaaaggc gaaaagcgcc    15600
cgcggcccga cagagaagag accctggtgt cacacaccga ggagccgccc tcttacgagg    15660
aggcagtcaa ggcggcctg cccaccactc gccccatagc ccccatggcc accggtgtgg    15720
tgggccacag gcaacacact cccgcaacac tagatctgcc ccgccgtcc gagccgccgc     15780 gccagccaaa ggcggcgacg gtgcccgctc cctccacttc cgccgccaac agagtgcccc    15840
tgcgccgcgc cgcgagcggc ccccgggcct cgcgagttag cggcaactgg cagagcacac    15900
tgaacagcat cgtgggcctg ggagtgagga gtgtgaagcg ccgccgttgc tactgaatga    15960
```

-continued

```
gcaagctagc taacgtgttg tatgtgtgta tgcgtcctat gtcgccgcca gaggagctgt    16020
tgagccgccg gcgccgtctg cactccagcg aatttcaaga tggcgacccc atcgatgatg    16080
cctcagtggt cgtacatgca catctcgggc caggacgctt cggagtacct gagccccggg    16140
ctggtgcagt tcgcccgcgc cacagacacc tacttcaaca tgagtaacaa gttcaggaac    16200
cccactgtgg cgcccaccca cgatgtgacc acggaccggt cgcagcgcct gacgctgcgg    16260
ttcatccccg tggatcggga ggacaccgcc tactcttaca aggcgcggtt cacgctggcc    16320
gtgggcgaca accgcgtgct ggacatggcc tccacttact ttgacatcag gggggtgctg    16380
gacaggggcc ccaccttcaa gccctactcg ggtactgcct acaactccct ggcccccaag    16440
ggcgctccca attcttgcga gtgggaacaa gatgaaccag ctcaggcagc aatagctgaa    16500
gatgaagaag aacttgaaga agaacaagct caggacgaac aggcgcccac taagaaaacc    16560
catgtatacg cccaggcacc tctttctggt gaaaaaatta ctaaggatgg tttgcaaata    16620
ggtgtggatg ccacacaggc gggagataac cctatatatg ctgataaaac attccaaccc    16680
gaacctcaga taggtgagtc tcagtggaac gaggctgatg ccacagtagc aggaggcaga    16740
gtcttaaaaa agaccacccc tatgagacct tgctatggat cctatgccaa acctactaat    16800
gccaatggcg gtcaagggat catggtggcc aatgatcagg gagcgcttga atctaaagtt    16860
gagatgcaat ttttctccac cacaacgtct cttaatgtaa gggaaggtga aaacaatctt    16920
cagccaaaag tagtgctata cagcgaagat gttaacttgg aatcccctga cactcatttg    16980
tcttacaaac ctaaaaagga tgacaccaac tctaaaatca tgttgggtca gcaagccatg    17040
cccaacagac ccaacctcat tgcttttagg gacaacttta ttggacttat gtactacaac    17100
agcacaggca acatgggagt gctggcagga caggcctccc agctaaacgc tgtggtagac    17160
ttgcaagaca gaaacacaga gctgtcatac caactgatgc ttgattccat ggagacagag    17220
tcaagatact tttccatgtg gaaccaggca gtggacagct atgacccaga tgtcagaatc    17280
attgaaaacc atgggggttga agatgagctg cccaactatt gctttccct gggcggtatt    17340 ggaattacag acacatacca gtgcataaaa ccaaccgcag ctgctaataa cactacatgg    17400
tctaaggatg aagaatttag tgatcgcaat gaaatagggg tgggaaacaa cttcgccatg    17460
gagatcaaca tccaggccaa cctctggagg aacttcctct atgcgaacgt ggggctctac    17520
ctgccagaca agctcaagta caaccccacc aacgtggaca tctctgacaa ccccaacacc    17580
tatgactaca tgaacaagcg tgtggtggct cccggcctgg tggactgctt tgtcaatgtg    17640
ggagccaggt ggtccctgga ctacatggac aacgtcaacc ccttcaacca ccaccgcaat    17700
gcgggtctgc gctaccgctc catgatcctg ggcaacgggc gctacgtgcc cttccacatt    17760
caggtgcccc agaagttctt tgccatcaag aacctcctcc tcctgccggg ctcctacact    17820
tacgagtgga acttcaggaa ggatgtcaac atggtcctgc agagctctct gggcaatgac    17880
cttagggtgg acggggccag catcaagttt gacagcgtca ccctctatgc taccttcttc    17940
cccatggctc acaacaccgc ctccacgctc gaggccatgc tgaggaacga caccaacgac    18000
cagtccttca atgactacct ctctggggcc aacatgctct accccatccc cgccaaggcc    18060
accaacgtgc ccatctccat tccctctcgc aactgggccg ccttcagagg ctgggccttt    18120
acccgcctta agaccaagga acccctcc ctgggctcgg ttttgacccc tactttgtc    18180 tactcgggat ccatcccta cctggatggc accttctacc tcaaccacac ttttaagaag    18240
atatccatca tgtatgactc ctccgtcagc tggccgggca tgaccgcct gctcacccc    18300 aatgagttcg aggtcaagcg cgccgtggac ggcgagggct acaacgtggc ccagtgcaac    18360
```

```
atgaccaagg actggttcct ggtgcagatg ctggccaact acaacatagg ctaccagggc     18420
ttctacatcc cagagagcta caaggacagg atgtactcct tcttcagaaa tttccaaccc     18480
atgagcaggc aggtggtgga cgagaccaaa tacaaggact atcaggccat tggcatcact     18540
caccagcaca acaactcggg attcgtgggc tacctggctc ccaccatgcg cgaggggcag     18600
gcctaccccg ccaacttccc ctacccgttg ataggcaaaa ccgcggtcga cagcgtcacc     18660
cagaaaaagt tcctctgcga ccgcaccctc tggcgcatcc ccttctctag caacttcatg     18720
tccatgggtg cgctcacgga cctgggccag aacctgctct atgccaactc cgcccatgcg     18780
ctggacatga cttttgaggt ggaccccatg gacgagccca cccttctcta tattgtgttt     18840
gaagtgttcg acgtggtcag agtgcaccag ccgcaccgcg tgtcatcga gaccgtgtac      18900 ctgcgcacgc ccttctcggc cggcaacgcc accacctaag gagacagcgc cgccgcctgc     18960
atgacgggtt ccaccgagca agagctcagg gccatcgcca gagacctggg atgcggaccc     19020 tatttttttgg gcacctatga caaacgcttc ccgggcttca tctcccgaga caagctcgcc    19080
tgcgccatcg tcaacacggc cgcgcgcgag accgggggcg tgcactggct ggcctttggc     19140
tgggacccgc gctccaaaac ctgctacctc ttcgacccct ttggcttctc cgatcagcgc     19200
ctcagacaga tctatgagtt tgagtacgag gggctgctgc ccgcagcgc gcttgcctcc      19260 tcgcccgacc gctgcatcac ccttgagaag tccaccgaga ccgtgcaggg gccccactcg     19320
gccgcctgcg gtctcttctg ctgcatgttt ttgcacgcct tgtgcgctg gccccagagt      19380 cccatggatc gcaaccccac catgaacttg ctcaaggag tgcccaacgc catgctccag      19440
agcccccagg tccagcccac cctgcgccac aaccaggaac agctctaccg cttcctggag     19500
cgccactccc cctacttccg cagtcacagc gcgcacatcc ggggggccac ctctttctgc     19560
cacttgcaag aaaacatgca agacggaaaa tgatgtacag ctcgcttttt aataaatgta     19620
aagactgtgc actttattta tacacgggct cttttctggtt atttattcaa caccgccgtc    19680
gccatctaga aatcgaaagg gttctgccgc gcgtcgccgt gcgccacggg cagagacacg     19740
ttgcgatact ggaagcggct cgcccactta aactcgggca ccaccatgcg gggcagtggt     19800
tcctcgggga agttctcgcc ccacaggggtg cgggtcagct gcagcgcgct caggaggtcg    19860
ggagccgaga tcttgaagtc gcagttgggg ccggaaccct gcgcgcgcga gttgcggtac     19920
acggggttgc agcactggaa caccagcagg gccggattat gcacgctggc cagcaggctc     19980
tcgtcgctga tcatgtcgct gtccagatcc tccgcgttgc tcagggcgaa cggggtcatc    20040
ttgcagacct gcctgcccag gaaaggcggc agcccgggct tgccgttgca gtcgcagcgc    20100
aggggcatca gcaggtgccc gcggcccgac tgcgcctgcg ggtacagcgc gcgcatgaag    20160
gcttcgatct gcctgaaagc cacctgcgtc ttggctccct ccgaaaagaa catcccacag    20220
gacttgctgg agaactggtt cgcgggacag ctggcatcgt gcaggcagca gcgcgcgtcg    20280
gtgttggcga tctgcaccac gttgcgaccc caccggttct tcactatctt ggccttggaa    20340
gcctgctcct tcagcgcgcg ctggccgttc tcgctggtca catccatctc tatcacctgc    20400
tccttgttga tcatgtttgt accgtgcaga cacttcaggt cgccctccgt ctgggtgcag    20460
cggtgctccc acagcgcgca accggtgggc tcccaatttt tgtgggtcac cccgcgtag    20520 gcctgcaggt aggcctgcaa gaagcgcccc atcatggcca caaaggtctt ctggctcgta    20580
aaggtcagct gcaggccgcg atgctcttcg ttcagccagg tcttgcagat ggcggccagc    20640
gcctcggtct gctcgggcag catcctaaaa tttgtcttca ggtcgttatc cacgtggtac    20700
ttgtccatca tggcgcgcgc cgcctccatg cccttctccc aggcggacac catgggcagg    20760
```

```
cttaggggt ttatcacttc caccggcgag gacaccgtac tttcgatttc ttcttcctcc   20820
ccctcttccc ggcgcgcgcc cacgctgctg cgcgctctca ccgcctgcac caagggtcg   20880 tcttcaggca agcgccgcac cgagcgcttg ccgcccttga cctgcttaat cagcaccggc   20940
gggttgctga agcccaccat ggtcagcgcc gcctgctctt cttcgtcttc gctgtctacc   21000
actatctctg gggaagggct tctccgctct gcggcggcgc gcttcttttt tttcttggga   21060
gcggccgtga tgggagtccgc cacggcgacg gaggtcgagg gcgtgggct ggggtgcgc    21120 ggtaccaggg cctcgtcgcc ctcggactct tcctctgact ccaggcggcg gcggagtcgc   21180
ttctttgggg gcgcgcgcgt cagcggcggc ggagacgggg acgggacgg ggacgggacg   21240 ccctccacag ggggtggtct tcgcgcagac ccgcggccgc gctcgggggt cttctcgagc   21300
tggtcttggt cccgactggc cattgtatcc tcctcctcct aggcagagag acataaggag   21360
tctatcatgc aagtcgagaa ggaggagagc ttaaccaccc cctctgagac cgccgatgcg   21420
cccgccgtcg ccgtcgcccc cgctgccgcc gacgcgcccg ccacaccgag cgacaccccc   21480 gcggacccc ccgccgacgc accctgttc gaggaagcgg ccgtggagca ggacccgggc    21540
tttgtctcgg cagaggagga tttgcgagag gaggaggata aggagaagaa gccctcagtg   21600
ccaaaagatg ataaagagca agacgagcac gacgcagatg cacaccaggg tgaagtcggg   21660 cgggggacg gagggcatga cggcgccgac tacctagacg aagggaacga cgtgctcttg   21720
aagcacctgc atcgtcagtg cgccattgtt tgcgacgctc tgcaggagcg cagcgaagtg   21780
cccctcagcg tggcggaggt cagccacgcc tacgagctca gcctcttctc ccccgggtg   21840 ccccccgcc gccgcgaaaa cggcacatgc gagcccaacc cgcgcctcaa cttctacccc   21900
gcctttgtgg tacccgaggt cctggccacc tatcacatct tctttcaaaa ttgcaagatc   21960
cccctctcgt gccgcgccaa ccgtagccgc gccgataaga tgctggccct gcgccagggc   22020
gaccacatac ctgatatcgc cgctttggaa gatgtaccaa agatcttcga gggtctgggt   22080
cgcaacgaga agcgggcagc aaactctctg caacaggaaa acagcgaaaa tgagagtcac   22140
accggggtac tggtggagct cgagggcgac aacgcccgcc tggcggtggt caagcgcagc   22200
atcgaggtca cccactttgc ctaccccgcg ctaaacctgc ccccaaagt catgaacgcg    22260 gccatggacg ggctgatcat gcgccgcggc cggcccctcg ctccagatgc aaacttgcat   22320
gaggagaccg aggacggcca gcccgtggtc agcgacgagc agctggcgcg ctggctggag   22380
accgcggacc ccgccgaact ggaggagcgg cgcaagatga tgatggccgt ggtgctggtc   22440
accgtagagc tggagtgtct gcagcgcttc ttcggcgacc ccgagatgca gagaaaggtc   22500
gaggagaccc tgcactacac cttccgccag ggctacgtgc gccaggcttg caagatctcc   22560
aacgtggagc tcagcaacct ggtgtcctac ctgggcatct tgcatgagaa ccgcctcggg   22620
cagagcgtgc tgcactccac cctgcgcggg gaggcgcgcc gcgactacgt gcgcgactgc   22680
gtttacctct tcctctgcta cacctggcag acggccatgg gggtctggca gcagtgcctg   22740
gaggagcgca acctcaagga gctggagaag ctcctgcagc gcgcgctcaa agatctctgg   22800
acgggctaca acgagcgctc ggtggccgcc gcgctggccg acctcatctt ccccgagcgc   22860
ctgctcaaaa ccctccagca ggggctgccc gacttcacca gccaaagcat gttgcaaaac   22920
ttcaggaact ttatcctgga gcgttctggc atcctacccg ccacctgctg cgccctgccc   22980
agcgactttg tccccctcgt gtaccgcgag tgccccccgc cgctgtgggg tcactgctac   23040
ctgttccaac tggccaacta cctgtcctac cacgcggacc tcatggagga ctccagcggc   23100 gagggggctca tggagtgcca ctgccgctgc aacctctgca cgccccaccg ctccctggtc   23160
```

```
tgcaacaccc aactgctcag cgagagtcag attatcggta ccttcgagct acagggtccg  23220
tcctcctcag acgagaagtc cgcggctccg gggctaaaac tcactccggg gctgtggact  23280
tccgcctacc tgcgcaaatt tgtacctgaa gactaccacg cccacgagat caggtttttac 23340 gaagaccaat cccgcccgcc caaggcgag ctgaccgcct gcgtcatcac ccagggcgag   23400
atcctaggcc aattgcaagc catccaaaaa gcccgccaag acttttttgct gaagaagggt 23460 cggggggtgt atctggaccc ccagtcgggt gaggagctca acccggttcc cccgctgccg  23520
ccgccgcggg accttgcttc ccaggataag catcgccatg gctcccagaa agaagcagca  23580
gcggccgcca ctgccgccac cccacatgct ggaggaagag gaggaatact gggacagtca  23640
ggcagaggag gtttcggacg aggaggagcc ggagacggag atggaagagt gggaggagga  23700
cagcttagac gaggaggctt ccgaagccga agaggcagac gcaacaccgt caccctcggc  23760
cgcagccccc tcgcaggcgc ccccgaagtc cgctcccagc atcagcagca acagcagcgc  23820
tataacctcc gctcctccac cgccgcgacc cacggccgac cgcagaccca accgtagatg  23880
ggacaccacc ggaaccgggg ccggtaagtc ctccgggaga ggcaagcaag cgcagcgcca  23940
aggctaccgc tcgtggcgcg ctcacaagaa cgccatagtc gcttgcttgc aagactgcgg  24000
ggggaacatc tccttcgccc gccgcttcct gctcttccac cacggtgtgg ccttcccccg  24060
taacgtcctg cattactacc gtcatctcta cagcccctac tgcggcggca gtgagccaga  24120
gacggtcggc ggcggcggcg gcgcccgttt cggcgcctag gaagacccag ggcaagactt  24180
cagccaagaa actcgcggcg gccgcggcga acgcggtcgc gggggccctg cgcctgacgg  24240
tgaacgaacc cctgtcgacc cgcgaactga ggaaccgaat cttccccact ctctatgcca  24300
tcttccagca gagcagaggg caggatcagg aactgaaagt aaaaaacagg tctctgcgct  24360
ccctcacccg cagctgtctg tatcacaaga gcgaagacca gcttcggcgc acgctggagg  24420
acgctgaggc actcttcagc aaatactgcg cgctcactct taaggactag ctccgcgccc  24480
ttctcgaatt taggcgggaa cgcctacgtc atcgcagcgc cgccgtcatg agcaaggaca  24540
ttcccacgcc atacatgtgg agctatcagc cgcagatggg actcgcggcg gcgcctccc   24600 aagactactc caccccgcatg aactggctca gtgccggccc acacatgatc tcacaggtta  24660
atgatatccg cacccatcga aaccaaatat tggtggagca ggcggcaatt accaccacgc  24720
cccgcaataa tcccaacccc agggagtggc ccgcgtccct ggtgtatcag gaaattcccg  24780
gccccaccac cgtactactt ccgcgtgatt cccaggccga agtccaaatg actaactcag  24840
gggcacagct cgcggggcggc tgtcgtcaca gggtgcggcc tcctcgccag gtataactc   24900 acctggagat ccgaggcaga ggtattcagc tcaacgacga gtcggtgagc tcctcgctcg  24960
gtctcagacc tgacgggacc ttccagatag ccggagccgg ccgatcttcc ttcacgcccc  25020
gccaggcgta cctgactctg caaagctcgt cctcggcgcc gcgctcgggc ggcatcggga  25080
ctctccagtt cgtgcaggag tttgtgccct cggtctactt caaccccttc tcgggctctc  25140
ccggtcgcta cccggaccag ttcatctcga actttgacgc cgcgagggac tcggtggacg  25200
gctacgactg aatgtcgggt ggacccggtg cagagcaact tcgcctgaag cacctcgacc  25260
actgccgccg ccctcagtgc tttgcccgct gtcagaccgg tgagttccag tacttttccc  25320
tgcccgactc gcacccggac ggcccggcgc acggggtgcg cttttttcatc ccgagtcagg  25380 tgcgctctac cctaatcagg gagtttaccg cccgtcccct actggcggag ttggaaaagg  25440
ggccttctat cctaaccatt gcctgcatct gctctaaccc tggattgcac caagatcttt  25500
gctgtcattt gtgtgctgag tataataaag gctgagatca gaatctactc gggctcctgt  25560
```

```
cgccatcctg tcaacgccac cgtccaagcc cggcccgatc agcccgaggt gaacctcacc   25620
tgcggtctgc accggcgcct gaggaaatac ctagcttggt actacaacag cactcccttt   25680
gtggtttaca acagctttga ccaggacggg gtctcactga gggataacct ctcgaacctg   25740
agctactcca tcaggaagaa cagcaccctc gagctacttc ctccttacct gcccgggact   25800
taccagtgtg tcaccggtcc ctgcacccac acccacctgt tgatcgtaaa cgactctctt   25860
ccgagaacag acctcaataa ctcctcttcg cagttcccca gaacaggagg tgagctcagg   25920
aaaccccggg taagaaggg tggacgagag ttaacacttg tggggtttct ggtgtatgtg   25980
acgctggtgg tggctctttt gattaaggct tttccttcca tgtctgaact ctccctcttc   26040
ttttatgaac aactcgacta gtgctaacgg gaccctaccc aacgaatcgg gattgaatat   26100
cggtaaccag gttgcagttt cacttttgat taccttcata gtcctcttcc tgctagtgct   26160
gtcgcttctg tgcctgcgga tcgggggctg ctgcatccac gtttatatct ggtgctggct   26220
gtttagaagg ttcggagacc atcgcaggta gaataaacat gctgctgctt accctctttg   26280
tcctggcgct ggccgccagc tgccaagcct tttccgaggc tgactttata gagccccagt   26340
gtaatgtgac ttttaaagcc catgcacagc gttgtcatac tataatcaaa tgtgccaccg   26400
aacacgatga ataccttatc cagtataaag ataaatcaca caaagtggca cttgttgaca   26460
tctggaaacc cgaagaccct ttggaataca atgtgaccgt tttccagggt gacctcttca   26520
aaatttacaa ttcactttc ccatttgacc agatgtgtga ctttgtcatg tacatggaaa   26580
agcagcacaa gctgtggcct ccgactcccc agggctgtgt ggaaaatcca ggctcttct   26640 gcatgatctc tctctgtgta actgtgctgg cactaatact cacgcttttg tatatcagat   26700
ttaaatcaag gcaaagcttc attgatgaaa agaaaatgcc ttaatcgctt tcacgcttga   26760
ttgctaacac cgggtttta tccgcagaat gattggaatc accctactaa tcacctccct   26820
ccttgcgatt gcccatgggt tggaacgaat cgaagtccct gtgggggcca atgttaccct   26880 ggtgggggcct gtcggcaatg ctacattaat gtgggaaaaa tatactaaaa atcaatgggt   26940
ctcttactgc actaacaaaa atagccacaa gcccagagcc atctgcgatg gcaaaatct   27000 aaccttgatt gatgttcaat tgctggatgc gggctactat tatgggcagc tgggtacaat   27060
gattaattac tggagacccc acagagatta catgctccac gtagtaaagg gtcccccttag  27120 cagcccaccc actaccacct ctactacccc cactaccacc actactccca ccaccagcac   27180
tgccgcccag cctcctcata gcagaacaac cacttttatc aattccaagt cccactcccc   27240
ccacattgcc ggcgggccct ccgcctcaga ctccgaaacc accgagatct gcttctgcaa   27300
atgctctgac gccattgccc aggatttgga agatcacgag gaagatgagc atgacttcgc   27360
agatgcatgc caggcatcag agccagaagc gctgccggtg gccctcaaac agtatgcaga   27420
cccccacacc acccccgacc ttcctccacc ttcccagaag ccaagtttcc tggggggaaaa   27480 tgaaactctg cctctctcca tactcgctct gacatctgtt gctatgttga ccgctctgct   27540
ggtgcttcta tgctctatat gctacctgat ctgctgcaga aagaaaaaat ctcacggcca   27600
tgctcaccag cccctcatgc acttcccttaa ccctccagag ctgggcgacc acaaactta   27660 agtctgcagt aactatctgc ccatcccttg tcagtcgaca gcgatgagcc ccactaatct   27720
aacggcctct ggacttacaa catcgtctct taatgagacc accgctcctc aagacctgta   27780
cgatggtgtc tccgcgctgg ttaaccagtg ggatcacctg gcatatggt ggctcctcat   27840 aggagcagtg accctgtgcc taatcctggt ctggatcatc tgctgcatca aaagcagaag   27900
acccaggcgg cggcccatct acaggccctt tgtcatcaca cctgaagatg atgatgacac   27960
```

```
cacttccagg ctgcagaggc taaagcagct actcttctct tttacagcat ggtaaattga    28020
atcatgcctc gcattttcat ctacttgtct ctccttccac tttttctggg ctcttctaca    28080
ttggccgctg tgtcccacat cgaggtagac tgcctcacgc ccttcacagt ctacctgctt    28140
ttcggctttg tcatctgcac cttgtctgc agcgttatca ctgtagtgat ctgcttcata    28200
cagtgcatcg actacgtctg cgtgcgggtg gcttacttta gacaccaccc ccagtatcgc    28260
aacagggaca tagcggctct cctaagactt gtttaaaatc atggccaaat taactgtgat    28320
tggtcttctg atcatctgct gcgtcctagc cgcgattggg actcaagctc ctaccaccac    28380
cagcgctccc agaaagagac atgtatcctg cagcttcaag cgtccctgga atataccca    28440 atgctttact gatgaacctg aaatctcttt ggcttggtac ttcagcgtca ccgcccttct    28500
tatcttctgc agtacggtta ttgcccttgc catctaccct tcccttgacc tgggctggaa    28560
tgctgtcaac tctatggaat atcccacctt cccagaacca gacctgccag acctggttgt    28620
tctaaacgcg tttcctcctc ctgctcccgt tcaaaatcag tttcgccctc cgtccccac     28680 gcccactgag gtcagctact ttaatctaac aggcggagat gactgaaaac ctagacctag    28740
aaatggacgg tctctgcagc gagcaacgca cactagagag gcgccggcaa aaagagctcg    28800
agcgtcttaa acaagagctc caagacgcgg tggccataca ccagtgcaaa aaggtgtct    28860 tctgtctggt aaaacaggcc acgctcacct atgaaaaac aggtgacacc caccgcctag     28920
gatacaagct gcccacacag cgccaaaagt tcgccctcat gataggcgaa caacccatca    28980
ccgtgaccca gcactccgtg gagacagaag gctgcataca tgctccctgt aggggcgctg    29040
actgcctcta caccttgatc aaaacccctct gcggtctcag agaccttatc cctttcaatt    29100
aatcataact gtaatcaata aaaaatcact tacttgaaat ctgatagcaa gcctctgtcc    29160
aattttttca gcaacacttc cttccctcc tcccaactct ggtactctag gcgcctcta     29220 gctgcaaact tcctccacag tctgaaggga atgtcagatt cctcctcctg tccctccgca    29280
cccacgatct tcatgttgtt gcagatgaaa cgcgcgagat cgtctgacga gccttcaac    29340 cccgtgtacc cctacgatac cgagatcgct ccgacttctg tccctttcct taccctcc      29400 tttgtgtcat ccgcaggaat gcaagaaaat ccagctgggg tgctgtccct gcacttgtca    29460 gagccccta ccacccacaa tgggggcctg actctaaaaa tggggggcgg cctgaccctg     29520
gacaaggaag ggaatctcac ttcccaaaac atcaccagtg tcgatccccc tctcaaaaaa    29580
agcaagaaca acatcagcct tcagaccgcc gcacccctcg ccgtcagctc cggggcccta    29640 acacttttg ccactccccc cctagcggtc agtggtgaca accttactgt gcagtctcag     29700
gcccctctca ctttggaaga ctcaaaacta actctggcca ccaaaggacc cctaactgtg    29760
tccgaaggca aacttgtcct agaaacagag gctcccctgc atgcaagtga cagcagcagc    29820
ctgggcctta gcgttacggc cccacttagc attaacaatg acagcctagg actagatctg    29880
caggcaccca ttgtctctca aaatggaaaa ctggctctaa atgtagcagg ccccctagct    29940
gtggccaatg gcattaatgc tttgacagta ggcacaggca aagtattgg tctaaatgaa    30000 accagcactc acttgcaagc aaagttggtc gcccccctag gctttgatac caatggcaac    30060
attaagctaa gcgttgcagg aggcatgaga ctaaataatg acacacttat actagatgta    30120
aactacccat ttgaagctca aggccaacta agtctaagag tgggccaggg tccgctgtat    30180
gtagattcta gcagccataa cctgaccatt agatgcctta gaggattata cataacatcg    30240
tctaataacc aaaccggtct agaggccaac ataaaactaa caaaaggcct tgtctatgat    30300
ggaaatgcca tagcagtcaa tgttggtcaa ggattgcaat acagcactac tgccacatcg    30360
```

```
gaaggtgtgt atcctataca gtctaagata ggtttgggaa tggaatatga taccaacgga   30420
gccatgatga caaaactagg ctctggacta agctttgaca attcaggagc cattgtagtg   30480
ggaaacaaaa atgatgacag gcttactctg tggactacac cagacccatc tcctaactgt   30540
agaatttatt ctgaaaaaga tactaaacta accttggtgc tgactaagtg tggcagccaa   30600
atcctaggca cagtatctgc ccttgctgtc agaggcagcc ttgcgcccat cactaatgca   30660
tccagcatag tccaaatatt tctaagattt gatgaaaatg gactattgat gagcaactca   30720
tcgctagacg gtgattactg gaattacaga aatggggact ccactaatag cacaccatat   30780
acaaatgcag taggctttat gcctaatcta gcagcctatc ctaaaggtca ggctacagct   30840
gcaaaaagca gtattgtaag ccaggtatac atggatggtg acactactaa acctataaca   30900
ctaaaaataa acttcaatgg cattgatgaa acaacagaaa ataccctgt  tagtaaatat   30960
tccatgacat tctcatggag ctggcccacc gcaagctaca taggccacac ttttgcaaca   31020
aactctttta ctttctccta catcgcccaa gaataaagaa agcacagaga tgcttgtttt   31080
gatttcaaaa ttgtgtgctt ttatttattt tcagcttaca gtatttccag tagtcattcg   31140
aataaagctt aatcaaactg catgagaacc cttccacata gcttaaatta gcaccagtgc   31200
aaatggagaa aagcctcgag gtcgttgcgc ggccgggatc ggtgatcacc gatccagaca   31260
tgataagata cattgatgag tttggacaaa ccacaactag aatgcagtga aaaaaatgct   31320
ttatttgtga aatttgtgat gctattgctt tatttgtaac cattataagc tgcaataaac   31380
aagttcccgg atcgcgatcc ggcccgaggc tgtagccgac gatggtgcgc caggagagtt   31440
gttgattcat tgtttgcctc cctgctgcgg ttttcaccg aagttcatgc cagtccagcg   31500
tttttgcagc agaaaagccg ccgacttcgg tttgcggtcg cgagtgaaga tcccttctct   31560
gttaccgcca acgcgcaata tgccttgcga ggtcgcaaaa tcggcgaaat tccatacctg   31620
ttcaccgacg acggcgctga cgcgatcaaa gacgcggtga tacatatcca gccatgcaca   31680
ctgatactct tcactccaca tgtcggtgta cattgagtgc agcccggcta acgtatccac   31740
gccgtattcg gtgatgataa tcggctgatg cagtttctcc tgccaggcca gaagttcttt   31800
ttccagtacc ttctctgccg tttccaaatc gccgctttgg acataccatc cgtaataacg   31860
gttcaggcac agcacatcaa agagatcgct gatggtatcg gtgtgagcgt cgcagaacat   31920
tacattgacg caggtgatcg gacgcgtcgg gtcgagttta cgcgttgctt ccgccagtgg   31980
cgcgaaatat tcccgtgcac cttgcggacg ggtatccggt tcgttggcaa tactccacat   32040
caccacgctt gggtggtttt tgtcacgcgc tatcagctct ttaatcgcct gtaagtgcgc   32100
ttgctgagtt tccccgttga ctgcctcttc gctgtacagt tctttcggct tgttgcccgc   32160
ttcgaaacca atgcctaaag agaggttaaa gccgacagca gcagtttcat caatcaccac   32220
gatgccatgt tcatctgccc agtcgagcat ctcttcagcg taagggtaat gcgaggtacg   32280
gtaggagttg gcccccaatcc agtccattaa tgcgtggtcg tgcaccatca gcacgttatc   32340
gaatcctttg ccacgcaagt ccgcatcttc atgacgacca aagccagtaa agtagaacgg   32400
tttgtggtta atcaggaact gttcgcccctt cactgccact gaccggatgc cgacgcgaag   32460
cgggtagata tcacactctg tctggctttt ggctgtgacg cacagttcat agagataacc   32520
ttcacccggt tgccagaggt gcggattcac cacttgcaaa gtcccgctag tgccttgtcc   32580
agttgcaacc acctgttgat ccgcatcacg cagttcaacg ctgacatcac cattggccac   32640
cacctgccag tcaacagacg cgtggttaca gtcttgcgcg acatgcgtca ccacggtgat   32700
atcgtccacc caggtgttcg gcgtggtgta gagcattacg ctgcgatgga ttccggcata   32760
```

```
gttaaagaaa tcatggaagt aagactgctt tttcttgccg ttttcgtcgg taatcaccat  32820
tcccggcggg atagtctgcc agttcagttc gttgttcaca caaacggtga tacgtacact  32880
tttcccggca ataacatacg gcgtgacatc ggcttcaaat ggcgtatagc cgccctgatg  32940
ctccatcact tcctgattat tgacccacac tttgccgtaa tgagtgaccg catcgaaacg  33000
cagcacgata cgctggcctg cccaaccttt cggtataaag acttcgcgct gataccagac  33060
gttgcccgca taattacgaa tatctgcatc ggcgaactga tcgttaaaac tgcctggcac  33120
agcaattgcc cggctttctt gtaacgcgct ttcccaccaa cgctgatcaa ttccacagtt  33180
ttcgcgatcc agactgaatg cccacaggcc gtcgagtttt ttgatttcac gggttggggt  33240
ttctacagga cggaccatgc gttcgacctt tctcttcttt tttgggccca tgatggcaga  33300
tccgtatagt gagtcgtatt agctggttct ttccgcctca gaagccatag agcccaccgc  33360
atccccagca tgcctgctat tgtcttccca atcctccccc ttgctgtcct gccccacccc  33420
acccccagaa atagaatgac acctactcag acaatgcgat gcaatttcct cattttatta  33480
ggaaaggaca gtgggagtgg caccttccag ggtcaaggaa ggcacggggg aggggcaaac  33540
aacagatggc tggcaactag aaggcacagt cgaggctgat cagcgagctc tagatgcatg  33600
ctcgagcggc cgcacgtcgt accggcaatt gccgcggcaa ttgccgacgc cgcgtaacta  33660
taacggtcct aaggtagcga gagggccaag tgccgaacga gtatatatag gaataaaaaa  33720
tgacgtaaat gtgtaaaggt cagaaaacgc ccagaaaaat acacagacca acgcccgaaa  33780 cgaaacccg  cgaaaaaata cccagaactt cctcaacaac cgccacttcc ggtttctcac  33840
ggtacgtcac ttccgcaaga aaagcaaaac tacatttccc acatgtgtaa aaacgaaacc  33900 ccgcccttg  taactgccca caacttacat catcaaaaca taaactccta cgtcacccgc  33960
cccgcctctc cccgcccacc tcattatcat attggccaca atccaaaata aggtatatta  34020
ttgatgatg                                                         34029
```

AFFENADENOVIRUS (GORILLA) OR ADENOVIRAL VECTORS AND METHODS OF USE

CROSS-REFERENCE TO RELATED APPLICATIONS

This patent application claims the benefit of U.S. Provisional Patent Application No. 61/543,638, filed Oct. 5, 2011, which is incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 285,313 Byte ASCII (Text) file named "716433_ST25.TXT," created on Mar. 28, 2014.

BACKGROUND OF THE INVENTION

In vivo delivery of proteins in biologically relevant forms and amounts has been an obstacle to drug and vaccine development for decades. One solution that has proven to be a successful alternative to traditional protein delivery approaches is the delivery of exogenous nucleic acid sequences for production of proteins in vivo. Gene transfer vectors ideally enter a wide variety of cell types, have the capacity to accept large nucleic acid sequences, are safe, and can be produced in quantities required for treating patients. Viral vectors are gene transfer vectors with these advantageous properties (see, e.g., Thomas et al., *Nature Review Genetics*, 4: 346-358 (2003)). Furthermore, while many viral vectors are engineered to infect a broad range of cell types, viral vectors also can be modified to target specific cell types, which can enhance the therapeutic efficacy of the vector (see, e.g., Kay et al., *Nature Medicine*, 7(1): 33-40 (2001).

Viral vectors that have been used with some success to deliver exogenous proteins to mammalian cells for therapeutic purposes include, for example, Retrovirus (see, e.g., Cavazzana-Calvo et al., *Science*, 288 (5466): 669-672 (2000)), Lentivirus (see, e.g., Cartier et al., *Science*, 326: 818-823 (2009)), Adeno-associated virus (AAV) (see, e.g., Mease et al., *Journal of Rheumatology*, 27(4): 692-703 (2010)), Herpes Simplex Virus (HSV) (see, e.g., Goins et al., *Gene Ther.*, 16(4): 558-569 (2009)), Vaccinia Virus (see, e.g., Mayrhofer et al., *J. Virol.*, 83(10): 5192-5203 (2009)), and Adenovirus (see, e.g., Lasaro and Ertl, *Molecular Therapy*, 17(8): 1333-1339 (2009)).

Despite their advantageous properties, widespread use of viral gene transfer vectors is hindered by several factors. In this respect, certain cells are not readily amenable to gene delivery by currently available viral vectors. For example, lymphocytes are impaired in the uptake of adenoviruses (Silver et al., *Virology*, 165: 377-387 (1988), and Horvath et al., *J. Virology*, 62(1): 341-345 (1988)). In addition, viral vectors that integrate into the host cell's genome (e.g., retroviral vectors) have the potential to cause insertion mutations in oncogenes (see, e.g., Cavazzana-Calvo et al., supra, and Hacein-Bey-Abina et al., *N. Engl. J. Med.*, 348: 255-256 (2003)).

The use of viral vectors for gene transfer also is impeded by the immunogenicity of viral vectors. A majority of the U.S. population has been exposed to wild-type forms of many of the viruses currently under development as gene transfer vectors (e.g., adenovirus). As a result, much of the U.S. population has developed pre-existing immunity to certain virus-based gene transfer vectors. Such vectors are quickly cleared from the bloodstream, thereby reducing the effectiveness of the vector in delivering biologically relevant amounts of a gene product. Moreover, the immunogenicity of certain viral vectors prevents efficient repeat dosing, which can be advantageous for "boosting" the immune system against pathogens when viral vectors are used in vaccine applications, thereby resulting in only a small fraction of a dose of the viral vector delivering its payload to host cells.

Thus, there remains a need for improved viral vectors that can be used to efficiently deliver genes to mammalian cells in vivo. The invention provides such viral vectors.

BRIEF SUMMARY OF THE INVENTION

The invention provides an adenovirus or adenoviral vector. The adenovirus or adenoviral vector comprises one or more of the nucleic acid sequences selected from the group consisting of (a) the nucleic acid sequence of SEQ ID NO: 1, (b) a nucleic acid sequence that is at least 98.5% identical to SEQ ID NO: 2, (c) a nucleic acid sequence that is at least 90% identical to SEQ ID NO: 3, (d) a nucleic acid sequence that is at least 80% identical to SEQ ID NO: 4, and (e) a nucleic acid sequence that is at least 89% identical to SEQ ID NO: 5.

The invention provides an adenovirus or adenoviral vector comprising one or more of the nucleic acid sequences selected from the group consisting of (a) a nucleic acid sequence that is at least 98.6% identical to SEQ ID NO: 6, (b) a nucleic acid sequence that is at least 99.06% identical to SEQ ID NO: 7, (c) a nucleic acid sequence that is at least 97.13% identical to SEQ ID NO: 8, (d) a nucleic acid sequence that is at least 90.7% identical to SEQ ID NO: 9, and (e) a nucleic acid sequence that is at least 96.6% identical to SEQ ID NO: 10.

The invention provides an adenovirus or adenoviral vector comprising one or more of the nucleic acid sequences selected from the group consisting of (a) a nucleic acid sequence comprising at least 121 contiguous nucleotides of SEQ ID NO: 6, (b) a nucleic acid sequence comprising at least 462 contiguous nucleotides of SEQ ID NO: 7, (c) a nucleic acid sequence comprising at least 234 contiguous nucleotides of SEQ ID NO: 8, (d) a nucleic acid sequence comprising at least 606 contiguous nucleotides of SEQ ID NO: 9, and (e) a nucleic acid sequence comprising at least 188 contiguous nucleotides of SEQ ID NO: 10.

The invention provides an adenovirus or adenoviral vector comprising one or more of the amino acid sequences selected from the group consisting of (a) the amino acid sequence of SEQ ID NO: 11, (b) an amino acid sequence that is at least 82% identical to SEQ ID NO: 13, (c) an amino acid sequence that is at least 80% identical to SEQ ID NO: 14, and (d) an amino acid sequence that is at least 83% identical to SEQ ID NO: 15.

The invention provides an adenovirus or adenoviral vector comprising one or more of the nucleic acid sequences selected from the group consisting of (a) a nucleic acid sequence encoding the amino acid sequence of SEQ ID NO: 11, (b) a nucleic acid sequence encoding an amino acid sequence that is at least 99% identical to SEQ ID NO: 12, (c) a nucleic acid sequence encoding an amino acid sequence that is at least 82% identical to SEQ ID NO: 13, (d) a nucleic acid sequence encoding an amino acid sequence that is at least 80% identical to SEQ ID NO: 14, and (e) a nucleic acid sequence encoding an amino acid sequence that is at least 83% identical to SEQ ID NO: 15.

The invention provides an adenovirus or adenoviral vector comprising one or more of the amino acid sequences selected from the group consisting of (a) the amino acid sequence of SEQ ID NO: 16, (b) an amino acid sequence that is at least 97.8% identical to SEQ ID NO: 18, (c) an amino acid that is at least 93.4% identical to SEQ ID NO: 19, and (d) an amino acid sequence that is at least 98.2% identical to SEQ ID NO: 20.

The invention provides an adenovirus or adenoviral vector comprising one or more of the nucleic acid sequences selected from the group consisting of (a) a nucleic acid sequence encoding the amino acid sequence of SEQ ID NO: 16, (b) a nucleic acid sequence encoding an amino acid sequence that is at least 99.78% identical to SEQ ID NO: 17, (c) a nucleic acid sequence encoding an amino acid sequence that is at least 97.8% identical to SEQ ID NO: 18, (d) a nucleic acid sequence encoding an amino acid that is at least 93.4% identical to SEQ ID NO: 19, and (e) a nucleic acid sequence encoding an amino acid sequence that is at least 98.2% identical to SEQ ID NO: 20.

The invention provides an adenovirus or adenoviral vector comprising one or more of the amino acid sequences selected from the group consisting of (a) an amino acid sequence comprising at least 89 contiguous amino acid residues of SEQ ID NO: 16, (b) an amino acid sequence comprising at least 247 contiguous amino acid residues of SEQ ID NO: 18, (c) an amino acid sequence comprising at least 370 contiguous amino acid residues of SEQ ID NO: 19, and (d) an amino acid sequence comprising at least 192 contiguous amino acid residues of SEQ ID NO: 20.

The invention provides an adenovirus or adenoviral vector comprising one or more of the nucleic acid sequences selected from the group consisting of (a) a nucleic acid sequence encoding an amino acid sequence comprising at least 89 contiguous amino acid residues of SEQ ID NO: 16, (b) a nucleic acid sequence encoding an amino acid sequence comprising at least 428 contiguous amino acid residues of SEQ ID NO: 17, (c) a nucleic acid sequence encoding an amino acid sequence comprising at least 247 contiguous amino acid residues of SEQ ID NO: 18, (d) a nucleic acid sequence encoding an amino acid sequence comprising at least 370 contiguous amino acid residues of SEQ ID NO: 19, and (e) a nucleic acid sequence encoding an amino acid sequence comprising at least 192 contiguous amino acid residues of SEQ ID NO: 20.

DETAILED DESCRIPTION OF THE INVENTION

Adenoviruses are generally associated with benign pathologies in humans, and the genomes of adenoviruses isolated from a variety of species, including humans, have been extensively studied. Adenovirus is a medium-sized (90-100 nm), nonenveloped icosohedral virus containing approximately 36 kb of double-stranded DNA. The adenovirus capsid mediates the key interactions of the early stages of the infection of a cell by the virus, and is required for packaging adenovirus genomes at the end of the adenovirus life cycle. The capsid comprises 252 capsomeres, which includes 240 hexons, 12 penton base proteins, and 12 fibers (Ginsberg et al., *Virology*, 28: 782-83 (1966)). The hexon comprises three identical proteins, namely polypeptide II (Roberts et al., *Science*, 232: 1148-51 (1986)). The penton base comprises five identical proteins and the fiber comprises three identical proteins. Proteins IIIa, VI, and IX are present in the adenoviral coat and are believed to stabilize the viral capsid (Stewart et al., *Cell*, 67: 145-54 (1991), and Stewart et al., *EMBO J.*, 12(7): 2589-99 (1993)). The expression of the capsid proteins, with the exception of pIX, is dependent on the adenovirus polymerase protein. Therefore, major components of an adenovirus particle are expressed from the genome only when the polymerase protein gene is present and expressed.

Several features of adenoviruses make them ideal vehicles for transferring genetic material to cells for therapeutic applications (i.e. "gene therapy"), or for use as antigen delivery systems for vaccine applications. For example, adenoviruses can be produced in high titers (e.g., about $10^{13}$ particle units (pu)), and can transfer genetic material to nonreplicating and replicating cells. The adenoviral genome can be manipulated to carry a large amount of exogenous DNA (up to about 8 kb), and the adenoviral capsid can potentiate the transfer of even longer sequences (Curiel et al., *Hum. Gene Ther.*, 3: 147-154 (1992)). Additionally, adenoviruses generally do not integrate into the host cell chromosome, but rather are maintained as a linear episome, thereby minimizing the likelihood that a recombinant adenovirus will interfere with normal cell function.

The invention is predicated, at least in part, on the discovery and isolation of an adenovirus that has not previously been identified or isolated. The adenovirus described herein was isolated from a gorilla. There are four widely recognized gorilla subspecies within the two species of Eastern Gorilla (*Gorilla beringei*) and Western Gorilla (*Gorilla gorilla*). The Western Gorilla species includes the subspecies Western Lowland Gorilla (*Gorilla gorilla gorilla*) and Cross River Gorilla (*Gorilla gorilla diehli*). The Eastern Gorilla species includes the subspecies Mountain Gorilla (*Gorilla beringei beringei*) and Eastern Lowland Gorilla (*Gorilla beringei graueri*) (see, e.g., Wilson and Reeder, eds., *Mammalian Species of the World*, $3^{rd}$ ed., Johns Hopkins University Press, Baltimore, Md. (2005)). The adenovirus of the invention was isolated from Mountain Gorilla (*Gorilla beringei beringei*).

The genomes of several such adenoviruses have been analyzed, and it has been determined that the adenovirus can have the nucleic acid sequence of, for example, SEQ ID NO: 21, SEQ ID NO: 22, SEQ ID NO: 23, SEQ ID NO: 24, or SEQ ID NO: 25, each of which includes a number of sub-sequences that serve to uniquely define the adenovirus, namely the nucleic acid sequences SEQ ID NOs: 1-10, and amino acid sequences SEQ ID NOs: 11-20. SEQ ID NOs: 6-10 encode the amino acid sequences of SEQ ID NOs: 16-20, respectively. SEQ ID NOs: 1-5 are a subset of the nucleic acid sequences of SEQ ID NOs: 6-10, respectively. SEQ ID NOs: 11-15 are a subset of the amino acid sequences of SEQ ID NOs: 16-20, respectively.

The adenovirus can be modified in the same manner as previously known adenoviruses to be used as an adenoviral vector, e.g., a gene delivery vehicle.

The term "adenovirus," as used herein, refers to an adenovirus that retains the ability to participate in the adenovirus life cycle and has not been physically inactivated by, for example, disruption (e.g., sonication), denaturing (e.g., using heat or solvents), or cross-linkage (e.g., via formalin cross-linking). The "adenovirus life cycle" includes (1) virus binding and entry into cells, (2) transcription of the adenoviral genome and translation of adenovirus proteins, (3) replication of the adenoviral genome, and (4) viral particle assembly (see, e.g., Fields Virology, $5^{th}$ ed., Knipe et al. (eds.), Lippincott Williams & Wilkins, Philadelphia, Pa. (2006)).

The term "adenoviral vector," as used herein, refers to an adenovirus in which the adenoviral genome has been manipulated to accommodate a nucleic acid sequence that is non-native with respect to the adenoviral genome. Typically, an adenoviral vector is generated by introducing one or more mutations (e.g., a deletion, insertion, or substitution) into the adenoviral genome of the adenovirus so as to accommodate the insertion of a non-native nucleic acid sequence, for example, for gene transfer, into the adenovirus.

The adenovirus and adenoviral vector can be replication-competent, conditionally replication-competent, or replication-deficient.

A replication-competent adenovirus or adenoviral vector can replicate in typical host cells, i.e., cells typically capable of being infected by an adenovirus. A replication-competent adenovirus or adenoviral vector can have one or more mutations as compared to the wild-type adenovirus (e.g., one or more deletions, insertions, and/or substitutions) in the adenoviral genome that do not inhibit viral replication in host cells. For example, the adenovirus or adenoviral vector can have a partial or entire deletion of the adenoviral early region known as the E3 region, which is not essential for propagation of the adenovirus or adenoviral genome.

A conditionally-replicating adenovirus or adenoviral vector is an adenovirus or adenoviral vector that has been engineered to replicate under pre-determined conditions. For example, replication-essential gene functions, e.g., gene functions encoded by the adenoviral early regions, can be operably linked to an inducible, repressible, or tissue-specific transcription control sequence, e.g., promoter. In such an embodiment, replication requires the presence or absence of specific factors that interact with the transcription control sequence. Conditionally-replicating adenoviral vectors are further described in U.S. Pat. No. 5,998,205.

A replication-deficient adenovirus or adenoviral vector is an adenovirus or adenoviral vector that requires complementation of one or more gene functions or regions of the adenoviral genome that are required for replication, as a result of, for example, a deficiency in one or more replication-essential gene function or regions, such that the adenovirus or adenoviral vector does not replicate in typical host cells, especially those in a human to be infected by the adenovirus or adenoviral vector.

A deficiency in a gene function or genomic region, as used herein, is defined as a disruption (e.g., deletion) of sufficient genetic material of the adenoviral genome to obliterate or impair the function of the gene (e.g., such that the function of the gene product is reduced by at least about 2-fold, 5-fold, 10-fold, 20-fold, 30-fold, or 50-fold) whose nucleic acid sequence was disrupted (e.g., deleted) in whole or in part. Deletion of an entire gene region often is not required for disruption of a replication-essential gene function. However, for the purpose of providing sufficient space in the adenoviral genome for one or more transgenes, removal of a majority of one or more gene regions may be desirable. While deletion of genetic material is preferred, mutation of genetic material by addition or substitution also is appropriate for disrupting gene function. Replication-essential gene functions are those gene functions that are required for adenovirus replication (e.g., propagation) and are encoded by, for example, the adenoviral early regions (e.g., the E1, E2, and E4 regions), late regions (e.g., the L1, L2, L3, L4, and L5 regions), genes involved in viral packaging (e.g., the IVa2 gene), and virus-associated RNAs (e.g., VA-RNA-1 and/or VA-RNA-2).

Whether the adenovirus or adenoviral vector is replication-competent or replication-deficient, the adenovirus or adenoviral vector retains at least a portion of the adenoviral genome. The adenovirus or adenoviral vector can comprise any portion of the adenoviral genome, including protein coding and non-protein coding regions. Desirably, the adenovirus or adenoviral vector comprises at least one nucleic acid sequence that encodes an adenovirus protein. The adenovirus or adenoviral vector can comprise a nucleic acid sequence that encodes any suitable adenovirus protein, such as, for example, a protein encoded by any one of the early region genes (i.e., E1A, E1B, E2A, E2B, E3, and/or E4 regions), or a protein encoded by any one of the late region genes, which encode the virus structural proteins (i.e., L1, L2, L3, L4, and L5 regions).

The adenovirus or adenoviral vector desirably comprises one or more nucleic acid sequences that encode the pIX protein, the DNA polymerase protein, the penton protein, the hexon protein, and/or the fiber protein. The adenovirus or adenoviral vector can comprise a full-length nucleic acid sequence that encodes a full-length amino acid sequence of an adenovirus protein. Alternatively, the adenovirus or adenoviral vector can comprise a portion of a full-length nucleic acid sequence that encodes a portion of a full-length amino acid sequence of an adenovirus protein.

A "portion" of a nucleic acid sequence comprises at least ten nucleotides (e.g., about 10 to about 5000 nucleotides). Preferably, a "portion" of a nucleic acid sequence comprises 10 or more (e.g., 15 or more, 20 or more, 25 or more, 30 or more, 35 or more, 40 or more, 45 or more, 50 or more, or 100 or more) nucleotides, but less than 5,000 (e.g., 4900 or less, 4000 or less, 3000 or less, 2000 or less, 1000 or less, 800 or less, 500 or less, 300 or less, or 100 or less) nucleotides. Preferably, a portion of a nucleic acid sequence is about 10 to about 3500 nucleotides (e.g., about 10, 20, 30, 50, 100, 300, 500, 700, 1000, 1500, 2000, 2500, or 3000 nucleotides), about 10 to about 1000 nucleotides (e.g., about 25, 55, 125, 325, 525, 725, or 925 nucleotides), or about 10 to about 500 nucleotides (e.g., about 15, 30, 40, 50, 60, 70, 80, 90, 150, 175, 250, 275, 350, 375, 450, 475, 480, 490, 495, or 499 nucleotides), or a range defined by any two of the foregoing values. More preferably, a "portion" of a nucleic acid sequence comprises no more than about 3200 nucleotides (e.g., about 10 to about 3200 nucleotides, about 10 to about 3000 nucleotides, or about 30 to about 500 nucleotides, or a range defined by any two of the foregoing values).

A "portion" of an amino acid sequence comprises at least three amino acids (e.g., about 3 to about 1,200 amino acids). Preferably, a "portion" of an amino acid sequence comprises 3 or more (e.g., 5 or more, 10 or more, 15 or more, 20 or more, 25 or more, 30 or more, 40 or more, or 50 or more) amino acids, but less than 1,200 (e.g., 1,000 or less, 800 or less, 700 or less, 600 or less, 500 or less, 400 or less, 300 or less, 200 or less, or 100 or less) amino acids. Preferably, a portion of an amino acid sequence is about 3 to about 500 amino acids (e.g., about 10, 100, 200, 300, 400, or 500 amino acids), about 3 to about 300 amino acids (e.g., about 20, 50, 75, 95, 150, 175, or 200 amino acids), or about 3 to about 100 amino acids (e.g., about 15, 25, 35, 40, 45, 60, 65, 70, 80, 85, 90, 95, or 99 amino acids), or a range defined by any two of the foregoing values. More preferably, a "portion" of an amino acid sequence comprises no more than about 500 amino acids (e.g., about 3 to about 400 amino acids, about 10 to about 250 amino acids, or about 50 to about 100 amino acids, or a range defined by any two of the foregoing values).

The adenovirus pIX protein is present in the adenovirus capsid, has been shown to strengthen hexon nonamer interactions, and is essential for the packaging of full-length genomes (see, e.g., Boulanger et al., *J. Gen. Virol.*, 44: 783-800 (1979); Horwitz M. S., "Adenoviridae and their replication" in *Virology*, $2^{nd}$ ed., B. N. Fields et al. (eds.), Raven Press, Ltd., New York, pp. 1679-1721 (1990), Ghosh-Choudhury et al., *EMBO J.*, 6: 1733-1739 (1987), and van Oostrum et al, *J. Virol.*, 56: 439-448 (1985)). In addition to its contribution to adenovirus structure, pIX also has been shown to exhibit transcriptional properties, such as stimulation of adenovirus major late promoter (MLP) activity (see, e.g., Lutz et al., *J. Virol.*, 71(7): 5102-5109 (1997)). Nucleic acid sequences that encode all or a portion of an adenovirus pIX protein include, for example, SEQ ID NO: 6 and SEQ ID NO: 1. Amino acid sequences that comprise a full-length pIX protein, or a portion thereof, include, for example, SEQ ID NO: 16 and SEQ ID NO: 11.

The adenovirus DNA polymerase protein is essential for viral DNA replication both in vitro and in vivo. The polymerase co-purifies in a complex with the precursor (pTP) of the terminal protein (TP), which is covalently attached to the 5' ends of adenovirus DNA (Field et al., *J. Biol. Chem.*, 259: 9487-9495 (1984)). Both the adenovirus DNA polymerase and pTP are encoded by the E2 region. The polymerase protein is required for the expression of all the structural proteins except for pIX. Without the gene sequence for polymerase protein, polymerase protein is not produced. As a result, the viral genome is not replicated, the Major Late Promoter is not activated, and the capsid proteins are not expressed. Nucleic acid sequences that encode all or a portion of an adenovirus DNA polymerase protein include, for example, SEQ ID NO: 7 and SEQ ID NO: 2. Amino acid sequences that comprise a full-length adenovirus DNA polymerase, or a portion thereof, include, for example, SEQ ID NO: 17 and SEQ ID NO: 12.

The adenovirus hexon protein is the largest and most abundant protein in the adenovirus capsid. The hexon protein is essential for virus capsid assembly, determination of the icosahedral symmetry of the capsid (which in turn defines the limits on capsid volume and DNA packaging size), and integrity of the capsid. In addition, hexon is a primary target for modification in order to reduce neutralization of adenoviral vectors (see, e.g., Gall et al., *J. Virol.*, 72: 10260-264 (1998), and Rux et al., *J. Virol.*, 77(17): 9553-9566 (2003)). The major structural features of the hexon protein are shared by adenoviruses across serotypes, but the hexon protein differs in size and immunological properties between serotypes (Jornvall et al., *J. Biol. Chem.*, 256(12): 6181-6186 (1981)). A comparison of 15 adenovirus hexon proteins revealed that the predominant antigenic and serotype-specific regions of the hexon appear to be in loops 1 and 2 (i.e., LI or l1, and LII or l2, respectively), within which are seven discrete hypervariable regions (HVR1 to HVR7) varying in length and sequence between adenoviral serotypes (Crawford-Miksza et al., *J. Virol.*, 70(3): 1836-1844 (1996)). Nucleic acid sequences that encode all or a portion of an adenovirus hexon protein include, for example, SEQ ID NO: 9 and SEQ ID NO: 4. Amino acid sequences that comprise a full-length adenovirus hexon protein, or a portion thereof, include, for example, SEQ ID NO: 19 and SEQ ID NO: 14.

The adenovirus fiber protein is a homotrimer of the adenoviral polypeptide IV that has three domains: the tail, shaft, and knob. (Devaux et al., *J. Molec. Biol.*, 215: 567-88 (1990), Yeh et al., *Virus Res.*, 33: 179-98 (1991)). The fiber protein mediates primary viral binding to receptors on the cell surface via the knob and the shaft domains (Henry et al., *J. Virol.*, 68(8): 5239-46 (1994)). The amino acid sequences for trimerization are located in the knob, which appears necessary for the amino terminus of the fiber (the tail) to properly associate with the penton base (Novelli et al., *Virology*, 185: 365-76 (1991)). In addition to recognizing cell receptors and binding the penton base, the fiber contributes to serotype identity. Fiber proteins from different adenoviral serotypes differ considerably (see, e.g., Green et al., *EMBO J.*, 2: 1357-65 (1983), Chroboczek et al., *Virology*, 186: 280-85 (1992), and Signas et al., *J. Virol.*, 53: 672-78 (1985)). Thus, the fiber protein has multiple functions key to the life cycle of adenovirus. Nucleic acid sequences that encode all or a portion of an adenovirus fiber protein include, for example, SEQ ID NO: 10 and SEQ ID NO: 5. Amino acid sequences that comprise a full-length adenovirus fiber protein, or a portion thereof, include, for example, SEQ ID NO: 20 and SEQ ID NO: 15.

The adenovirus penton base protein is located at the vertices of the icosahedral capsid and comprises five identical monomers. The penton base protein provides a structure for bridging the hexon proteins on multiple facets of the icosahedral capsid, and provides the essential interface for the fiber protein to be incorporated in the capsid. Each monomer of the penton base contains an RGD tripeptide motif (Neumann et al., *Gene*, 69: 153-157 (1988)). The RGD tripeptide mediates binding to αv integrins and adenoviruses that have point mutations in the RGD sequence of the penton base are restricted in their ability to infect cells (Bai et al., *J. Virol.*, 67: 5198-5205 (1993)). Thus, the penton base protein is essential for the architecture of the capsid and for maximum efficiency of virus-cell interaction. Nucleic acid sequences that encode all or a portion of an adenovirus penton base protein include, for example, SEQ ID NO: 8 and SEQ ID NO: 3. Amino acid sequences that comprise a full-length adenovirus penton base protein, or a portion thereof, include, for example, SEQ ID NO: 18 and SEQ ID NO: 13.

Nucleic acid or amino acid sequence "identity," as described herein, can be determined by comparing a nucleic acid or amino acid sequence of interest to a reference nucleic acid or amino acid sequence. The number of nucleotides or amino acid residues that have been changed and/or modified (such as, e.g., by point mutations, insertions, or deletions) in the reference sequence so as to result in the sequence of interest are counted. The total number of such changes is subtracted from the total length of the sequence of interest, and the difference is divided by the length of the sequence of interest and expressed as a percentage. A number of mathematical algorithms for obtaining the optimal alignment and calculating identity between two or more sequences are known and incorporated into a number of available software programs. Examples of such programs include CLUSTAL-W, T-Coffee, and ALIGN (for alignment of nucleic acid and amino acid sequences), BLAST programs (e.g., BLAST 2.1, BL2SEQ, and later versions thereof) and FASTA programs (e.g., FASTA3x, FASTM, and SSEARCH) (for sequence alignment and sequence similarity searches). Sequence alignment algorithms also are disclosed in, for example, Altschul et al., *J. Molecular Biol.*, 215(3): 403-410 (1990), Beigert et al., *Proc. Natl. Acad. Sci. USA,* 106(10): 3770-3775 (2009), Durbin et al., eds., *Biological Sequence Analysis: Probalistic Models of Proteins and Nucleic Acids*, Cambridge University Press, Cambridge, UK (2009), Soding, *Bioinformatics,* 21(7): 951-960 (2005), Altschul et al., *Nucleic Acids Res.,* 25(17): 3389-3402 (1997), and Gusfield, *Algorithms on Strings, Trees and Sequences*, Cambridge University Press, Cambridge UK (1997)).

In one embodiment, the adenovirus or adenoviral vector comprises one or more of the following nucleic acid sequences: (a) the nucleic acid sequence of SEQ ID NO: 1, (b) a nucleic acid sequence that is at least 98.5% identical (e.g., at least 98.73%, at least 98.96%, at least 99.18%, at least 99.41%, at least 99.64%, at least 99.87%, or 100% identical) to SEQ ID NO: 2, (c) a nucleic acid sequence that is at least 90% identical (e.g., at least 92.94%, at least 95.88%, 98.82%, or 100% identical) to SEQ ID NO: 3, (d) a nucleic acid sequence that is at least 80% identical (e.g., at least 80.83%, at least 83.06%, at least 85.28%, at least 87.50%, at least 89.72%, at least 91.94%, at least 94.17%, at least 96.39%, at least 98.61%, or 100% identical) to SEQ ID NO: 4, and (e) a nucleic acid sequence that is at least 89% identical (e.g., at least 92.33%, at least 95.67%, at least 99%, or 100% identical) to SEQ ID NO: 5.

The adenovirus or adenoviral vector can comprise one, two, three, four, or all five of the aforementioned sequences alone or in any combination. In this respect, the adenovirus or adenoviral vector can comprise any combination of any two of the aforementioned sequences, any combination of any three of the aforementioned sequences, any combination of any four of the aforementioned sequences, or all five of the aforementioned sequences. For example, the adenovirus or adenoviral vector can comprise the nucleic acid sequence of SEQ ID NO: 1. The adenovirus or adenoviral vector can comprise a nucleic acid sequence that is at least 98.5% identical to SEQ ID NO: 2 and a nucleic acid sequence that is at least 90% identical to SEQ ID NO: 3. The adenovirus or adenoviral vector can comprise the nucleic acid sequence of SEQ ID NO: 1, a nucleic acid sequence that is at least 90% identical to SEQ ID NO: 3, and a nucleic acid sequence that is at least 89% identical to SEQ ID NO: 5. The adenovirus or adenoviral vector can comprise (a) the nucleic acid sequence of SEQ ID NO: 1, (b) the nucleic acid sequence SEQ ID NO: 2, (c) the nucleic acid sequence of SEQ ID NO: 3, (d) the nucleic acid sequence of SEQ ID NO: 4, or (e) the nucleic acid sequence of SEQ ID NO: 5. The adenovirus or adenoviral vector can comprise (a) the nucleic acid sequence of SEQ ID NO: 1, (b) a nucleic acid sequence that is at least 98.5% identical to SEQ ID NO: 2, (c) a nucleic acid sequence that is at least 90% identical to SEQ ID NO: 3, (d) a nucleic acid sequence that is at least 80% identical to SEQ ID NO: 4, and (e) a nucleic acid sequence that is at least 89% identical to SEQ ID NO: 5. The adenovirus or adenoviral vector can comprise (a) the nucleic acid sequence of SEQ ID NO: 1, (b) the nucleic acid sequence SEQ ID NO: 2, (c) the nucleic acid sequence of SEQ ID NO: 3, (d) the nucleic acid sequence of SEQ ID NO: 4, and (e) the nucleic acid sequence of SEQ ID NO: 5.

In another embodiment, the adenovirus or adenoviral vector comprises one or more of the following nucleic acid sequences: (a) a nucleic acid sequence that is at least 98.6% identical (e.g., at least 98.85%, at least 99.10%, at least 99.35%, at least 99.60%, or 100% identical) to SEQ ID NO: 6, (b) a nucleic acid sequence that is at least 99.06% identical (e.g., at least 99.09%, at least 99.12%, at least 99.15%, at least 99.19%, at least 99.22%, at least 99.25%, at least 99.28%, at least 99.31%, at least 99.34%, at least 99.38%, at least 99.41%, at least 99.44%, at least 99.47%, at least 99.50%, at least 99.53%, at least 99.57%, at least 99.60%, at least 99.63%, at least 99.66%, at least 99.69%, at least 99.72%, at least 99.75%, at least 99.79%, at least 99.82%, at least 99.85%, at least 99.88%, at least 99.91%, at least 99.94%, at least 99.98%, or 100% identical) to SEQ ID NO: 7, (c) a nucleic acid sequence that is at least 97.13% identical (e.g., at least 97.18%, at least 97.23%, at least 97.28%, at least 97.33%, at least 97.38%, at least 97.43%, at least 97.48%, at least 97.5% at least 97.54%, at least 97.59%, at least 97.6%, at least 97.64%, at least 97.69%, at least 97.7%, at least 97.74%, at least 97.79%, at least 97.8%, at least 97.84%, at least 97.89%, at least 97.9%, at least 97.94%, at least 97.99%, at least 98%, at least 98.04%, at least 98.09%, at least 98.1%, at least 98.14%, at least 98.19%, at least 98.2%, at least 98.24%, at least 98.30%, at least 98.35%, at least 98.40%, at least 98.45%, at least 98.50%, at least 98.55%, at least 98.60%, at least 98.70%, at least 98.75%, at least 98.80%, at least 98.85%, at least 98.90%, at least 98.95%, at least 99.00%, at least 99.06%, at least 99.11%, at least 99.16%, at least 99.2%, at least 99.21%, at least 99.26%, at least 99.3%, at least 99.31%, at least 99.36%, at least 99.4%, at least 99.41%, at least 99.46%, at least 99.5%, at least 99.51%, at least 99.56%, at least 99.6%, at least 99.61%, at least 99.66%, at least 99.7%, at least 99.71%, at least 99.76%, at least 99.8%, at least 99.81%, at least 99.87%, at least 99.9%, at least 99.92%, at least 99.95%, at least 99.97%, or 100% identical) to SEQ ID NO: 8, (d) a nucleic acid sequence that is at least 90.7% identical (e.g., at least 90.73%, at least 90.77%, at least 90.80%, at least 90.84%, at least 90.87%, at least 90.91%, at least 90.94%, at least 90.98%, at least 91.01%, at least 91.05%, at least 91.08%, at least 91.12%, at least 91.15%, at least 91.19%, at least 91.22%, at least 91.26%, at least 91.29%, at least 91.33%, at least 91.36%, at least 91.40%, at least 91.43%, at least 91.46%, at least 91.50%, at least 91.53%, at least 91.57%, at least 91.60%, at least 91.64%, at least 91.67%, at least 91.71%, at least 91.74%, at least 91.78%, at least 91.81%, at least 91.85%, at least 91.88%, at least 91.92%, at least 91.95%, at least 91.99%, at least 92.02%, at least 92.06%, at least 92.09%, at least 92.13%, at least 92.16%, at least 92.19%, at least 92.23%, at least 92.26%, at least 92.30%, at least 92.33%, at least 92.37%, at least 92.40%, at least 92.44%, at least 92.47%, at least 92.51%, at least 92.54%, at least 92.58%, at least 92.61%, at least 92.65%, at least 92.68%, at least 92.72%, at least 92.75%, at least 92.79%, at least 92.82%, at least 92.86%, at least 92.89%, at least 92.92%, at least 92.96%, at least 92.99%, at least 93.03%, at least 93.06%, at least 93.10%, at least 93.13%, at least 93.17%, at least 93.20%, at least 93.24%, at least 93.27%, at least 93.31%, at least 93.34%, at least 93.38%, at least 93.41%, at least 93.45%, at least 93.48%, at least 93.52%, at least 93.55%, at least 93.58%, at least 93.62%, at least 93.65%, at least 93.69%, at least 93.72%, at least 93.76%, at least 93.79%, at least 93.83%, at least 93.86%, at least 93.90%, at least 93.93%, at least 93.97%, at least 94.00%, at least 94.04%, at least 94.07%, at least 94.11%, at least 94.14%, at least 94.18%, at least 94.21%, at least 94.25%, at least 94.28%, at least 94.31%, at least 94.35%, at least 94.38%, at least 94.42%, at least 94.45%, at least 94.49%, at least 94.52%, at least 94.56%, at least 94.59%, at least 94.63%, at least 94.66%, at least 94.70%, at least 94.73%, at least 94.77%, at least 94.80%, at least 94.84%, at least 94.87%, at least 94.91%, at least 94.94%, at least 94.98%, at least 95.01%, at least 95.04%, at least 95.08%, at least 95.11%, at least 95.15%, at least 95.18%, at least 95.22%, at least 95.25%, at least 95.29%, at least 95.32%, at least 95.36%, at least 95.39%, at least 95.43%, at least 95.46%, at least 95.50%, at least 95.53%, at least 95.57%, at least 95.60%, at least 95.64%, at least 95.67%, at least 95.71%, at least 95.74%, at least 95.77%, at least 95.81%, at least 95.84%, at least 95.88%, at least 95.91%, at least 95.95%, at least 95.98%, at least 96.02%, at least 96.05%, at least 96.09%, at least 96.12%, at least 96.16%, at least 96.19%, at least 96.23%, at least 96.26%, at least 96.30%, at least 96.33%, at least 96.37%, at least 96.40%, at least 96.44%, at least 96.47%, at least 96.50%, at least 96.54%, at least 96.57%, at least 96.61%, at least 96.64%, at least 96.68%, at least 96.71%, at least 96.75%, at least 96.78%, at least 96.82%, at least 96.85%, at least 96.89%, at least 96.92%, at least 96.96%, at least 96.99%, at least 97.03%, at least 97.06%, at least 97.10%, at least 97.13%, at least 97.17%, at least 97.20%, at least 97.23%, at least 97.27%, at least 97.30%, at least 97.34%, at least 97.37%, at least 97.41%, at least 97.44%, at least 97.48%, at least 97.51%, at least 97.55%, at least 97.58%, at least 97.62%, at least 97.65%, at least 97.69%, at least 97.72%, at least 97.76%, at least 97.79%, at least 97.83%, at least 97.86%, at least 97.89%, at least 97.93%, at least 97.96%, at least 98.00%, at least 98.03%, at least 98.07%, at least 98.10%, at least 98.14%, at least 98.17%, at least 98.21%, at least 98.24%, at least 98.28%, at least 98.31%, at least 98.35%, at least 98.38%, at least 98.42%, at least 98.45%, at least 98.49%, at least 98.52%, at least 98.56%, at least 98.59%, at least 98.62%, at least 98.66%, at least 98.69%, at least 98.73%, at least 98.76%, at least 98.80%, at least 98.83%, at least 98.87%, at least 98.90%, at least 98.94%, at least 98.97%, at least 99.01%, at least 99.04%, at least 99.08%, at least 99.11%, at least 99.15%, at least 99.18%, at least 99.22%, at least 99.25%, at least 99.29%, at least 99.32%, at least 99.35%, at least 99.39%, at least 99.42%, at least 99.46%, at least 99.49%, at least 99.53%, at least 99.56%, at least 99.60%, at least 99.63%, at least 99.67%, at least 99.70%, at least 99.74%, at least 99.77%, at least 99.81%, at least 99.84%, at least 99.88%, at least 99.91%, at least 99.95%, at least 99.98%, or 100% identical) to SEQ ID NO: 9, and (e) a nucleic acid sequence that is at least 96.6% identical (e.g., at least 96.66%, at least 96.71%, at least 96.77%, at least 96.83%, at least 96.89%, at least 96.94%, at least 97.00%, at least 97.06%, at least 97.11%, at least 97.17%, at least 97.23%, at least 97.29%, at least 97.34%, at least 97.40%, at least 97.46%, at least 97.51%, at least 97.57%, at least 97.63%, at least 97.69%, at least 97.74%, at least 97.80%, at least 97.86%, at least 97.92%, at least 97.97%, at least 98.03%, at least 98.09%, at least 98.14%, at least 98.20%, at least 98.26%, at least 98.32%, at least 98.37%, at least 98.43%, at least 98.49%, at least 98.54%, at least 98.60%, at least 98.66%, at least 98.72%, at least 98.77%, at least 98.83%, at least 98.89%, at least 98.94%, at least 99.00%, at least 99.06%, at least 99.12%, at least 99.17%, at least 99.23%, at least 99.29%, at least 99.34%, at least 99.40%, at least 99.46%, at least 99.52%, at least 99.57%, at least 99.63%, at least 99.69%, at least 99.74%, at least at least 99.80%, at least 99.86%, at least 99.92%, at least 99.97%, or 100% identical) to SEQ ID NO: 10.

The adenovirus or adenoviral vector can comprise one, two, three, four, or all five of the aforementioned sequences alone or in any combination. In this respect, the adenovirus or adenoviral vector can comprise any combination of any two of the aforementioned sequences, any combination of any three of the aforementioned sequences, any combination of any four of the aforementioned sequences, or all five of the aforementioned sequences. For example, the adenovirus or adenoviral vector can comprise a nucleic acid sequence that is at least 98.6% identical to SEQ ID NO: 6. The adenovirus or adenoviral vector can comprise a nucleic acid sequence that is at least 99.06% identical to SEQ ID NO: 7 and a nucleic acid sequence that is at least 97.13% identical to SEQ ID NO: 8. The adenovirus or adenoviral vector can comprise a nucleic acid sequence that is at least 97.13% identical to SEQ ID NO: 8, a nucleic acid sequence that is at least 90.7% identical to SEQ ID NO: 9, and a nucleic acid sequence that is at least 96.6% identical to SEQ ID NO: 10. The adenovirus or adenoviral vector can comprise (a) the nucleic acid sequence of SEQ ID NO: 6, (b) the nucleic acid sequence SEQ ID NO: 7, (c) the nucleic acid sequence of SEQ ID NO: 8, (d) the nucleic acid sequence of SEQ ID NO: 9, or (e) the nucleic acid sequence of SEQ ID NO: 10. The adenovirus or adenoviral vector can comprise (a) a nucleic acid sequence that is at least 98.6% identical to SEQ ID NO: 6, (b) a nucleic acid sequence that is at least 99.06% identical to SEQ ID NO: 7, (c) a nucleic acid sequence that is at least 97.13% identical to SEQ ID NO: 8, (d) a nucleic acid sequence that is at least 90.7% identical to SEQ ID NO: 9, and (e) a nucleic acid sequence that is at least 96.6% identical to SEQ ID NO: 10. The adenovirus or adenoviral vector can comprise (a) the nucleic acid sequence of SEQ ID NO: 6, (b) the nucleic acid sequence SEQ ID NO: 7, (c) the nucleic acid sequence of SEQ ID NO: 8, (d) the nucleic acid sequence of SEQ ID NO: 9, and (e) the nucleic acid sequence of SEQ ID NO: 10.

In another embodiment, the adenovirus or adenoviral vector comprises one or more of the following nucleic acid sequences: (a) a nucleic acid sequence comprising at least 121 contiguous nucleotides of SEQ ID NO: 6, (b) a nucleic acid sequence comprising at least 462 contiguous nucleotides of SEQ ID NO: 7, (c) a nucleic acid sequence comprising at least 234 contiguous nucleotides of SEQ ID NO: 8, (d) a nucleic acid sequence comprising at least 606 contiguous nucleotides of SEQ ID NO: 9, or (e) a nucleic acid sequence comprising at least 188 contiguous nucleotides of SEQ ID NO: 10.

The adenovirus or adenoviral vector can comprise a nucleic acid sequence comprising at least 121 (e.g., 125 or more, 130 or more, 150 or more, 200 or more, 250 or more, or 300 or more) contiguous nucleotides of SEQ ID NO: 6, but no more than 399 (e.g., 398 or less, 350 or less, or 275 or less) contiguous nucleotides of SEQ ID NO: 6. Preferably, the adenovirus or adenoviral vector comprises a nucleic acid sequence comprising 121 to 300 contiguous nucleotides (e.g., 125, 150, 175, 200, 250, or 275 contiguous nucleotides), 121 to 200 contiguous nucleotides (e.g., 130, 140, 145, 160, 165, 170, 180, 185, 190, 195, or 199 contiguous nucleotides), or 121 to 150 contiguous nucleotides (e.g., 122, 123, 124, 125, 126, 127, 128, 129, 130, 131, 132, 133, 134, 135, 136, 137, 138, 139, 140, 141, 142, 143, 144, 145, 146, 147, 148, or 149 contiguous nucleotides) of SEQ ID NO: 6, or a range defined by any two of the foregoing values.

The adenovirus or adenoviral vector can comprise a nucleic acid sequence comprising at least 462 (e.g., 470 or more, 500 or more, 600 or more, 700 or more, 800 or more, 900 or more, or 1,000 or more) contiguous nucleotides of SEQ ID NO: 7, but no more than 3168 (e.g., 3,100 or less, 3,000 or less, 2,500 or less, 2,000 or less, or 1,500 or less) contiguous nucleotides of SEQ ID NO: 7. Preferably, the adenovirus or adenoviral vector comprises a nucleic acid sequence comprising 462 to 2,000 contiguous nucleotides (e.g., 475, 500, 700, 1,000, 1,200, 1,500, or 1,700 contiguous nucleotides), 462 to 1,000 contiguous nucleotides (e.g., 490, 525, 575, 600, 650, 675, 725, 750, 800, 850, 900, or 950 contiguous nucleotides), or 462 to 800 contiguous nucleotides (e.g., 480, 485, 490, 495, 499, 510, 515, 530, 540, 550, 560, 565, 570, 580, 585, 590, 595, 615, 625, 630, 640, 660, 665, 670, 680, 685, 690, 695, 705, 715, 730, 740, 755, 760, 765, 770, 775, 780, 785, 790, 795, or 799 contiguous nucleotides) of SEQ ID NO: 7, or a range defined by any two of the foregoing values.

The adenovirus or adenoviral vector can comprise a nucleic acid sequence comprising at least 234 (e.g., 235 or more, 250 or more, 300 or more, 350 or more, 400 or more, 450 or more, or 500 or more) contiguous nucleotides of SEQ ID NO: 8, but no more than 1,974 (e.g., 1,900 or less, 1,800 or less, 1,500 or less, 1,200 or less, 1,000 or less, 850 or less, 800 or less, 750 or less, or 700 or less) contiguous nucleotides of SEQ ID NO: 8. Preferably, the adenovirus or adenoviral vector comprises a nucleic acid sequence comprising 234 to 1,500 contiguous nucleotides (e.g., 290, 300, 400, 500, 600, 700, 800, 900, 1,000, or 1,200 contiguous nucleotides), 234 to 1,000 contiguous nucleotides (e.g., 295, 350, 450, 550, 650, 750, 850, or 950 contiguous nucleotides), or 234 to 500 contiguous nucleotides (e.g., 290, 305, 310, 315, 325, 340, 345, 360, 365, 370, 375, 380, 385, 390, 395, 405, 425, 430, 440, 455, 460, 465, 470, 475, 480, 485, 490, 495, or 499 contiguous nucleotides) of SEQ ID NO: 8, or a range defined by any two of the foregoing values.

The adenovirus or adenoviral vector can comprise a nucleic acid sequence comprising at least 606 (e.g., 610 or more, 650 or more, 700 or more, 800 or more, or 1,000 or more) contiguous nucleotides of SEQ ID NO: 9, but no more than 2877 (2,800 or less, 2,500 or less, 2,000 or less, 1,800 or less, or 1,500 or less) contiguous nucleotides of SEQ ID NO: 9. Preferably, the adenovirus or adenoviral vector comprises a nucleic acid sequence comprising 606 to 2,000 contiguous nucleotides (e.g., 615, 650, 700, 800, 900, 1,000, 1,200, 1,500, 1,700, or 1,900 contiguous nucleotides), 606 to 1,000 contiguous nucleotides (e.g., 630, 645, 665, 675, 725, 750, 775, 825, 850, 875, 925, 950, or 975 contiguous nucleotides), or 606 to 800 contiguous nucleotides (e.g., 620, 635, 640, 655, 660, 670, 680, 685, 690, 695, 699, 705, 715, 730, 735, 740, 745, 755, 760, 765, 770, 785, 790, 795, or 799 contiguous nucleotides) of SEQ ID NO: 9, or a range defined by any two of the foregoing values.

The adenovirus or adenoviral vector can comprise a nucleic acid sequence comprising at least 188 (e.g., 189 or more, 200 or more, 300 or more, 500 or more, 700 or more, or 900 or more) contiguous nucleotides of SEQ ID NO: 10, but no more than 1,749 (1,700 or less, 1,500 or less, 1,200 or less, or 1,000 or less) contiguous nucleotides of SEQ ID NO: 10. Preferably, the adenovirus or adenoviral vector comprises a nucleic acid sequence comprising 188 to 1,500 contiguous nucleotides (e.g., 200, 400, 600, 800, 1,000, 1,200, or 1,400 contiguous nucleotides), 188 to 1,000 contiguous nucleotides (e.g., 195, 250, 350, 450, 550, 650, 750, 850, or 950 contiguous nucleotides), or 188 to 500 contiguous nucleotides (e.g., 190, 225, 230, 240, 255, 260, 265, 270, 275, 315, 325, 330, 340, 355, 360, 365, 370, 375, 380, 385, 390, 395, 415, 425, 430, 440, 455, 460, 465, 470, 475, 480, 485, 490, 495, or 499 contiguous nucleotides) of SEQ ID NO: 10, or a range defined by any two of the foregoing values.

The adenovirus or adenoviral vector can comprise one, two, three, four, or all five of the aforementioned sequences alone, or in any combination. In this respect, the adenovirus or adenoviral vector can comprise any combination of any two of the aforementioned sequences, any combination of any three of the aforementioned sequences, any combination of any four of the aforementioned sequences, or all five of the aforementioned sequences. For example, the adenovirus or adenoviral vector can comprise a nucleic acid sequence comprising at least 121 contiguous nucleotides of SEQ ID NO: 6. The adenovirus or adenoviral vector can comprise a nucleic acid sequence comprising at least 234 contiguous nucleotides of SEQ ID NO: 8, and a nucleic acid sequence comprising at least 188 contiguous nucleotides of SEQ ID NO: 10. The adenovirus or adenoviral vector can comprise a nucleic acid sequence comprising at least 462 contiguous nucleotides of SEQ ID NO: 7, a nucleic acid sequence comprising at least 606 contiguous nucleotides of SEQ ID NO: 9, and a nucleic acid sequence comprising at least 188 contiguous nucleotides of SEQ ID NO: 10. The adenovirus or adenoviral vector can comprise a nucleic acid sequence comprising at least 121 contiguous nucleotides of SEQ ID NO: 6, a nucleic acid sequence comprising at least 462 contiguous nucleotides of SEQ ID NO: 7, a nucleic acid sequence comprising at least 234 contiguous nucleotides of SEQ ID NO: 8, and a nucleic acid sequence comprising at least 606 contiguous nucleotides of SEQ ID NO: 9. The adenovirus or adenoviral vector can comprise (a) a nucleic acid sequence comprising at least 121 contiguous nucleotides of SEQ ID NO: 6, (b) a nucleic acid sequence comprising at least 462 contiguous nucleotides of SEQ ID NO: 7, (c) a nucleic acid sequence comprising at least 234 contiguous nucleotides of SEQ ID NO: 8, (d) a nucleic acid sequence comprising at least 606 contiguous nucleotides of SEQ ID NO: 9, and (e) a nucleic acid sequence comprising at least 188 contiguous nucleotides of SEQ ID NO: 10.

In another embodiment, the adenovirus or adenoviral vector comprises one or more of the following amino acid sequences: (a) the amino acid sequence of SEQ ID NO: 11, (b) an amino acid sequence that is at least 82% identical (e.g., at least 88.67%, at least 95.33%, or 100% identical) to SEQ ID NO: 13, (c) an amino acid sequence that is at least 80% identical (e.g., at least 81%, at least 82%, at least 83%, at least 83.06%, at least 84%, at least 85%, at least 85.28%, at least 86%, at least 87%, at least 87.5%, at least 88%, at least 88.67%, at least 89%, at least 89.72% at least 90%, at least 91%, at least 91.94%, at least 92%, at least 92.33%, at least 93%, at least 94%, at least 94.17%, at least 95%, at least 95.33%, at least 95.67%, at least 96%, at least 96.39%, at least 97%, at least 98%, at least 98.61%, at least 99%, at least 99.5%, or 100% identical) to SEQ ID NO: 14, and (d) an amino acid sequence that is at least 83% identical (e.g., at least 89.67%, at least 96.33%, or 100% identical) to SEQ ID NO: 15.

The adenovirus or adenoviral vector can comprise one, two, three, or all four of the aforementioned amino acid sequences alone or in any combination. In this respect, the adenovirus or adenoviral vector can comprise any combination of any two of the aforementioned sequences, any combination of any three of the aforementioned sequences, or all four of the aforementioned sequences. For example, the adenovirus or adenoviral vector can comprise the amino acid sequence of SEQ ID NO: 11. The adenovirus or adenoviral vector can comprise an amino acid sequence of SEQ ID NO: 11, and an amino acid sequence that is at least 82% identical to SEQ ID NO: 13. The adenovirus or adenoviral vector can comprise the amino acid sequence of SEQ ID NO: 11, an amino acid sequence that is at least 82% identical to SEQ ID NO: 13, and an amino acid sequence that is at least 83% identical to SEQ ID NO: 15. The adenovirus or adenoviral vector can comprise (a) the amino acid sequence of SEQ ID NO: 11, (b) the amino acid sequence of SEQ ID NO: 13, (c) the amino acid sequence of SEQ ID NO: 14, or (d) the amino acid sequence of SEQ ID NO: 15. The adenovirus or adenoviral vector can comprise (a) the amino acid sequence of SEQ ID NO: 11, (b) an amino acid sequence that is at least 82% identical to SEQ ID NO: 13, (c) an amino acid sequence that is at least 80% identical to SEQ ID NO: 14, and (d) an amino acid sequence that is at least 83% identical to SEQ ID NO: 15. The adenovirus or adenoviral vector can comprise (a) the amino acid sequence of SEQ ID NO: 11, (b) the amino acid sequence of SEQ ID NO: 13, (c) the amino acid sequence of SEQ ID NO: 14, and (d) the amino acid sequence of SEQ ID NO: 15.

In another embodiment, the adenovirus or adenoviral vector comprises one or more of the following amino acid sequences: (a) the amino acid sequence of SEQ ID NO: 16, (b) an amino acid sequence that is at least 97.8% identical (e.g., at least 97.95%, at least 98.10%, at least 98.26%, at least 98.41%, at least 98.56%, at least 98.71%, at least 98.86%, at least 99.02%, at least 99.17%, at least 99.32%, at least 99.47%, at least 99.62%, at least 99.78%, or 100% identical) to SEQ ID NO: 18, (c) an amino acid sequence that is at least 93.4% identical (e.g., at least 93.50%, at least 93.61%, at least 93.71%, at least 93.82%, at least 93.92%, at least 94.03%, at least 94.13%, at least 94.23%, at least 94.34%, at least 94.44%, at least 94.55%, at least 94.65%, at least 94.76%, at least 94.86%, at least 94.96%, at least 95.07%, at least 95.17%, at least 95.28%, at least 95.38%, at least 95.49%, at least 95.59%, at least 95.69%, at least 95.80%, at least 95.90%, at least 96.01%, at least 96.11%, at least 96.22%, at least 96.32%, at least 96.42%, at least 96.53%, at least 96.63%, at least 96.74%, at least 96.84%, at least 96.95%, at least 97.05%, at least 97.15%, at least 97.26%, at least 97.36%, at least 97.47%, at least 97.57%, at least 97.68%, at least 97.78%, at least 97.88%, at least 97.99%, at least 98.09%, at least 98.20%, at least 98.30%, at least 98.41%, at least 98.51%, at least 98.61%, at least 98.72%, at least 98.82%, at least 98.93%, at least 99.03%, at least 99.14%, at least 99.24%, at least 99.34%, at least 99.45%, at least 99.55%, at least 99.66%, at least 99.76%, at least 99.87%, at least 99.97%, or 100% identical) to SEQ ID NO: 19, and (d) an amino acid sequence that is at least 98.2% identical (e.g., at least 98.37%, at least 98.54%, at least 98.71%, at least 98.89%, at least 99.06%, at least 99.23%, at least 99.40%, at least 99.57%, at least 99.74%, at least 99.92%, or 100% identical) to SEQ ID NO: 20.

The adenovirus or adenoviral vector can comprise one, two, three, or all four of the aforementioned amino acid sequences alone or in any combination. In this respect, the adenovirus or adenoviral vector can comprise any combination of any two of the aforementioned sequences, any combination of any three of the aforementioned sequences, or all four of the aforementioned sequences. For example, the adenovirus or adenoviral vector can comprise the amino acid sequence of SEQ ID NO: 16. The adenovirus or adenoviral vector can comprise the amino acid sequence of SEQ ID NO: 16, and an amino acid sequence that is at least 93.4% identical to SEQ ID NO: 19. The adenovirus or adenoviral vector can comprise the amino acid sequence of SEQ ID NO: 16, an amino acid sequence that is at least 93.4% identical to SEQ ID NO: 19, and an amino acid sequence that is at least 98.2% identical to SEQ ID NO: 20. The adenovirus or adenoviral vector can comprise (a) the amino acid sequence of SEQ ID NO: 16, (b) the amino acid sequence of SEQ ID NO: 18, (c) the amino acid sequence of SEQ ID NO: 19, or (d) the amino acid sequence of SEQ ID NO: 20. The adenovirus or adenoviral vector can comprise (a) the amino acid sequence of SEQ ID NO: 16, (b) an amino acid sequence that is at least 97.8% identical to SEQ ID NO: 18, (c) an amino acid that is at least 93.4% identical to SEQ ID NO: 19, and (d) an amino acid sequence that is at least 98.2% identical to SEQ ID NO: 20. The adenovirus or adenoviral vector can comprise (a) the amino acid sequence of SEQ ID NO: 16, (b) the amino acid sequence of SEQ ID NO: 18, (c) the amino acid sequence of SEQ ID NO: 19, and (d) the amino acid sequence of SEQ ID NO: 20.

In another embodiment, the adenovirus or adenoviral vector comprises one or more of the following amino acid sequences: (a) an amino acid sequence comprising at least 89 contiguous amino acid residues of SEQ ID NO: 16, (b) an amino acid sequence comprising at least 247 contiguous amino acid residues of SEQ ID NO: 18, (c) an amino acid sequence comprising at least 370 contiguous amino acid residues of SEQ ID NO: 19, and (d) an amino acid sequence comprising at least 192 contiguous amino acid residues of SEQ ID NO: 20.

The adenovirus or adenoviral vector can comprise an amino acid sequence comprising at least 89 (e.g., 90 or more, 100 or more, or 110 or more) contiguous amino acid residues of SEQ ID NO: 16, but no more than 133 (e.g., 130 or less, 125 or less, 120 or less, or 115 or less) contiguous amino acid residues of SEQ ID NO: 16. Preferably, the adenovirus or adenoviral vector comprises an amino acid sequence comprising 89 to 130 contiguous amino acid residues (e.g., 90, 100, 110, 115, 120, or 125 contiguous amino acid residues) of SEQ ID NO: 16, 89 to 115 contiguous amino acid residues of SEQ ID NO: 16 (e.g., 95, 110, or 112 contiguous amino acid residues), or 89 to 100 contiguous amino acid residues (e.g., 89, 90, 91, 92, 93, 94, 95, 96, 97, 98, or 99 contiguous amino acid residues) of SEQ ID NO: 16, or a range defined by any two of the foregoing values.

The adenovirus or adenoviral vector can comprise an amino acid sequence comprising at least 247 (e.g., 250 or more, 275 or more, 300 or more, or 400 or more) contiguous amino acid residues of SEQ ID NO: 18, but no more than 658 (e.g., 650 or less, 550 or less, or 450 or less) contiguous amino acid residues of SEQ ID NO: 18. Preferably, the adenovirus or adenoviral vector comprises an acid sequence comprising 247 to 600 contiguous amino acid residues (e.g., 255, 275, 300, 400, or 500 contiguous amino acid residues) of SEQ ID NO: 18, 247 to 500 contiguous amino acid residues of SEQ ID NO: 18 (e.g., 325, 350, 375, 425, 450, or 475 contiguous amino acid residues), or 247 to 400 contiguous amino acid residues (e.g., 265, 280, 285, 290, 295, 360, 365, 380, 385, 390, 395, or 399 contiguous amino acid residues) of SEQ ID NO: 18, or a range defined by any two of the foregoing values.

The adenovirus or adenoviral vector can comprise an amino acid sequence comprising at least 370 (e.g., 380 or more, 400 or more, or 500 or more) contiguous amino acid residues of SEQ ID NO: 19, but no more than 959 (e.g., 950 or less, 900 or less, 800 or less, 700 or less, or 600 or less) contiguous amino acid residues of SEQ ID NO: 19. Preferably, the adenovirus or adenoviral vector comprises an acid sequence comprising 370 to 800 contiguous amino acid residues (e.g., 390, 400, 500, 600, or 700 contiguous amino acid residues) of SEQ ID NO: 19, 370 to 600 contiguous amino acid residues (e.g., 375, 385, 395, 425, 445, 450, 465, 475, 525, 545, 550, 565 or 575 contiguous amino acid residues) of SEQ ID NO: 19, or 370 to 500 contiguous amino acid residues (e.g., 385, 389, 395, 399, 415, 435, 440, 460, 470, 480, or 499 contiguous amino acid residues) of SEQ ID NO: 19, or a range defined by any two of the foregoing values.

The adenovirus or adenoviral vector can comprise an amino acid sequence comprising at least 192 (e.g., 193 or more, 200 or more, or 300 or more) contiguous amino acid residues of SEQ ID NO: 20, but no more than 583 (e.g., 580 or less, 550 or less, 500 or less, 450 or less, or 400 or less) contiguous amino acid residues of SEQ ID NO: 20. Preferably, the adenovirus or adenoviral vector comprises an acid sequence comprising 192 to 500 contiguous amino acid residues (e.g., 198, 200, 300, or 400 contiguous amino acid residues) of SEQ ID NO: 20, 192 to 300 contiguous amino acid residues (e.g., 194, 196, 200, 210, 220, 230, 240, 250, 260, 270, 280, or 290 contiguous amino acid residues) of SEQ ID NO: 20, or 192 to 250 contiguous amino acid residues (e.g., 195, 199, 215, 225, 235, or 245 contiguous amino acid residues) of SEQ ID NO: 20, or a range defined by any two of the foregoing values.

The adenovirus or adenoviral vector can comprise one, two, three, or all four of the aforementioned amino acid sequences alone or in any combination. In this respect, the adenovirus or adenoviral vector can comprise any combination of any two of the aforementioned sequences, any combination of any three of the aforementioned sequences, or all four of the aforementioned sequences. For example, the adenovirus or adenoviral vector can comprise an amino acid sequence comprising at least 89 contiguous amino acid residues of SEQ ID NO: 16. The adenovirus or adenoviral vector can comprise an amino acid sequence comprising at least 89 contiguous amino acid residues of SEQ ID NO: 16, and an amino acid sequence comprising at least 370 contiguous amino acid residues of SEQ ID NO: 19. The adenovirus or adenoviral vector can comprise an amino acid sequence comprising at least 89 contiguous amino acid residues of SEQ ID NO: 16, an amino acid sequence comprising at least 247 contiguous amino acid residues of SEQ ID NO: 18, and an amino acid sequence comprising at least 370 contiguous amino acid residues of SEQ ID NO: 19. The adenovirus or adenoviral vector can comprise an amino acid sequence comprising at least 89 contiguous amino acid residues of SEQ ID NO: 16, an amino acid sequence comprising at least 247 contiguous amino acid residues of SEQ ID NO: 18, and an amino acid sequence comprising at least 192 contiguous amino acid residues of SEQ ID NO: 20. The adenovirus or adenoviral vector can comprise (a) an amino acid sequence comprising at least 89 contiguous amino acid residues of SEQ ID NO: 16, (b) an amino acid sequence comprising at least 247 contiguous amino acid residues of SEQ ID NO: 18, (c) an amino acid sequence comprising at least 370 contiguous amino acid residues of SEQ ID NO: 19, and (d) an amino acid sequence comprising at least 192 contiguous amino acid residues of SEQ ID NO: 20.

In other embodiments, the adenovirus or adenoviral vector comprises one or more nucleic acid sequences that encode one or more of any of the aforementioned amino acid sequences, e.g., the amino acid sequences of any of SEQ ID NOs: 11-20 or any of the variants and/or portions thereof as described herein. For example, the adenovirus or adenoviral vector can comprise a nucleic acid sequence encoding an amino acid sequence that is at least 99.78% identical (e.g., at least 99.87%, at least 99.97%, or 100% identical) to SEQ ID NO: 17, or a nucleic acid sequence encoding an amino acid sequence that is at least 99% identical (e.g., at least 99.68% or 100% identical) to SEQ ID NO: 12.

The adenovirus or adenoviral vector can comprise the nucleic acid sequence of, for example, SEQ ID NO: 21, SEQ ID NO: 22, SEQ ID NO: 23, SEQ ID NO: 24, or SEQ ID NO: 25.

As discussed herein, the adenovirus or adenoviral vector can be replication-competent, conditionally-replicating, or replication-deficient. Preferably, the adenovirus or adenoviral vector is replication-deficient, such that the replication-deficient adenovirus or adenoviral vector requires complementation of at least one replication-essential gene function of one or more regions of the adenoviral genome for propagation (e.g., to form adenoviral vector particles).

The replication-deficient adenovirus or adenoviral vector can be modified in any suitable manner to cause the deficiencies in the one or more replication-essential gene functions in one or more regions of the adenoviral genome for propagation. The complementation of the deficiencies in the one or more replication-essential gene functions of one or more regions of the adenoviral genome refers to the use of exogenous means to provide the deficient replication-essential gene functions. Such complementation can be effected in any suitable manner, for example, by using complementing cells and/or exogenous DNA (e.g., helper adenovirus) encoding the disrupted replication-essential gene functions.

The adenovirus or adenoviral vector can be deficient in one or more replication-essential gene functions of only the early regions (i.e., E1-E4 regions) of the adenoviral genome, only the late regions (i.e., L1-L5 regions) of the adenoviral genome, both the early and late regions of the adenoviral genome, or all adenoviral genes (i.e., a high capacity adenovector (HC-Ad). See Morsy et al., *Proc. Natl. Acad. Sci. USA*, 95: 965-976 (1998); Chen et al., *Proc. Natl. Acad. Sci. USA*, 94: 1645-1650 (1997); and Kochanek et al., *Hum. Gene Ther.*, 10: 2451-2459 (1999). Examples of replication-deficient adenoviral vectors are disclosed in U.S. Pat. Nos. 5,837,511; 5,851,806; 5,994,106; 6,127,175; 6,482,616; and 7,195,896, and International Patent Application Publications WO 1994/028152, WO 1995/002697, WO 1995/016772, WO 1995/034671, WO 1996/022378, WO 1997/012986, WO 1997/021826, and WO 2003/022311.

The early regions of the adenoviral genome include the E1, E2, E3, and E4 regions. The E1 region comprises the E1A and E1B subregions, and one or more deficiencies in replication-essential gene functions in the E1 region can include one or more deficiencies in replication-essential gene functions in either or both of the E1A and E1B subregions, thereby requiring complementation of the E1A subregion and/or the E1B subregion of the adenoviral genome for the adenovirus or adenoviral vector to propagate (e.g., to form adenoviral vector particles). The E2 region comprises the E2A and E2B subregions, and one or more deficiencies in replication-essential gene functions in the E2 region can include one or more deficiencies in replication-essential gene functions in either or both of the E2A and E2B subregions, thereby requiring complementation of the E2A subregion and/or the E2B subregion of the adenoviral genome for the adenovirus or adenoviral vector to propagate (e.g., to form adenoviral vector particles).

The E3 region does not include any replication-essential gene functions, such that a deletion of the E3 region in part or in whole does not require complementation of any gene functions in the E3 region for the adenovirus or adenoviral vector to propagate (e.g., to form adenoviral vector particles). In the context of the invention, the E3 region is defined as the region that initiates with the open reading frame that encodes a protein with high homology to the 12.5K protein from the E3 region of human adenovirus 5 (NCBI reference sequence AP_000218) and ends with the open reading frame that encodes a protein with high homology to the 14.7K protein from the E3 region of human adenovirus 5 (NCBI reference sequence AP_000224.1). The E3 region may be deleted in whole or in part, or retained in whole or in part. The size of the deletion may be tailored so as to retain an adenovirus or adenoviral vector whose genome closely matches the optimum genome packaging size. A larger deletion will accommodate the insertion of larger heterologous nucleic acid sequences in the adenovirus or adenoviral genome. In one embodiment of the invention, the L4 polyadenylation signal sequences, which reside in the E3 region, are retained.

The E4 region comprises multiple open reading frames (ORFs). An adenovirus or adenoviral vector with a deletion of all of the open reading frames of the E4 region except ORF6, and in some cases ORF3, does not require complementation of any gene functions in the E4 region for the adenovirus or adenoviral vector to propagate (e.g., to form adenoviral vector particles). Conversely, an adenovirus or adenoviral vector with a disruption or deletion of ORF6, and in some cases ORF3, of the E4 region (e.g., with a deficiency in a replication-essential gene function based in ORF6 and/or ORF3 of the E4 region), with or without a disruption or deletion of any of the other open reading frames of the E4 region or the native E4 promoter, polyadenylation sequence, and/or the right-side inverted terminal repeat (ITR), requires complementation of the E4 region (specifically, of ORF6 and/or ORF3 of the E4 region) for the adenovirus or adenoviral vector to propagate (e.g., to form adenoviral vector particles). The late regions of the adenoviral genome include the L1, L2, L3, L4, and L5 regions. The adenovirus or adenoviral vector also can have a mutation in the major late promoter (MLP), as discussed in International Patent Application Publication WO 2000/000628, which can render the adenovirus or adenoviral vector replication-deficient if desired.

The one or more regions of the adenoviral genome that contain one or more deficiencies in replication-essential gene functions desirably are one or more early regions of the adenoviral genome, i.e., the E1, E2, and/or E4 regions, optionally with the deletion in part or in whole of the E3 region.

The replication-deficient adenovirus or adenoviral vector also can have one or more mutations as compared to the wild-type adenovirus (e.g., one or more deletions, insertions, and/or substitutions) in the adenoviral genome that do not inhibit viral replication in host cells. Thus, in addition to one or more deficiencies in replication-essential gene functions, the adenovirus or adenoviral vector can be deficient in other respects that are not replication-essential. For example, the adenovirus or adenoviral vector can have a partial or entire deletion of the adenoviral early region known as the E3 region, which is not essential for propagation of the adenovirus or adenoviral genome.

In one embodiment, the adenovirus or adenoviral vector is replication-deficient and requires, at most, complementation of the E1 region or the E4 region of the adenoviral genome, for propagation (e.g., to form adenoviral vector particles). Thus, the replication-deficient adenovirus or adenoviral vector requires complementation of at least one replication-essential gene function of the E1A subregion and/or the E1B region of the adenoviral genome (denoted an E1-deficient adenoviral vector) or the E4 region of the adenoviral genome (denoted an E4-deficient adenoviral vector) for propagation (e.g., to form adenoviral vector particles). The adenovirus or adenoviral vector can be deficient in at least one replication-essential gene function (desirably all replication-essential gene functions) of the E1 region of the adenoviral genome and at least one gene function of the nonessential E3 region of the adenoviral genome (denoted an E1/E3-deficient adenoviral vector). The adenovirus or adenoviral vector can be deficient in at least one replication-essential gene function (desirably all replication-essential gene functions) of the E4 region of the adenoviral genome and at least one gene function of the nonessential E3 region of the adenoviral genome (denoted an E3/E4-deficient adenoviral vector).

In one embodiment, the adenovirus or adenoviral vector is replication-deficient and requires, at most, complementation of the E2 region, preferably the E2A subregion, of the adenoviral genome, for propagation (e.g., to form adenoviral vector particles). Thus, the replication-deficient adenovirus or adenoviral vector requires complementation of at least one replication-essential gene function of the E2A subregion of the adenoviral genome (denoted an E2A-deficient adenoviral vector) for propagation (e.g., to form adenoviral vector particles). The adenovirus or adenoviral vector can be deficient in at least one replication-essential gene function (desirably all replication-essential gene functions) of the E2A region of the adenoviral genome and at least one gene function of the nonessential E3 region of the adenoviral genome (denoted an E2A/E3-deficient adenoviral vector).

In one embodiment, the adenovirus or adenoviral vector is replication-deficient and requires, at most, complementation of the E1 and E4 regions of the adenoviral genome for propagation (e.g., to form adenoviral vector particles). Thus, the replication-deficient adenovirus or adenoviral vector requires complementation of at least one replication-essential gene function of both the E1 and E4 regions of the adenoviral genome (denoted an E1/E4-deficient adenoviral vector) for propagation (e.g., to form adenoviral vector particles). The adenovirus or adenoviral vector can be deficient in at least one replication-essential gene function (desirably all replication-essential gene functions) of the E1 region of the adenoviral genome, at least one replication-essential gene function of the E4 region of the adenoviral genome, and at least one gene function of the nonessential E3 region of the adenoviral genome (denoted an E1/E3/E4-deficient adenoviral vector). The adenovirus or adenoviral vector preferably requires, at most, complementation of the E1 region of the adenoviral genome for propagation, and does not require complementation of any other deficiency of the adenoviral genome for propagation. More preferably, the adenovirus or adenoviral vector requires, at most, complementation of the E1 and E4 regions of the adenoviral genome for propagation, and does not require complementation of any other deficiency of the adenoviral genome for propagation.

The adenovirus or adenoviral vector, when deficient in multiple replication-essential gene functions of the adenoviral genome (e.g., an E1/E4-deficient adenoviral vector), can include a spacer sequence to provide viral growth in a complementing cell line similar to that achieved by adenoviruses or adenoviral vectors deficient in a single replication-essential gene function (e.g., an E1-deficient adenoviral vector). The spacer sequence can contain any nucleotide sequence or sequences which are of a desired length, such as sequences at least about 15 base pairs (e.g., between about 15 nucleotides and about 12,000 nucleotides), preferably about 100 nucleotides to about 10,000 nucleotides, more preferably about 500 nucleotides to about 8,000 nucleotides, even more preferably about 1,500 nucleotides to about 6,000 nucleotides, and most preferably about 2,000 to about 3,000 nucleotides in length, or a range defined by any two of the foregoing values. The spacer sequence can be coding or non-coding and native or non-native with respect to the adenoviral genome, but does not restore the replication-essential function to the deficient region. The spacer also can contain an expression cassette. More preferably, the spacer comprises a polyadenylation sequence and/or a gene that is non-native with respect to the adenovirus or adenoviral vector. The use of a spacer in an adenoviral vector is further described in, for example, U.S. Pat. No. 5,851,806 and International Patent Application Publication WO 1997/021826.

By removing all or part of the adenoviral genome, for example, the E1, E3, and E4 regions of the adenoviral genome, the resulting adenovirus or adenoviral vector is able to accept inserts of exogenous nucleic acid sequences while retaining the ability to be packaged into adenoviral capsids. An exogenous nucleic acid sequence can be inserted at any position in the adenoviral genome so long as insertion in the position allows for the formation of adenovirus or the adenoviral vector particle. The exogenous nucleic acid sequence preferably is positioned in the E1 region, the E3 region, or the E4 region of the adenoviral genome.

The replication-deficient adenovirus or adenoviral vector of the invention can be produced in complementing cell lines that provide gene functions not present in the replication-deficient adenovirus or adenoviral vector, but required for viral propagation, at appropriate levels in order to generate high titers of viral vector stock. Such complementing cell lines are known and include, but are not limited to, 293 cells (described in, e.g., Graham et al., *J. Gen. Virol.*, 36: 59-72 (1977)), PER.C6 cells (described in, e.g., International Patent Application Publication WO 1997/000326, and U.S. Pat. Nos. 5,994,128 and 6,033,908), and 293-ORF6 cells (described in, e.g., International Patent Application Publication WO 95/34671 and Brough et al., *J. Virol.*, 71: 9206-9213 (1997)). Other suitable complementing cell lines to produce the replication-deficient adenovirus or adenoviral vector of the invention include complementing cells that have been generated to propagate adenoviral vectors encoding transgenes whose expression inhibits viral growth in host cells (see, e.g., U.S. Patent Application Publication No. 2008/0233650). Additional suitable complementing cells are described in, for example, U.S. Pat. Nos. 6,677,156 and 6,682,929, and International Patent Application Publication WO 2003/020879. In some instances, the cellular genome need not comprise nucleic acid sequences, the gene products of which complement for all of the deficiencies of a replication-deficient adenoviral vector. One or more replication-essential gene functions lacking in a replication-deficient adenoviral vector can be supplied by a helper virus, e.g., an adenoviral vector that supplies in trans one or more essential gene functions required for replication of the replication-deficient adenovirus or adenoviral vector. Alternatively, the inventive adenovirus or adenoviral vector can comprise a non-native replication-essential gene that complements for the one or more replication-essential gene functions lacking in the inventive replication-deficient adenovirus or adenoviral vector. For example, an E1/E4-deficient adenoviral vector can be engineered to contain a nucleic acid sequence encoding E4 ORF 6 that is obtained or derived from a different adenovirus (e.g., an adenovirus of a different serotype than the inventive adenovirus or adenoviral vector, or an adenovirus of a different species than the inventive adenovirus or adenoviral vector).

The adenovirus or adenoviral vector can further comprise a transgene. The term "transgene" is defined herein as a non-native nucleic acid sequence that is operably linked to appropriate regulatory elements (e.g., a promoter), such that the non-native nucleic acid sequence can be expressed to produce a protein (e.g., peptide or polypeptide). The regulatory elements (e.g., promoter) can be native or non-native to the adenovirus or adenoviral vector.

A "non-native" nucleic acid sequence is any nucleic acid sequence (e.g., DNA, RNA, or cDNA sequence) that is not a naturally occurring nucleic acid sequence of an adenovirus in a naturally occurring position. Thus, the non-native nucleic acid sequence can be naturally found in an adenovirus, but located at a non-native position within the adenoviral genome and/or operably linked to a non-native promoter. The terms "non-native nucleic acid sequence," "heterologous nucleic acid sequence," and "exogenous nucleic acid sequence" are synonymous and can be used interchangeably in the context of the invention. The non-native nucleic acid sequence preferably is DNA and preferably encodes a protein (i.e., one or more nucleic acid sequences encoding one or more proteins).

The non-native nucleic acid sequence can encode a therapeutic protein that can be used to prophylactically or therapeutically treat a mammal for a disease. Examples of suitable therapeutic proteins include cytokines, toxins, tumor suppressor proteins, growth factors, hormones, receptors, mitogens, immunoglobulins, neuropeptides, neurotransmitters, and enzymes. Alternatively, the non-native nucleic acid sequence can encode an antigen of a pathogen (e.g., a bacterium or a virus), and the adenovirus or adenoviral vector can be used as a vaccine.

The invention provides a composition comprising the adenovirus or adenoviral vector described herein and a carrier therefor (e.g., a pharmaceutically acceptable carrier). The composition desirably is a physiologically acceptable (e.g., pharmaceutically acceptable) composition, which comprises a carrier, preferably a physiologically (e.g., pharmaceutically) acceptable carrier, and the adenovirus or adenoviral vector. Any suitable carrier can be used within the context of the invention, and such carriers are well known in the art. The choice of carrier will be determined, in part, by the particular use of the composition (e.g., administration to an animal) and the particular method used to administer the composition.

Ideally, in the context of replication-deficient adenoviral vectors, the pharmaceutical composition preferably is free of replication-competent adenovirus. The pharmaceutical composition optionally can be sterile.

Suitable compositions include aqueous and non-aqueous isotonic sterile solutions, which can contain anti-oxidants, buffers, and bacteriostats, and aqueous and non-aqueous sterile suspensions that can include suspending agents, solubilizers, thickening agents, stabilizers, and preservatives. The composition can be presented in unit-dose or multi-dose sealed containers, such as ampules and vials, and can be stored in a freeze-dried (lyophilized) condition requiring only the addition of the sterile liquid carrier, for example, water, immediately prior to use. Extemporaneous solutions and suspensions can be prepared from sterile powders, granules, and tablets. Preferably, the carrier is a buffered saline solution. More preferably, the adenovirus or adenoviral vector is part of a composition formulated to protect the adenovirus or adenoviral vector from damage prior to administration. For example, the composition can be formulated to reduce loss of the adenovirus or adenoviral vector on devices used to prepare, store, or administer the adenovirus or adenoviral vector, such as glassware, syringes, or needles. The composition can be formulated to decrease the light sensitivity and/or temperature sensitivity of the adenovirus or adenoviral vector. To this end, the composition preferably comprises a pharmaceutically acceptable liquid carrier, such as, for example, those described above, and a stabilizing agent selected from the group consisting of polysorbate 80, L-arginine, polyvinylpyrrolidone, trehalose, and combinations thereof. Use of such a composition will extend the shelf life of the adenovirus or adenoviral vector, and facilitate its administration. Formulations for adenovirus or adenoviral vector-containing compositions are further described in, for example, U.S. Pat. Nos. 6,225,289, 6,514,943, and International Patent Application Publication WO 2000/034444.

The composition also can be formulated to enhance transduction efficiency. In addition, one of ordinary skill in the art will appreciate that the adenovirus or adenoviral vector can be present in a composition with other therapeutic or biologically-active agents. For example, factors that control inflammation, such as ibuprofen or steroids, can be part of the composition to reduce swelling and inflammation associated with in vivo administration of the adenovirus or adenoviral vector. If the adenovirus or adenoviral vector is used to deliver an antigen-encoding nucleic acid sequence to a host, immune system stimulators or adjuvants, e.g., interleukins, lipopolysaccharide, or double-stranded RNA, can be administered to enhance or modify any immune response to the antigen. Antibiotics, i.e., microbicides and fungicides, can be present to treat existing infection and/or reduce the risk of future infection, such as infection associated with gene transfer procedures.

The following examples further illustrate the present invention and, of course, should not be construed as in any way limiting its scope.

EXAMPLE 1

This example demonstrates the immunogenicity of an adenoviral vector encoding a Respiratory Syncytial Virus (RSV) F protein in cotton rats.

A gorilla adenovirus having the nucleic acid sequence of SEQ ID NO: 22 was modified by genetic engineering to (1) be rendered replication-deficient by deletion of the E1 region, and (2) express the human Respiratory Syncytial Virus (RSV) Fusion (F) glycoprotein. Because RSV replicates in the cytoplasm of cells, the gene encoding the F protein was modified for expression in a cell nucleus by removing RNA processing signals (e.g., RNA splicing sites), and was codon-optimized for expression in a mammalian cell. The expression of the F protein from the adenoviral vector was verified by infection of HEK-293 cells in vitro, and by a Western blot assay using protein extracts of the infected cells and a commercially available anti-RSV polyclonal antibody (Pab7133P, Maine Biotechnology, Portland, Me.).

Cotton rats (*Sigmodon hispidus*) were injected in the tibialis muscle with a single administration of $10^7$ particle units (pu) of the E1-deleted adenoviral vector expressing the RSV F glycoprotein. The animals were then challenged 28 days later with live human RSV ($10^6$ particle forming units (pfu) administered intranasally). At 5 days post-challenge, the viral load of RSV in the lungs of the animals was measured. The animals that were immunized with the adenoviral vector expressing the F protein did not have detectable RSV in the lungs (limit of detection 70 pfu/gram of lung tissue).

The results of this example demonstrate that the inventive adenoviral vector encoding an RSV F protein is immunogenic in vivo and can confer complete protection against RSV infection in cotton rats.

All references, including publications, patent applications, and patents, cited herein are hereby incorporated by reference to the same extent as if each reference were individually and specifically indicated to be incorporated by reference and were set forth in its entirety herein.

The use of the terms “a” and “an” and “the” and similar referents in the context of describing the invention (especially in the context of the following claims) are to be construed to cover both the singular and the plural, unless otherwise indicated herein or clearly contradicted by context. The terms “comprising,” “having,” “including,” and “containing” are to be construed as open-ended terms (i.e., meaning “including, but not limited to,”) unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., “such as”) provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An adenovirus or adenoviral vector comprising a non-native nucleic acid sequence and one or more of the nucleic acid sequences selected from the group consisting of:
    (a) a nucleic acid sequence that is at least 98.6% identical to SEQ ID NO: 6,
    (b) a nucleic acid sequence that is at least 99.06% identical to SEQ ID NO: 7,
    (c) a nucleic acid sequence that is at least 97.13% identical to SEQ ID NO: 8,
    (d) a nucleic acid sequence that is at least 91.6% identical to SEQ ID NO: 9, and
    (e) a nucleic acid sequence that is at least 96.83% identical to SEQ ID NO: 10.

2. The adenovirus or adenoviral vector of claim 1, which comprises a nucleic acid sequence that is at least 98.6% identical to SEQ ID NO: 6.

3. The adenovirus or adenoviral vector of claim 2, which comprises the nucleic acid sequence of SEQ ID NO: 6.

4. The adenovirus or adenoviral vector of claim 1, which comprises a nucleic acid sequence that is at least 99.06% identical to SEQ ID NO: 7.

5. The adenovirus or adenoviral vector of claim 4, which comprises the nucleic acid sequence of SEQ ID NO: 7.

6. The adenovirus or adenoviral vector of claim 1, which comprises a nucleic acid sequence that is at least 97.13% identical to SEQ ID NO: 8.

7. The adenovirus or adenoviral vector of claim 6, which comprises the nucleic acid sequence of SEQ ID NO: 8.

8. The adenovirus or adenoviral vector of claim 1, which comprises a nucleic acid sequence that is at least 91.6% identical to SEQ ID NO: 9.

9. The adenovirus or adenoviral vector of claim 8, which comprises the nucleic acid sequence of SEQ ID NO: 9.

10. The adenovirus or adenoviral vector of claim 1, which comprises a nucleic acid sequence that is at least 96.83% identical to SEQ ID NO: 10.

11. The adenovirus or adenoviral vector of claim 10, which comprises the nucleic acid sequence of SEQ ID NO: 10.

12. An adenovirus or adenoviral vector comprising a non-native nucleic acid sequence and one or more of the nucleic acid sequences selected from the group consisting of:
    (a) a nucleic acid sequence comprising at least 121 contiguous nucleotides of SEQ ID NO: 6,
    (b) a nucleic acid sequence comprising at least 462 contiguous nucleotides of SEQ ID NO: 7,
    (c) a nucleic acid sequence comprising at least 234 contiguous nucleotides of SEQ ID NO: 8,
    (d) a nucleic acid sequence comprising at least 606 contiguous nucleotides of SEQ ID NO: 9, and
    (e) a nucleic acid sequence comprising at least 188 contiguous nucleotides of SEQ ID NO: 10.

13. The adenovirus or adenoviral vector of claim 12, which comprises a nucleic acid sequence comprising at least 121 contiguous nucleotides of SEQ ID NO: 6.

14. The adenovirus or adenoviral vector of claim 13, which comprises the nucleic acid sequence of SEQ ID NO: 6.

15. The adenovirus or adenoviral vector of claim 12, which comprises a nucleic acid sequence comprising at least 462 contiguous nucleotides of SEQ ID NO: 7.

16. The adenovirus or adenoviral vector of claim 15, which comprises the nucleic acid sequence of SEQ ID NO: 7.

17. The adenovirus or adenoviral vector of claim 12, which comprises a nucleic acid sequence comprising at least 234 contiguous nucleotides of SEQ ID NO: 8.

18. The adenovirus or adenoviral vector of claim 17, which comprises the nucleic acid sequence of SEQ ID NO: 8.

19. The adenovirus or adenoviral vector of claim 12, which comprises a nucleic acid sequence comprising at least 606 contiguous nucleotides of SEQ ID NO: 9.

20. The adenovirus or adenoviral vector of claim 19, which comprises the nucleic acid sequence of SEQ ID NO: 9.

21. The adenovirus or adenoviral vector of claim 12, which comprises a nucleic acid sequence comprising at least 188 contiguous nucleotides of SEQ ID NO: 10.

22. The adenovirus or adenoviral vector of claim 21, which comprises the nucleic acid sequence of SEQ ID NO: 10.

23. An adenovirus or adenoviral vector comprising a non-native nucleic acid sequence and one or more of the amino acid sequences selected from the group consisting of:
   (a) the amino acid sequence of SEQ ID NO: 16,
   (b) an amino acid sequence that is at least 97.8% identical to SEQ ID NO: 18,
   (c) an amino acid sequence that is at least 93.4% identical to SEQ ID NO: 19, and
   (d) an amino acid sequence that is at least 98.2% identical to SEQ ID NO: 20.

24. The adenovirus or adenoviral vector of claim 23, which comprises the amino acid sequence of SEQ ID NO: 16.

25. The adenovirus or adenoviral vector of claim 23, which comprises an amino acid sequence that is at least 97.8% identical to SEQ ID NO: 18.

26. The adenovirus or adenoviral vector of claim 25, which comprises the amino acid sequence of SEQ ID NO: 18.

27. The adenovirus or adenoviral vector of claim 23, which comprises an amino acid sequence that is at least 93.4% identical to SEQ ID NO: 19.

28. The adenovirus or adenoviral vector of claim 27, which comprises the amino acid sequence of SEQ ID NO: 19.

29. The adenovirus or adenoviral vector of claim 23, which comprises an amino acid sequence that is at least 98.2% identical to SEQ ID NO: 20.

30. The adenovirus or adenoviral vector of claim 29, which comprises the amino acid sequence of SEQ ID NO: 20.

31. An adenovirus or adenoviral vector comprising a non-native nucleic acid sequence and one or more of the nucleic acid sequences selected from the group consisting of:
   (a) a nucleic acid sequence encoding the amino acid sequence of SEQ ID NO: 16,
   (b) a nucleic acid sequence encoding an amino acid sequence that is at least 99.78% identical to SEQ ID NO: 17,
   (c) a nucleic acid sequence encoding an amino acid sequence that is at least 97.8% identical to SEQ ID NO: 18,
   (d) a nucleic acid sequence encoding an amino acid sequence that is at least 93.4% identical to SEQ ID NO: 19, and
   (e) a nucleic acid sequence encoding an amino acid sequence that is at least 98.2% identical to SEQ ID NO: 20.

32. The adenovirus or adenoviral vector of claim 31, which comprises a nucleic acid sequence encoding the amino acid sequence of SEQ ID NO: 16.

33. The adenovirus or adenoviral vector of claim 31, which comprises a nucleic acid sequence encoding an amino acid sequence that is at least 99.78% identical to SEQ ID NO: 17.

34. The adenovirus or adenoviral vector of claim 33, which comprises a nucleic acid sequence encoding the amino acid sequence of SEQ ID NO: 17.

35. The adenovirus or adenoviral vector of claim 31, which comprises a nucleic acid sequence encoding an amino acid sequence that is at least 97.8% identical to SEQ ID NO: 18.

36. The adenovirus or adenoviral vector of claim 35, which comprises a nucleic acid sequence encoding the amino acid sequence of SEQ ID NO: 18.

37. The adenovirus or adenoviral vector of claim 31, which comprises a nucleic acid sequence encoding an amino acid sequence that is at least 93.4% identical to SEQ ID NO: 19.

38. The adenovirus or adenoviral vector of claim 37, which comprises a nucleic acid sequence encoding the amino acid sequence of SEQ ID NO: 19.

39. The adenovirus or adenoviral vector of claim 31, which comprises an amino acid sequence that is at least 98.2% identical to SEQ ID NO: 20.

40. The adenovirus or adenoviral vector of claim 39, which comprises the amino acid sequence of SEQ ID NO: 20.

41. An adenovirus or adenoviral vector comprising a non-native nucleic acid sequence and one or more of the amino acid sequences selected from the group consisting of:
   (a) an amino acid sequence comprising at least 89 contiguous amino acid residues of SEQ ID NO: 16,
   (b) an amino acid sequence comprising at least 247 contiguous amino acid residues of SEQ ID NO: 18,
   (c) an amino acid sequence comprising at least 370 contiguous amino acid residues of SEQ ID NO: 19, and
   (d) an amino acid sequence comprising at least 192 contiguous amino acid residues of SEQ ID NO: 20.

42. The adenovirus or adenoviral vector of claim 41, which comprises an amino acid sequence comprising at least 89 contiguous amino acid residues of SEQ ID NO: 16.

43. The adenovirus or adenoviral vector of claim 42, which comprises the amino acid sequence of SEQ ID NO: 16.

44. The adenovirus or adenoviral vector of claim 41, which comprises an amino acid sequence comprising at least 247 contiguous amino acid residues of SEQ ID NO: 18.

45. The adenovirus or adenoviral vector of claim 44, which comprises the amino acid sequence of SEQ ID NO: 18.

46. The adenovirus or adenoviral vector of claim 41, which comprises an amino acid sequence comprising at least 370 contiguous amino acid residues of SEQ ID NO: 19.

47. The adenovirus or adenoviral vector of claim 46, which comprises the amino acid sequence of SEQ ID NO: 19.

48. The adenovirus or adenoviral vector of claim 41, which comprises an amino acid sequence comprising at least 192 contiguous amino acid residues of SEQ ID NO: 20.

49. The adenovirus or adenoviral vector of claim 48, which comprises the amino acid sequence of SEQ ID NO: 20.

50. An adenovirus or adenoviral vector comprising a non-native nucleic acid sequence and one or more of the nucleic acid sequences selected from the group consisting of:
   (a) a nucleic acid sequence encoding an amino acid sequence comprising at least 89 contiguous amino acid residues of SEQ ID NO: 16,
   (b) a nucleic acid sequence encoding an amino acid sequence comprising at least 428 contiguous amino acid residues of SEQ ID NO: 17, (c) a nucleic acid sequence encoding an amino acid sequence comprising at least 247 contiguous amino acid residues of SEQ ID NO: 18, (d) a nucleic acid sequence encoding an amino acid sequence comprising at least 370 contiguous amino acid residues of SEQ ID NO: 19, and (e) a nucleic acid sequence encoding an amino acid sequence comprising at least 192 contiguous amino acid residues of SEQ ID NO: 20.

51. The adenovirus or adenoviral vector of claim 50, which comprises a nucleic acid sequence encoding an amino acid sequence comprising at least 89 contiguous amino acid residues of SEQ ID NO: 16.

52. The adenovirus or adenoviral vector of claim 51, which comprises a nucleic acid sequence encoding the amino acid sequence of SEQ ID NO: 16.

53. The adenovirus or adenoviral vector of claim 50, which comprises a nucleic acid sequence encoding an amino acid sequence comprising at least 428 contiguous amino acid residues of SEQ ID NO: 17.

54. The adenovirus or adenoviral vector of claim 53, which comprises a nucleic acid sequence encoding the amino acid sequence of SEQ ID NO: 17.

55. The adenovirus or adenoviral vector of claim 50, which comprises a nucleic acid sequence encoding an amino acid sequence comprising at least 247 contiguous amino acid residues of SEQ ID NO: 18.

56. The adenovirus or adenoviral vector of claim 55, which comprises a nucleic acid sequence encoding the amino acid sequence of SEQ ID NO: 18.

57. The adenovirus or adenoviral vector of claim 50, which comprises a nucleic acid sequence encoding an amino acid sequence comprising at least 370 contiguous amino acid residues of SEQ ID NO: 19.

58. The adenovirus or adenoviral vector of claim 57, which comprises a nucleic acid sequence encoding the amino acid sequence of SEQ ID NO: 19.

59. The adenovirus or adenoviral vector of claim 50, which comprises a nucleic acid sequence encoding an amino acid sequence comprising at least 192 contiguous amino acid residues of SEQ ID NO: 20.

60. The adenovirus or adenoviral vector of claim 59, which comprises a nucleic acid sequence encoding the amino acid sequence of SEQ ID NO: 20.

61. The adenovirus or adenoviral vector of claim 12, wherein the adenovirus or adenoviral vector requires complementation of a deficiency in one or more early regions of the adenoviral genome for propagation and does not require complementation of any other deficiency of the adenoviral genome for propagation.

62. The adenovirus or adenoviral vector of claim 12, wherein the non-native nucleic acid sequence is a transgene.

63. A composition comprising the adenovirus or adenoviral vector of claim 12, and a pharmaceutically acceptable carrier.

64. The adenovirus or adenoviral vector of claim 1, wherein the non-native nucleic acid sequence is a transgene or a nucleic acid sequence naturally found in an adenovirus but located at a non-native position within the adenoviral genome.

65. The adenovirus or adenoviral vector of claim 12, wherein the non-native nucleic acid sequence is naturally found in an adenovirus but located at a non-native position within the adenoviral genome.

66. The adenovirus or adenoviral vector of claim 23, wherein the non-native nucleic acid sequence is a transgene or a nucleic acid sequence naturally found in an adenovirus but located at a non-native position within the adenoviral genome.

67. The adenovirus or adenoviral vector of claim 31, wherein the non-native nucleic acid sequence is a transgene or a nucleic acid sequence naturally found in an adenovirus but located at a non-native position within the adenoviral genome.

68. The adenovirus or adenoviral vector of claim 41, wherein the non-native nucleic acid sequence is a transgene or a nucleic acid sequence naturally found in an adenovirus but located at a non-native position within the adenoviral genome.

69. The adenovirus or adenoviral vector of claim 50, wherein the non-native nucleic acid sequence is a transgene or a nucleic acid sequence naturally found in an adenovirus but located at a non-native position within the adenoviral genome.

70. The adenovirus or adenoviral vector of claim 1, which comprises a nucleic acid sequence that is at least 99.10% identical to SEQ ID NO: 6.

71. The adenovirus or adenoviral vector of claim 1, which comprises a nucleic acid sequence that is at least 99.50% identical to SEQ ID NO: 7.

72. The adenovirus or adenoviral vector of claim 1, which comprises a nucleic acid sequence that is at least 98% identical to SEQ ID NO: 8.

73. The adenovirus or adenoviral vector of claim 1, which comprises a nucleic acid sequence that is at least 94% identical to SEQ ID NO: 9.

74. The adenovirus or adenoviral vector of claim 1, which comprises a nucleic acid sequence that is at least 98% identical to SEQ ID NO: 10.

75. The adenovirus or adenoviral vector of claim 1, which comprises (a) a nucleic acid sequence that is at least 98.6% identical to SEQ ID NO: 6, (b) a nucleic acid sequence that is at least 99.06% identical to SEQ ID NO: 7, (c) a nucleic acid sequence that is at least 97.13% identical to SEQ ID NO: 8, (d) a nucleic acid sequence that is at least 91.6% identical to SEQ ID NO: 9, and (e) a nucleic acid sequence that is at least 96.83% identical to SEQ ID NO: 10.

76. A composition comprising the adenovirus or adenoviral vector of claim 1, and a pharmaceutically acceptable carrier.

77. The adenovirus or adenoviral vector of claim 12, which comprises a nucleic acid sequence comprising at least 150 contiguous nucleotides of SEQ ID NO: 6.

78. The adenovirus or adenoviral vector of claim 12, which comprises a nucleic acid sequence comprising at least 600 contiguous nucleotides of SEQ ID NO: 7.

79. The adenovirus or adenoviral vector of claim 12, which comprises a nucleic acid sequence comprising at least 300 contiguous nucleotides of SEQ ID NO: 8.

80. The adenovirus or adenoviral vector of claim 12, which comprises a nucleic acid sequence comprising at least 700 contiguous nucleotides of SEQ ID NO: 9.

81. The adenovirus or adenoviral vector of claim 12, which comprises a nucleic acid sequence comprising at least 300 contiguous nucleotides of SEQ ID NO: 10.

82. The adenovirus or adenoviral vector of claim 12, which comprises (a) a nucleic acid sequence comprising at least 121 contiguous nucleotides of SEQ ID NO: 6, (b) a nucleic acid sequence comprising at least 462 contiguous nucleotides of SEQ ID NO: 7, (c) a nucleic acid sequence comprising at least 234 contiguous nucleotides of SEQ ID NO: 8, (d) a nucleic acid sequence comprising at least 606 contiguous nucleotides of SEQ ID NO: 9, and (e) a nucleic acid sequence comprising at least 188 contiguous nucleotides of SEQ ID NO: 10.

83. The adenovirus or adenoviral vector of claim 23, which comprises an amino acid sequence that is at least 98.86% identical to SEQ ID NO: 18.

84. The adenovirus or adenoviral vector of claim 23, which comprises an amino acid sequence that is at least 96.01% identical to SEQ ID NO: 19.

85. The adenovirus or adenoviral vector of claim 23, which comprises an amino acid sequence that is at least 99.06% identical to SEQ ID NO: 20.

86. The adenovirus or adenoviral vector of claim 23, which comprises (a) the amino acid sequence of SEQ ID NO: 16, (b) an amino acid sequence that is at least 97.8% identical to SEQ ID NO: 18, (c) an amino acid that is at least 93.4% identical to SEQ ID NO: 19, and (d) an amino acid sequence that is at least 98.2% identical to SEQ ID NO: 20.

87. A composition comprising the adenovirus or adenoviral vector of claim 23, and a pharmaceutically acceptable carrier.

88. The adenovirus or adenoviral vector of claim 31, which comprises a nucleic acid sequence encoding an amino acid sequence that is at least 99.87% identical to SEQ ID NO: 17.

89. The adenovirus or adenoviral vector of claim 31, which comprises a nucleic acid sequence encoding an amino acid sequence that is at least 98.86% identical to SEQ ID NO: 18.

90. The adenovirus or adenoviral vector of claim 31, which comprises a nucleic acid sequence encoding an amino acid sequence that is at least 96.01% identical to SEQ ID NO: 19.

91. The adenovirus or adenoviral vector of claim 31, which comprises a nucleic acid sequence encoding an amino acid sequence that is at least 99.06% identical to SEQ ID NO: 20.

92. The adenovirus or adenoviral vector of claim 31, which comprises (a) a nucleic acid sequence encoding the amino acid sequence of SEQ ID NO: 16, (b) a nucleic acid sequence encoding an amino acid sequence that is at least 99.78% identical to SEQ ID NO: 17, (c) a nucleic acid sequence encoding an amino acid sequence that is at least 97.8% identical to SEQ ID NO: 18, (d) a nucleic acid sequence encoding an amino acid sequence that is at least 93.4% identical to SEQ ID NO: 19, and (e) a nucleic acid sequence encoding an amino acid sequence that is at least 98.2% identical to SEQ ID NO: 20.

93. A composition comprising the adenovirus or adenoviral vector of claim 31, and a pharmaceutically acceptable carrier.

94. The adenovirus or adenoviral vector of claim 41, which comprises an amino acid sequence comprising at least 100 contiguous amino acid residues of SEQ ID NO: 16.

95. The adenovirus or adenoviral vector of claim 41, which comprises an amino acid sequence comprising at least 275 contiguous amino acid residues of SEQ ID NO: 18.

96. The adenovirus or adenoviral vector of claim 41, which comprises an amino acid sequence comprising at least 400 contiguous amino acid residues of SEQ ID NO: 19.

97. The adenovirus or adenoviral vector of claim 41, which comprises an amino acid sequence comprising at least 200 contiguous amino acid residues of SEQ ID NO: 20.

98. The adenovirus or adenoviral vector of claim 41, which comprises (a) an amino acid sequence comprising at least 89 contiguous amino acid residues of SEQ ID NO: 16, (b) an amino acid sequence comprising at least 247 contiguous amino acid residues of SEQ ID NO: 18, (c) an amino acid sequence comprising at least 370 contiguous amino acid residues of SEQ ID NO: 19, and (d) an amino acid sequence comprising at least 192 contiguous amino acid residues of SEQ ID NO: 20.

99. A composition comprising the adenovirus or adenoviral vector of claim 41, and a pharmaceutically acceptable carrier.

100. The adenovirus or adenoviral vector of claim 50, which comprises a nucleic acid sequence encoding an amino acid sequence comprising at least 100 contiguous amino acid residues of SEQ ID NO: 16.

101. The adenovirus or adenoviral vector of claim 50, which comprises a nucleic acid sequence encoding an amino acid sequence comprising at least 275 contiguous amino acid residues of SEQ ID NO: 18.

102. The adenovirus or adenoviral vector of claim 50, which comprises a nucleic acid sequence encoding an amino acid sequence comprising at least 400 contiguous amino acid residues of SEQ ID NO: 19.

103. The adenovirus or adenoviral vector of claim 50, which comprises a nucleic acid sequence encoding an amino acid sequence comprising at least 200 contiguous amino acid residues of SEQ ID NO: 20.

104. The adenovirus or adenoviral vector of claim 50, which comprises (a) a nucleic acid sequence encoding an amino acid sequence comprising at least 89 contiguous amino acid residues of SEQ ID NO: 16, (b) a nucleic acid sequence encoding an amino acid sequence comprising at least 428 contiguous amino acid residues of SEQ ID NO: 17, (c) a nucleic acid sequence encoding an amino acid sequence comprising at least 247 contiguous amino acid residues of SEQ ID NO: 18, (d) a nucleic acid sequence encoding an amino acid sequence comprising at least 370 contiguous amino acid residues of SEQ ID NO: 19, and (e) a nucleic acid sequence encoding an amino acid sequence comprising at least 192 contiguous amino acid residues of SEQ ID NO: 20.

105. A composition comprising the adenovirus or adenoviral vector of claim 50, and a pharmaceutically acceptable carrier.

106. The adenovirus or adenoviral vector of claim 1, wherein the non-native nucleic acid sequence is a transgene.

107. The adenovirus or adenoviral vector of claim 23, wherein the non-native nucleic acid sequence is a transgene.

108. The adenovirus or adenoviral vector of claim 31, wherein the non-native nucleic acid sequence is a transgene.

109. The adenovirus or adenoviral vector of claim 41, wherein the non-native nucleic acid sequence is a transgene.

110. The adenovirus or adenoviral vector of claim 50, wherein the non-native nucleic acid sequence is a transgene.

111. The adenovirus or adenoviral vector of claim 1, wherein the adenovirus or adenoviral vector requires complementation of a deficiency in one or more early regions of the adenoviral genome for propagation and does not require complementation of any other deficiency of the adenoviral genome for propagation.

112. The adenovirus or adenoviral vector of claim 23, wherein the adenovirus or adenoviral vector requires complementation of a deficiency in one or more early regions of the adenoviral genome for propagation and does not require complementation of any other deficiency of the adenoviral genome for propagation.

113. The adenovirus or adenoviral vector of claim 31, wherein the adenovirus or adenoviral vector requires complementation of a deficiency in one or more early regions of the adenoviral genome for propagation and does not require complementation of any other deficiency of the adenoviral genome for propagation.

114. The adenovirus or adenoviral vector of claim 41, wherein the adenovirus or adenoviral vector requires complementation of a deficiency in one or more early regions of the adenoviral genome for propagation and does not require complementation of any other deficiency of the adenoviral genome for propagation.

115. The adenovirus or adenoviral vector of claim 50, wherein the adenovirus or adenoviral vector requires complementation of a deficiency in one or more early regions of the adenoviral genome for propagation and does not require complementation of any other deficiency of the adenoviral genome for propagation.

* * * * *